United States Patent
Konteatis et al.

(10) Patent No.: US 12,077,534 B2
(45) Date of Patent: Sep. 3, 2024

(54) AZA-HETEROBICYCLIC INHIBITORS OF MAT2A AND METHODS OF USE FOR TREATING CANCER

(71) Applicant: Les Laboratoires Servier SAS, Suresnes (FR)

(72) Inventors: Zenon D. Konteatis, Chatham, NJ (US); Mingzong Li, Medford, MA (US); Samuel K. Reznik, Cambridge, MA (US); Zhihua Sui, Suresnes (FR)

(73) Assignee: LES LABORATOIRES SERVIER, Suresnes (FR)

( * ) Notice: Subject to any disclaimer, the term of this patent is extended or adjusted under 35 U.S.C. 154(b) by 670 days.

(21) Appl. No.: 17/418,442

(22) PCT Filed: Dec. 27, 2019

(86) PCT No.: PCT/US2019/068652
§ 371 (c)(1),
(2) Date: Jun. 25, 2021

(87) PCT Pub. No.: WO2020/139991
PCT Pub. Date: Jul. 2, 2020

(65) Prior Publication Data
US 2022/0144820 A1     May 12, 2022

Related U.S. Application Data

(60) Provisional application No. 62/785,519, filed on Dec. 27, 2018.

(51) Int. Cl.
*C07D 471/04*     (2006.01)
*A61P 35/00*      (2006.01)
*C07D 519/00*     (2006.01)

(52) U.S. Cl.
CPC ............ *C07D 471/04* (2013.01); *A61P 35/00* (2018.01); *C07D 519/00* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 10,329,298 B2 * | 6/2019 | Konteatis | C07D 487/04 |
| 10,800,782 B2 * | 10/2020 | Konteatis | A61P 35/02 |
| 11,325,914 B1 * | 5/2022 | Konteatis | A61P 35/02 |
| 11,524,960 B2 * | 12/2022 | Konteatis | C07D 471/20 |
| 2003/0055044 A1 | 3/2003 | Davies et al. | |
| 2004/0122029 A1 | 6/2004 | Liu et al. | |
| 2021/0115045 A1 | 4/2021 | Konteatis et al. | |
| 2022/0098203 A1 * | 3/2022 | Konteatis | C07D 487/04 |
| 2022/0251081 A1 * | 8/2022 | Konteatis | C07D 471/04 |

FOREIGN PATENT DOCUMENTS

| | | |
|---|---|---|
| AU | 2001293784 B2 | 8/2007 |
| JP | 2004-509113 A | 3/2004 |
| JP | 2021-519783 A | 8/2021 |
| RU | 2345077 C2 | 1/2009 |
| WO | 99/67634 A1 | 12/1999 |
| WO | 2002/018380 A1 | 3/2002 |
| WO | 2012/103457 A2 | 8/2012 |
| WO | 2016/064960 A1 | 4/2016 |
| WO | 2018/045071 A1 | 3/2018 |
| WO | 2019/191470 A1 | 10/2019 |

OTHER PUBLICATIONS

Li et al., J. Med. Chem. 2022, 65, 14, 9531-9547 Publication Date:Jul. 7, 2022 (Year: 2022).*
Abdelrazek F.M. et al., "A novel synthesis and molluscicidal activity of some functionally substituted pyridine, pyrido[3,2-c]pyridazine, and pyrido[3,2-c]pyridazino[2',3'-a]quinazoline derivatives", Arch Pharm Chem., Apr. 2005, vol. 338, No. 7, pp. 329-334.
Wardakhan et al., "Uses of 2-diazo-4,5,6,7-tetrahydrobenzo[b]thiophene derivatives in the synthesis of azoles, azines, and their fused derivatives", Heteroatom Chemistry, vol. 13, No. 2, 2002, pp. 108-115.
Cai et al., "Differential Expression of Methionine Adenosyltransferase Genes Influences the Rate of Growth of Human Hepatocellular Carcinoma Cells", Cancer Res., 1998, 58, 1444-1450.
Cairns et al., "Frequency of homozygous deletion at p16/CDKN2 in primary human tumours", Nat. Gen. 1995, 11, 210-212.
Chen et al., "Role of Methionine Adenosyltransferase 2A and S-adenosylmethionine in Mitogen-Induced Growth of Human Colon Cancer Cells", Gastroenterology, 2007, 133, 207-218.
Frau et al., "Pleiotropic effects of methionine adenosyltransferases deregulation as determinants of liver cancer progression and prognosis", J. Hepatol., 2013, 59, 830-841.
Frau et al., "Role of Transcriptional and Posttranscriptional Regulation of Methionine Adenosyltransferases in Liver Cancer Progression", Hepatology, 2012, 56, 165-175.
Garcia-Castellano et al., "Methylthioadenosine Phosphorylase Gene Deletions Are Common in Osteosarcoma", Clin. Cancer Res., 2002, 8(3), 782-787.
Jani et al., "Inhibition of methionine adenosyltransferase II induces FasL expression, Fas-DISC formation and caspase-8-dependent apoptotic death in T leukemic cells", Cell Res., 2009, 19, 358-369.
Li et al., "Multi-target siRNA: Therapeutic Strategy for Hepatocellular Carcinoma", J. Cancer, 2016, 7(10), 1317-1327.

(Continued)

*Primary Examiner* — Jeffrey S Lundgren
*Assistant Examiner* — Anthony Joseph Seitz
(74) *Attorney, Agent, or Firm* — BakerHostetler

(57) ABSTRACT

The present disclosure provides for compounds according to Formula I and their pharmaceutically acceptable salts, tautomers, and/or isotopologues as described in the disclosure. The compounds are inhibitors of methionine adenosyltransferase isoform 2A (MAT2A). Also provided are pharmaceutical compositions and methods of using the compounds for treating cancers, including some cancers in which the gene encoding methylthioadenosine phosphorylase (MTAP) is deleted.

35 Claims, No Drawings

(56) References Cited

OTHER PUBLICATIONS

Liu et al., "Silencing MAT2A gene by RNA interference inhibited cell growth and induced apoptosis in human hepatoma cells", Hepatol. Res., 2007, 37, 376-388.
Lu et al., "Hijacking the E3 Ubiquitin Ligase Cereblon to Efficiently Target BRD4", Chemistry & Biology, 2015, 22, 755-763.
Marjon et al., "MTAP Deletions in Cancer Create Vulnerability to Targeting of the MAT2A/PRMT5/RIOK1 Axis", Cell Reports, 2016, 15(3), 574-587.
Pascale et al., "Deregulation of methionine metabolism as determinant of progression and prognosis of hepatocellular carcinoma", Transl. Gastroenterol. Hepatol, 2018, 3, 36.
Pomerantz et al., "The Ink4a Tumor Suppressor Gene Product, p19Arf, Interacts with MDM2 and Neutralizes MDM2's Inhibition of p53", Cell, 1998, 92, 713-723.
Vazquez-Chantada et al., "HuR/Methyl-HuR and AUF1 regulate the MAT expressed during liver proliferation, differentiation and carcinogenesis", Gastroenterology, 2010, 138, 1943-1953.
Wermuth, The Practice of Medicinal Chemistry, Molecular Variaitons Based on Isosteric Replacements, Academic Press, 1996, p. 203-213.
Bastin R. J. et al., "Salt selection and optimisation procedures for pharmaceutical new chemical entities", Organic process research & development, 2000, vol. 4, No. 5, pp. 427-435.
Blass B.E. et al., "A facile, KF/Al2O3 mediated method for the preparation of functionalized pyrido[2,3-d]pyrimidin-7(8H)-ones", Tetrahedron Letters, 2006, vol. 47, No. 18, pp. 3177-3180.

\* cited by examiner

AZA-HETEROBICYCLIC INHIBITORS OF MAT2A AND METHODS OF USE FOR TREATING CANCER

CROSS-REFERENCE TO RELATED APPLICATIONS

This application is the National Stage Application of International Patent Application No. PCT/US2019/068652, filed Dec. 27, 2019, which claims priority to U.S. Provisional Patent Application No. 62/785,519, filed Dec. 27, 2018, the disclosures of which are incorporated by reference herein in their entireties.

BACKGROUND

Methionine adenosyltransferase (MAT), which is also known as S-adenosylmethionine synthetase, is a cellular enzyme that catalyzes the synthesis of S-adenosyl methionine (SAM or AdoMet) from methionine and ATP; the catalysis is considered to be rate-limiting step of the methionine cycle. SAM is the propylamino donor in polyamine biosynthesis, the principal methyl donor for DNA methylation, and is involved in gene transcription and cellular proliferation as well as the production of secondary metabolites.

Two genes designated as MAT1A and MAT2A encode two distinct catalytic MAT isoforms, respectively. A third gene, MAT2B, encodes a MAT2A regulatory subunit. MAT1A is specifically expressed in the adult liver, whereas MAT2A is widely distributed. Because MAT isoforms differ in catalytic kinetics and regulatory properties, MAT1A-expressing cells have considerably higher SAM levels than do MAT2A-expressing cells. It has been found that hypomethylation of the MAT2A promoter and histone acetylation causes upregulation of MAT2A expression. See, e.g. M. Vázquez-Chantada et al., *Gastroenterology* 138 (2010) 1943-53; M. Frau et al., *J. Hepatol.* 59 (2013) 830-41; M. Frau et al., *Hepatology* 56 (2012) 165-75; and R. M. Pascale et al., *Transl. Gastroenterol. Hepatol.* 3 (2018) 36.

In hepatocellular carcinoma (HCC), the downregulation of MAT1A and the up-regulation of MAT2A occur, which is known as the MAT1A:MAT2A switch. The switch, accompanied with up-regulation of MAT2B, results in lower SAM contents, which provide a growth advantage to hepatoma cells. Because MAT2A plays a crucial role in facilitating the growth of hepatoma cells, it is a target for antineoplastic therapy. Recent studies have shown that silencing by using small interfering RNA substantially suppresses growth and induces apoptosis in hepatoma cells. See, e.g., T. Li et al., *J. Cancer* 7(10) (2016) 1317-1327.

Some cancer cell lines that are MTAP deficient are particularly sensitive to inhibition of MAT2A. Marjon et al. (Cell Reports 15(3) (2016) 574-587). MTAP (methylthioadenosine phosphorylase) is an enzyme widely expressed in normal tissues that catalyzes the conversion of methylthioadenosine (MTA) into adenine and 5-methylthioribose-1-phosphate. The adenine is salvaged to generate adenosine monophosphate, and the 5-methylthioribose-1-phosphate is converted to methionine and formate. Because of this salvage pathway, MTA can serve as an alternative purine source when de novo purine synthesis is blocked, e.g., with antimetabolites, such as L-alanosine.

MAT2A is dysregulated in additional cancers that lack MTAP-deletion, including hepatocellular carcinoma and leukemia. J. Cai et al., *Cancer Res.* 58 (1998) 1444-1450; T. S. Jani et al., *Cell. Res.* 19 (2009) 358-369. Silencing of MAT2A expression via RNA-interference results in antiproliferative effects in several cancer models. H. Chen et al., *Gastroenterology* 133 (2007) 207-218; Q. Liu et al. *Hepatol. Res.* 37 (2007) 376-388.

Many human and murine malignant cells lack MTAP activity. MTAP deficiency is found not only in tissue culture cells but the deficiency is also present in primary leukemias, gliomas, melanomas, pancreatic cancers, non-small cell lung cancers (NSCLC), bladder cancers, astrocytomas, osteosarcomas, head and neck cancers, myxoid chondrosarcomas, ovarian cancers, endometrial cancers, breast cancers, soft tissue sarcomas, non-Hodgkin lymphoma, and mesotheliomas. The gene encoding for human MTAP maps to region 9p21 on human chromosome 9p. This region also contains the tumor suppressor genes p16INK4A (also known as CDKN2A) and p15INK4B. These genes code for p16 and p15, which are inhibitors of the cyclin D-dependent kinases cdk4 and cdk6, respectively.

The p16INK4A transcript can alternatively be alternative reading frame (ARF) spliced into a transcript encoding p14ARF. p14ARF binds to MDM2 and prevents degradation of p53 (Pomerantz et al. (1998) Cell 92:713-723). The 9p21 chromosomal region is of interest because it is frequently homozygously deleted in a variety of cancers, including leukemias, NSLC, pancreatic cancers, gliomas, melanomas, and mesothelioma. The deletions often inactivate more than one gene. For example, Cairns et al. ((1995) *Nat. Gen.* 11:210-212) reported that after studying more than 500 primary tumors, almost all the deletions identified in such tumors involved a 170 kb region containing MTAP, p14ARF and P16INK4A. Carson et al. (WO 99/67634) reported that a correlation exists between the stage of tumor development and loss of homozygosity of the gene encoding MTAP and the gene encoding p16. For example, deletion of the MTAP gene, but not p16INK4A was reported to be indicative of a cancer at an early stage of development, whereas deletion of the genes encoding for p16 and MTAP was reported to be indicative of a cancer at a more advanced stage of tumor development. In some osteosarcoma patients, the MTAP gene was present at diagnosis but was deleted at a later time point (Garcia-Castellano et al., *Clin. Cancer Res.* 8(3) 2002 782-787).

SUMMARY

The present disclosure provides compounds that inhibit MAT2A. The compounds and their pharmaceutical compositions are useful in methods for treating various cancers, including those that are refractory to standard treatments, such as surgery, radiation therapy, chemotherapy, and hormonal therapy.

Thus, in accordance with some embodiments, the present disclosure provides a compound according to formula I or a pharmaceutically acceptable salt, tautomer, and/or isotopologue thereof.

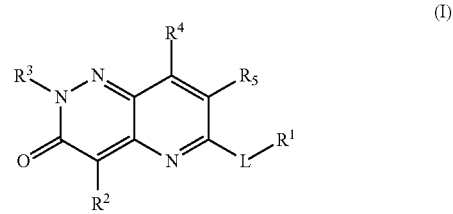

In Formula I, L is O, S, NR, or a bond. R is H or $C_1$-$C_6$-alkyl.

$R^1$ is selected from the group consisting of $C_1$-$C_6$-alkyl, $C_2$-$C_6$-alkenyl, $C_3$-$C_6$-carbocyclyl, —($C_1$-$C_6$-alkyl)($C_3$-$C_6$-carbocyclyl), and —($C_1$-$C_6$-alkyl)($C_3$-$C_6$-cycloalkenyl) wherein any alkyl in $R^1$ is straight or branched. In an embodiment, $R^1$ is optionally substituted by 1-6 halo or 1-6 deuterium.

Alternatively, in an embodiment, when L is NR, then R and $R^1$ in combination with L represent a 3- to 6-membered heterocycloalkyl (wherein 1-4 ring members are independently selected from N, O, and S) optionally substituted by one or more $R^A$.

$R^2$ and $R^3$ are independently selected from the group consisting of $C_2$-$C_6$-alkynyl, $C_6$-$C_{10}$-aryl, $C_3$-$C_6$-carbocyclyl, 5- to 10-membered heteroaryl (wherein 1-4 heteroaryl members are independently selected from N, O, and S), and 3- to 14-membered heterocycloalkyl (wherein 1-4 heterocycloalkyl members are independently selected from N, O, and S). $R^2$ and $R^3$ are independently and optionally substituted by one or more substituents that are selected from the group consisting of $R^A$, $OR^A$, halo, —N=N—$R^A$, —$NR^AR^B$, —($C_1$-$C_6$-alkyl)$NR^AR^B$, —C(O)$OR^A$, —C(O)$NR^AR^B$, —OC(O)$R^A$, —Si($C_1$-$C_6$-alkyl)$_3$ and —CN.

$R^4$ is selected from the group consisting of H, $C_1$-$C_6$-alkyl (optionally substituted by one or more halo, hydroxy or 3- to 14-membered heterocycloalkoxy (wherein 1-4 heterocycloalkoxy members are independently selected from N, O, and S)), —O($C_1$-$C_6$-alkyl) (optionally substituted by one or more halo), —OH, halo, —CN, —($C_1$-$C_6$-alkyl)$NR^AR^B$, and —$NR^AR^B$.

$R^5$ is selected from the group consisting of H, $C_1$-$C_6$-alkyl, $C_1$-$C_6$-alkoxy, $C_2$-$C_6$-alkenyl, $C_2$-$C_6$-alkynyl, halo, —CN, and —$NR^CR^D$.

$R^A$ and $R^B$ are independently selected from the group consisting of H, —CN, -hydroxy, oxo, $C_1$-$C_6$-alkyl, $C_1$-$C_6$-alkoxy, $C_2$-$C_6$-alkenyl, $C_2$-$C_6$-alkynyl, —$NH_2$, —S(O)$_{0-2}$—($C_1$-$C_6$-alkyl), —S(O)$_{0-2}$—($C_6$-$C_{10}$-aryl), —C(O)($C_1$-$C_6$-alkyl), —C(O)($C_3$-$C_{14}$-carbocyclyl), —$C_3$-$C_{14}$-carbocyclyl, —($C_1$-$C_6$-alkyl)($C_3$-$C_{14}$-carbocyclyl), $C_6$-$C_{10}$-aryl, 3- to 14-membered heterocycloalkyl and —($C_1$-$C_6$-alkyl)-(3- to 14-membered heterocycloalkyl) (wherein 1-4 heterocycloalkyl members are independently selected from N, O, and S), and 5- to 10-membered heteroaryl (wherein 1-4 heteroaryl members are independently selected from N, O, and S).

Each alkyl, alkoxy, alkenyl, alkynyl, aryl, carbocyclyl, heterocycloalkyl, and heteroaryl moiety of $R^A$ and $R^B$ is optionally substituted with one or more substituents selected from the group consisting of deuterium, hydroxy, halo, —NR'$_2$ (wherein each R' is independently selected from the group consisting of $C_1$-$C_6$-alkyl, $C_2$-$C_6$-alkenyl, $C_2$-$C_6$-alkynyl, $C_6$-$C_{10}$-aryl, 3- to 14-membered heterocycloalkyl and —($C_1$-$C_6$-alkyl)-(3- to 14-membered heterocycloalkyl) (wherein 1-4 ring members are independently selected from N, O, and S), and 5- to 10-membered heteroaryl (wherein 1-4 heteroaryl members are independently selected from N, O, and S)), —NHC(O)(O$C_1$-$C_6$-alkyl), —$NO_2$, —CN, oxo, —C(O)OH, —C(O)O($C_1$-$C_6$-alkyl), —$C_1$-$C_6$-alkyl($C_1$-$C_6$-alkoxy), —C(O)$NH_2$, $C_1$-$C_6$-alkyl, —C(O)$C_1$-$C_6$-alkyl, —O$C_1$-$C_6$-alkyl, —Si($C_1$-$C_6$-alkyl)$_3$, —S(O)$_{0-2}$—($C_1$-$C_6$-alkyl), $C_6$-$C_{10}$-aryl, —($C_1$-$C_6$-alkyl)($C_6$-$C_{10}$-aryl), 3- to 14-membered heterocycloalkyl, and —($C_1$-$C_6$-alkyl)-(3- to 14-membered heterocycle) (wherein 1-4 heterocycle members are independently selected from N, O, and S), and —O($C_6$-$C_{14}$-aryl). Each alkyl, alkenyl, aryl, and heterocycloalkyl substituent in $R^A$ and $R^B$ is optionally substituted with one or more substituents selected from the group consisting of deuterium, hydroxy, —O$C_1$-$C_6$-alkyl, halo, —$NH_2$, —($C_1$-$C_6$-alkyl)$NH_2$, —C(O)OH, CN, and oxo.

$R^C$ and $R^D$ are each independently selected from H and $C_1$-$C_6$-alkyl.

The disclosure provides in another embodiment a pharmaceutical composition comprising a therapeutically effective amount of a compound or a pharmaceutically acceptable salt, tautomer, and/or isotopologue thereof as described herein, and a pharmaceutically acceptable carrier.

In another embodiment, the disclosure provides a method for treating a cancer in a subject suffering therefrom, comprising administering to the subject an effective amount of a MAT2A inhibitor compound as described herein.

Yet another embodiment of the disclosure is a method for inhibiting the synthesis of S-adenosyl methionine (SAM) in a cell, comprising introducing into the cell an effective amount of a compound, or a pharmaceutically acceptable salt, tautomer, and/or isotopologue thereof, as described herein.

The disclosure, in another embodiment, relates to a method for inhibiting the synthesis of S-adenosyl methionine (SAM) in a subject, comprising administering to the subject an effective amount of at least one compound or a salt, tautomer, and/or isotopologue thereof as described herein.

In an embodiment, the disclosure provides a method for treating a cancer in a subject suffering therefrom, wherein the cancer is characterized by a reduction or absence of methylthioadenosine phosphorylase (MTAP) gene expression, the absence of the MTAP gene, or reduced function of MTAP protein, as compared to cancers where the MTAP gene or protein is present and/or fully functioning, the method comprising administering to the subject a therapeutically effective amount of a compound, or a pharmaceutically acceptable salt, tautomer, and/or isotopologue thereof, as described herein.

The disclosure also provides in another embodiment a compound or a pharmaceutically acceptable salt, tautomer, and/or isotopologue thereof, as described herein, for inhibiting the synthesis of S-adenosyl methionine (SAM).

In still a further embodiment, the disclosure provides a compound or a pharmaceutically acceptable salt, tautomer, and/or isotopologue thereof, as described herein, for use in treating a cancer in a subject suffering therefrom.

The disclosure also provides the use of a compound as described herein, or a pharmaceutically acceptable salt thereof, for the manufacture of a medicament for treating cancer.

DETAILED DESCRIPTION

The compounds described herein are inhibitors of MAT2A. The present disclosure thus relates not only to such compounds in conformity with Formula I, but also to their pharmaceutical compositions, tautomers, and isotopologues. The compounds and compositions are useful in treating cancers. Some cancers include various MTAP-deleted cancers, i.e., those cancers characterized by the absence or deletion of the MTAP gene/protein or reduced function of the MTAP protein.

Definitions

"Alkyl" refers to straight, branched chain hydrocarbyl groups, from 1 to about 20 carbon atoms. For instance, an alkyl can have from 1 to 10 carbon atoms or 1 to 6 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, and the like. Thus, alkyl groups include primary alkyl groups, secondary alkyl groups, and tertiary alkyl groups. An alkyl group can be unsubstituted or optionally substituted with one or more substituents as described herein below.

The phrase "substituted alkyl" refers to alkyl substituted at one or more positions, for example, 1, 2, 3, 4, 5, or even 6 positions, which substituents are attached at any available atom to produce a stable compound, with substitution as described herein. "Optionally substituted alkyl" refers to alkyl or substituted alkyl.

Each of the terms "halogen," "halide," and "halo" refers to —F, —Cl, —Br, or —I.

The term "alkenyl" refers to straight or branched chain hydrocarbyl groups including from 2 to about 20 carbon atoms having 1-3, 1-2, or at least one carbon to carbon double bond. An alkenyl group can be unsubstituted or optionally substituted with one or more substituents as described herein below.

"Substituted alkenyl" refers to alkenyl substituted at 1 or more, e.g., 1, 2, 3, 4, 5, or even 6 positions, which substituents are attached at any available atom to produce a stable compound, with substitution as described herein. "Optionally substituted alkenyl" refers to alkenyl or substituted alkenyl.

"Alkyne or "alkynyl" refers to a straight or branched chain unsaturated hydrocarbon having the indicated number of carbon atoms and at least one triple bond. Examples of an alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

"Substituted alkynyl" refers to an alkynyl substituted at 1 or more, e.g., 1, 2, 3, 4, 5, or even 6 positions, which substituents are attached at any available atom to produce a stable compound, with substitution as described herein. "Optionally substituted alkynyl" refers to alkynyl or substituted alkynyl.

The term "alkoxy" refers to an —O-alkyl group having the indicated number of carbon atoms. For example, a ($C_1$-$C_6$)alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "carbocyclyl" refers to a monocyclic, bicyclic, tricyclic, or polycyclic, 3- to 14-membered ring system, which is either saturated, such as "cycloalkyl," or unsaturated, such as "cycloalkenyl." The term "cycloalkenyl" refers specifically to cyclic alkenyl, such as $C_3$-$C_6$-cycloalkenyl. The carbocyclyl may be attached via any atom. Carbocyclyl, for instance, also contemplates fused rings wherein, for instance, a carbocyclyl is fused to an aryl or heteroaryl ring as defined herein. Representative examples of carbocyclyl include, but are not limited to cyclopropyl, cyclobutyl, cyclopentyl, cyclohexyl, cyclopropenyl, cyclobutenyl, cyclopentenyl, cyclohexenyl, phenyl, naphthyl, anthracyl, benzofuranyl, and benzothiophenyl. A carbocyclyl group can be unsubstituted or optionally substituted with one or more substituents as described herein below.

"Substituted carbocyclyl" refers to carbocyclyl substituted at 1 or more, e.g., 1, 2, 3, 4, 5, or even 6 positions, which substituents are attached at any available atom to produce a stable compound, with substitution as described herein. "Optionally substituted carbocyclyl" refers to carbocyclyl or substituted carbocyclyl.

"Aryl" when used alone or as part of another term means a carbocyclic aromatic group whether or not fused having the number of carbon atoms designated or if no number is designated, up to 14 carbon atoms, such as a $C_6$-$C_{14}$-aryl. Particular aryl groups are phenyl, naphthyl, biphenyl, phenanthrenyl, naphthacenyl, and the like (see e.g. Lang's Handbook of Chemistry (Dean, J. A., ed) 13$^{th}$ ed. Table 7-2 [1985]). A particular aryl is phenyl. "Aryl" also includes aromatic ring systems that are optionally fused with a carbocyclyl ring, as herein defined. An aryl group can be unsubstituted or optionally substituted with one or more substituents as described herein below.

A "substituted aryl" is an aryl that is independently substituted with one or more substituents attached at any available atom to produce a stable compound, wherein the substituents are as described herein. "Optionally substituted aryl" refers to aryl or substituted aryl.

The term "heteroatom" refers to N, O, and S. Compounds that contain N or S atoms can be optionally oxidized to the corresponding N-oxide, sulfoxide, or sulfone compounds.

"Heteroaryl," alone or in combination with any other moiety described herein, refers to a monocyclic aromatic ring structure containing 5 to 10, such as 5 or 6 ring atoms, or a bicyclic aromatic group having 8 to 10 atoms, containing one or more, such as 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or heteroatom is the point of attachment of the heteroaryl ring structure such that a stable compound is produced. Examples of heteroaryl groups include, but are not limited to, pyridinyl, pyridazinyl, pyrazinyl, quinoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. A heteroaryl group can be unsubstituted or optionally substituted with one or more substituents as described herein below.

A "substituted heteroaryl" is a heteroaryl that is independently substituted, unless indicated otherwise, with one or more, e.g., 1, 2, 3, 4 or 5, also 1, 2, or 3 substituents, also 1 substituent, attached at any available atom to produce a stable compound, wherein the substituents are as described herein. "Optionally substituted heteroaryl" refers to heteroaryl or substituted heteroaryl.

"Heterocycloalkyl" means a saturated or unsaturated non-aromatic monocyclic, bicyclic, tricyclic or polycyclic ring system that has from 3 to 14, such as 3 to 6, atoms in which from 1 to 4 carbon atoms in the ring are replaced by heteroatoms of O, S or N. A heterocycloalkyl is optionally fused with aryl or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl. A heterocycloalkyl group can be unsubstituted or optionally substituted with one or more substituents as described herein below.

"Optionally substituted heterocycloalkyl" denotes a heterocycloalkyl that is substituted with 1 to 3 substituents, e.g., 1, 2 or 3 substituents, attached at any available atom to produce a stable compound, wherein the substituents are as described herein.

"Heterocycloalkoxy" refers to an —O-heterocycloalkyl group having the indicated number of member atoms in a monocyclic, bicyclic, tricyclic or polycyclic ring system and where 1 to 4 carbon atoms in the ring are replaced by heteroatoms of O, S or N.

"Optionally substituted heterocycloalkoxy" refers to a heterocycloalkoxy group that is substituted with 1 to 3 substituents, e.g., 1, 2 or 3 substituents, attached at any available atom to produce a stable compound, wherein the substituents are as described herein.

The term "nitrile" or "cyano" can be used interchangeably and refer to a —CN group which is bound to a carbon atom of a heteroaryl ring, aryl ring and a heterocycloalkyl ring.

The term "oxo" refers to a =O atom attached to a saturated or unsaturated moiety. The =O atom can be attached to a carbon, sulfur, or nitrogen atom that is part of a cyclic or acyclic moiety.

A "hydroxyl" or "hydroxy" refers to an —OH group.

The substituent —CO$_2$H may be replaced with bioisosteric replacements such as:

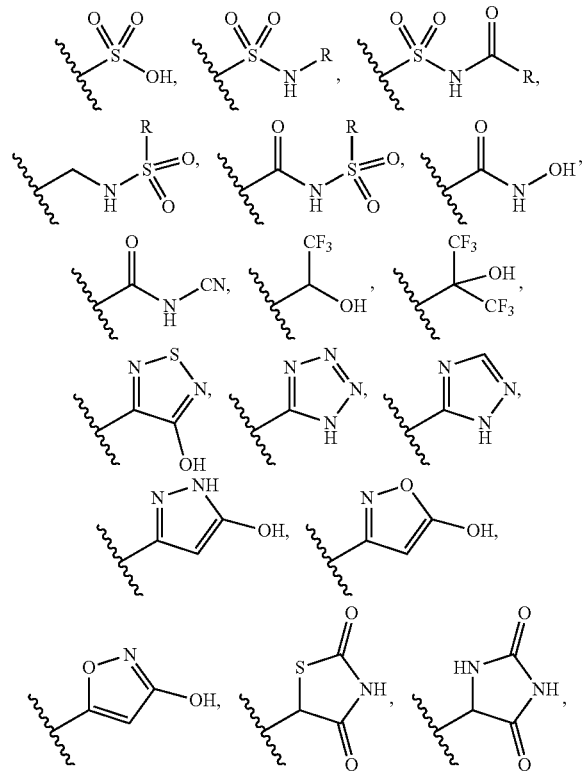

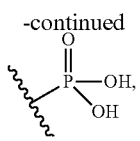

and the like, wherein R has the same definition as R$^4$ as defined herein. See, e.g., THE PRACTICE OF MEDICINAL CHEMISTRY (Academic Press: New York, 1996), at page 203.

Compounds described herein can exist in various isomeric forms, including configurational, geometric, and conformational isomers, including, for example, cis- or trans-conformations. The compounds may also exist in one or more tautomeric forms, including both single tautomers and mixtures of tautomers. The term "isomer" is intended to encompass all isomeric forms of a compound of this disclosure, including tautomeric forms of the compound. The compounds of the present disclosure may also exist in open-chain or cyclized forms. In some cases, one or more of the cyclized forms may result from the loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the disclosure.

Some compounds described herein can have asymmetric centers and therefore exist in different enantiomeric and diastereomeric forms. A compound of the disclosure can be in the form of an optical isomer or a diastereomer. Accordingly, the disclosure encompasses compounds and their uses as described herein in the form of their optical isomers, diastereoisomers and mixtures thereof, including a racemic mixture. Optical isomers of the compounds of the disclosure can be obtained by known techniques such as asymmetric synthesis, chiral chromatography, simulated moving bed technology or via chemical separation of stereoisomers through the employment of optically active resolving agents.

Unless otherwise indicated, the term "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound. The stereoisomer as described above can be viewed as composition comprising two stereoisomers that are present in their respective weight percentages described herein.

As used herein, the term "isotopologue" is an isotopically enriched compound. As used herein, and unless otherwise indicated, the term "isotopically enriched" refers to an atom having an isotopic composition other than the naturally abundant isotopic composition of that atom. "Isotopically enriched" may also refer to a compound containing at least one atom having an isotopic composition other than the natural isotopic composition of that atom. In an isotopologue, "isotopic enrichment" refers to the percentage of incorporation of an amount of a specific isotope of a given atom in a molecule in the place of that atom's natural isotopic composition. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%.

Thus, as used herein, and unless otherwise indicated, the term "isotopic enrichment factor" refers to the ratio between the isotopic composition and the natural isotopic composition of a specified isotope.

With regard to the compounds provided herein, when a particular atom's position is designated as having deuterium or "D" or "$H^2$", it is understood that the abundance of deuterium at that position is substantially greater than the natural abundance of deuterium, which is about 0.015%. A position designated as having deuterium typically has a minimum isotopic enrichment factor of, in particular embodiments, at least 1000 (15% deuterium incorporation), at least 2000 (30% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium atom. The isotopic enrichment and isotopic enrichment factor of the compounds provided herein can be determined using conventional analytical methods known to one of ordinary skill in the art, including mass spectrometry and nuclear magnetic resonance spectroscopy.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

As used herein, and unless otherwise specified to the contrary, the term "compound" is inclusive in that it encompasses a compound or a pharmaceutically acceptable salt, stereoisomer, isotopologue, and/or tautomer thereof. Thus, for instance, a compound of Formula I or II includes a pharmaceutically acceptable salt of an isotopologue of the compound.

In this description, a "pharmaceutically acceptable salt" is a pharmaceutically acceptable, organic or inorganic acid or base salt of a compound of the disclosure. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycolylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

The term "effective amount" refers to an amount of a compound of the disclosure or other active ingredient sufficient to provide a therapeutic or prophylactic benefit in the treatment or prevention of a disease or to delay or minimize symptoms associated with a disease. Further, a therapeutically effective amount with respect to a compound of the disclosure means that amount of therapeutic agent alone, or in combination with other therapies, that provides a therapeutic benefit in the treatment or prevention of a disease. Used in connection with a compound of the disclosure, the term can encompass an amount that improves overall therapy, reduces or avoids symptoms or causes of disease, or enhances the therapeutic efficacy of or synergizes with another therapeutic agent.

A "patient" or subject" includes an animal, such as a human, cow, horse, sheep, lamb, pig, chicken, turkey, quail, cat, dog, mouse, rat, rabbit or guinea pig. In accordance with some embodiments, the animal is a mammal such as a non-primate and a primate (e.g., monkey and human). In one embodiment, a patient is a human, such as a human infant, child, adolescent or adult.

"Inhibitor" means a compound which prevents or reduces the amount of synthesis of SAM. In an embodiment, an inhibitor binds to MAT2A. In one embodiment, the inhibitor inhibits the function of MAT2A.

Compounds

As described generally above, the present disclosure provides compounds and pharmaceutically acceptable salts, tautomers, and/or isotopologues thereof, wherein the compounds conform to formula I.

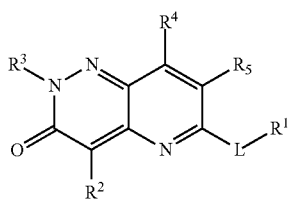
(I)

In Formula I, L is O, S, NR, or a bond. R is H or $C_1$-$C_6$-alkyl.

$R^1$ is selected from the group consisting of $C_1$-$C_6$-alkyl, $C_2$-$C_6$-alkenyl, $C_3$-$C_6$-carbocyclyl, —($C_1$-$C_6$-alkyl)($C_3$-$C_6$-carbocyclyl), and —($C_1$-$C_6$-alkyl)($C_3$-$C_6$-cycloalkenyl) wherein any alkyl in $R^1$ is straight or branched. In an embodiment, $R^1$ is optionally substituted by 1-6 halo or 1-6 deuterium.

Alternatively, in an embodiment, when L is NR, then R and $R^1$ in combination with L represent a 3- to 6-membered heterocycloalkyl (wherein 1-4 ring members are independently selected from N, O, and S) optionally substituted by one or more $R^A$.

$R^2$ and $R^3$ are independently selected from the group consisting of $C_2$-$C_6$-alkynyl, $C_6$-$C_{10}$-aryl, $C_3$-$C_6$-carbocyclyl, 5- to 10-membered heteroaryl (wherein 1-4 heteroaryl members are independently selected from N, O, and S), and 3- to 14-membered heterocycloalkyl (wherein 1-4 heterocycloalkyl members are independently selected from N, O, and S). $R^2$ and $R^3$ are independently and optionally substituted by one or more substituents that are selected from the group consisting of $R^A$, $OR^A$, halo, —N=N—$R^A$, —$NR^AR^B$, —($C_1$-$C_6$-alkyl)$NR^AR^B$, —C(O)$OR^A$, —C(O)$NR^AR^B$, —OC(O)$R^A$, —Si($C_1$-$C_6$-alkyl)$_3$ and —CN.

$R^4$ is selected from the group consisting of H, $C_1$-$C_6$-alkyl (optionally substituted by one or more halo, hydroxy or 3- to 14-membered heterocycloalkoxy (wherein 1-4 heterocycloalkoxy members are independently selected from N, O, and S)), —O($C_1$-$C_6$-alkyl) (optionally substituted by one or more halo), —OH, halo, —CN, —($C_1$-$C_6$-alkyl)$NR^AR^B$, and —$NR^AR^B$.

$R^5$ is selected from the group consisting of H, $C_1$-$C_6$-alkyl, $C_1$-$C_6$-alkoxy, $C_2$-$C_6$-alkenyl, $C_2$-$C_6$-alkynyl, halo, —CN, and —$NR^CR^D$.

$R^A$ and $R^B$ are independently selected from the group consisting of H, —CN, -hydroxy, oxo, $C_1$-$C_6$-alkyl, $C_1$-$C_6$-alkoxy, $C_2$-$C_6$-alkenyl, $C_2$-$C_6$-alkynyl, —$NH_2$, —$S(O)_{0-2}$—($C_1$-$C_6$-alkyl), —$S(O)_{0-2}$—($C_6$-$C_{10}$-aryl), —C(O)($C_1$-$C_6$-alkyl), —C(O)($C_3$-$C_{14}$-carbocyclyl), —$C_3$-$C_{14}$-carbocyclyl, —($C_1$-$C_6$-alkyl)($C_3$-$C_{14}$-carbocyclyl), $C_6$-$C_{10}$-aryl, 3- to 14-membered heterocycloalkyl and —($C_1$-$C_6$-alkyl)-(3- to 14-membered heterocycloalkyl) (wherein 1-4 heterocycloalkyl members are independently selected from N, O, and S), and 5- to 10-membered heteroaryl (wherein 1-4 heteroaryl members are independently selected from N, O, and S).

Each alkyl, alkoxy, alkenyl, alkynyl, aryl, carbocyclyl, heterocycloalkyl, and heteroaryl moiety of $R^A$ and $R^B$ is optionally substituted with one or more substituents selected from the group consisting of deuterium, hydroxy, halo, —$NR'_2$ (wherein each R' is independently selected from the group consisting of $C_1$-$C_6$-alkyl, $C_2$-$C_6$-alkenyl, $C_2$-$C_6$-alkynyl, $C_6$-$C_{10}$-aryl, 3- to 14-membered heterocycloalkyl and —($C_1$-$C_6$-alkyl)-(3- to 14-membered heterocycloalkyl) (wherein 1-4 ring members are independently selected from N, O, and S), and 5- to 10-membered heteroaryl (wherein 1-4 heteroaryl members are independently selected from N, O, and S), —NHC(O)(O$C_1$-$C_6$-alkyl), —$NO_2$, —CN, oxo, —C(O)OH, —C(O)O($C_1$-$C_6$-alkyl), —$C_1$-$C_6$-alkyl($C_1$-$C_6$-alkoxy), —C(O)$NH_2$, $C_1$-$C_6$-alkyl, —C(O)$C_1$-$C_6$-alkyl, —O$C_1$-$C_6$-alkyl, —Si($C_1$-$C_6$-alkyl)$_3$, —$S(O)_{0-2}$—($C_1$-$C_6$-alkyl), $C_6$-$C_{10}$-aryl, —($C_1$-$C_6$-alkyl)($C_6$-$C_{10}$-aryl), 3- to 14-membered heterocycloalkyl, and —($C_1$-$C_6$-alkyl)-(3- to 14-membered heterocycle) (wherein 1-4 heterocycle members are independently selected from N, O, and S), and —O($C_6$-$C_{14}$-aryl). Each alkyl, alkenyl, aryl, and heterocycloalkyl substituent in $R^A$ and $R^B$ is optionally substituted with one or more substituents selected from the group consisting of hydroxy, —O$C_1$-$C_6$-alkyl, halo, —$NH_2$, —($C_1$-$C_6$-alkyl)$NH_2$, —C(O)OH, CN, and oxo.

$R^C$ and $R^D$ are each independently selected from H and $C_1$-$C_6$-alkyl.

In some embodiments, $R^4$ is selected from the group consisting of H, $C_1$-$C_6$-alkyl (optionally substituted by one or more halo, hydroxy or 3- to 14-membered heterocycloalkoxy (wherein 1-4 heterocycloalkoxy members are independently selected from N, O, and S)), —O($C_1$-$C_6$-alkyl), —($C_1$-$C_6$-alkyl)$NR^AR^B$, and —$NR^AR^B$ (wherein $R^A$ and $R^B$ are independently selected from H and $C_1$-$C_6$-alkyl); and $R^5$ is selected from the group consisting of H, $C_1$-$C_6$-alkyl, $C_1$-$C_6$-alkoxy, and —$NR^CR^D$.

In other embodiments, at least one of $R^4$ and $R^5$ is H. For instance, $R^4$ is H or $R^5$ is H. Alternatively, each of $R^4$ and $R^5$ is H.

Optionally in combination with any other embodiment herein described, various embodiments provide for a Formula I compound wherein $R^2$ is optionally substituted $C_6$-$C_{10}$-aryl or optionally substituted 5- to 10-membered heteroaryl. In one embodiment, $R^2$ is optionally substituted $C_6$-$C_{10}$-aryl, such as optionally substituted phenyl. In another embodiment, $R^2$ is optionally substituted 5- to 10-membered heteroaryl, and wherein 1 ring member is N. For instance, $R^2$ is an optionally substituted 5- or 6-membered heteroaryl, or an optionally substituted 6-membered heteroaryl, an example of which is optionally substituted pyridyl.

In some embodiments, optionally in combination with any other described herein, $R^3$ is optionally substituted 3- to 14-membered heterocycloalkyl or optionally substituted 5- to 10-membered heteroaryl. Non-limiting examples of $R^3$ are selected from the group consisting of benzothiazolyl, benzoisothiazolyl, benzoxazolyl, pyridinyl, pyridinonyl, pyridazinyl, benzimidazolyl, benzotriazolyl, indazolyl, quinoxalinyl, quinolinyl, quinazolinyl, imidazopyridinyl, pyrazolopyridinyl, triazolopyridinyl, cinnolinyl, isoxazolyl, pyrazolyl, benzofuranyl, dihydrobenzofuranyl, dihydrobenzodioxinyl, and tetrahydrobenzodioxinyl, each of which may be optionally substituted.

In other embodiments, $R^3$ is optionally substituted $C_6$-$C_{10}$-aryl. An example is optionally substituted phenyl.

The disclosure provides some Formula I compounds wherein $R^2$ is optionally substituted phenyl and $R^3$ is optionally substituted 3- to 14-membered heterocycloalkyl or optionally substituted 5- to 10-membered heteroaryl.

In various embodiments, the disclosure provides a Formula I compound wherein L is O or NR. Further, in accordance with additional embodiments, $R^1$ is optionally substituted $C_1$-$C_6$-alkyl or optionally substituted $C_3$-$C_6$-carbocyclyl. An example of $R^1$ is $C_1$-$C_3$-alkyl that is optionally substituted by 1-3 F.

A subset of Formula I compounds, according to an embodiment, are those in which L is O or NR and R is H; $R^1$ is $C_1$-$C_3$-alkyl that is optionally substituted by 1-3 F; $R^2$ is optionally substituted 3- to 14-membered heterocycloalkyl or optionally substituted 5- to 10-membered heteroaryl (wherein 1 heterocycloalkyl or heteroaryl member is N) or optionally substituted $C_6$-$C_{10}$-aryl; $R^3$ is optionally substituted 3- to 14-membered heterocycloalkyl or optionally substituted 5- to 10-membered heteroaryl wherein 1 to 3 heterocycloalkyl or heteroaryl members are independently selected from N, O, and S; and each of $R^4$ and $R^5$ is H. In some embodiments, L is NR.

In various embodiments, the disclosure provides specific examples of Formula I compounds, and their pharmaceutically acceptable salts, tautomers, and/or isotopologues as set forth in Table 1 below:

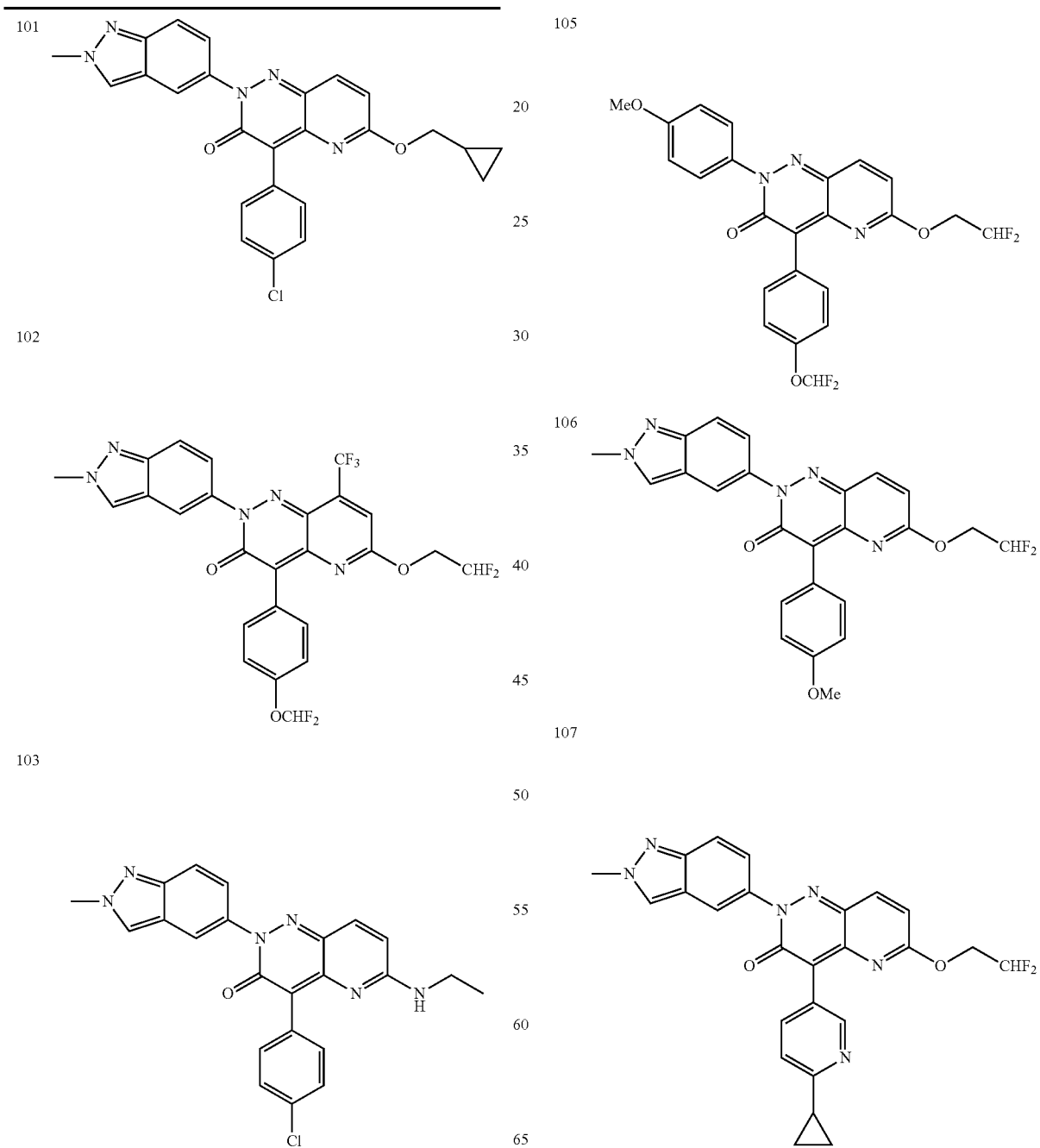

TABLE 1-continued
108 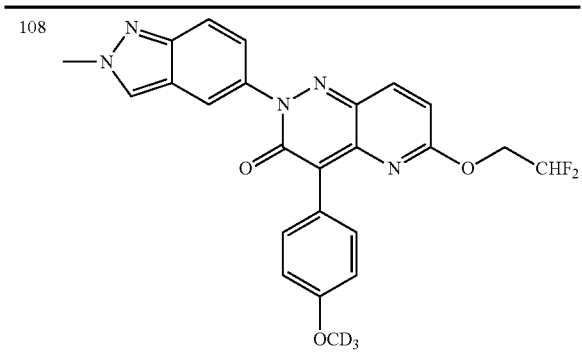
109 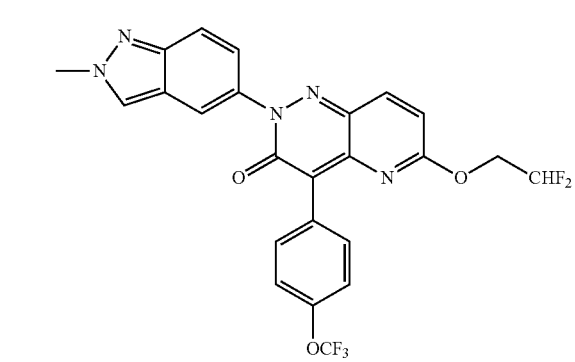
110 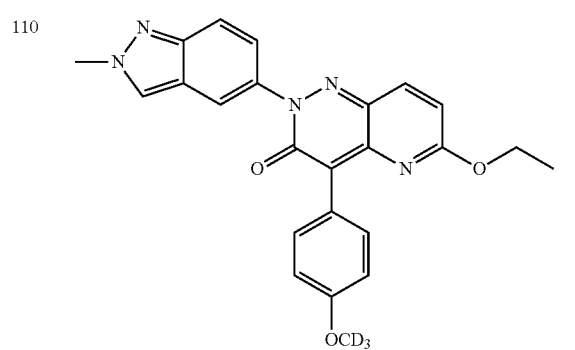
111 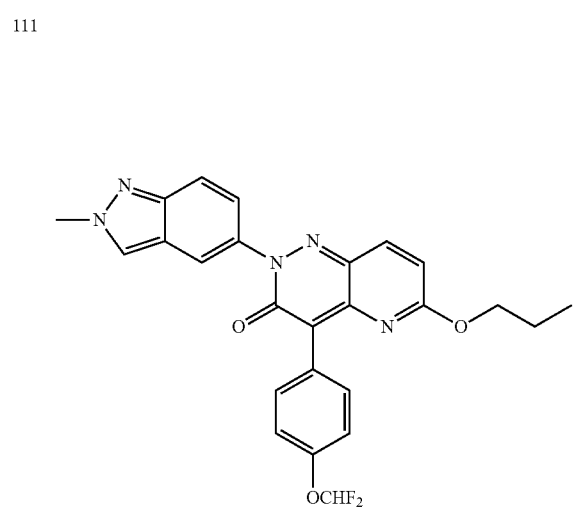
112 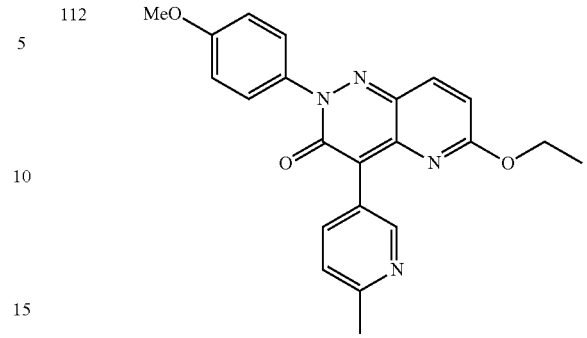
113 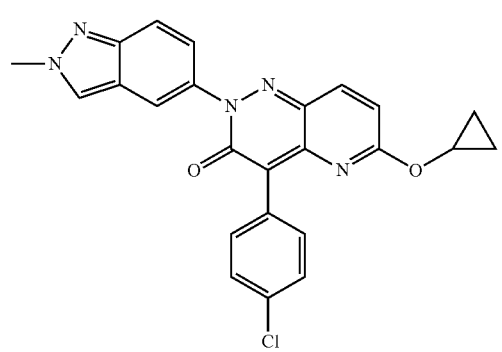 [SMILES: Cn1cc2cc(-n3nc4ccc(OC5CC5)nc4c(-c4ccc(Cl)cc4)c3=O)ccc2n1]
114 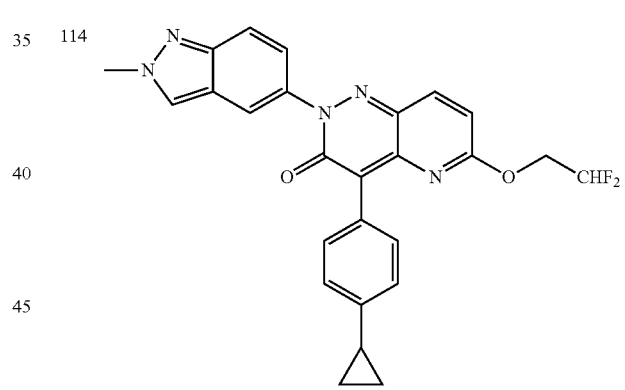
115 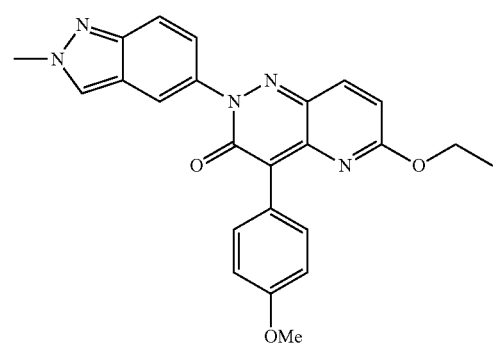 [SMILES: CCOc1ccc2nn(-c3ccc4nn(C)cc4c3)c(=O)c(-c3ccc(OC)cc3)c2n1]

TABLE 1-continued
116 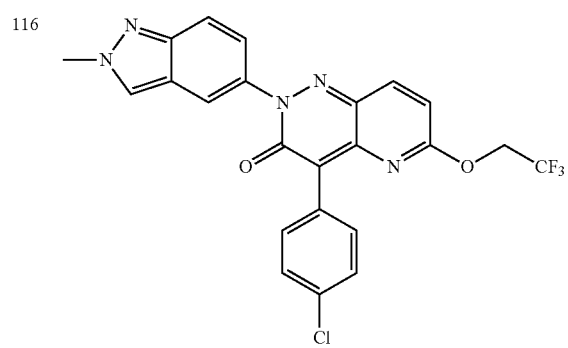
117 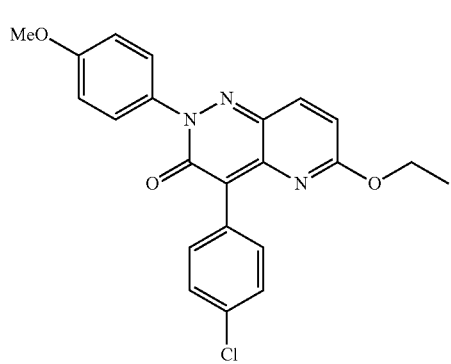 [SMILES: CCOc1ccc2nn(-c3ccc(OC)cc3)c(=O)c(-c3ccc(Cl)cc3)c2n1]
118 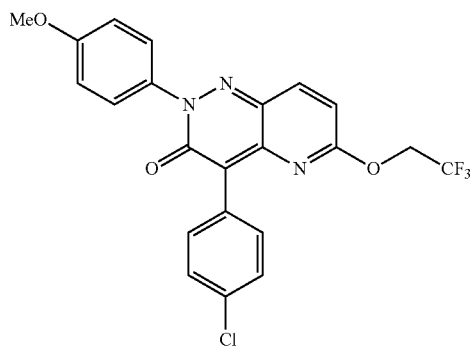 [SMILES: COc1ccc(-n2nc3ccc(OCC(F)(F)F)nc3c(-c3ccc(Cl)cc3)c2=O)cc1]
119 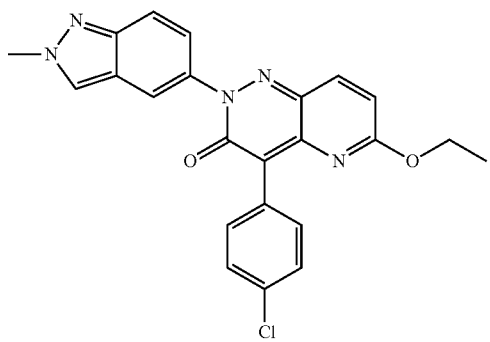 [SMILES: CCOc1ccc2nn(-c3ccc4nn(C)cc4c3)c(=O)c(-c3ccc(Cl)cc3)c2n1]
TABLE 1-continued
120 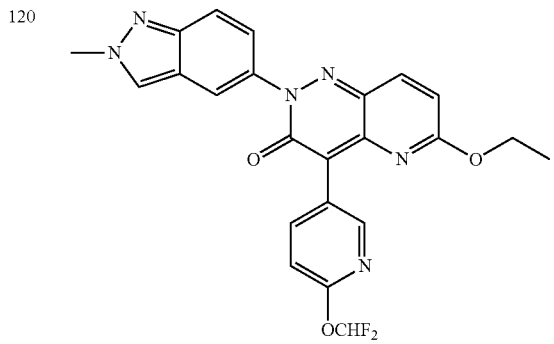
121 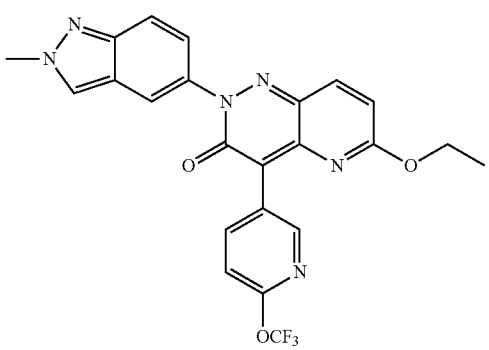
122
123 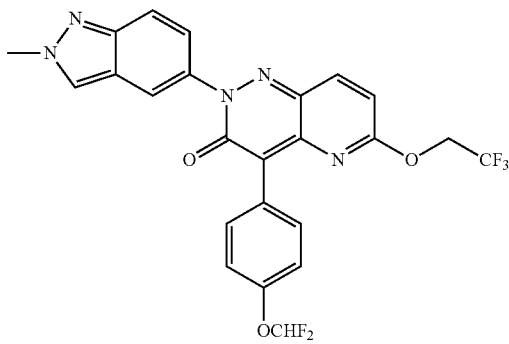 [SMILES: Cn1cc2cc(-n3nc4ccc(OCC(F)(F)F)nc4c(-c4ccc(OC(F)F)cc4)c3=O)ccc2n1]

TABLE 1-continued
124 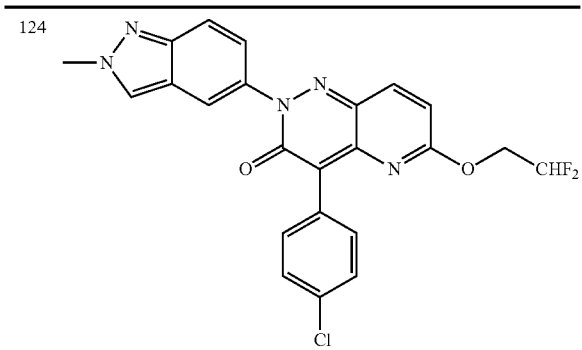
125 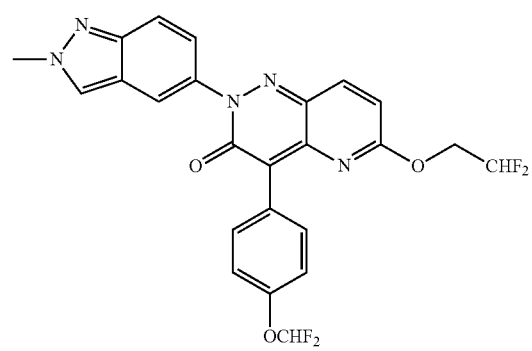
126 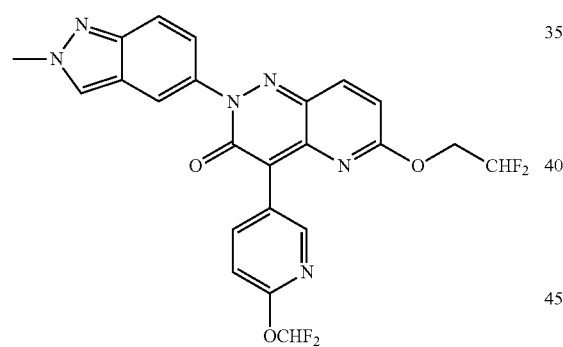
127 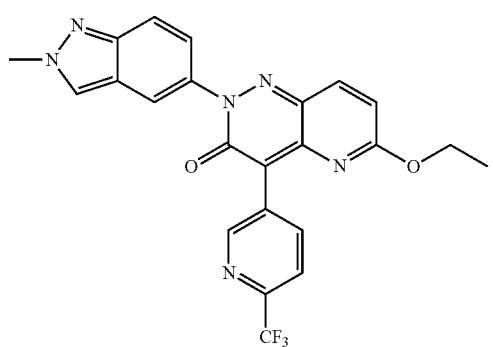
128 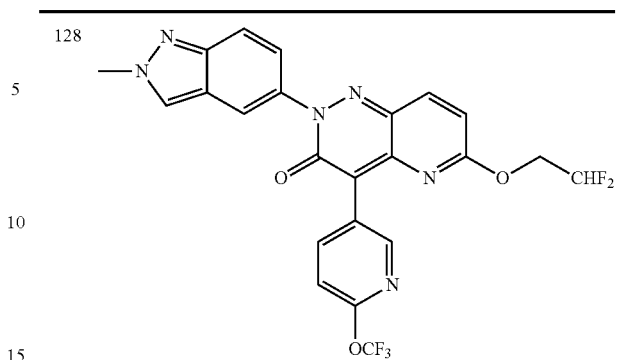
129 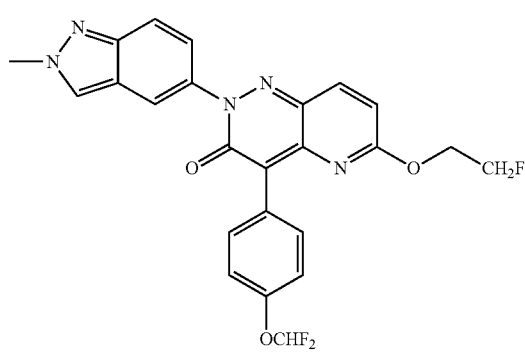 [SMILES: Cn1cc2cc(-n3nc4ccc(OCC(F)F)nc4c(-c4ccc(OC(F)F)cc4)c3=O)ccc2n1]
130 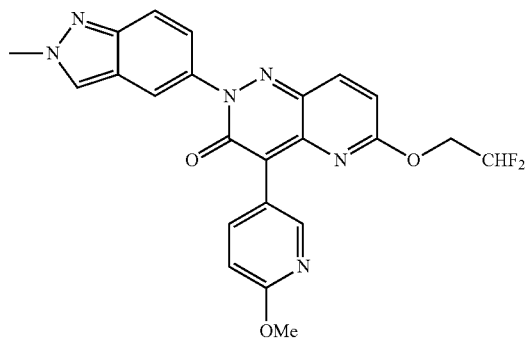 [SMILES: COc1ccc(-c2c(=O)n(-c3ccc4nn(C)cc4c3)nc3ccc(OCC(F)F)nc23)cn1]
131 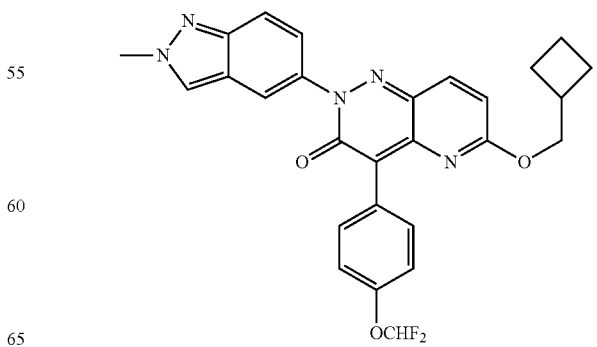

TABLE 1-continued
132 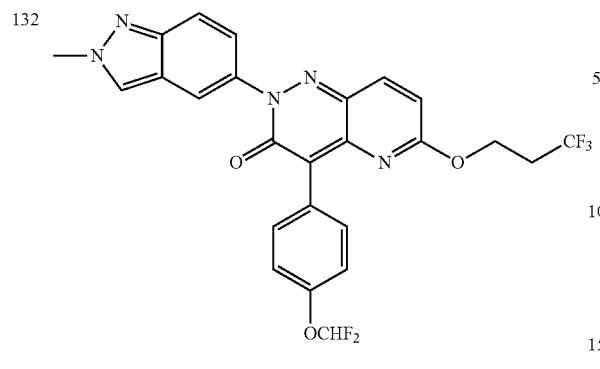
133 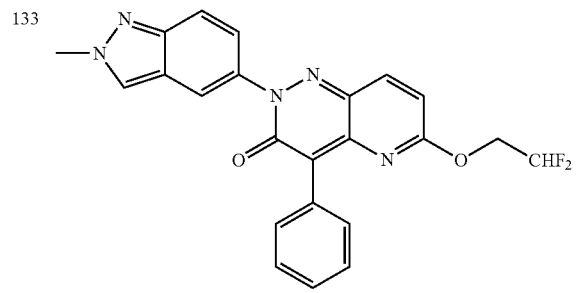
134 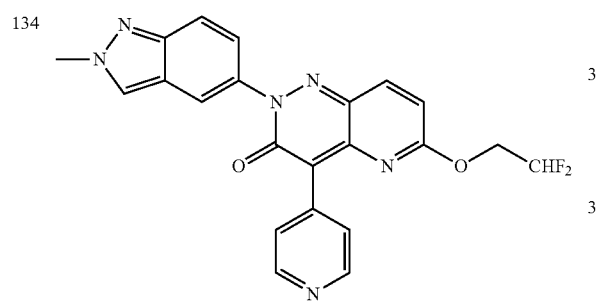
135 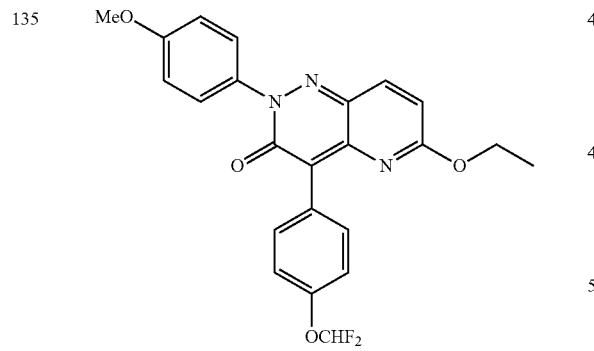
136 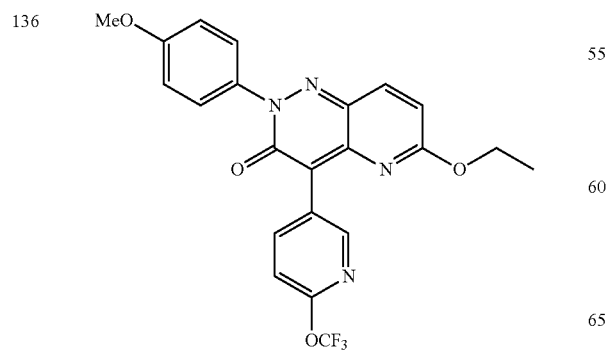
TABLE 1-continued
137 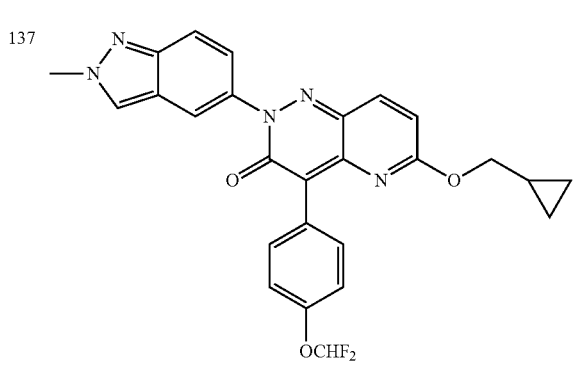
138 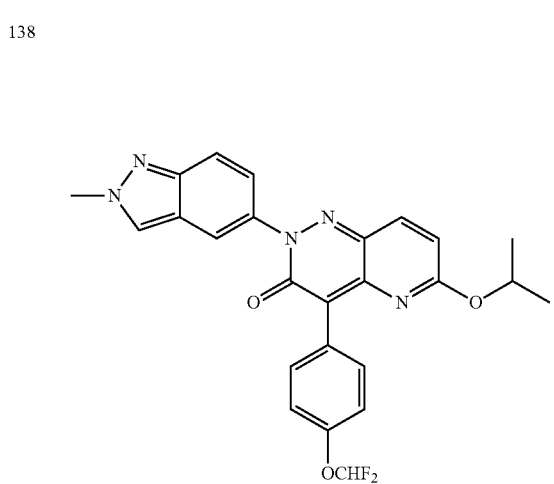
139 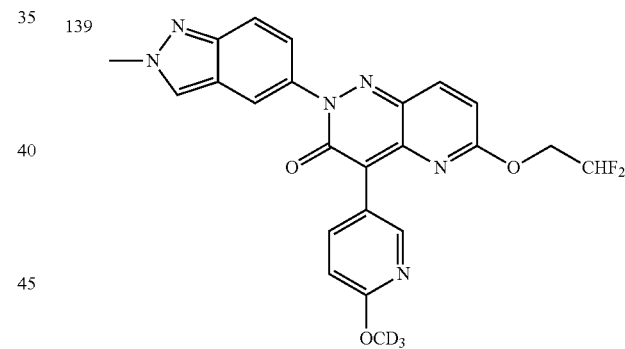
140 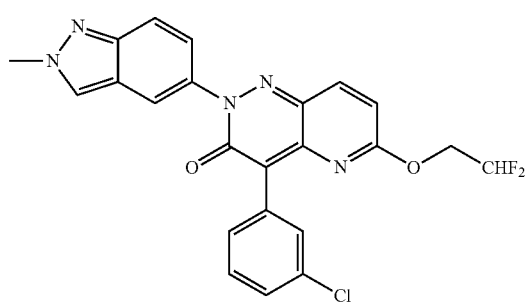 [SMILES: Cn1cc2cc(-n3nc4ccc(OCC(F)F)nc4c(-c4cccc(Cl)c4)c3=O)ccc2n1]

TABLE 1-continued
141
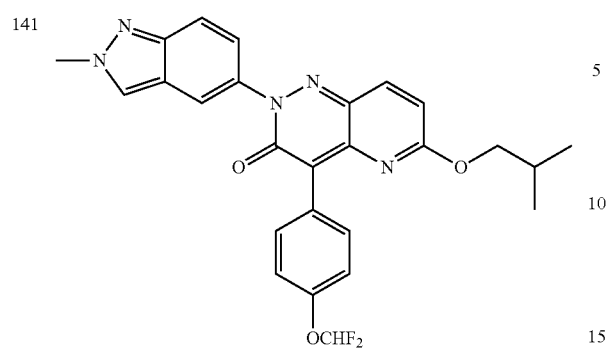
142
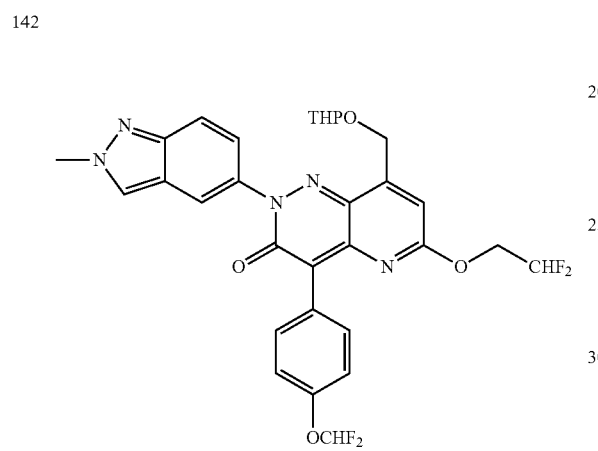
143
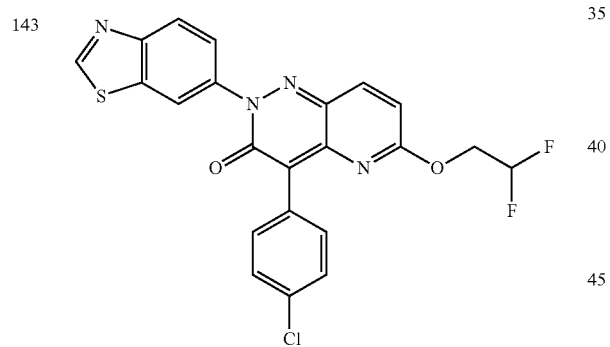
144
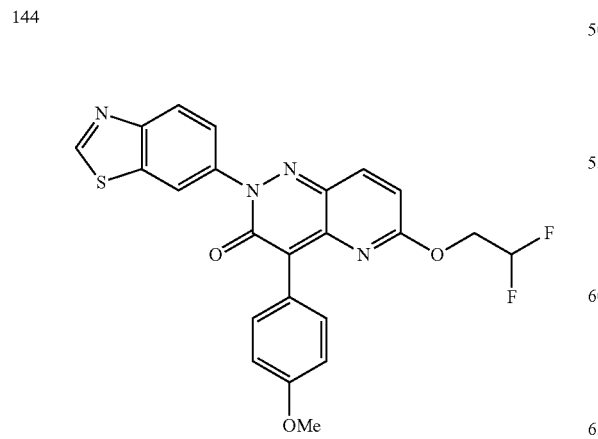
TABLE 1-continued
145
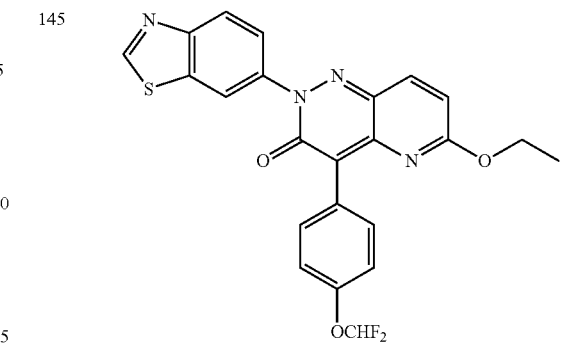
146
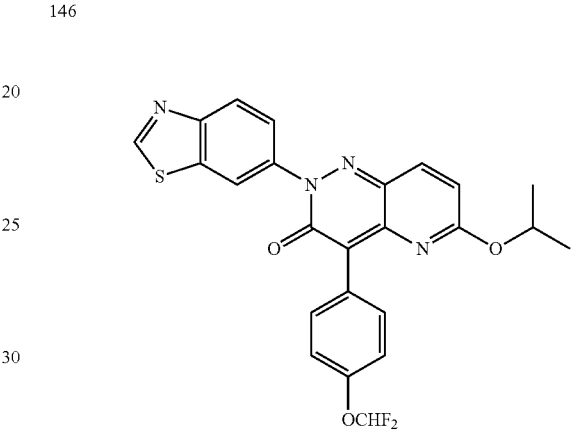
147
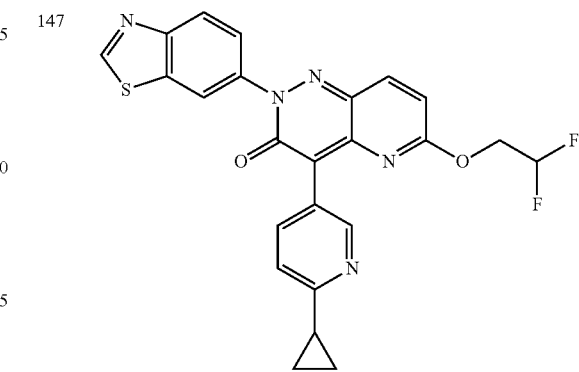
148
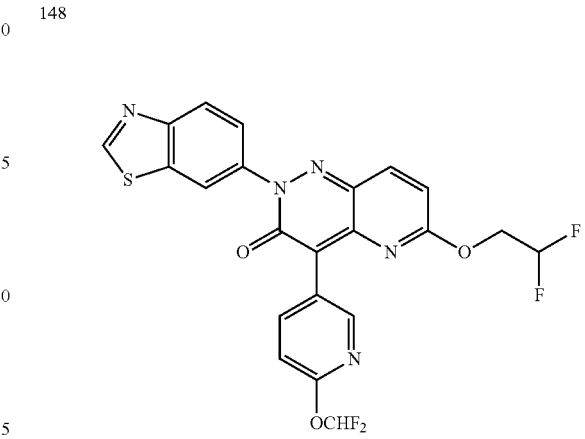

TABLE 1-continued
149 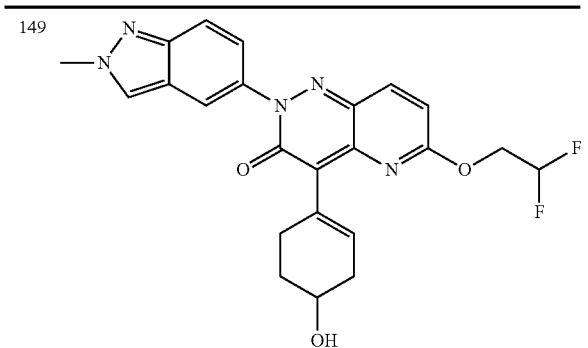
150 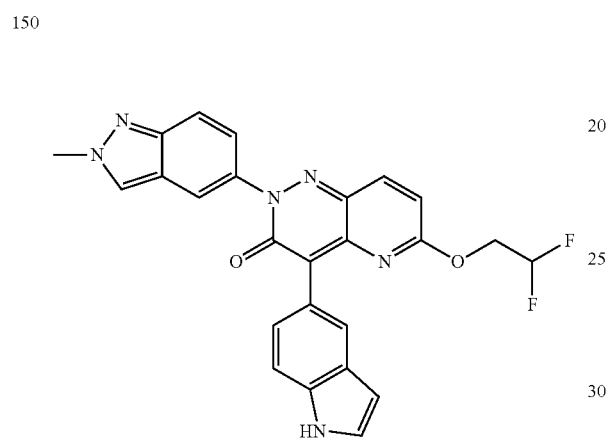
151 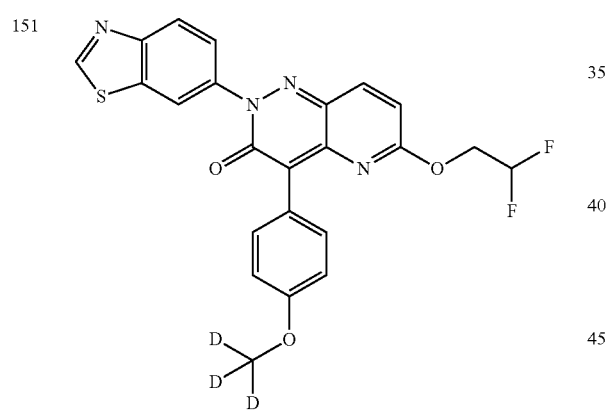
152 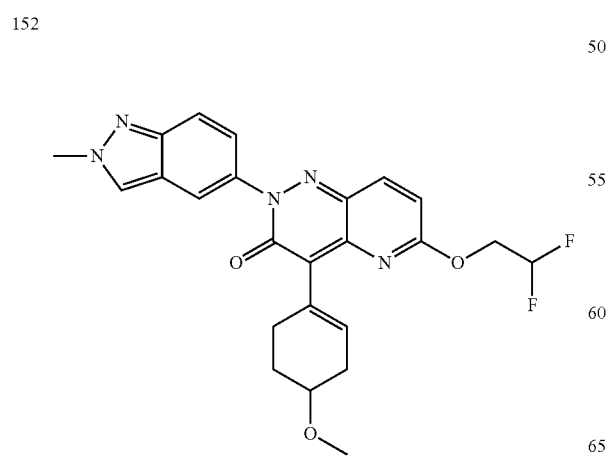
TABLE 1-continued
153 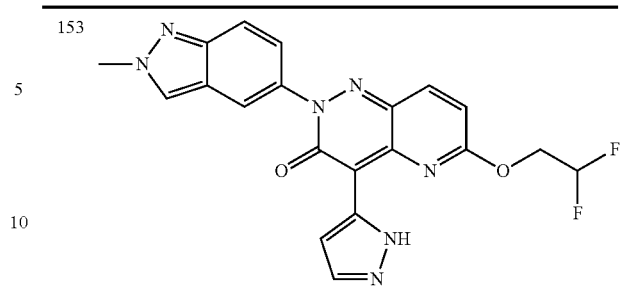
154 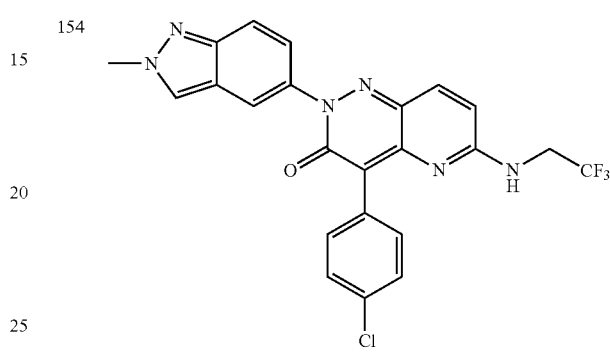
155 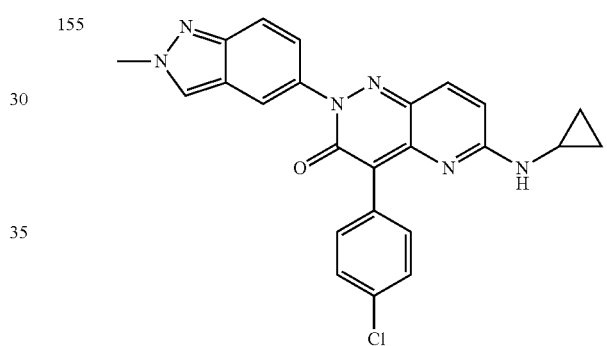
156 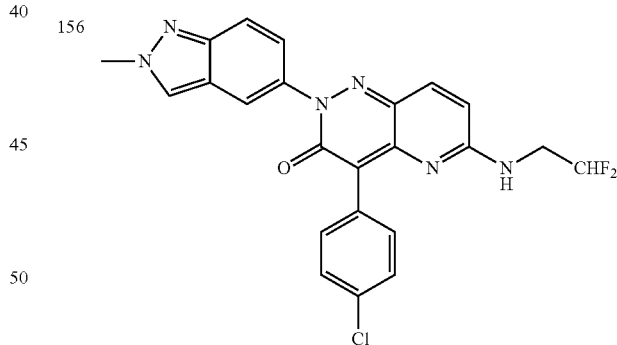
157 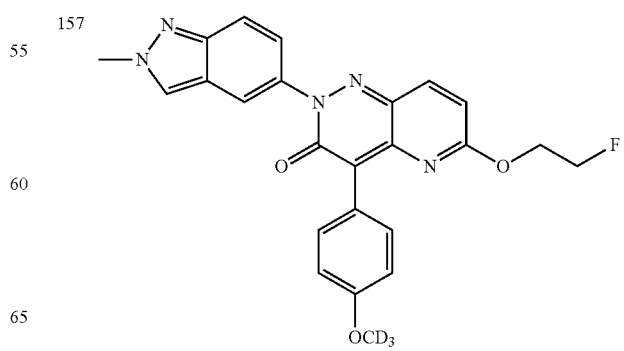

TABLE 1-continued
158 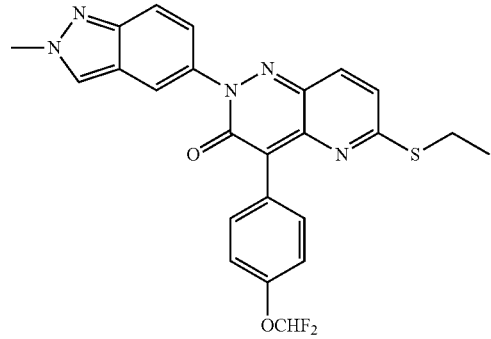
159 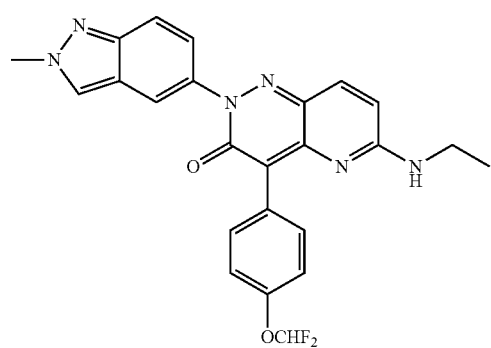 [SMILES: CCNc1ccc2nn(-c3ccc4nn(C)cc4c3)c(=O)c(-c3ccc(OC(F)F)cc3)c2n1]
160 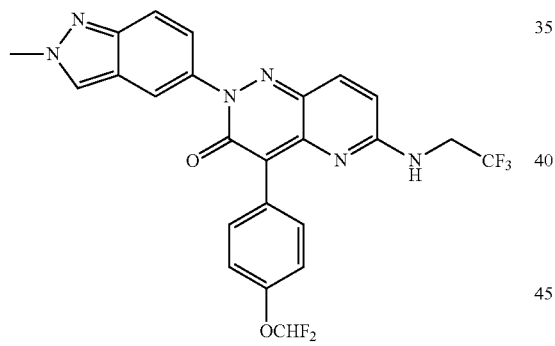
161 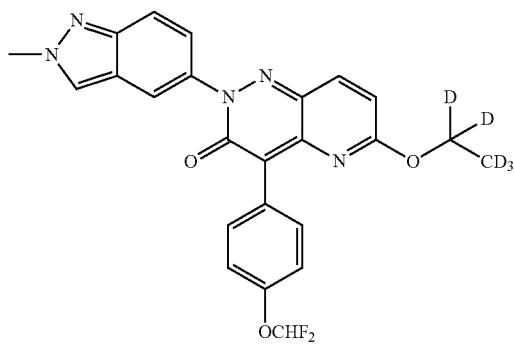 [SMILES: [2H]C([2H])([2H])C([2H])([2H])Oc1ccc2nn(-c3ccc4nn(C)cc4c3)c(=O)c(-c3ccc(OC(F)F)cc3)c2n1]
TABLE 1-continued
162 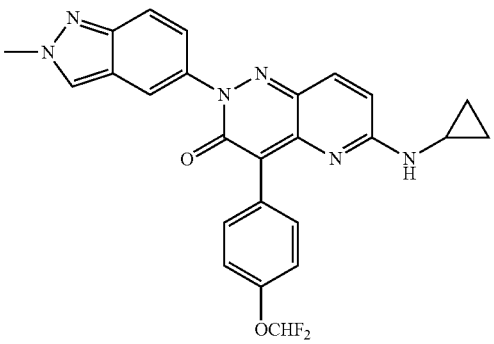 [SMILES: Cn1cc2cc(-n3nc4ccc(NC5CC5)nc4c(-c4ccc(OC(F)F)cc4)c3=O)ccc2n1]
163 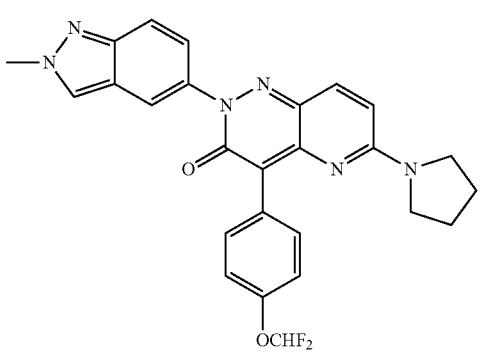 [SMILES: Cn1cc2cc(-n3nc4ccc(N5CCCC5)nc4c(-c4ccc(OC(F)F)cc4)c3=O)ccc2n1]
164 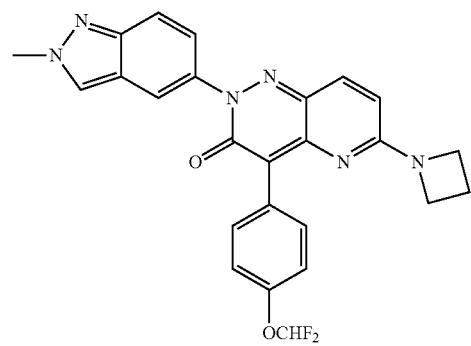
165 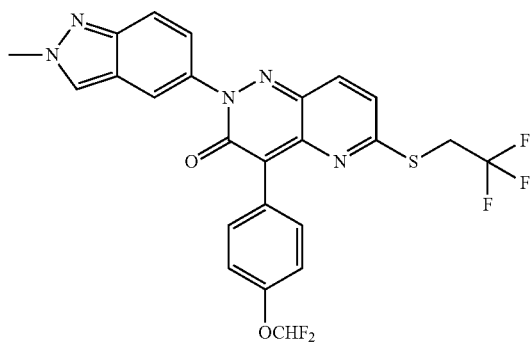 [SMILES: Cn1cc2cc(-n3nc4ccc(SCC(F)(F)F)nc4c(-c4ccc(OC(F)F)cc4)c3=O)ccc2n1]

TABLE 1-continued
166 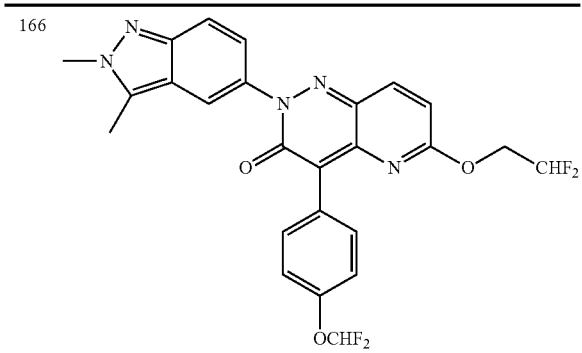
167 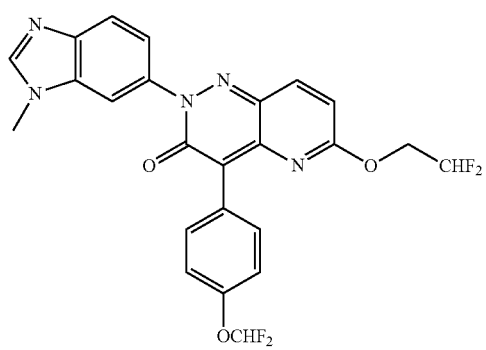
168 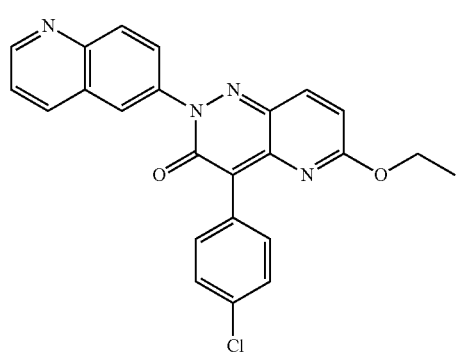 [SMILES: CCOc1ccc2nn(-c3ccc4ncccc4c3)c(=O)c(-c3ccc(Cl)cc3)c2n1]
169 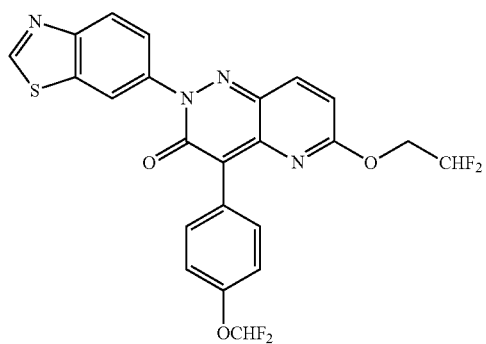 [SMILES: O=c1c(-c2ccc(OC(F)F)cc2)c2nc(OCC(F)F)ccc2nn1-c1ccc2ncsc2c1]
170 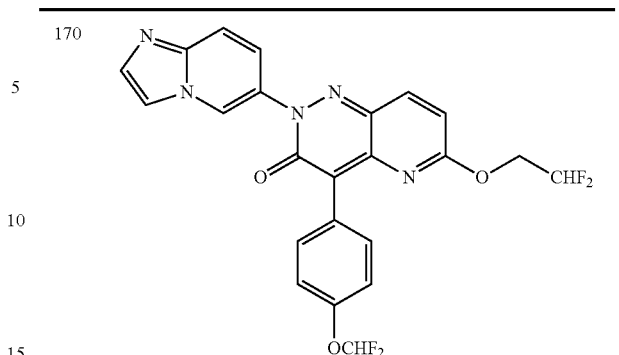
171 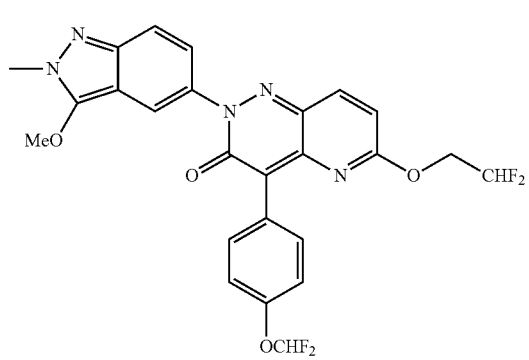 [SMILES: COc1c2cc(-n3nc4ccc(OCC(F)F)nc4c(-c4ccc(OC(F)F)cc4)c3=O)ccc2nn1C]
172 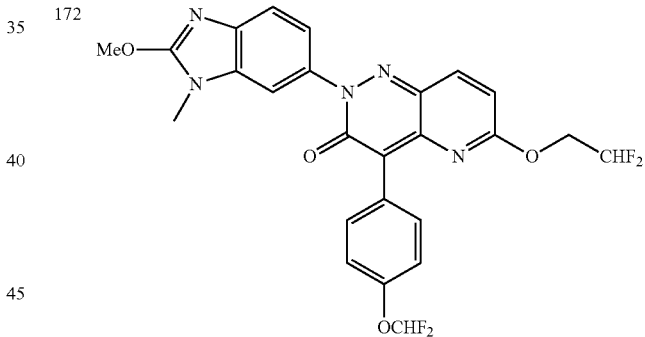
173 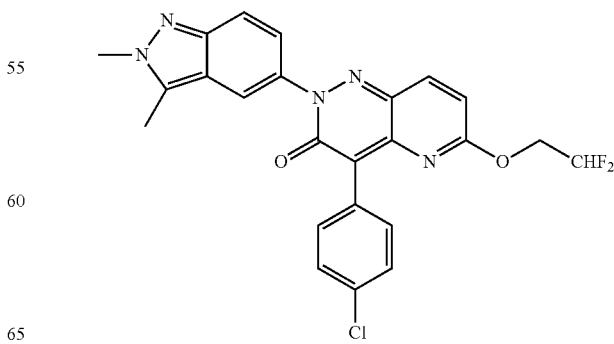

TABLE 1-continued
174 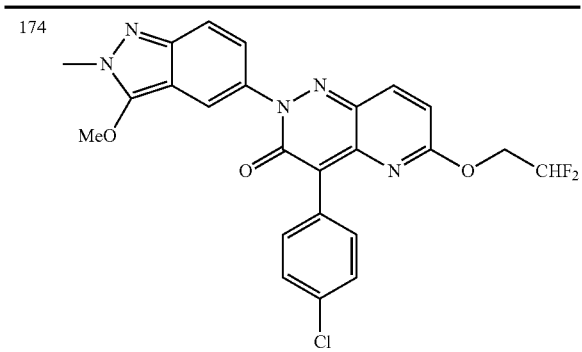
175 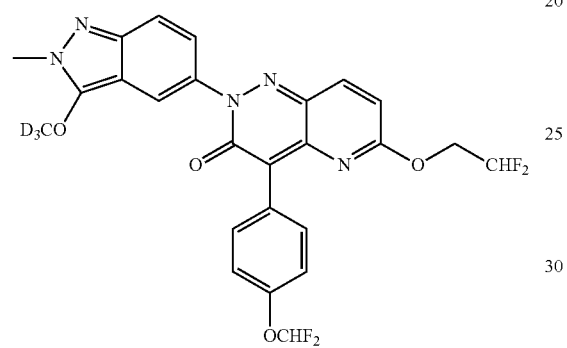
176 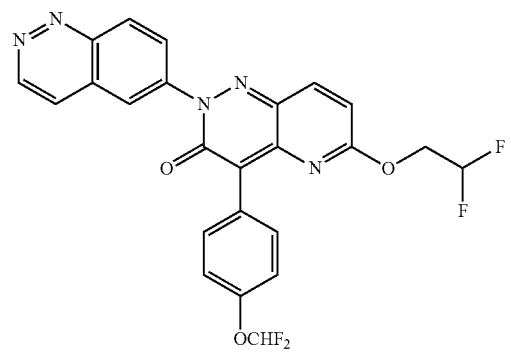 [SMILES: O=c1c(-c2ccc(OC(F)F)cc2)c2nc(OCC(F)F)ccc2nn1-c1ccc2nnccc2c1]
177 
TABLE 1-continued
178 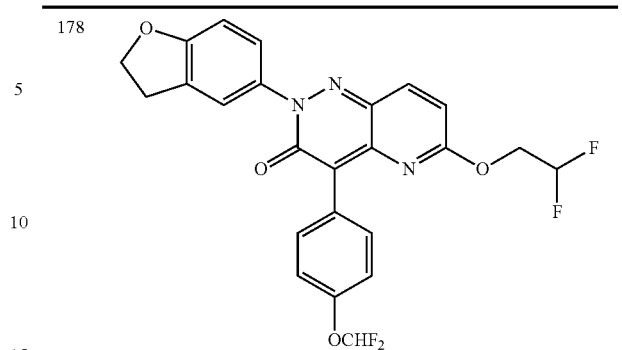
179 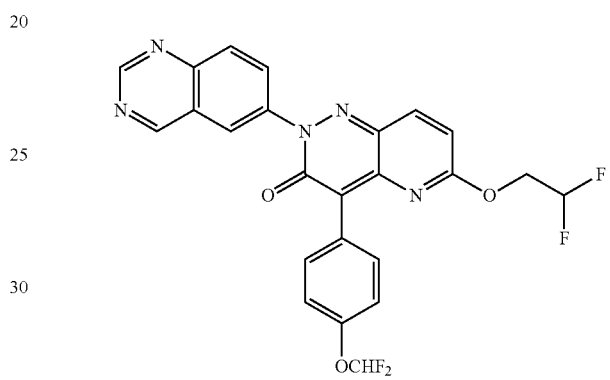
180 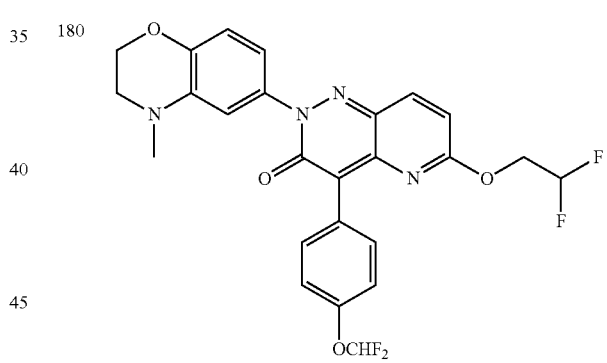
181 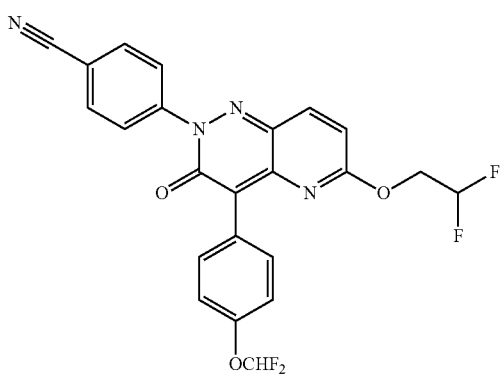 [SMILES: N#Cc1ccc(-n2nc3ccc(OCC(F)F)nc3c(-c3ccc(OC(F)F)cc3)c2=O)cc1]

TABLE 1-continued
182
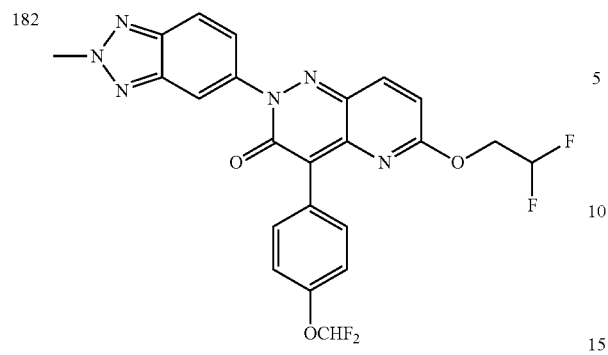
183
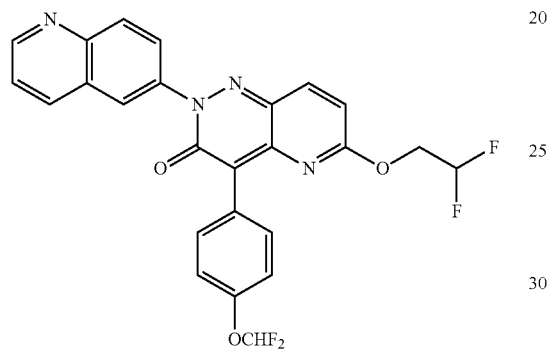
184
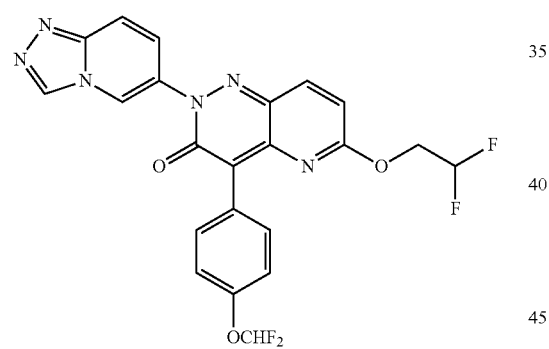
185
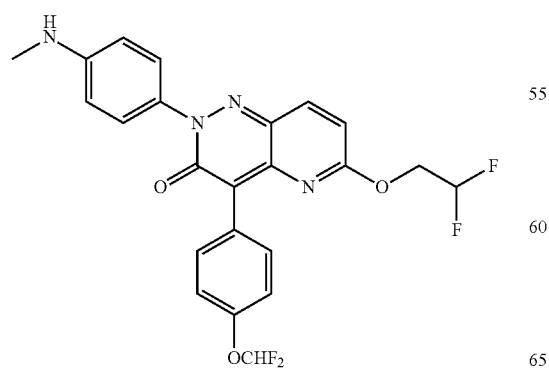
TABLE 1-continued
186
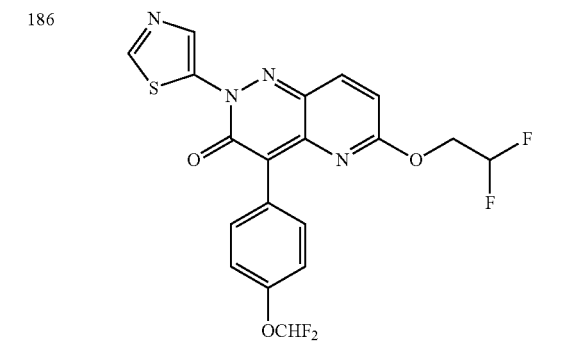
187
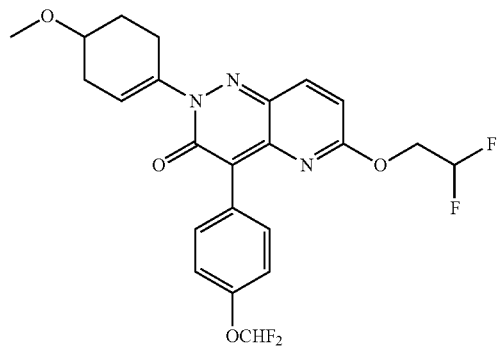 [SMILES: COC1CC=C(n2nc3ccc(OCC(F)F)nc3c(-c3ccc(OC(F)F)cc3)c2=O)CC1]
188
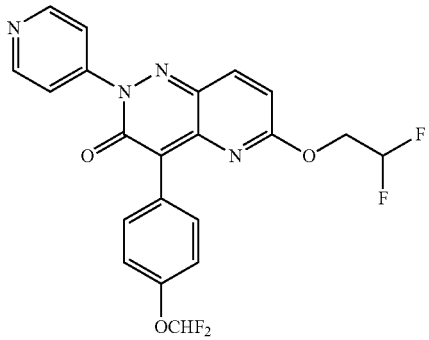
189
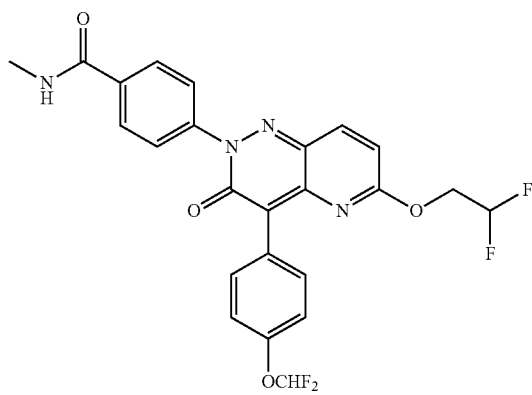 [SMILES: CNC(=O)c1ccc(-n2nc3ccc(OCC(F)F)nc3c(-c3ccc(OC(F)F)cc3)c2=O)cc1]

TABLE 1-continued
190
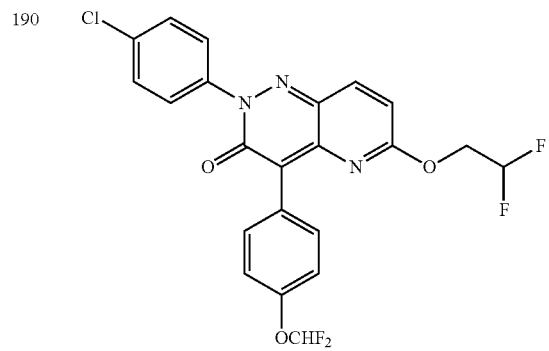
191
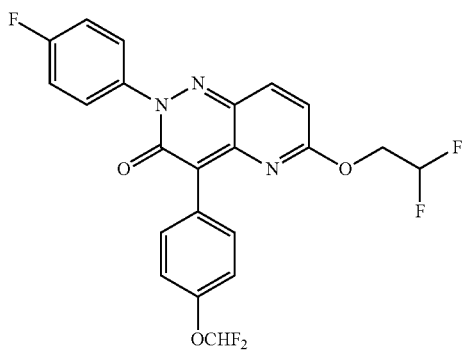
192
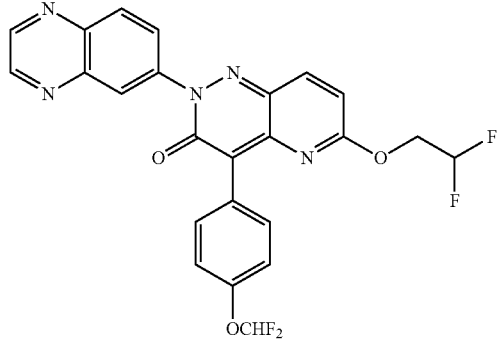
193
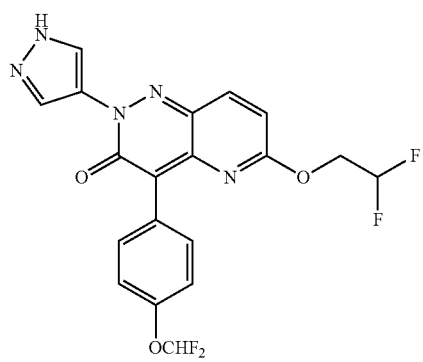 [SMILES: O=c1c(-c2ccc(OC(F)F)cc2)c2nc(OCC(F)F)ccc2nn1-c1cn[nH]c1]
TABLE 1-continued
194
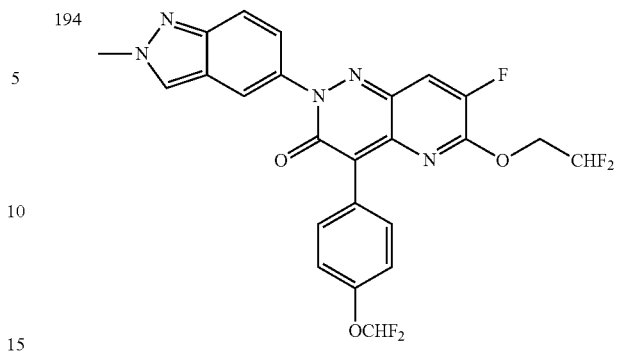
195
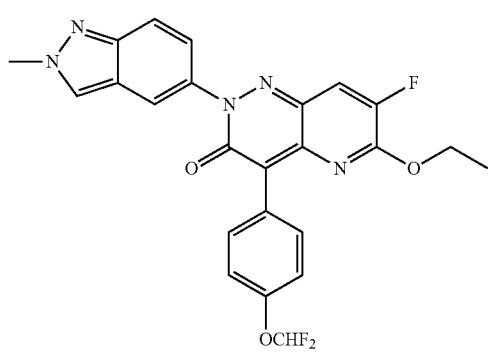
196
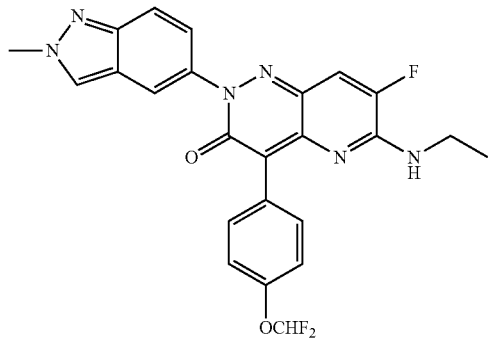 [SMILES: CCNc1nc2c(-c3ccc(OC(F)F)cc3)c(=O)n(-c3ccc4nn(C)cc4c3)nc2cc1F]
197
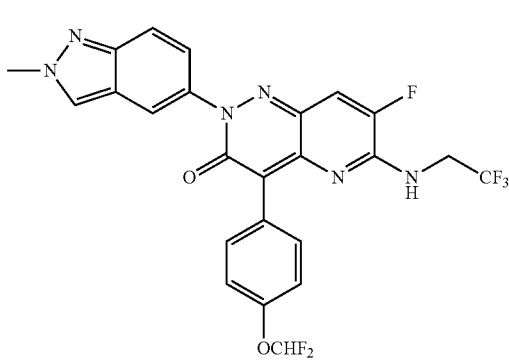 [SMILES: Cn1cc2cc(-n3nc4cc(F)c(NCC(F)(F)F)nc4c(-c4ccc(OC(F)F)cc4)c3=O)ccc2n1]

TABLE 1-continued
198 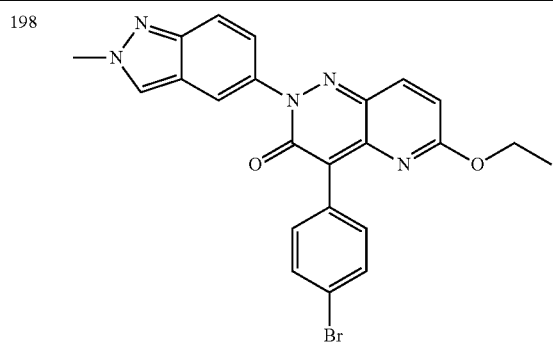
199 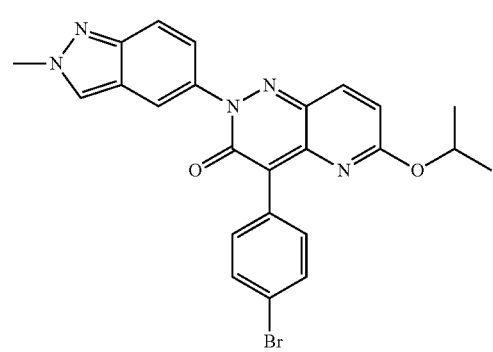 [SMILES: CC(C)Oc1ccc2nn(-c3ccc4nn(C)cc4c3)c(=O)c(-c3ccc(Br)cc3)c2n1]
200 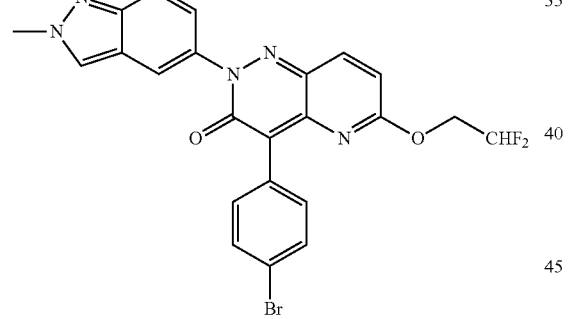
201 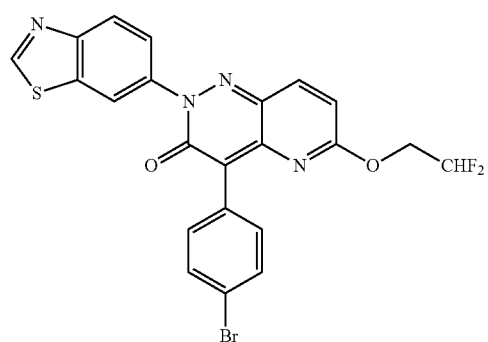 [SMILES: O=c1c(-c2ccc(Br)cc2)c2nc(OCC(F)F)ccc2nn1-c1ccc2ncsc2c1]
TABLE 1-continued
202 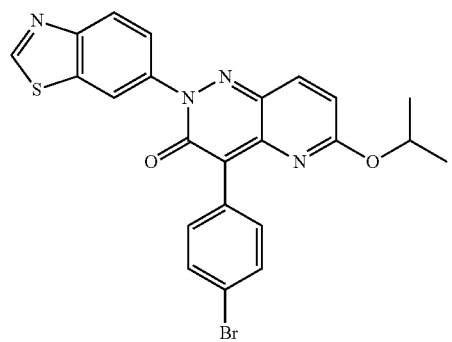 [SMILES: CC(C)Oc1ccc2nn(-c3ccc4ncsc4c3)c(=O)c(-c3ccc(Br)cc3)c2n1]
203 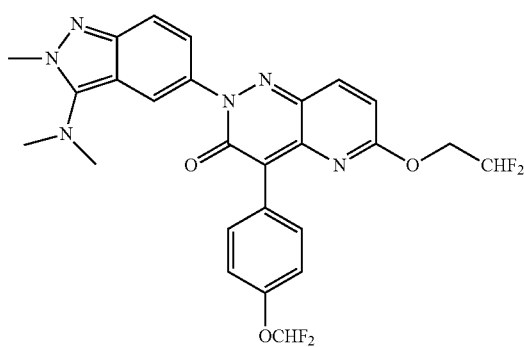 [SMILES: CN(C)c1c2cc(-n3nc4ccc(OCC(F)F)nc4c(-c4ccc(OC(F)F)cc4)c3=O)ccc2nn1C]
204 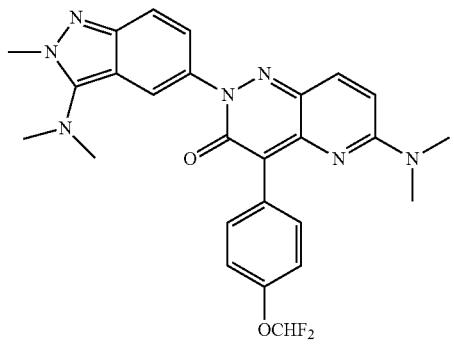
205 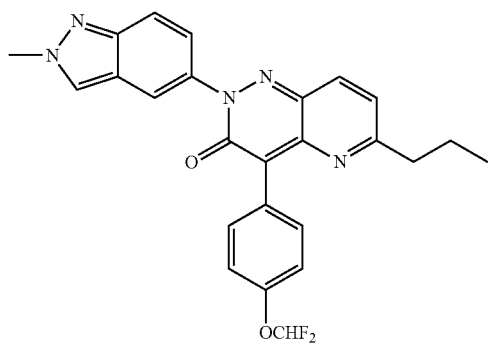 [SMILES: CCCc1ccc2nn(-c3ccc4nn(C)cc4c3)c(=O)c(-c3ccc(OC(F)F)cc3)c2n1]

TABLE 1-continued
206 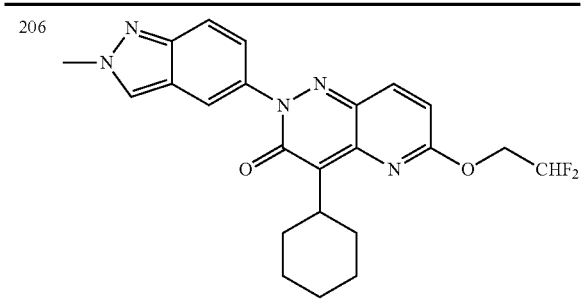
207 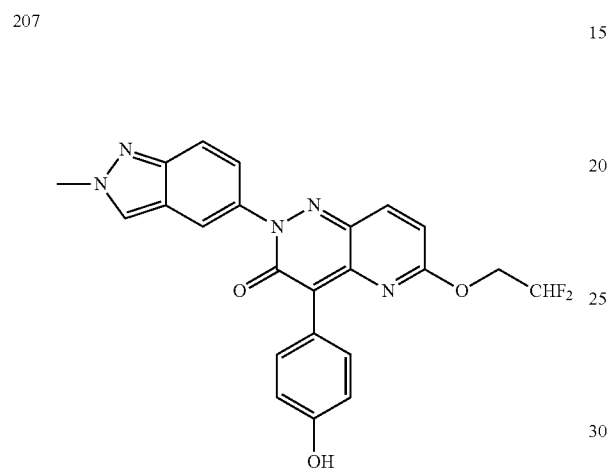
208 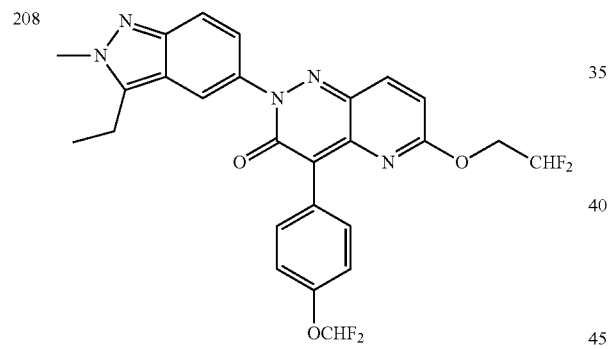
209 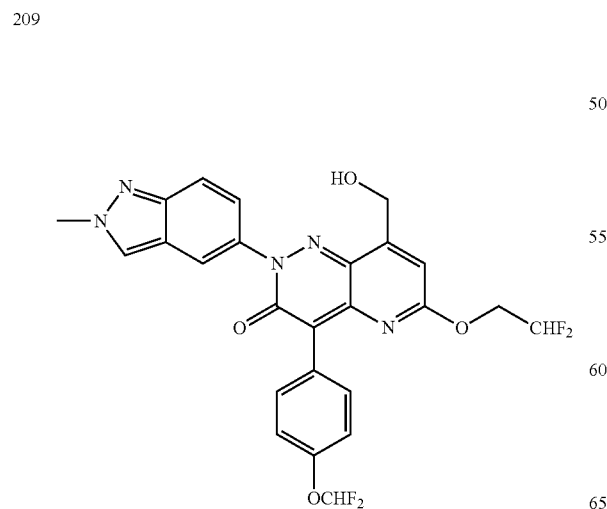
TABLE 1-continued
210 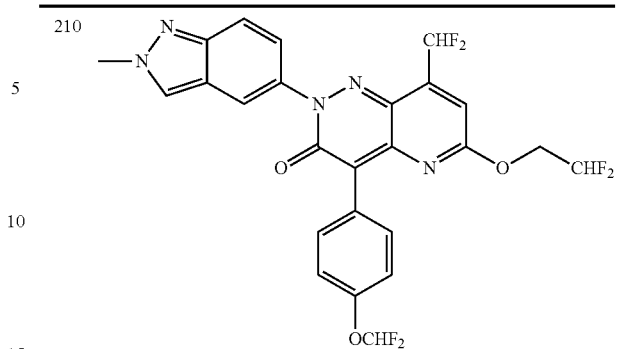
211 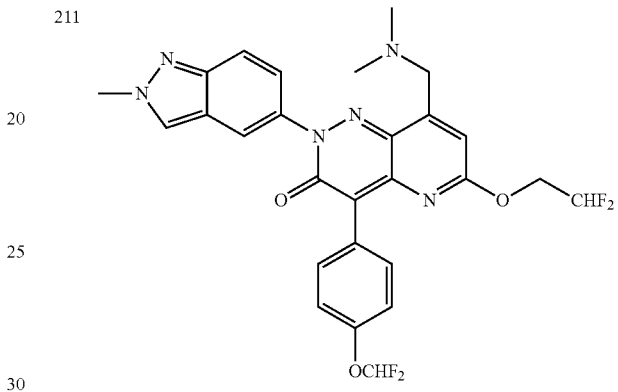
212 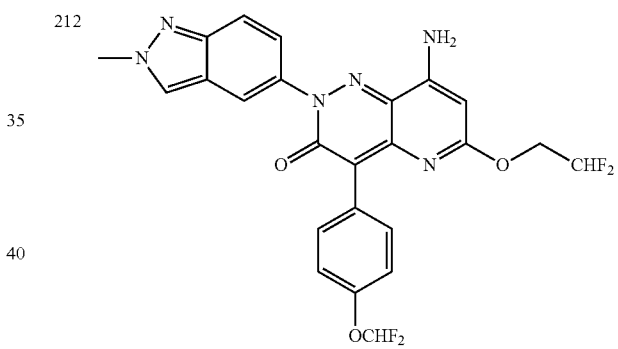
213
214 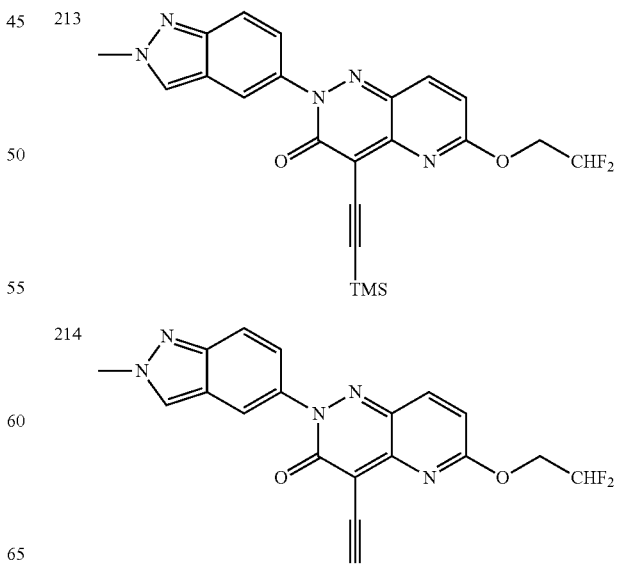

TABLE 1-continued
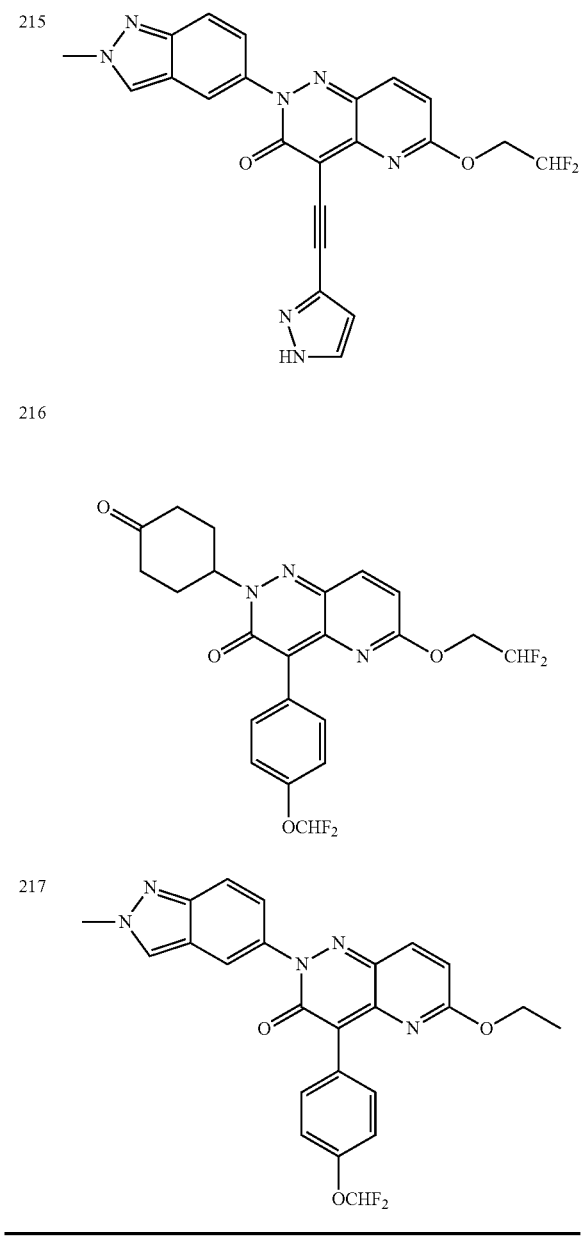
In other various embodiments, the disclosure provides additional specific examples of Formula I compounds, and their pharmaceutically acceptable salts, tautomers, and/or isotopologues as set forth in Table 2 below.
TABLE 2
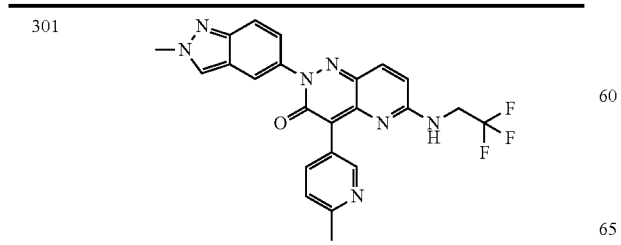
TABLE 2-continued
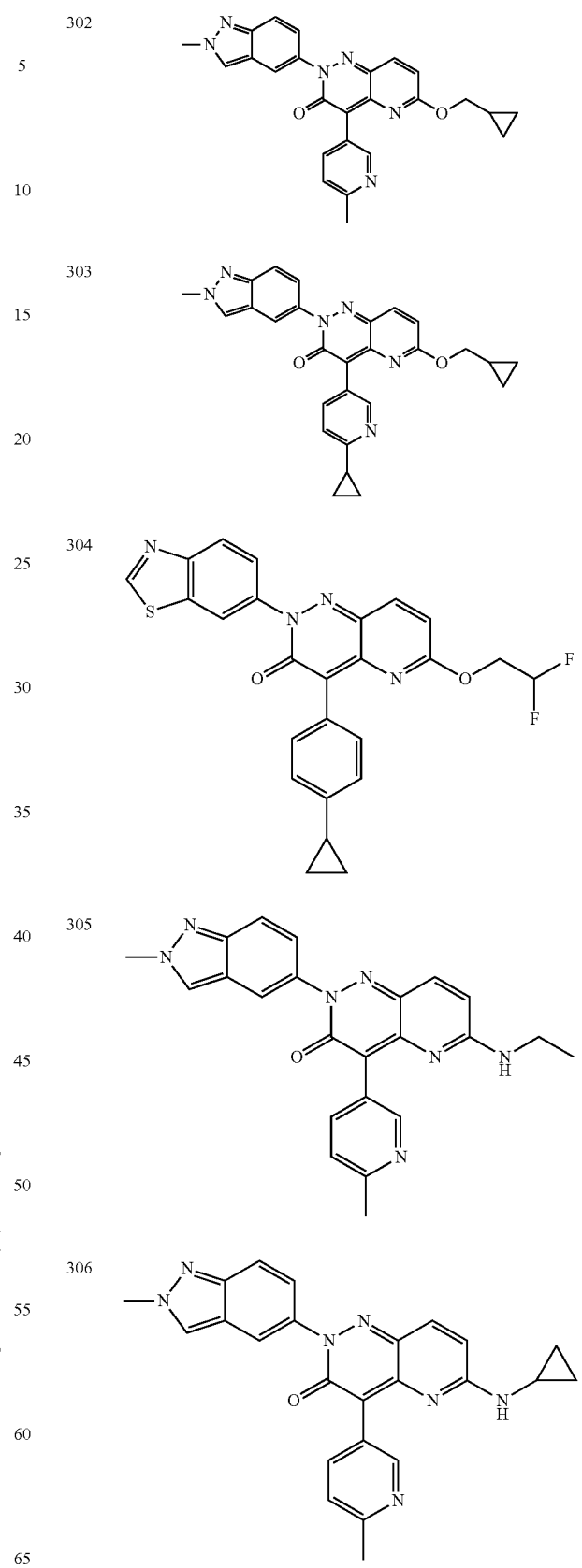

TABLE 2-continued
307 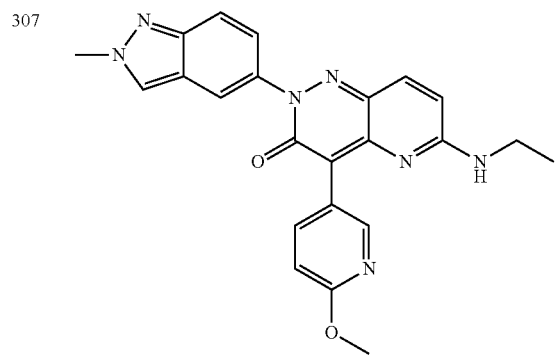
308 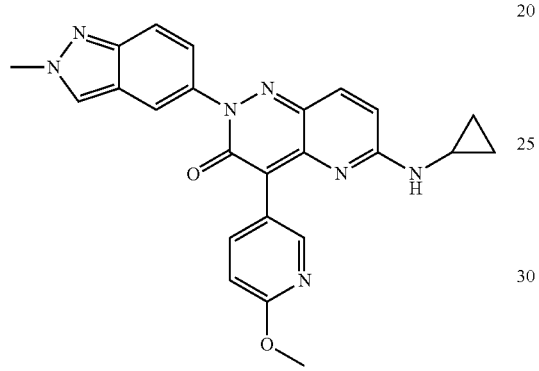
309 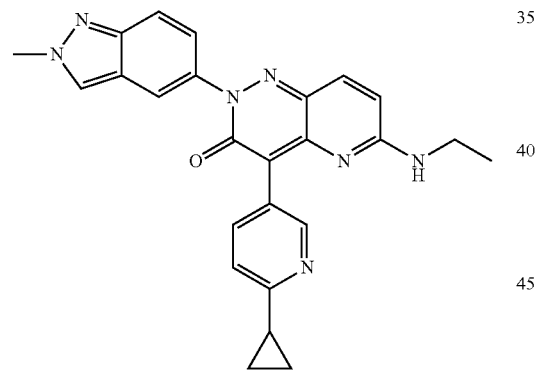
310 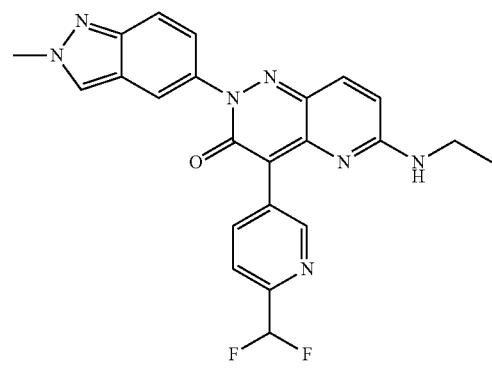
TABLE 2-continued
311 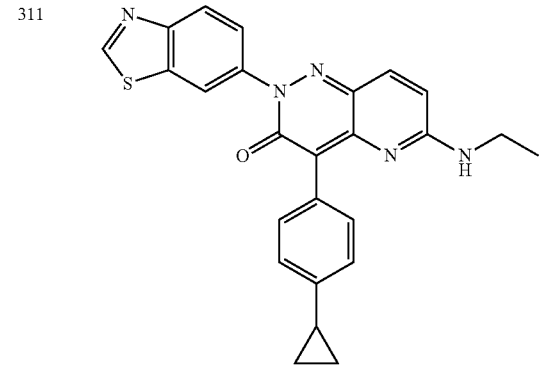
312 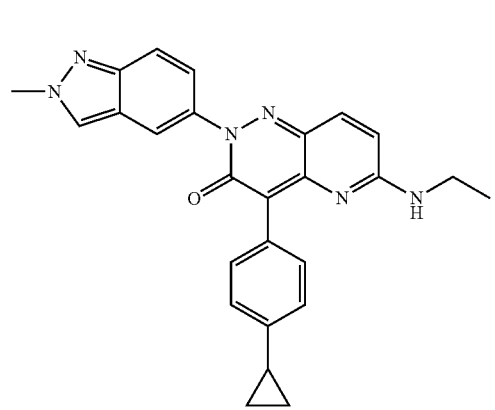
313 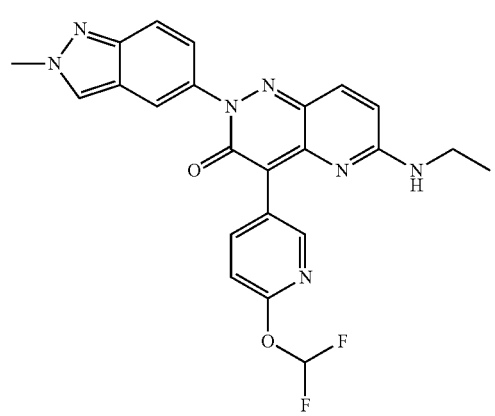
314 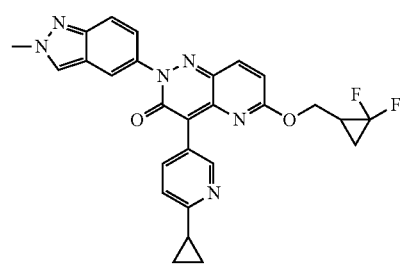

TABLE 2-continued
| 315 | 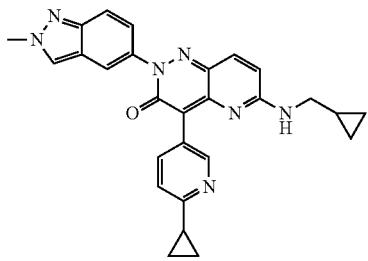 |
| --- | --- |
| 316 | 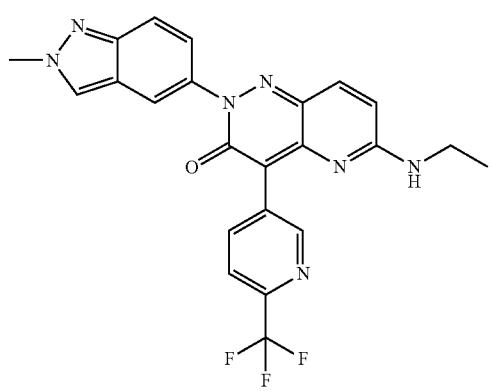 |
| 317 | 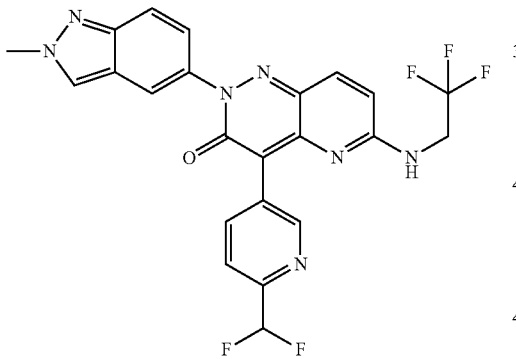 |
| 318 | 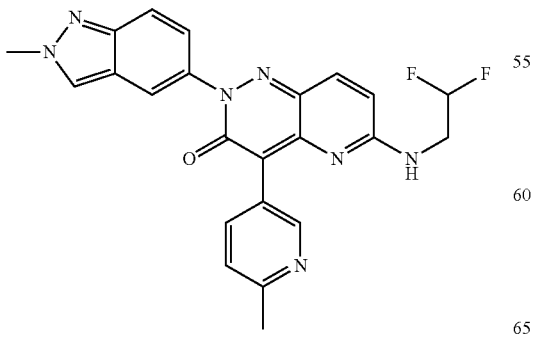 |
TABLE 2-continued
| 319 | 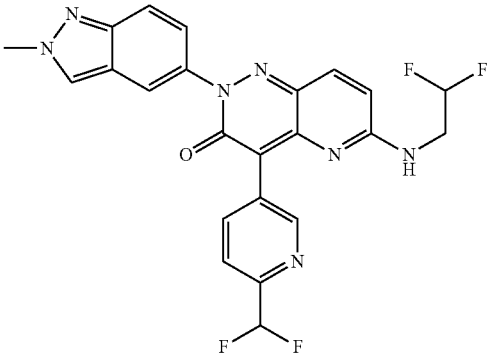 |
| --- | --- |
| 320 | 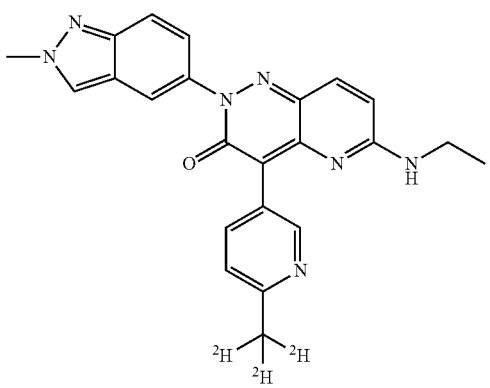 |
| 321 | 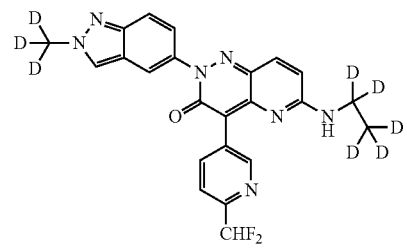 |
| 322 | 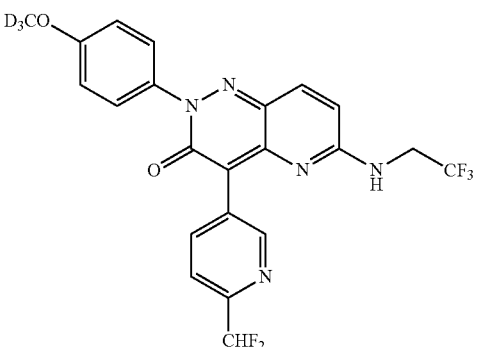 |
| 323 | 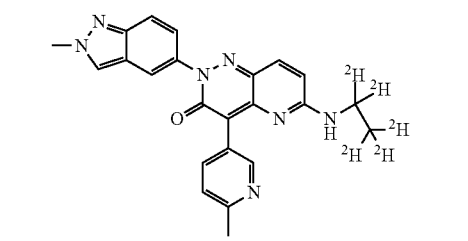 |

TABLE 2-continued

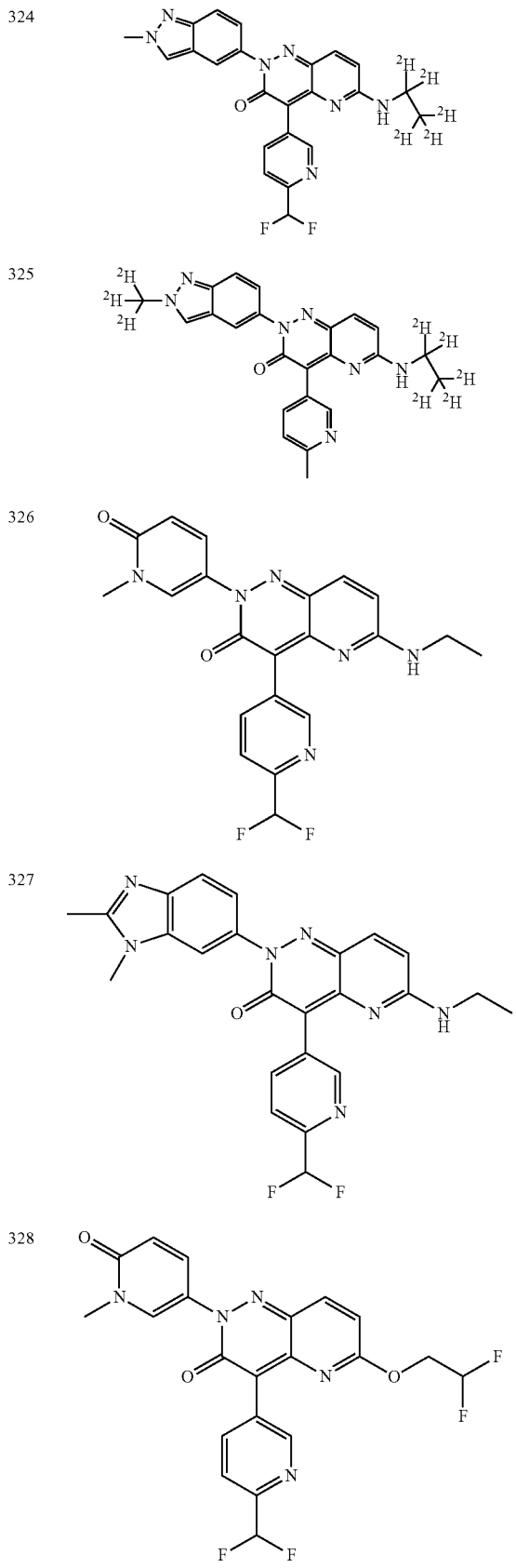

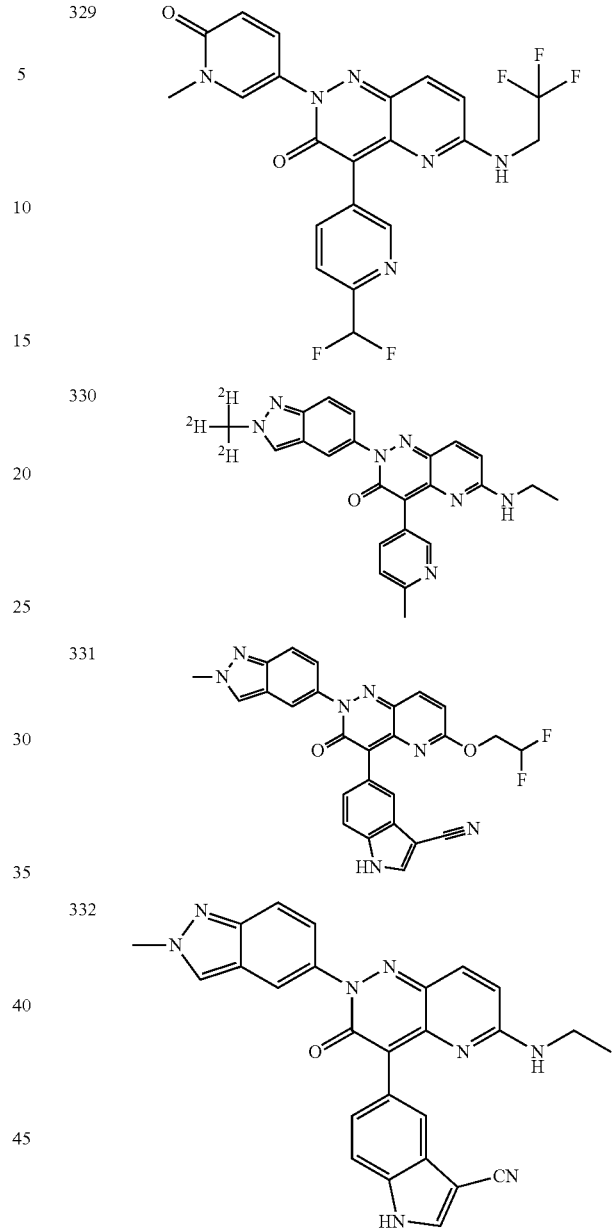

Pharmaceutical Composition

The disclosure also provides a pharmaceutical composition comprising a therapeutically effective amount of one or more compounds according to Formula I or a pharmaceutically acceptable salt, stereoisomer, tautomer, and/or isotopologue, in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

In one embodiment, the pharmaceutical composition comprises a compound selected from those illustrated in Table 1 or a pharmaceutically acceptable salt, stereoisomer, tautomer, and/or isotopologue thereof, and a pharmaceutically acceptable carrier.

The pharmaceutical composition of the present disclosure is formulated, dosed, and administered in a fashion consistent with good medical practice. Factors for consideration in this context include the particular disorder being treated, the particular subject being treated, the clinical condition of the subject, the cause of the disorder, the site of delivery of the agent, the method of administration, the scheduling of administration, and other factors known to medical practitioners.

The "therapeutically effective amount" of a compound (or a pharmaceutically acceptable salt, stereoisomer, tautomer, and/or isotopologue thereof that is administered is governed by such considerations, and is the minimum amount necessary to exert a cytotoxic effect on a cancer, or to inhibit MAT2A activity, or both. Such amount may be below the amount that is toxic to normal cells, or the subject as a whole. Generally, the initial therapeutically effective amount of a compound (or a pharmaceutically acceptable salt, stereoisomer, or tautomer thereof) of the present disclosure that is administered is in the range of about 0.01 to about 200 mg/kg or about 0.1 to about 20 mg/kg of patient body weight per day, with the typical initial range being about 0.3 to about 15 mg/kg/day. Oral unit dosage forms, such as tablets and capsules, may contain from about 1 mg to about 1000 mg of a compound (or a pharmaceutically acceptable salt, stereoisomer, or tautomer thereof) of the present disclosure. In another embodiment, such dosage forms contain from about 50 mg to about 500 mg of a compound (or a pharmaceutically acceptable salt, stereoisomer, or tautomer thereof) of the present disclosure. In yet another embodiment, such dosage forms contain from about 25 mg to about 200 mg of a compound (or a pharmaceutically acceptable salt, stereoisomer, or tautomer thereof) of the present disclosure. In still another embodiment, such dosage forms contain from about 10 mg to about 100 mg of a compound (or a pharmaceutically acceptable salt, stereoisomer, or tautomer thereof) of the present disclosure. In a further embodiment such dosage forms contain from about 5 mg to about 50 mg of a compound (or a pharmaceutically acceptable salt, stereoisomer, or tautomer thereof) of the present disclosure.

The compositions can be administered orally, topically, parenterally, by inhalation or spray or rectally in dosage unit formulations. The term parenteral as used herein includes subcutaneous injections, intravenous, intramuscular, intrasternal injection or infusion techniques.

Suitable oral compositions in accordance with the disclosure include without limitation tablets, troches, lozenges, aqueous or oily suspensions, dispersible powders or granules, emulsion, hard or soft capsules, syrups or elixirs.

Encompassed within the scope of the disclosure are pharmaceutical compositions suitable for single unit dosages that comprise a compound of the disclosure or its pharmaceutically acceptable stereoisomer, salt, or tautomer and a pharmaceutically acceptable carrier.

Compositions suitable for oral use may be prepared according to any method known to the art for the manufacture of pharmaceutical compositions. For instance, liquid formulations of the compounds contain one or more agents selected from the group consisting of sweetening agents, flavoring agents, coloring agents and preserving agents in order to provide pharmaceutically palatable preparations of the MAT2A inhibitor.

For tablet compositions, a compound of the present disclosure in admixture with non-toxic pharmaceutically acceptable excipients is used for the manufacture of tablets. Examples of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions, a compound of the present disclosure is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending a compound of the present disclosure in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide a compound of the present disclosure in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the present disclosure may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions for parenteral administrations are administered in a sterile medium. Depending on the vehicle used and concentration the concentration of the drug in the formulation, the parenteral formulation can either be a suspension or a solution containing dissolved drug. Adjuvants such as local anesthetics, preservatives and buffering agents can also be added to parenteral compositions.

Methods of Use

The MAT2A enzyme catalyzes the synthesis of S-adenosyl methionine (SAM) from methionine and ATP in cells. Accordingly, in another embodiment of the present disclosure there is provided a method of inhibiting in a cell the synthesis of SAM comprising introducing into the cell an effective amount of a compound of Formula I or a pharmaceutically acceptable salt, stereoisomer, tautomer, and/or isotopologue thereof. In an embodiment, the cell is in a subject. In some embodiments, a Formula I compound is used to identify other compounds that are inhibitors of MAT2A, for example, in a competition assay for binding to MAT2A or for the inhibition of SAM production. Binding to MAT2A or the inhibition of SAM production by a test compound having a detectable label can be measured with and without the presence of an unlabeled compound of the present disclosure.

The present disclosure also provides a method for treating a cancer in a subject suffering therefrom, comprising administering to the subject an effective amount of a MAT2A inhibitor compound as described herein. In some embodiments, the MAT2A inhibitor is a compound of Formula I or a pharmaceutically acceptable salt thereof. In an embodiment, optionally in combination with any other embodiment, the subject is a mammal, such as a human.

In an embodiment, the cancer is an MTAP-deleted cancer. In some embodiments, the cancer as one selected from the group consisting of mesothelioma, neuroblastoma, intestine carcinoma such as rectum carcinoma, colon carcinoma, familiarly adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, bladder carcinoma, testis carcinoma, breast carcinoma, urinary carcinoma, melanoma, brain tumors, head and neck cancer, lymphoma, acute lymphatic leukemia (ALL), chronic lymphatic leukemia (CLL), acute myeloid leukemia (AML), chronic myeloid leukemia (CML), hepatocellular carcinoma, gall bladder carcinoma, bronchial carcinoma, small cell lung carcinoma (SCLC), non-small cell lung carcinoma (NSCLC), multiple myeloma (MM), basalioma, teratoma, retinoblastoma, choroidea melanoma, seminoma, rhabdomyo sarcoma, osteosarcoma, chondrosarcoma, myosarcoma, liposarcoma, fibrosarcoma, Ewing sarcoma, and plasmocytoma.

In other embodiments, the cancer is selected from lung cancer, non-small cell lung cancer, bronchioloalviolar cell lung cancer, bone cancer, pancreatic cancer, skin cancer, head and neck cancer, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphoma, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including resistant and/or refractory versions of any of the above cancers, and a combination of one or more of the above cancers.

In some embodiments, the cancer is selected from the group consisting of B-cell acute lymphocytic leukemia (B-ALL), mesothelioma, lymphoma, pancreatic carcinoma, lung cancer, gastric cancer, esophageal cancer, bladder carcinoma, brain cancer, head and neck cancer, melanoma and breast cancer.

In other embodiments the lung cancer is non-small cell lung cancer, small cell lung cancer, adenocarcinoma of the lung, and squamous cell carcinoma of the lung.

In other embodiments the breast cancer is triple negative breast cancer (TNBC).

In other embodiments, the brain cancer is a brain tumor selected from the group consisting of glioma, glioblastoma, astrocytoma, meningioma, medulloblastoma, peripheral neuroectodermal tumors, and craniopharyngioma.

In still other embodiments, the cancer is a lymphoma selected from the group consisting of mantle cell lymphoma, Hodgkin lymphoma, non-Hodgkin lymphoma, Burkitt lymphoma, diffuse large B-cell lymphoma (DLBCL), and adult T-cell leukemia/lymphoma (ATLL). As used herein, the expression adult T-cell leukemia/lymphoma refers to a rare and often aggressive T-cell lymphoma that can be found in the blood (leukemia), lymph nodes (lymphoma), skin, or multiple areas of the body.

As described generally above, methylthioadenosine phosphorylase (MTAP) is an enzyme found in all normal tissues that catalyzes the conversion of methylthioadenosine (MTA) into adenine and 5-methylthioribose-1-phosphate. The adenine is salvaged to generate adenosine monophosphate, and the 5-methylthioribose-1-phosphate is converted to methionine and formate. Because of this salvage pathway, MTA can serve as an alternative purine source when de novo purine synthesis is blocked, e.g., with antimetabolites, such as L-alanosine. Many human and murine malignant cells lack MTAP activity. MTAP deficiency is not only found in tissue culture cells but the deficiency is also present in primary leukemias, gliomas, melanomas, pancreatic cancers, non-small cell lung cancers (NSCLC), bladder cancers, astrocytomas, osteosarcomas, head and neck cancers, myxoid chondrosarcomas, ovarian cancers, endometrial cancers, breast cancers, soft tissue sarcomas, non-Hodgkin lymphomas, and mesotheliomas. For example, proliferation of cancer cells that are MTAP null, i.e., MTAP-deleted, is inhibited by knocking down MAT2A expression with shRNA which was confirmed using small molecule inhibitors of MAT2A. K. Marjon et al., *Cell Reports* 15 (2016) 574-587, incorporated herein by reference. An MTAP null or MTAP-deleted cancer is a cancer in which the MTAP gene has been deleted or lost or otherwise deactivated or a cancer in which the MTAP protein has a reduced or impaired function, or a reduced presence.

Accordingly, in an embodiment of the present disclosure there is provided a method for treating a cancer in a subject wherein the cancer is characterized by a reduction or absence of MTAP expression or absence of the MTAP gene or reduced function of MTAP protein as compared to cancers where the MTAP gene and/or protein is present and fully functioning, or as compared to cancers with the wild type MTAP gene. The method comprises administering to the subject a therapeutically effective amount of a compound of Formula I or a pharmaceutically acceptable salt, tautomer, and/or isotopologue thereof.

In another embodiment, there is provided a method of treating an MTAP deleted cancer in a subject comprising administering to the subject an effective amount of a compound of Formula I or a pharmaceutically acceptable salt thereof. In an embodiment, the MTAP deleted cancer is selected from leukemia, glioma, melanoma, pancreatic cancer, non-small cell lung cancer (NSCLC), bladder cancer, astrocytoma, osteosarcoma, head and neck cancer, myxoid chondrosarcoma, ovarian cancer, endometrial cancer, breast cancer, soft tissue sarcoma, lymphoma, and mesothelioma.

In an embodiment, the MTAP deleted cancer is pancreatic cancer. In another embodiment, the MTAP deleted cancer is selected from bladder cancer, melanoma, brain cancer, lung cancer, pancreatic cancer, breast cancer, liver cancer, esophageal cancer, gastric cancer, colon cancer, head and neck cancer, kidney cancer, colon cancer, diffuse large B cell lymphoma (DLBCL), acute lymphoblastic leukemia (ALL), mantle cell lymphoma (MCL), glioblastoma multiforme (GBM), and non-small cell lung cancer (NSCLC).

Genomic analysis of MTAP null cell lines revealed that cell lines incorporating a KRAS mutation or a p53 mutation were sensitive to MAT2A inhibition. Accordingly, an embodiment of the present disclosure provides a method for treating a cancer in a subject wherein the cancer is characterized by reduction or absence of MTAP expression or absence of the MTAP gene or reduced function of MTAP protein, the method comprising administering to the subject a therapeutically effective amount of a compound of Formula I, wherein said cancer is further characterized by the presence of mutant KRAS or mutant p53. In an embodiment, there is provided a method of treating an MTAP null cancer having a mutant KRAS or mutant p53 in a subject, comprising administering to the subject an effective amount of a compound of Formula I or a pharmaceutically acceptable salt, tautomer, and/or isotopologue thereof. For example, the cancer is MTAP null and KRAS mutant, MTAP null and p53 mutant, or each of MTAP null, KRAS mutant and p53 mutant.

The term "mutant KRAS" or "KRAS mutation" refers to a KRAS protein incorporating an activating mutation that alters its normal function and the gene encoding such a protein. For example, a mutant KRAS protein may incorporate a single amino acid substitution at position 12 or 13. In a particular embodiment, the KRAS mutant incorporates a G12X or G13X substitution, wherein X represents any amino acid change at the indicated position. In a particular embodiment, the substitution is GT2V, GT2R, GT2C or GT3D. In another embodiment, the substitution is GT3D. By "mutant p53" or "p53 mutation" is meant p53 protein (or gene encoding said protein) incorporating a mutation that inhibits or eliminates its tumor suppressor function. In an embodiment, said p53 mutation is, Y126_splice, K132Q, M133K, R174fs, R175H, R196*, C238S, C242Y, G245S, R248W, R248Q, I255T, D259V, S261_splice, R267P, R273C, R282W, A159V or R280K. In an embodiment, the foregoing cancer is non-small cell lung cancer (NSCLC), pancreatic cancer, head and neck cancer, gastric cancer, breast cancer, colon cancer or ovarian cancer.

In another embodiment, the compounds disclosed herein are useful as ligands for degradation of disease-associated proteins. An example of this approach is PROTACs (PROteolysis TArgeting Chimeras). PROTACs are bifunctional molecules that comprise both a ligand moiety selected from one of the compounds disclosed herein, which is capable of binding the target protein, and a ligase targeting moiety, such as a peptide portion (referred to as the degron) that is recognized and polyubiquitinated by E3 ligase. Thus, the PROTAC non-covalently binds to a target protein, and recruits E3 ligase via the degron, which results in polyubiquination and degradation of the bound target. A number of publications describe the pre-clinical use of PROTACs in a variety of therapeutic areas including oncology. See, e.g., Lu et al. *Chemistry & Biology* 22 (2015) 755-763.

Aspects

Aspect 1. A compound according to Formula I.

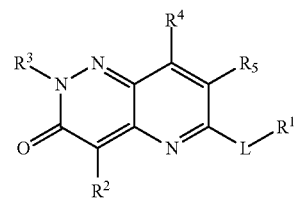

(I)

wherein

L is O, S, NR, or a bond;

R is H or $C_1$-$C_6$-alkyl;

$R^1$ is selected from the group consisting of $C_1$-$C_6$-alkyl, $C_2$-$C_6$-alkenyl, $C_3$-$C_6$-carbocyclyl, —($C_1$-$C_6$-alkyl)($C_3$-$C_6$-carbocyclyl), and —($C_1$-$C_6$-alkyl)($C_3$-$C_6$-cycloalkenyl) wherein
any alkyl in $R^1$ is straight or branched, and
$R^1$ is optionally substituted by 1-6 halo;
or when L is NR, then R and $R^1$ in combination with L represent a 3- to 6-membered heterocycloalkyl (wherein 1-4 ring members are independently selected from N, O, and S) optionally substituted by one or more $R^A$;
$R^2$ and $R^3$ are independently selected from the group consisting of $C_6$-$C_{10}$-aryl, $C_3$-$C_6$-carbocyclyl, 5- to 10-membered heteroaryl (wherein 1-4 heteroaryl members are independently selected from N, O, and S), and 3- to 14-membered heterocycloalkyl (wherein 1-4 heterocycloalkyl members are independently selected from N, O, and S),
wherein $R^2$ and $R^3$ are independently and optionally substituted by one or more substituents that are selected from the group consisting of $R^A$, $OR^A$, halo, —N=N—$R^A$, $NR^AR^B$, —($C_1$-$C_6$-alkyl)$NR^AR^B$, —C(O)$OR^A$, —C(O)$NR^AR^B$, —OC(O)$R^A$, and —CN;
$R^4$ is selected from the group consisting of H, $C_1$-$C_6$-alkyl (optionally substituted by one or more halo), —O($C_1$-$C_6$-alkyl) (optionally substituted by one or more halo), —OH, halo, —CN, —($C_1$-$C_6$-alkyl)$NR^AR^B$, and —$NR^AR^B$;
$R^5$ is selected from the group consisting of H, $C_1$-$C_6$-alkyl, $C_1$-$C_6$-alkoxy, $C_2$-$C_6$-alkenyl, $C_2$-$C_6$-alkynyl, halo, —CN, and —$NR^CR^D$;
$R^A$ and $R^B$ are independently selected from the group consisting of H, —CN, -hydroxy, oxo, $C_1$-$C_6$-alkyl, $C_1$-$C_6$-alkoxy, $C_2$-$C_6$-alkenyl, $C_2$-$C_6$-alkynyl, —NH$_2$, —S(O)$_{0-2}$—($C_1$-$C_6$-alkyl), —S(O)$_{0-2}$—($C_6$-$C_{10}$-aryl), —C(O)($C_1$-$C_6$-alkyl), —C(O)($C_3$-$C_{14}$-carbocyclyl), —$C_3$-$C_{14}$-carbocyclyl, —($C_1$-$C_6$-alkyl)($C_3$-$C_{14}$-carbocyclyl), $C_6$-$C_{10}$-aryl, 3- to 14-membered heterocycloalkyl and —($C_1$-$C_6$-alkyl)-(3- to 14-membered heterocycloalkyl) (wherein 1-4 heterocycloalkyl members are independently selected from N, O, and S), and 5- to 10-membered heteroaryl (wherein 1-4 heteroaryl members are independently selected from N, O, and S);
wherein each alkyl, alkoxy, alkenyl, alkynyl, aryl, carbocyclyl, heterocycloalkyl, and heteroaryl moiety of $R^A$ and $R^B$ is optionally substituted with one or more substituents selected from the group consisting of hydroxy, halo, —NR'$_2$ (wherein each R' is independently selected from the group consisting of $C_1$-$C_6$-alkyl, $C_2$-$C_6$-alkenyl, $C_2$-$C_6$-alkynyl, $C_6$-$C_{10}$-aryl, 3- to 14-membered heterocycloalkyl and —($C_1$-$C_6$-alkyl)-(3- to 14-membered heterocycloalkyl) (wherein 1-4 ring members are independently selected from N, O, and S), and 5- to 10-membered heteroaryl (wherein 1-4 heteroaryl members are independently selected from N, O, and S), —NHC(O)(O$C_1$-$C_6$-alkyl), —NO$_2$, —CN, oxo, —C(O)OH, —C(O)O($C_1$-$C_6$-alkyl), —$C_1$-$C_6$-alkyl($C_1$-$C_6$-alkoxy), —C(O)NH$_2$, $C_1$-$C_6$-alkyl, —C(O) $C_1$-$C_6$-alkyl, —O$C_1$-$C_6$-alkyl, —Si($C_1$-$C_6$-alkyl)$_3$, —S(O)$_{0-2}$—($C_1$-$C_6$-alkyl), $C_6$-$C_{10}$-aryl, —($C_1$-$C_6$-alkyl)($C_6$-$C_{10}$-aryl), 3- to 14-membered heterocycloalkyl, and —($C_1$-$C_6$-alkyl)-(3- to 14-membered heterocycle) (wherein 1-4 heterocycle members are independently selected from N, O, and S), and —O($C_6$-$C_{14}$-aryl), wherein each alkyl, alkenyl, aryl, and heterocycloalkyl in $R^A$ and $R^B$ is optionally substituted with one or more substituents selected from the group consisting of hydroxy, —O$C_1$-$C_6$-alkyl, halo, —NH$_2$, —($C_1$-$C_6$-alkyl)NH$_2$, —C(O)OH, CN, and oxo,
$R^C$ and $R^D$ are each independently selected from H and $C_1$-$C_6$-alkyl;
or a pharmaceutically acceptable salt thereof.

Aspect 2. The compound according to Aspect 1, wherein $R^4$ is selected from the group consisting of H, $C_1$-$C_6$-alkyl optionally substituted by one or more halo, —O($C_1$-$C_6$-alkyl), —($C_1$-$C_6$-alkyl)$NR^AR^B$, and —$NR^AR^B$ (wherein $R^A$ and $R^B$ are independently selected from H and $C_1$-$C_6$-alkyl); and
$R^5$ is selected from the group consisting of H, $C_1$-$C_6$-alkyl, $C_1$-$C_6$-alkoxy, and —$NR^CR^D$.

Aspect 3. The compound according to Aspect 1 or 2, wherein at least one of $R^4$ and $R^5$ is H.

Aspect 4. The compound according to any one of Aspects 1-3, wherein $R^4$ is H.

Aspect 5. The compound according to any one of Aspects 1-4, wherein $R^5$ is H.

Aspect 6. The compound according to any one of Aspects 1-5, wherein each of $R^4$ and $R^5$ is H.

Aspect 7. The compound according to any one of Aspects 1 to 6, wherein $R^2$ is $C_6$-$C_{10}$-aryl or 5- to 10-membered heteroaryl.

Aspect 8. The compound according to Aspect 7, wherein $R^2$ is $C_6$-$C_{10}$-aryl.

Aspect 9. The compound according to Aspect 8, wherein $R^2$ is phenyl.

Aspect 10. The compound according to Aspect 7, wherein $R^2$ is 5- to 10-membered heteroaryl, and wherein 1 ring member is N.

Aspect 11. The compound according to Aspect 10, wherein $R^2$ is a 5- or 6-membered heteroaryl.

Aspect 12. The compound according to Aspect 10 or 11, wherein $R^2$ is a 6-membered heteroaryl.

Aspect 13. The compound according to any one of Aspects 10-12, wherein $R^2$ is pyridyl.

Aspect 14. The compound according to any one of Aspects 1 to 12, wherein $R^3$ is 3- to 14-membered heterocycloalkyl or 5- to 10-membered heteroaryl.

Aspect 15. The compound according to Aspect 14, wherein $R^3$ is selected from the group consisting of benzothiazolyl, benzoisothiazolyl, benzoxazolyl, pyridinyl, pyridinonyl, pyradazinyl, benzimidazolyl, benzotriazolyl, indazolyl, quinoxalinyl, quinolinyl, quinazolinyl, imidazopyridinyl, pyrazolopyridinyl, triazolopyridinyl, cinnolinyl, isoxazolyl, pyrazolyl, benzofuranyl, dihydrobenzofuranyl, dihydrobenzodioxinyl, and tetrahydrobenzodioxinyl.

Aspect 16. The compound according to any one of Aspects 1 to 12, wherein $R^3$ is $C_6$-$C_{10}$-aryl.

Aspect 17. The compound according to Aspect 16, wherein $R^3$ is phenyl.

Aspect 18. The compound according to any one of Aspects 1 to 6, wherein $R^2$ is phenyl and $R^3$ is 3- to 14-membered heterocycloalkyl or 5- to 10-membered heteroaryl.

Aspect 19. The compound according to any one of Aspects 1 to 18, wherein L is O or NR.

Aspect 20. The compound according to Aspect 19, wherein $R^1$ is $C_1$-$C_6$-alkyl or $C_3$-$C_6$-carbocyclyl.

Aspect 21. The compound according to Aspect 19 or 20, wherein $R^1$ is $C_1$-$C_3$-alkyl that is optionally substituted by 1-3 F.

Aspect 22. The compound according to Aspect 1, wherein L is O or NR and R is H;
$R^1$ is $C_1$-$C_3$-alkyl that is optionally substituted by 1-3 F;

$R^2$ is 3- to 14-membered heterocycloalkyl or 5- to 10-membered heteroaryl (wherein 1 heterocycloalkyl or heteroaryl member is N) or $C_6$-$C_{10}$-aryl;

$R^3$ is 3- to 14-membered heterocycloalkyl or 5- to 10-membered heteroaryl wherein 1 to 3 heterocycloalkyl or heteroaryl members are independently selected from N, O, and S; and each of $R^4$ and $R^5$ is H.

Aspect 23. The compound according to Aspect 22, wherein L is NR.

Aspect 24. The compound according to Aspect 1, wherein the compound is selected from the following table:

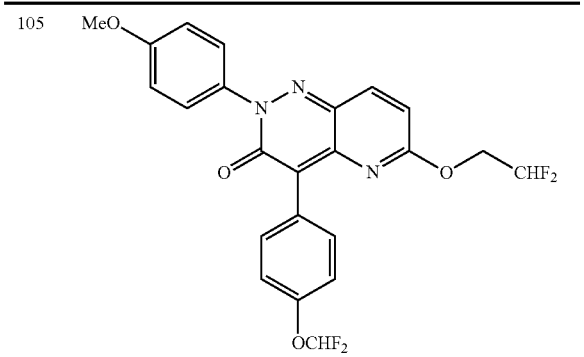

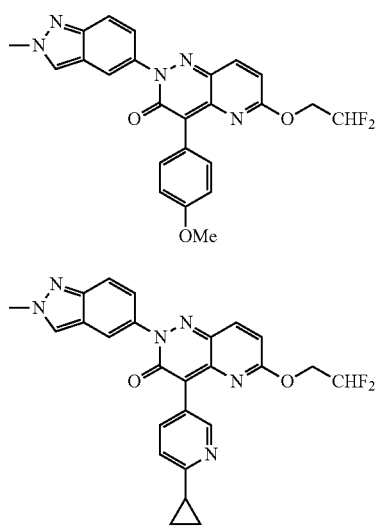

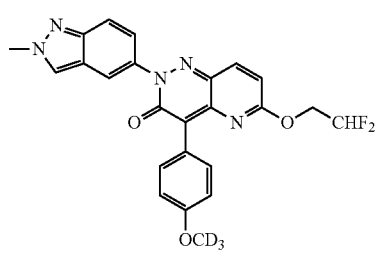

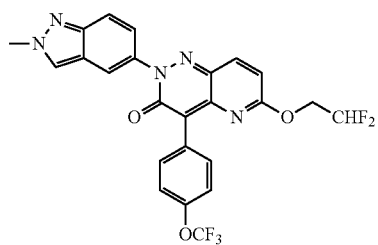

-continued
| | |
|---|---|
| 110 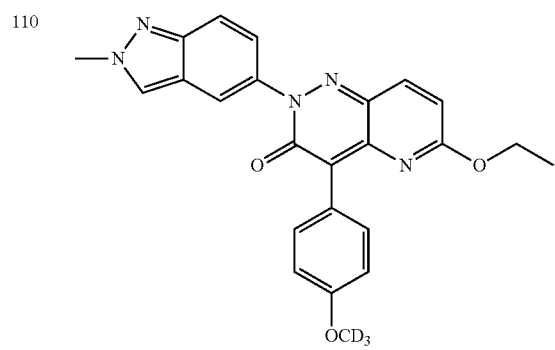 | 115 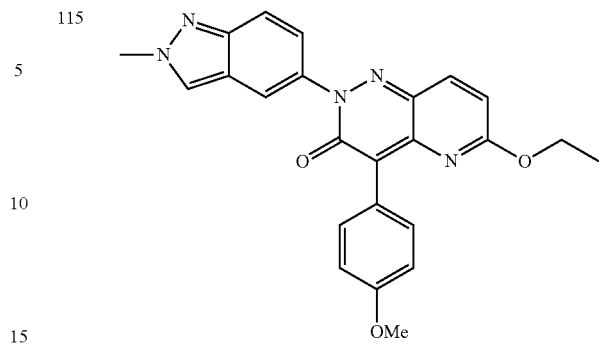 |
| 111 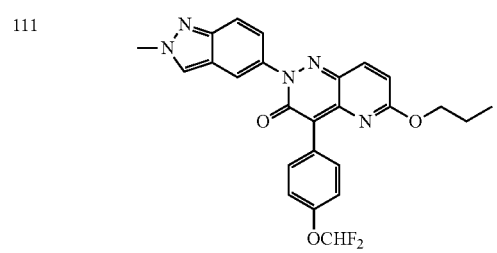 | 116 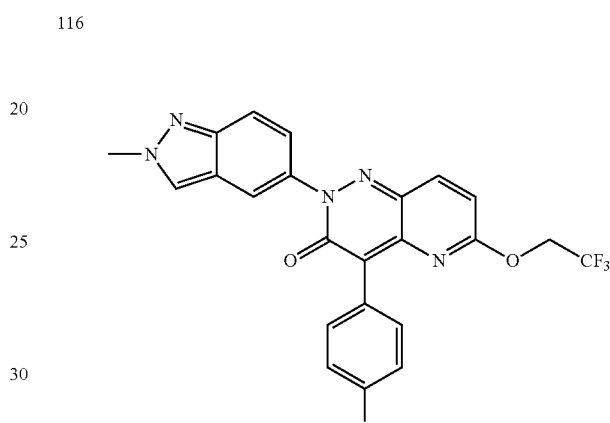 |
| 112 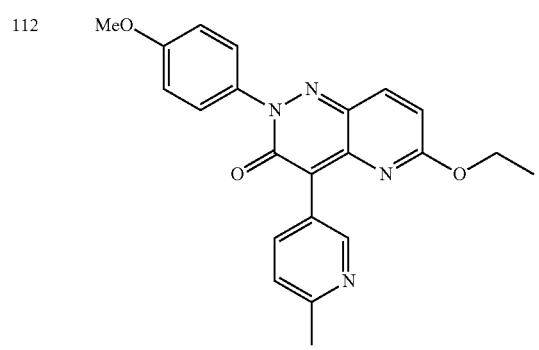 | 117 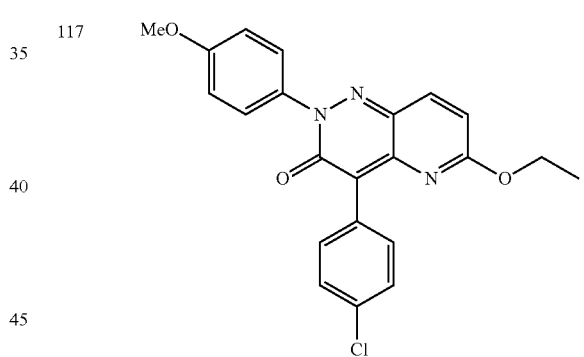 |
| 113 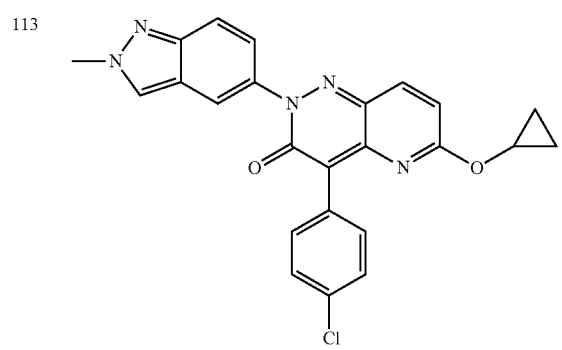 | 118 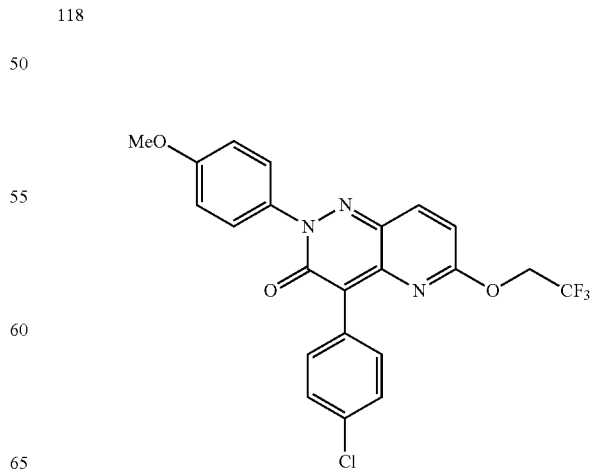 |
| 114 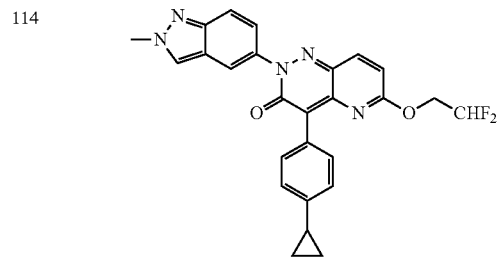 | |

| | |
|---|---|
| 119 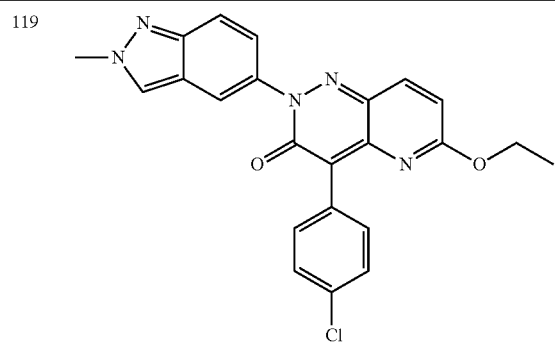 | 123 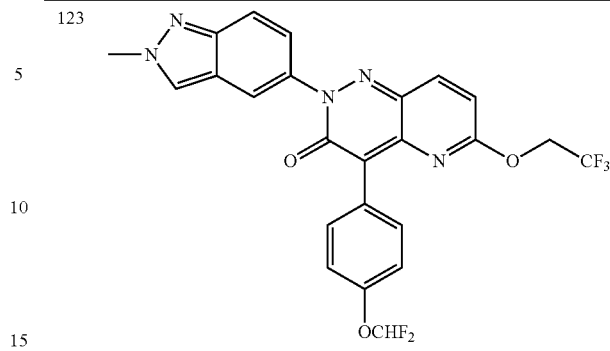 |
| 120 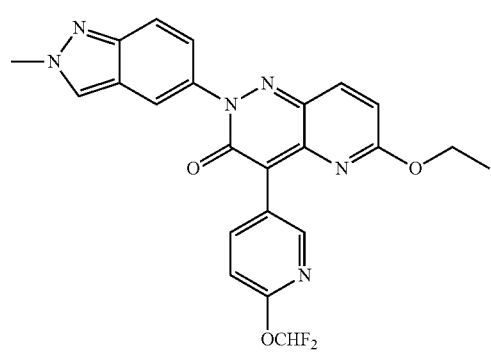 | 124 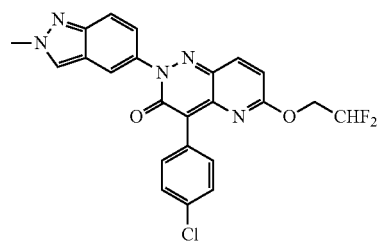 |
| 121 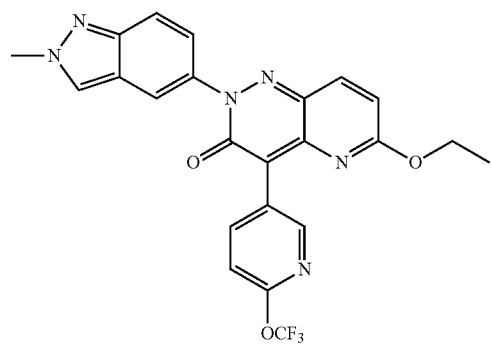 | 125 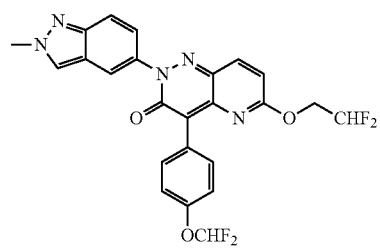 |
| 122 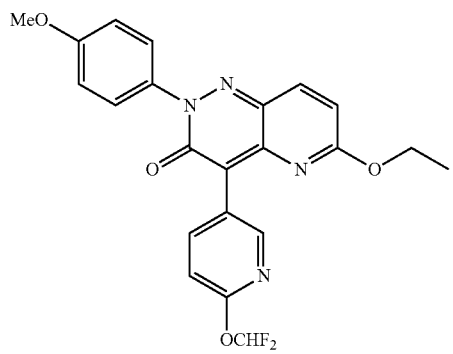 | 126 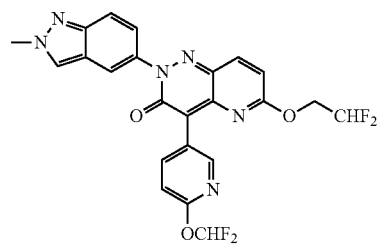 |
| | 127 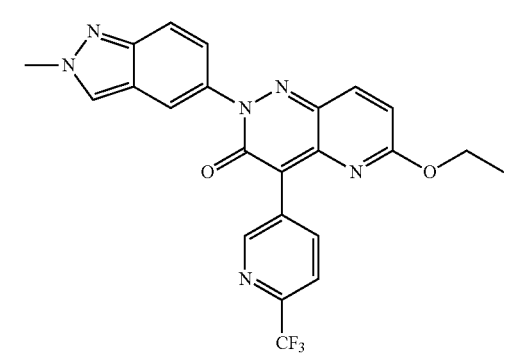 |

128 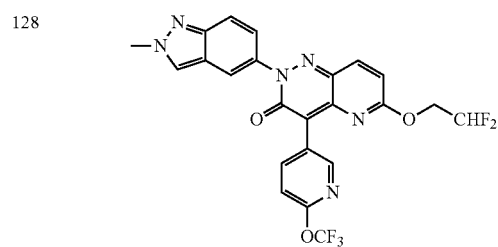
129 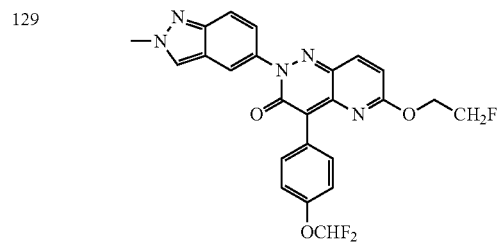
130 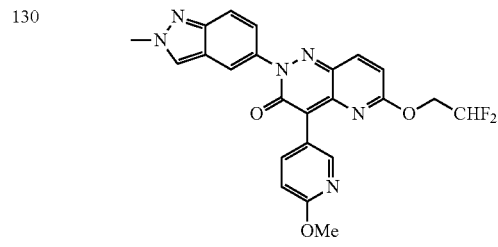
131 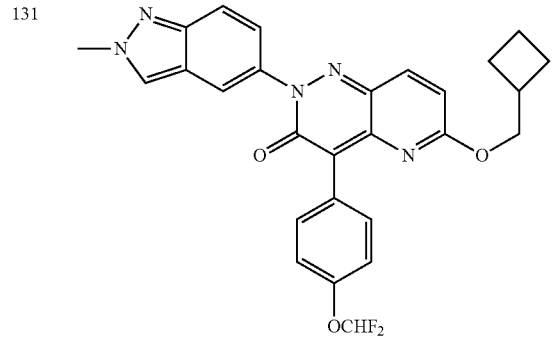
132 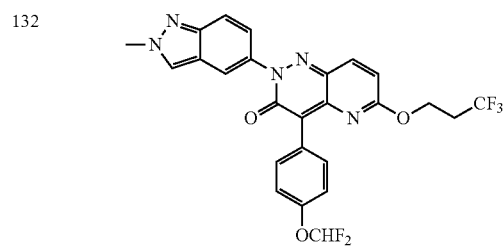
133 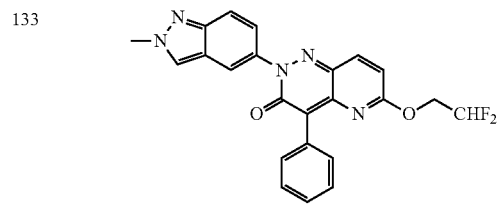
134 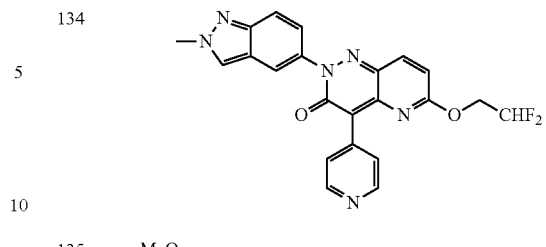
135 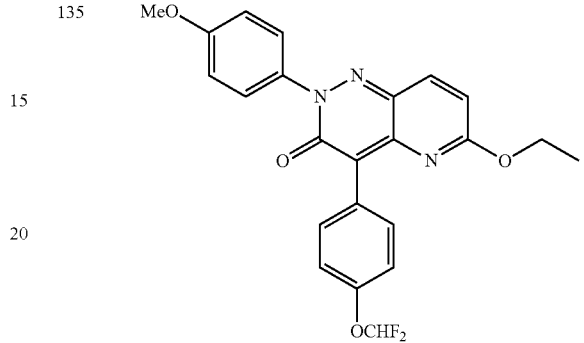
136 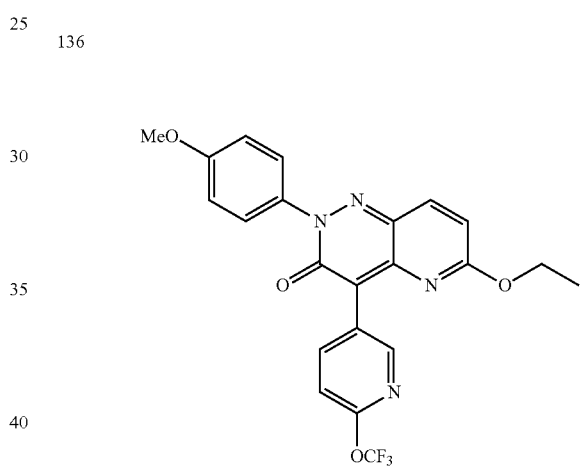
137 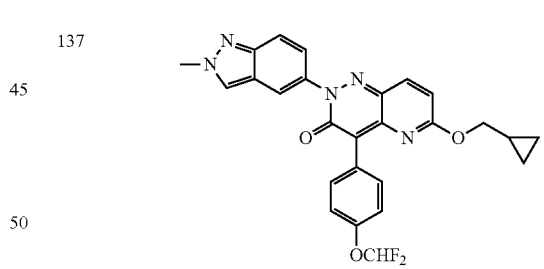
138 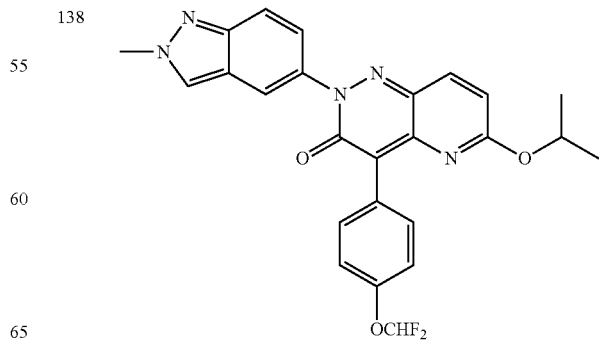

| | |
|---|---|
| 139 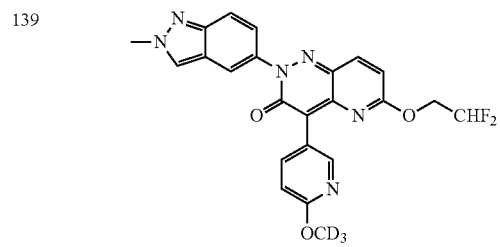 | 144 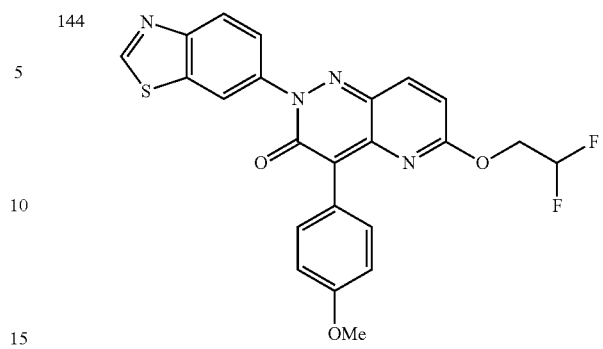 |
| 140 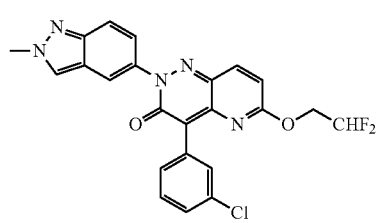 | |
| 141 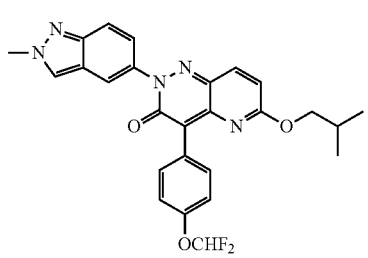 | 145 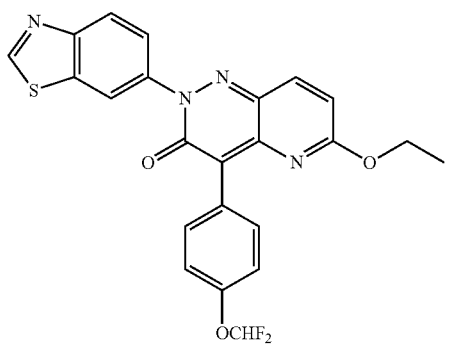 |
| 142 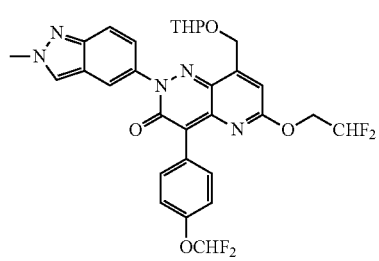 | 146 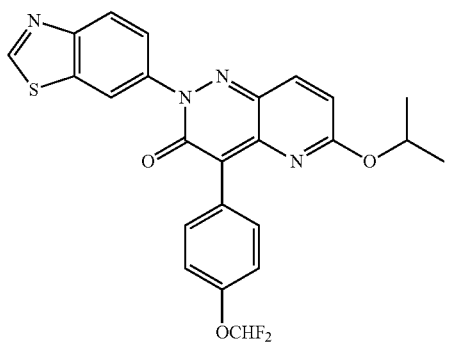 |
| 143 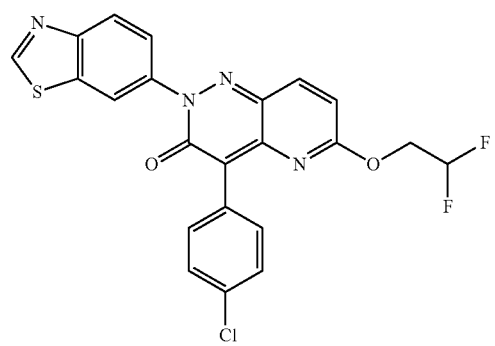 | 147 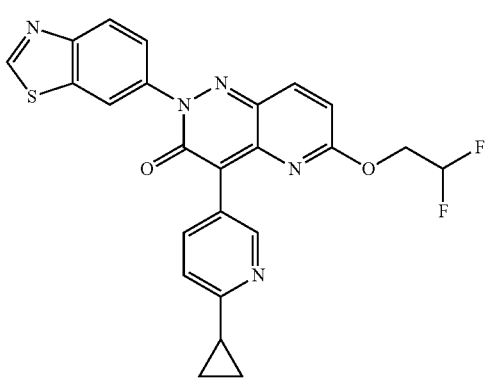 |

-continued
148 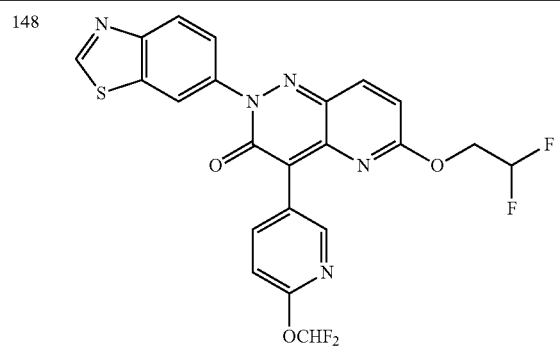
149 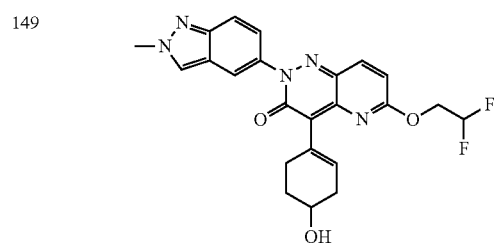
150 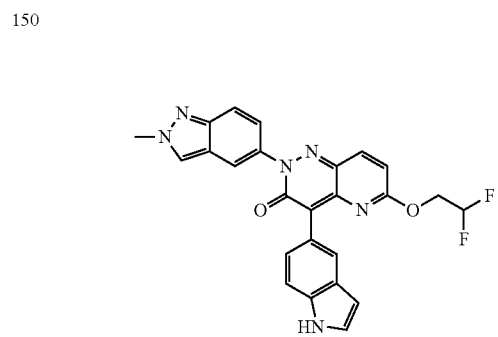
151 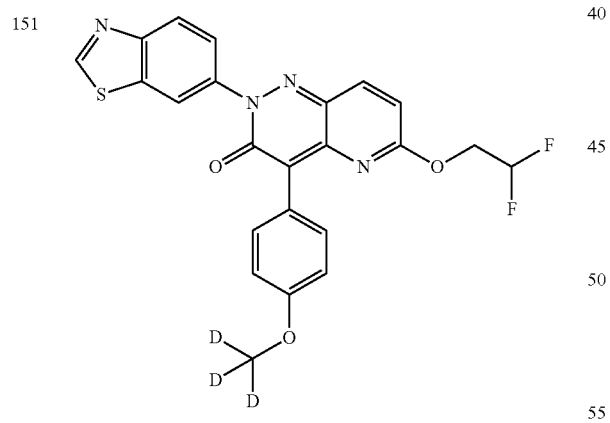
152 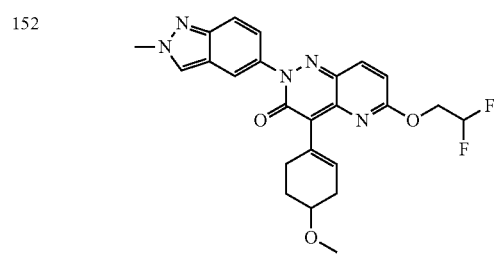
-continued
153 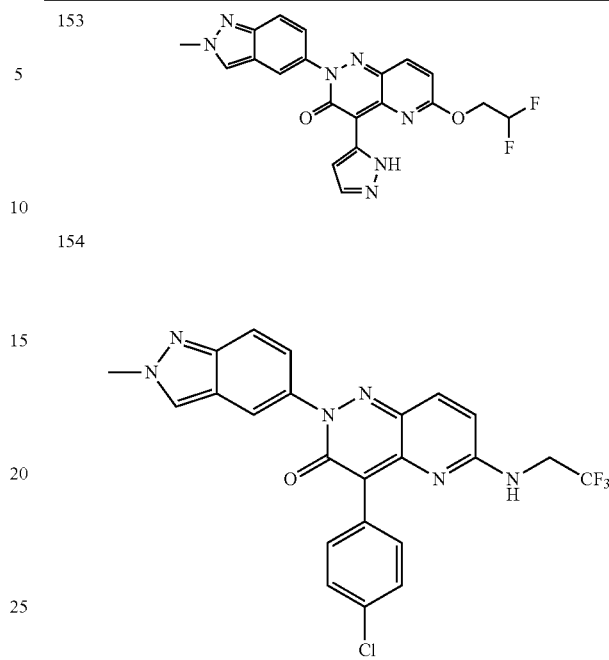
154
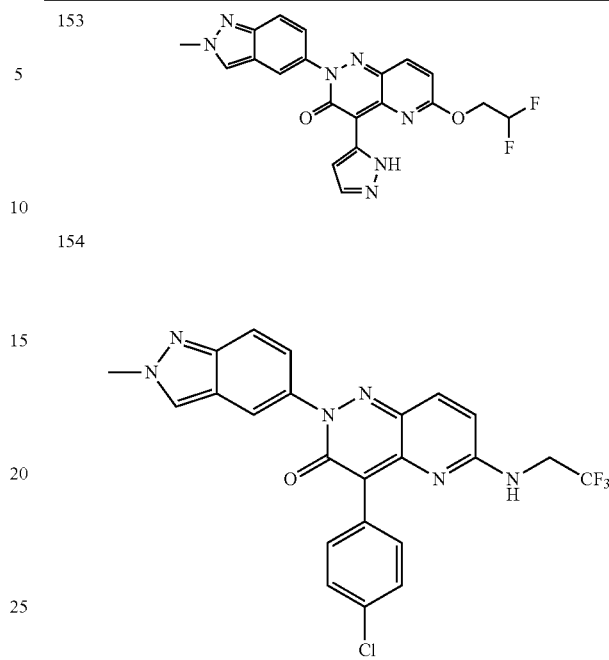
155 
156 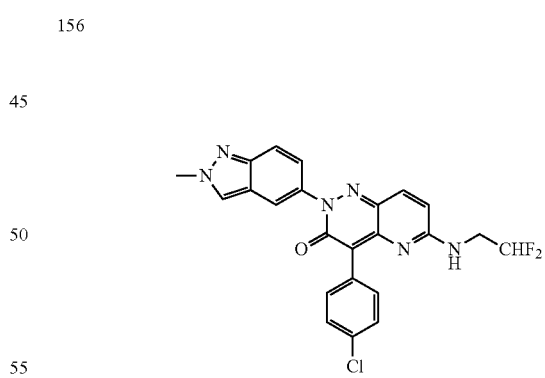
157 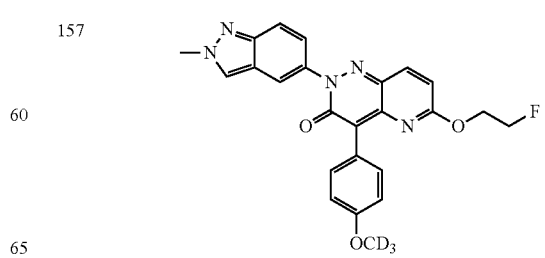

-continued
158 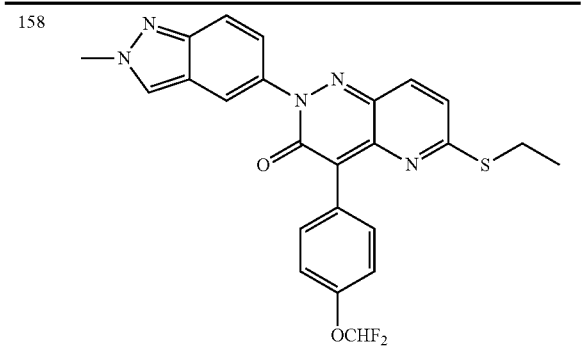
159 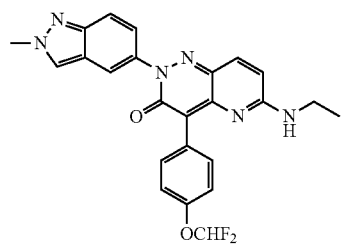
160 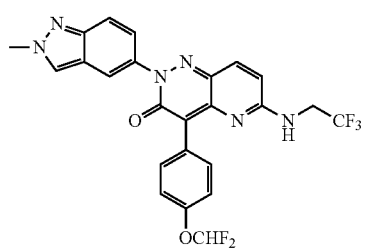
161 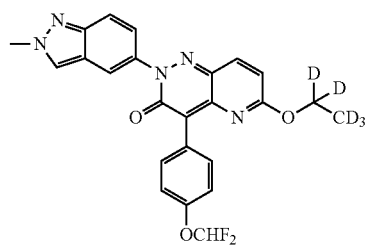
162 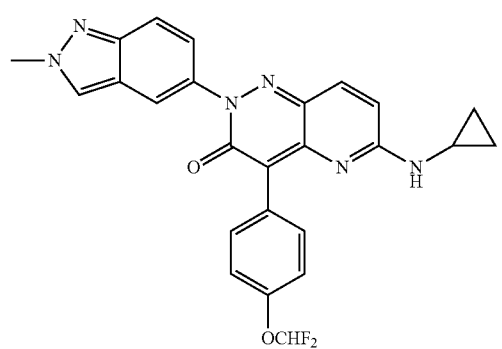
-continued
163 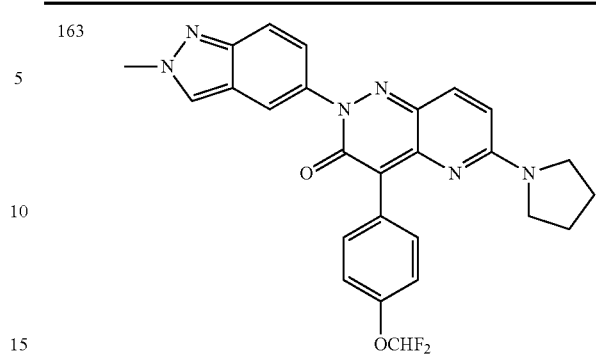
164 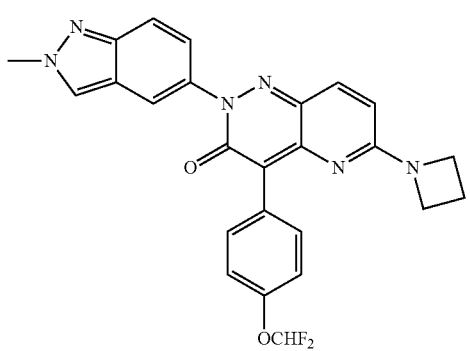
165 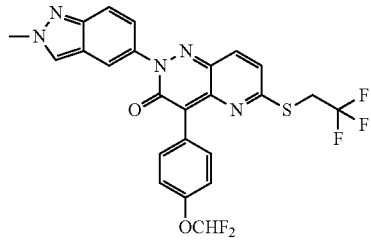
166 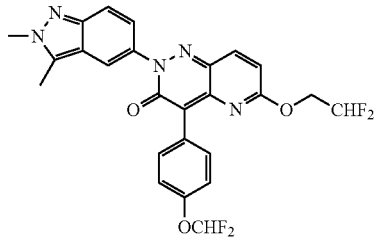
167 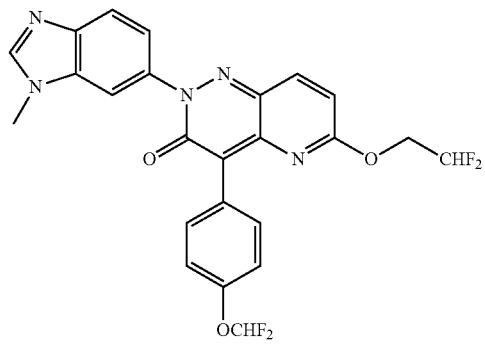

| | | | |
|---|---|---|---|
| 168 | 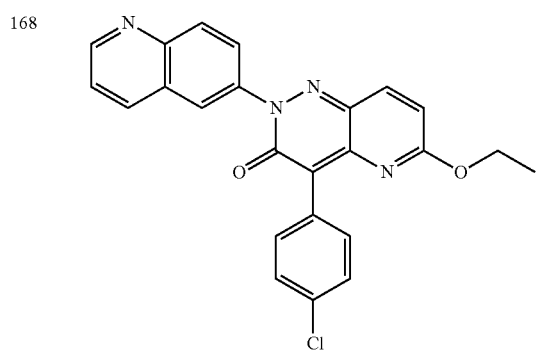 | 173 | 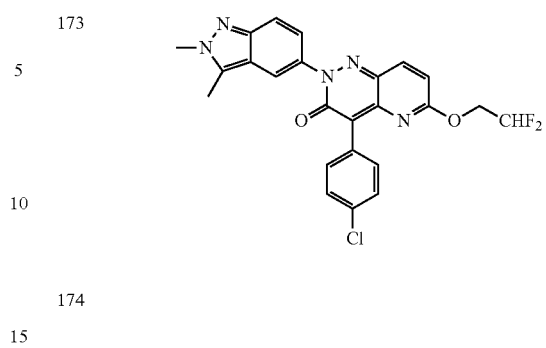 |
| 169 | 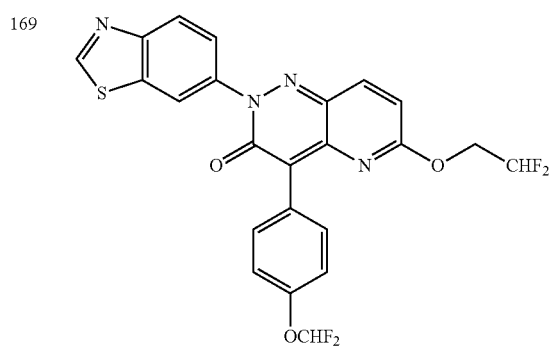 | 174 | 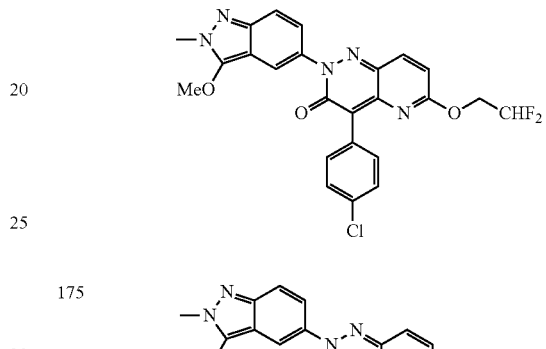 |
| 170 | 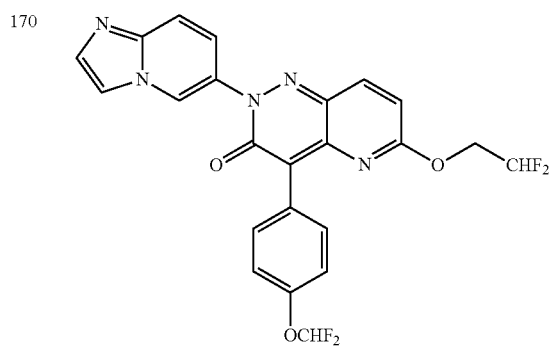 | 175 | 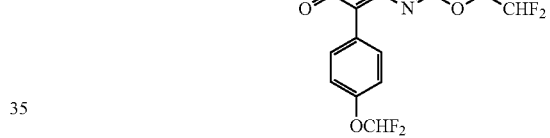 |
| 171 | 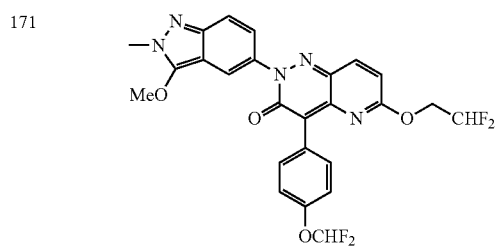 | 176 | 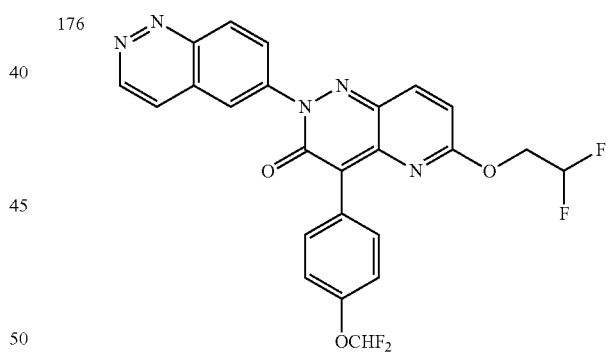 |
| 172 | 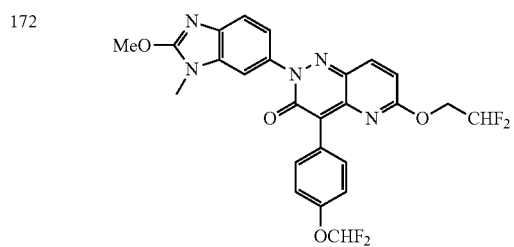 | 177 | 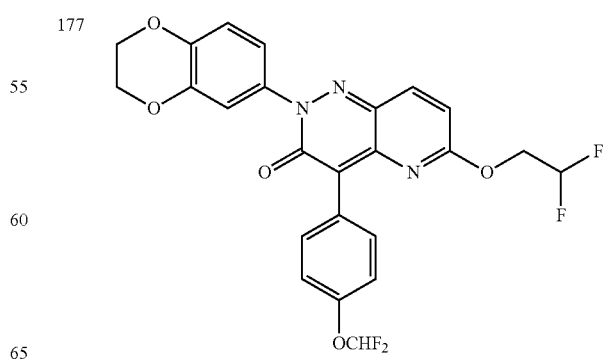 |

| 178 | 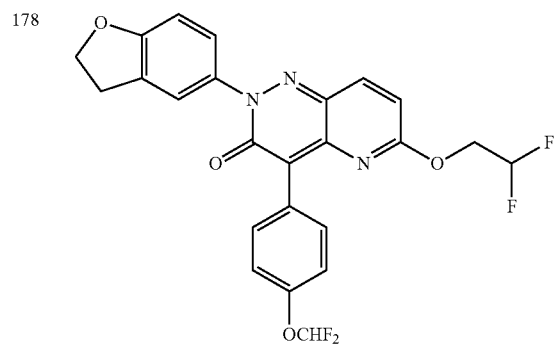 | 182 | 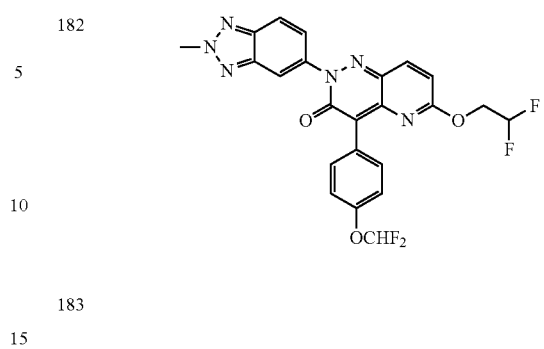 |
| --- | --- | --- | --- |
| 179 | 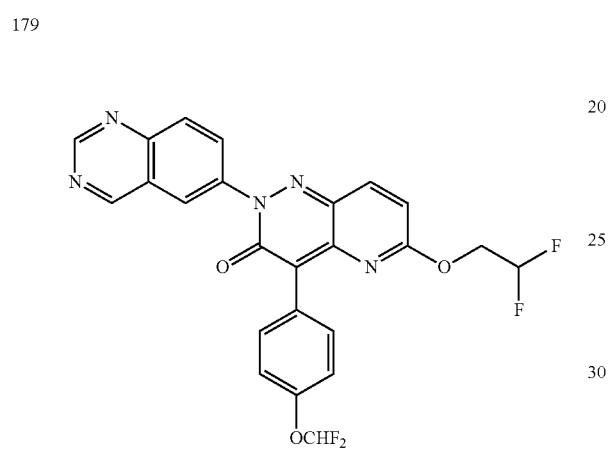 | 183 | 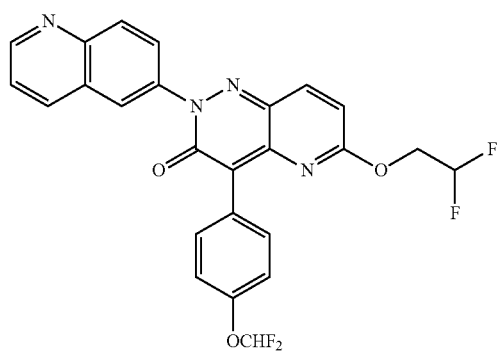 |
| 180 | 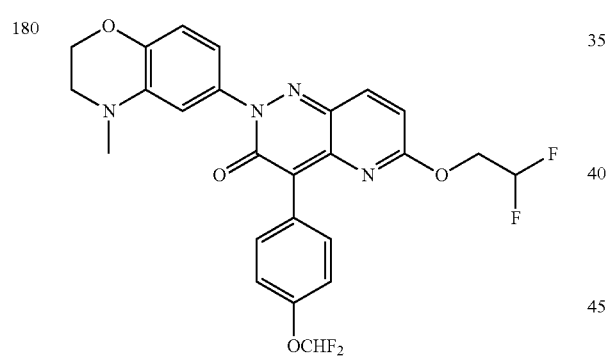 | 184 | 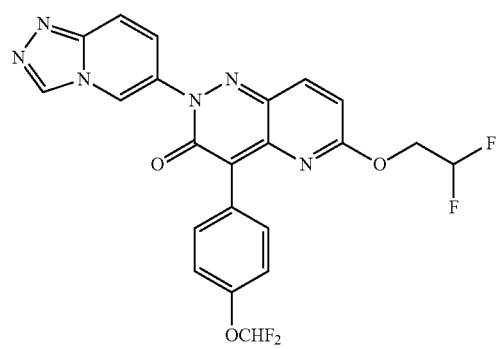 |
| 181 | 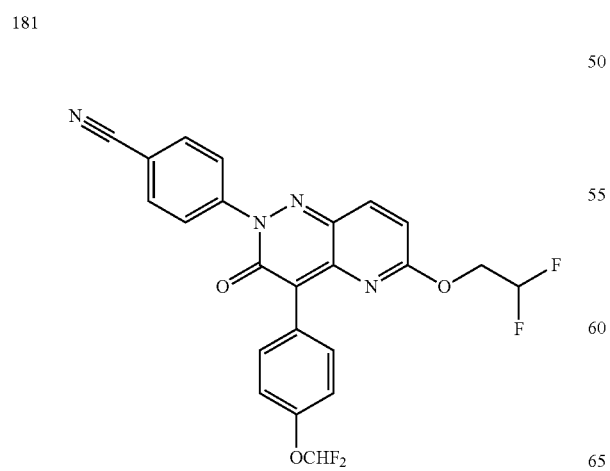 | 185 | 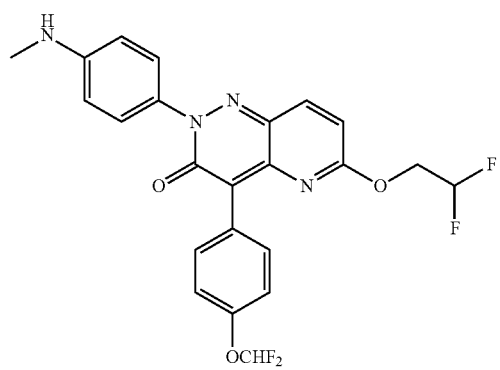 |

| 186 | 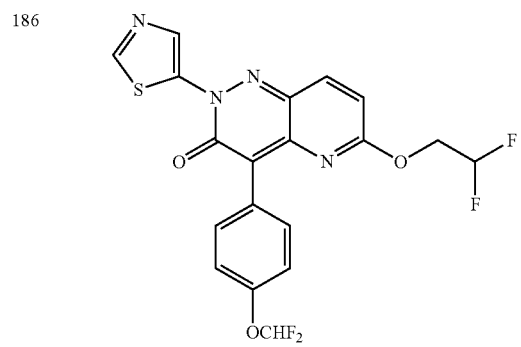 | 190 | 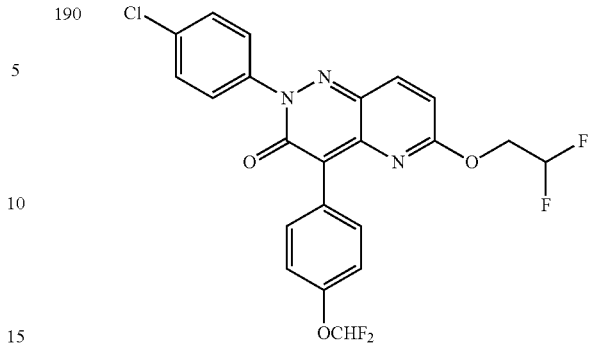 |
| --- | --- | --- | --- |
| 187 | 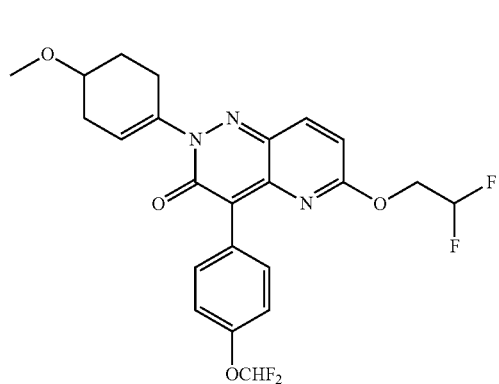 | 191 | 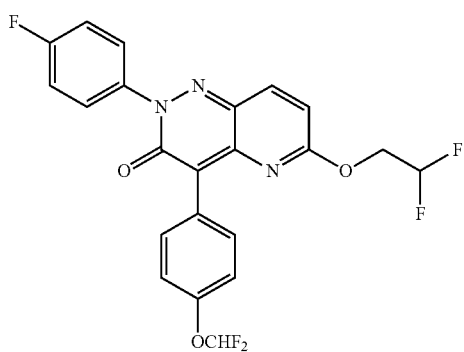 |
| 188 | 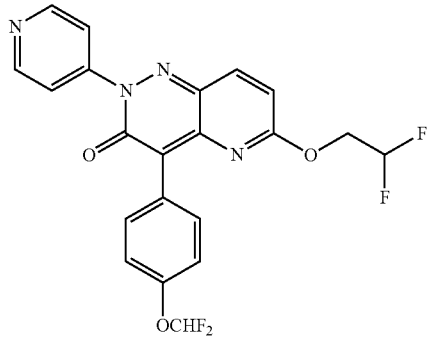 | 192 | 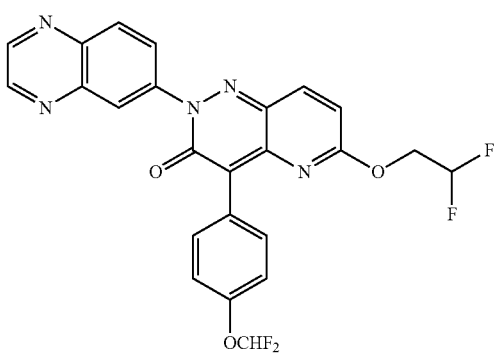 |
| 189 | 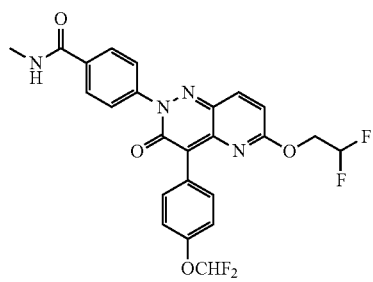 | 193 | 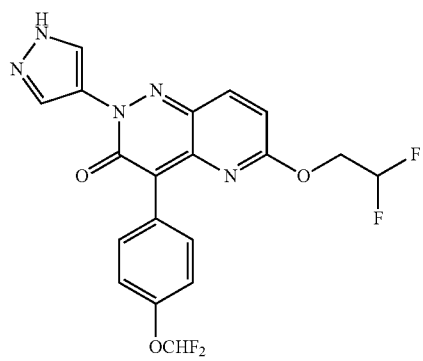 |

-continued
194 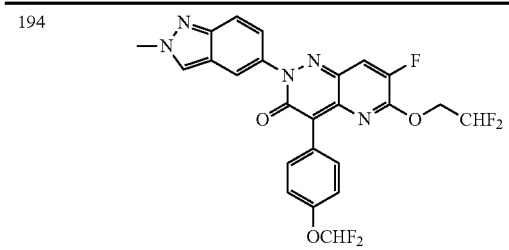
195 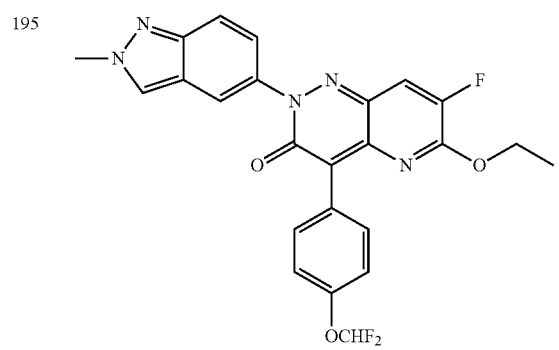
196 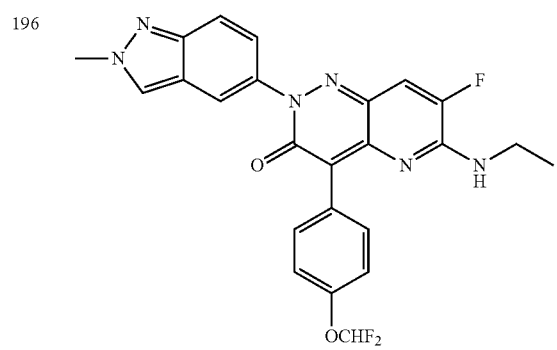
197 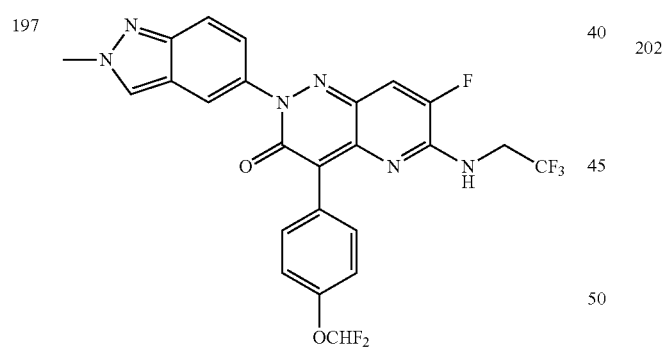
198 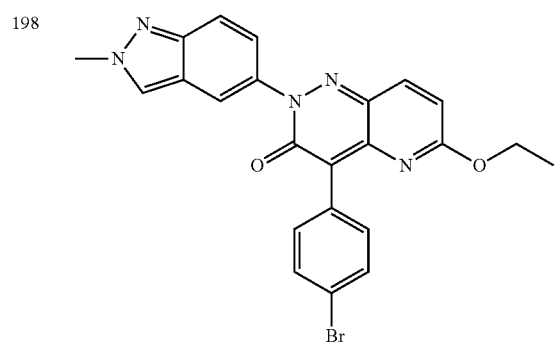
-continued
199 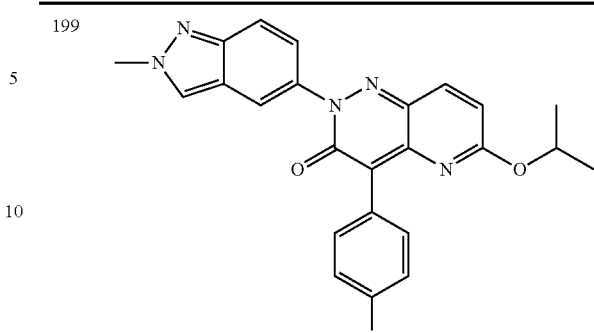
200 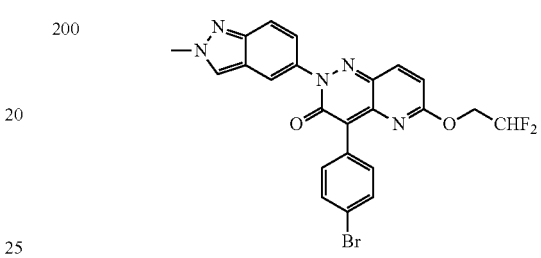
201 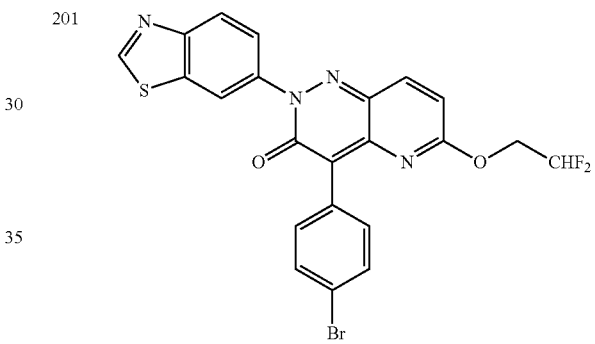
202 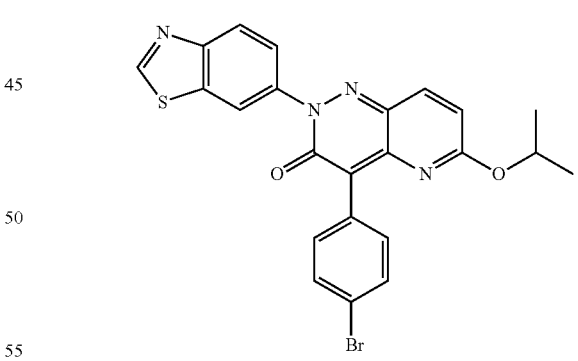
203 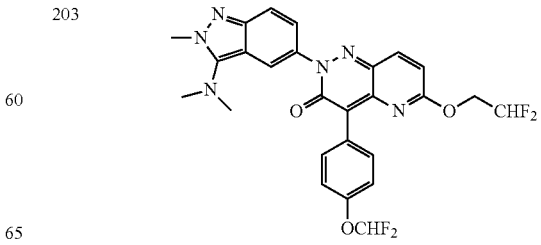

| | | | |
|---|---|---|---|
| 204 | 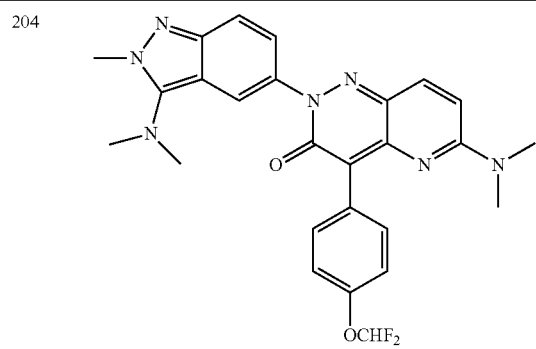 | 209 | 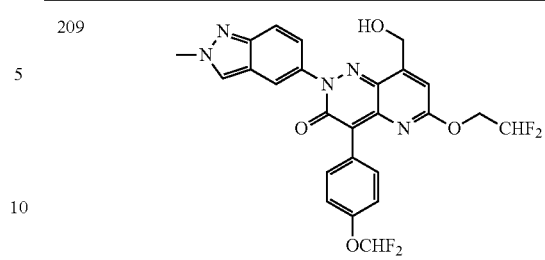 |
| 205 | 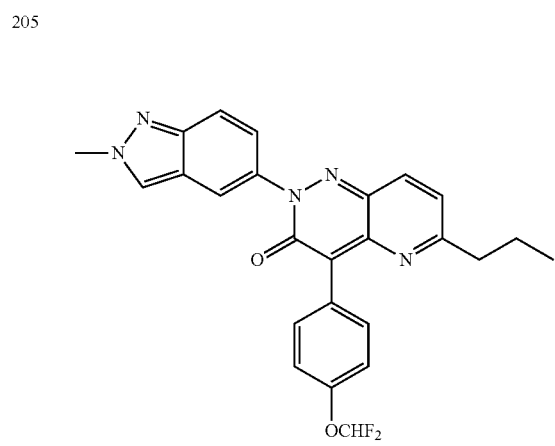 | 210 | 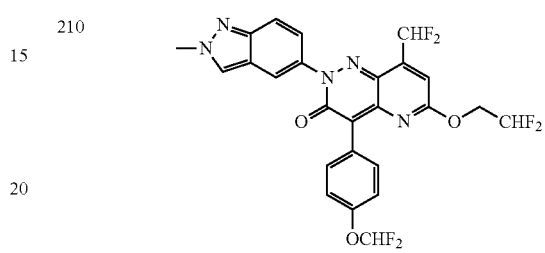 |
| 206 | 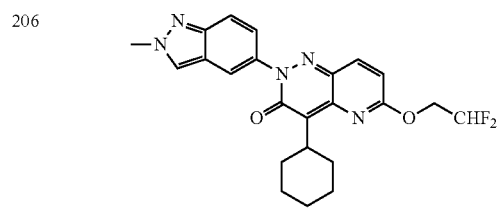 | 211 | 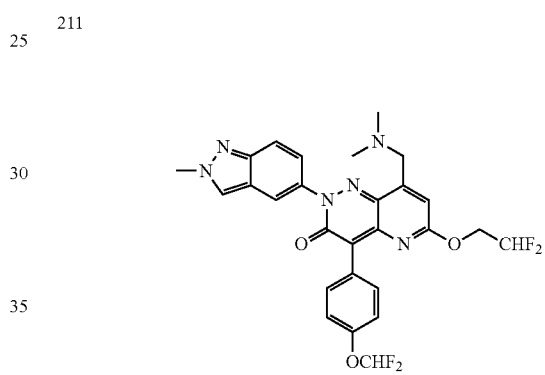 |
| 207 | 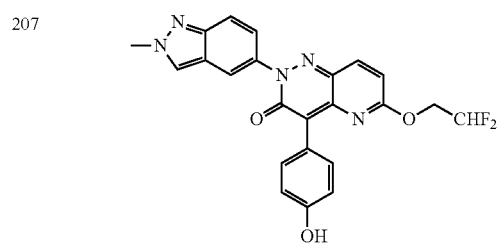 | 212 | 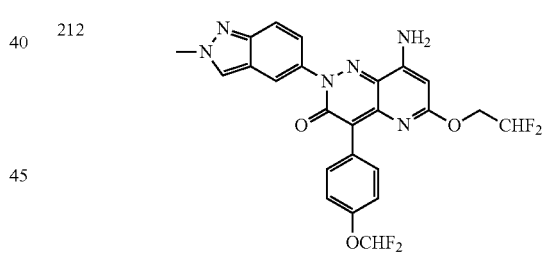 |
| 208 | 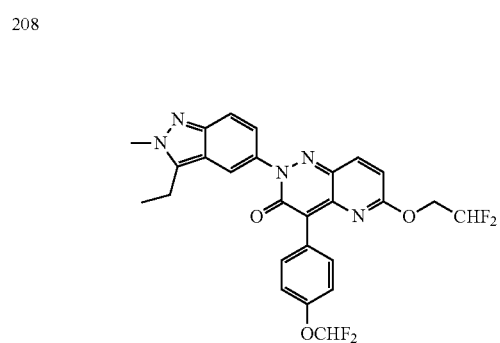 | 213 | 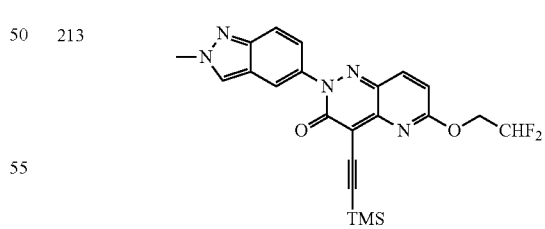 |
| | | 214 | 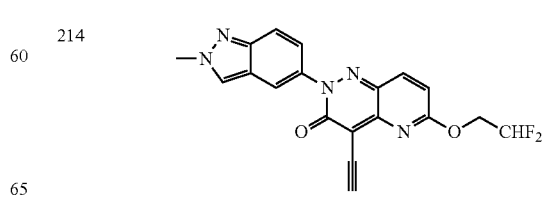 |

215 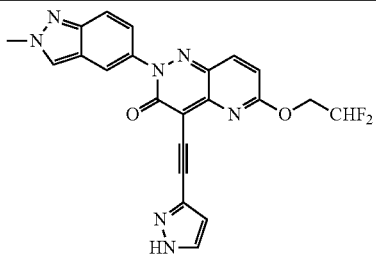

216 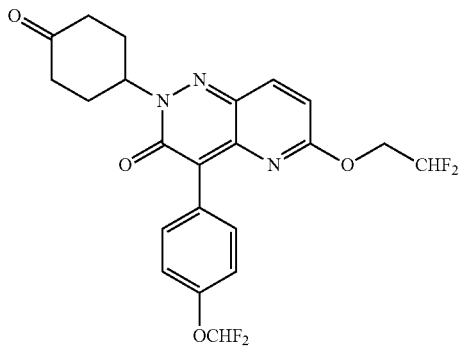 [SMILES: O=C1CCC(n2nc3ccc(OCC(F)F)nc3c(-c3ccc(OC(F)F)cc3)c2=O)CC1]

217 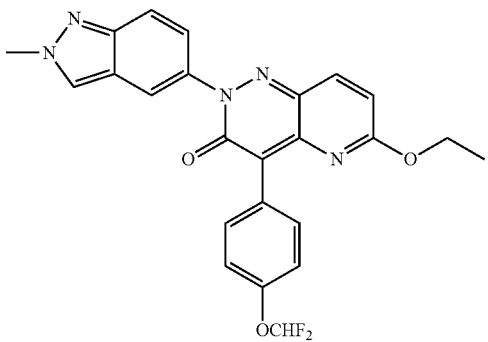

Aspect 25. A pharmaceutical composition comprising a therapeutically effective amount of a compound according to any one of Aspects 1 to 24 or a pharmaceutically acceptable salt thereof, and a pharmaceutically acceptable carrier.

Aspect 26. A method for treating a cancer in a subject suffering therefrom, comprising administering to the subject an effective amount of a MAT2A inhibitor compound according to any one of Aspects 1-24.

Aspect 27. The method according to Aspect 26, wherein the cancer is an MTAP-deleted cancer.

Aspect 28. A method for inhibiting the synthesis of S-adenosyl methionine (SAM) in a cell, comprising introducing into the cell an effective amount of a compound, or a pharmaceutically acceptable salt thereof, according to any one of Aspects 1 to 24.

Aspect 29. The method according to Aspect 28, wherein the cell is in a subject.

Aspect 30. A method for inhibiting the synthesis of S-adenosyl methionine (SAM) in a subject, comprising administering to the subject an effective amount of at least one compound or a salt thereof according to any one of Aspects 1 to 24.

Aspect 31. A method for treating a cancer in a subject suffering therefrom, comprising administering to the subject an effective amount of a compound according to any one of Aspects 1 to 24.

Aspect 32. The method according to Aspect 31, wherein the cancer is an MTAP-deleted cancer.

Aspect 33. The method according to any one of Aspects 26, 27, 31, and 32, wherein the cancer is selected from the group consisting of mesothelioma, neuroblastoma, rectum carcinoma, colon carcinoma, familiarly adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, bladder carcinoma, testis carcinoma, breast carcinoma, urinary carcinoma, melanoma, brain tumors, lymphoma, head and neck cancer, acute lymphatic leukemia (ALL), chronic lymphatic leukemia (CLL), acute myeloid leukemia (AML), chronic myeloid leukemia (CML), hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, osteosarcoma, chondrosarcoma, myosarcoma, liposarcoma, fibrosarcoma, Ewing sarcoma, and plasmocytoma.

Aspect 34. The method according to Aspect 31 or 32, wherein the cancer is selected from the group consisting of B-cell acute lymphocytic leukemia (B-ALL), mesothelioma, lymphoma, pancreatic carcinoma, lung cancer, gastric cancer, esophageal cancer, bladder carcinoma, brain cancer, head and neck cancer, melanoma, and breast cancer.

Aspect 35. The method according to Aspect 34, wherein the cancer is a lung cancer selected from the group consisting of non-small cell lung cancer, small cell lung cancer, adenocarcinoma of the lung, and squamous cell carcinoma of the lung.

Aspect 36. The method according to Aspect 34, wherein cancer is a brain tumor selected from the group consisting of glioma, glioblastoma, astrocytoma, meningioma, medulloblastoma, peripheral neuroectodermal tumors, and craniopharyngioma.

Aspect 37. The method according to Aspect 34, wherein the cancer is triple negative breast cancer (TNBC).

Aspect 38. The method according to Aspect 34, wherein the cancer is a lymphoma selected from the group consisting of mantle cell lymphoma, Hodgkin lymphoma, non-Hodgkin lymphoma, Burkitt lymphoma, diffuse large B-cell lymphoma, and adult T-cell leukemia/lymphoma.

Aspect 39. A method for treating a cancer in a subject suffering therefrom, wherein the cancer is characterized by a reduction or absence of methylthioadenosine phosphorylase (MTAP) gene expression, the absence of the MTAP gene, or reduced function of MTAP protein, as compared to cancers where the MTAP gene or protein is present and/or fully functioning, the method comprising administering to the subject a therapeutically effective amount of a compound, or a pharmaceutically acceptable salt thereof, according to any one of Aspects 1 to 24.

Aspect 40. A compound according to any one of Aspects 1 to 24, or a pharmaceutically acceptable salt thereof, for inhibiting the synthesis of S-adenosyl methionine (SAM).

Aspect 41. A compound according to any one of Aspects 1 to 24, or a pharmaceutically acceptable salt thereof, for treating a cancer in a subject suffering therefrom.

Aspect 42. The compound according to Aspect 41, wherein the cancer is an MTAP-deleted cancer.

Aspect 43. The compound according to Aspect 41 or 42, wherein the cancer is selected from the group consisting of mesothelioma, neuroblastoma, rectum carcinoma, colon carcinoma, familiarly adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, bladder carcinoma, testis carcinoma, breast carcinoma, urinary carcinoma, melanoma, brain tumors, lymphoma, head and neck cancer, acute lymphatic leukemia (ALL), chronic lymphatic leukemia (CLL), acute myeloid leukemia (AML), chronic myeloid leukemia (CML), hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, osteosarcoma, chondrosarcoma, myosarcoma, liposarcoma, fibrosarcoma, Ewing sarcoma, and plasmocytoma.

Aspect 44. The compound according to Aspect 41 or 42, wherein the cancer is selected from the group consisting of B-cell acute lymphocytic leukemia (B-ALL), mesothelioma, lymphoma, pancreatic carcinoma, lung cancer, gastric cancer, esophageal cancer, bladder carcinoma, brain cancer, head and neck cancer, melanoma, and breast cancer.

Aspect 45. The compound according to Aspect 44, wherein the cancer is a lung cancer selected from the group consisting of non-small cell lung cancer, small cell lung cancer, adenocarcinoma of the lung, and squamous cell carcinoma of the lung.

Aspect 46. The compound according to Aspect 44, wherein the cancer is triple negative breast cancer (TNBC).

Aspect 47. The compound according to Aspect 44, wherein the cancer is a brain tumor selected from the group consisting of glioma, glioblastoma, astrocytoma, meningioma, medulloblastoma, peripheral neuroectodermal tumors, and craniopharyngioma.

Aspect 48. The compound according to any one of Aspects 41 to 43, wherein the cancer is a lymphoma selected from the group consisting of mantle cell lymphoma, Hodgkin lymphoma, non-Hodgkin lymphoma, Burkitt lymphoma, diffuse large B-cell lymphoma (DLBCL), and adult T-cell leukemia/lymphoma.

EXAMPLES

The present disclosure will be more fully understood by reference to the following examples. The examples should not, however, be construed as limiting the scope of the present disclosure.

Units and Terms List:
  anhy. anhydrous
  aq. aqueous
  min minute(s)
  mL milliliter
  mmol millimole(s)
  mol mole(s)
  MS mass spectrometry
  NMR nuclear magnetic resonance
  TLC thin layer chromatography
  HPLC high-performance liquid chromatography
  RT(r.t.) room temperature NMR Spectra
  Hz hertz
  δ chemical shift
  J coupling constant
  s singlet
  d doublet
  t triplet
  q quartet
  m multiplet
  br broad
  qd quartet of doublets
  dquin doublet of quintets
  dd doublet of doublets
  dt doublet of triplets Solvents and Reagents:
  $CHCl_3$ chloroform
  DCM dichloromethane
  DMF dimethylformamide
  $Et_2O$ diethyl ether
  EtOH ethyl alcohol
  EtOAc ethyl acetate
  EA ethyl acetate
  MeOH methyl alcohol
  MeCN acetonitrile
  PE petroleum ether
  THF tetrahydrofuran
  AcOH acetic acid
  HCl hydrochloric acid
  $H_2SO_4$ sulfuric acid
  $NH_4Cl$ ammonium chloride
  KOH potassium hydroxide
  NaOH sodium hydroxide
  $K_2CO_3$ potassium carbonate
  $Na_2CO_3$ sodium carbonate
  TFA trifluoroacetic acid
  $Na_2SO_4$ sodium sulfate
  $NaBH_4$ sodium borohydride
  $NaHCO_3$ sodium bicarbonate
  LiHMDS lithium hexamethyldisilylamide
  NaHMDS sodium hexamethyldisilylamide
  LAH lithium aluminum hydride
  $NaBH_4$ sodium borohydride
  LDA lithium diisopropylamide
  $Et_3N$ triethylamine
  DMAP 4-(dimethylamino)pyridine
  DIPEA N,N-diisopropylethylamine
  $NH_4OH$ ammonium hydroxide
  EDCI 1-ethyl-3-(3-dimethylaminopropyl)carbodiimide
  HOBt 1-hydroxybenzotriazole
  HATU O-(7-azabenzotriazol-1-yl)-N,N,N',N'-tetramethyluronium
  Xphos 2-Dicyclohexylphosphino-2',4',6'-triisopropylbiphenyl
  BINAP 2,2'-bis(diphenylphosphanyl)-1,1'-binaphthyl General Experimental In the following examples, the reagents and solvents were purchased from commercial sources (such as Alfa, Acros, Sigma Aldrich, TCI and Shanghai Chemical Reagent Company), and used without further purification unless otherwise specified. Flash chromatography was performed on an Ez Purifier III using column with silica gel particles of 200-300 mesh. Analytical and preparative thin layer chromatography (TLC) plates were HSGF 254 (0.15-0.2 mm thickness, Shanghai Anbang Company, China). Nuclear magnetic resonance (NMR) spectra were obtained on a Brucker AMX-400 NMR (Brucker, Switzerland). Chemical shifts were reported in parts per million (ppm, δ) downfield from tetramethylsilane. Mass spectra were given with electrospray ionization (ESI) from a Waters LCT TOF Mass Spectrometer (Waters, USA). HPLC chromatographs were record on an Agilent 1200 Liquid Chromatography (Agilent, USA, column: Ultimate 4.6 mm×50 mm, 5 μm, mobile phase A: 0.1% formic acid in water; mobile phase B: acetonitrile). Microwave reactions were run on an Initiator 2.5 Microwave Synthesizer (Biotage, Sweden).

General Procedure I:

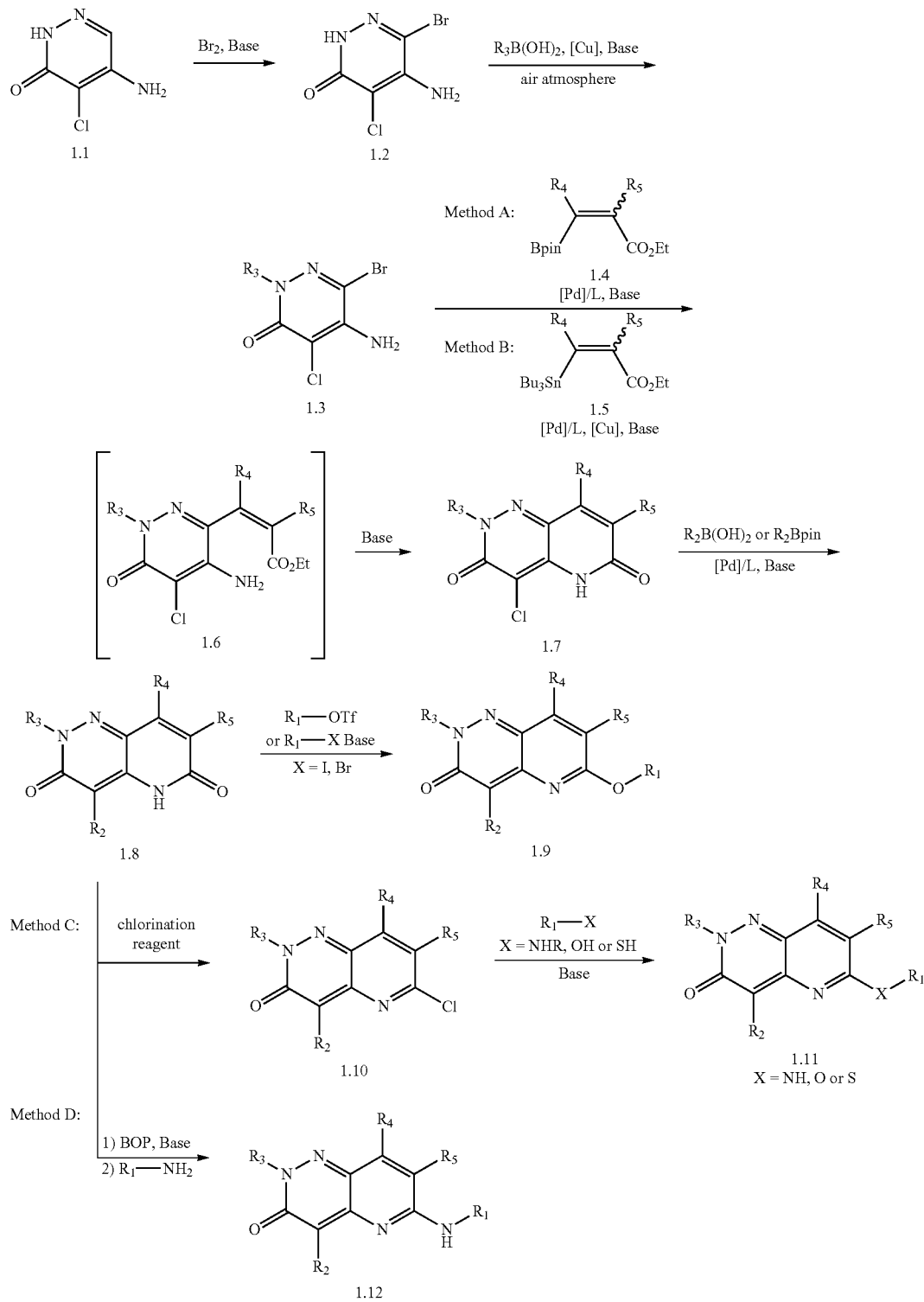

Compounds of structure 1.9, 1.11 and 1.12 were obtained through the scheme depicted as General Procedure I. Beginning with pyridazinone 1.1, electrophilic bromination was used to generate heterocyclic bromide 1.2. The desired $R_3$ group was installed using a Chan-Lam coupling to generate compound 1.3. At this stage, the desired $R_4$ and $R_5$ groups were installed by using either a Suzuki cross-coupling with reagent 1.4 (Method A), or a Stille cross-coupling with reagent 1.5 (Method B). The resulting intermediate 1.6 was then cyclized to the desired bicyclic core 1.7 under basic conditions. The desired $R_2$ group was installed using a Suzuki cross-coupling to generate compound 1.8. Compound 1.8 was then alkylated to install the desired $R_1$ group and provide final compounds of structure 1.9. Alternatively, compound 1.8 was chlorinated to give aryl-chloride 1.10, and the desired $R_1$ was installed via nucleophilic aromatic substitution to yield final compounds of structure 1.11 (Method C). Alternatively, compound 1.8 was activated using BOP, and the desired N-linked $R_1$ was installed via nucleophilic aromatic substitution to yield final compounds of structure 1.12 (Method D).

Preparation of Example 101 Via General Procedure I (Method A)

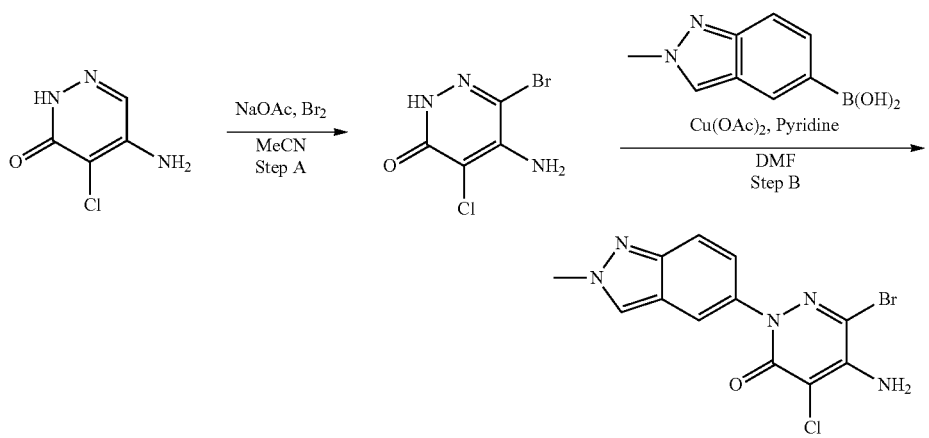

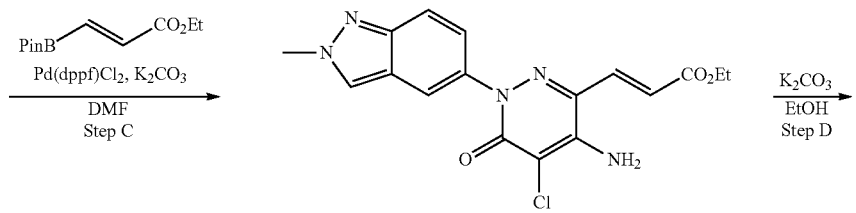

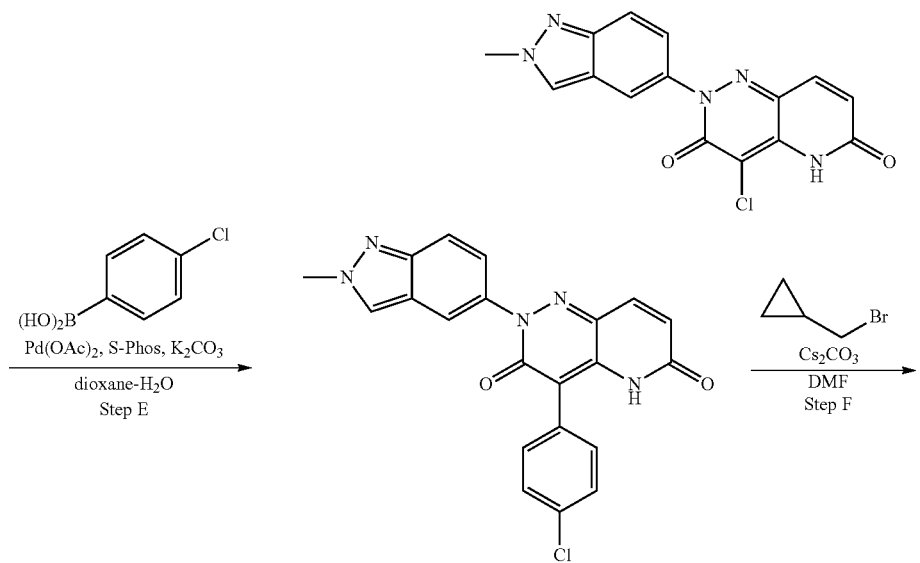

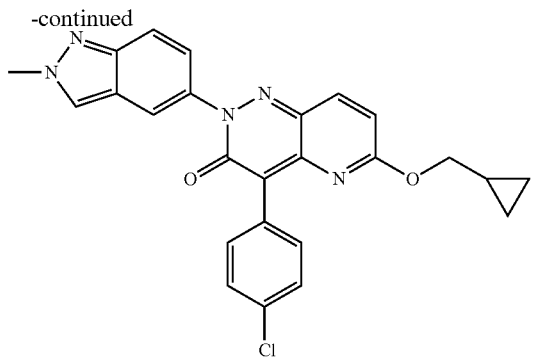

Step A:
5-amino-6-bromo-4-chloropyridazin-3(2H)-one

To a suspension of 5-amino-4-chloropyridazin-3(2H)-one (1.2 g, 8.2 mmol, 1.0 eq.) and NaOAc (0.74 g, 9.1 mmol, 1.1 eq.) in MeCN (40 mL) was added $Br_2$ (1.45 g, 9.1 mmol, 1.1 eq.) at 80° C. over 5 min via a syringe. The resulting mixture was stirred at 80° C. for additional 1 hr. After cooling to room temperature, the volatiles were removed under reduced pressure, diluted with ice-cooled $H_2O$ (20 mL), the resulting white precipitate was filtered, and the filter cake was collected and dried under reduced pressure to give 5-amino-6-bromo-4-chloropyridazin-3(2H)-one (1.48 g, 80% yield) as a white solid. LC-MS (ESI): m/z 224, 226 $[M+H]^+$.

Step B: 5-amino-6-bromo-4-chloro-2-(2-methyl-2H-indazol-5-yl)pyridazin-3(2H)-one To a suspension of 5-amino-6-bromo-4-chloropyridazin-3(2H)-one (590 mg, 2.63 mmol, 1.0 eq.) in DMF (15 mL) was added (2-methyl-2H-indazol-5-yl)boronic acid (555 mg, 3.15 mmol, 1.2 eq.), $Cu(OAc)_2$ (478 mg, 2.63 mmol, 1.0 eq.) and pyridine (422 µL, 5.26 mmol, 2.0 eq.). The resulting mixture was stirred at 50° C. (air atmosphere) for 8 h, and the reaction was monitored by TLC. After completion, the reaction mixture was diluted with $H_2O$ (30 mL), the resulting suspension was stirred additional 30 min, the precipitate was collected and washed over ice-cooled $H_2O$ (30 mL×3) and dried under reduced pressure to afford 5-amino-6-bromo-4-chloro-2-(2-methyl-2H-indazol-5-yl)pyridazin-3(2H)-one (770 mg, 82% yield) as a gray-white solid. LC-MS (ESI): m/z 354, 356 $[M+H]^+$.

Step C: ethyl (E)-3-(4-amino-5-chloro-1-(2-methyl-2H-indazol-5-yl)-6-oxo-1,6-dihydropyridazin-3-yl)acrylate To a solution of 5-amino-6-bromo-4-chloro-2-(2-methyl-2H-indazol-5-yl)pyridazin-3(2H)-one (500 mg, 1.41 mmol, 1.0 eq.) in DMF (10 mL) was added ethyl (E)-3-(4,4,5,5-tetramethyl-1,3,2-dioxaborolan-2-yl)acrylate (350 mg, 1.55 mmol, 1.1 eq.), $Pd(dppf)Cl_2$ (103 mg, 0.14 mmol, 0.1 eq.) and $K_2CO_3$ (389 mg, 2.82 mmol, 2.0 eq.). The reaction mixture was stirred at 80° C. for 16 hrs under $N_2$ atmosphere. The reaction mixture was poured into ice water (30 mL) and extracted with EtOAc (50 mL×3). The combined organic layers were dried over $Na_2SO_4$, concentrated under reduced pressure, the crude residue was purified by flash column chromatography on silica gel to give ethyl (E)-3-(4-amino-5-chloro-1-(2-methyl-2H-indazol-5-yl)-6-oxo-1, 6-dihydropyridazin-3-yl)acrylate (316 mg, 60% yield) as a yellow solid. LC-MS (ESI): m/z 374 $[M+H]^+$.

Step D: 4-chloro-2-(2-methyl-2H-indazol-5-yl)pyrido[3,2-c]pyridazine-3,6(2H,5H)-dione To a solution of ethyl (E)-3-(4-amino-5-chloro-1-(2-methyl-2H-indazol-5-yl)-6-oxo-1,6-dihydropyridazin-3-yl)acrylate (400 mg, 1.07 mmol, 1.0 eq.) in EtOH (10 mL) was added $K_2CO_3$ (295 mg, 2.14 mmol, 2.0 eq.) at room temperature. The reaction mixture was stirred at 80° C. for 3 hrs. Then ice water (30 mL) was added and the mixture was extracted with EtOAc (30 mL×3). The combined organic layers were dried over $Na_2SO_4$, concentrated under reduced pressure, the crude residue was purified by flash column chromatography on silica gel to give 4-chloro-2-(2-methyl-2H-indazol-5-yl)pyrido[3,2-c]pyridazine-3,6(2H,5H)-dione (319 mg, 85% yield) as a yellow solid. LC-MS (ESI): m/z 328 $[M+H]^+$.

Step E: 4-(4-chlorophenyl)-2-(2-methyl-2H-indazol-5-yl)pyrido[3,2-c]pyridazine-3,6(2H,5H)-dione A solution of 4-chloro-2-(2-methyl-2H-indazol-5-yl)pyrido[3,2-c]pyridazine-3,6(2H,5H)-dione (1 g, 3.05 mmol, 1.0 eq.), (4-chlorophenyl)boronic acid (954 mg, 6.1 mmol, 2.0 eq.), $Pd(OAc)_2$ (68 mg, 0.3 mmol, 0.1 eq.), S-Phos (251 mg, 0.61 mmol, 0.2 eq.) and $K_2CO_3$ (1.26 g, 9.15 mmol, 3.0 eq.) in dioxane/$H_2O$ (110 mL, 10/1, v/v) was stirred at 110° C. under $N_2$ atmosphere for 2 hrs. Ice water (30 mL) was added and the mixture was extracted with EtOAc (30 mL×3), the combined organic layers were dried over $Na_2SO_4$, concentrated under reduced pressure, the crude residue was purified by flash column chromatography on silica gel to give 4-(4-chlorophenyl)-2-(2-methyl-2H-indazol-5-yl)pyrido[3,2-c]pyridazine-3,6(2H,5H)-dione (700 mg, 57% yield) as a yellow solid. LC-MS: m/z 404 $[M+H]^+$.

Step F: 4-(4-chlorophenyl)-6-(cyclopropylmethoxy)-2-(2-methyl-2H-indazol-5-yl)pyrido[3,2-c]pyridazin-3(2H)-one A solution of 4-(4-chlorophenyl)-2-(2-methyl-2H-indazol-5-yl)pyrido[3,2-c]pyridazine-3,6(2H,5H)-dione (200 mg, 0.495 mmol, 1.0 eq.), (bromomethyl)cyclopropane (0.2 mL, 2.0 mmol, 4.0 eq.), $Cs_2CO_3$ (484 mg, 1.5 mmol, 3.0 eq.) in DMF (3 mL) was stirred at room temperature for 16 hrs. The reaction mixture was concentrated under reduced pressure and the resulting residue was purified by prep-HPLC to give 4-(4-chlorophenyl)-6-(cyclopropylmethoxy)-2-(2-methyl-2H-indazol-5-yl)pyrido[3,2-c]pyridazin-3(2H)-one (Example 101).

$^1$H NMR (400 MHz, DMSO-d$_6$) δ: 8.55 (s, 1H), 8.07 (d, J=2.0 Hz, 1H), 8.04 (d, J=9.6 Hz, 1H), 7.86 (d, J=8.8 Hz, 2H), 7.76 (d, J=9.2 Hz, 1H), 7.56 (d, J=8.4 Hz, 2H), 7.51 (dd, J=9.2 Hz, 1.6 Hz, 1H), 7.04 (d, J=9.2 Hz, 1H), 4.28 (s, 3H), 4.21 (d, J=7.2 Hz, 2H), 1.36-1.19 (m, 1H), 0.64-0.57 (m, 2H), 0.37-0.33 (m, 2H).

LC-MS (ESI): m/z 458 [M+H]$^+$

Preparation of Example 102 via General Procedure I (Method B)

Method B:

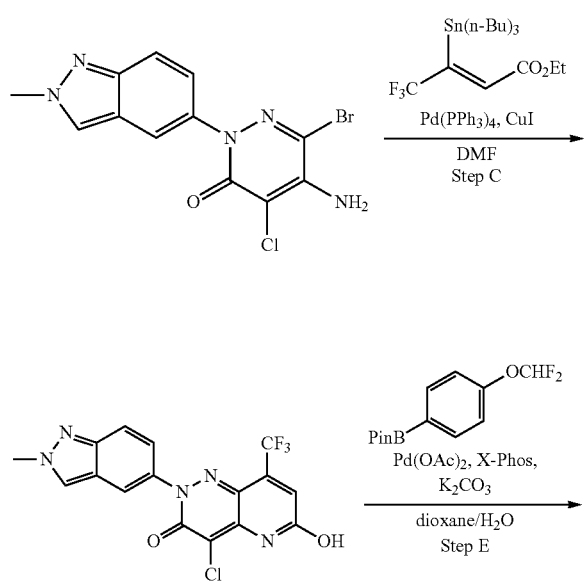

Step C: 4-chloro-6-hydroxy-2-(2-methyl-2H-indazol-5-yl)-8-(trifluoromethyl)pyrido[3,2-c]pyridazin-3(2H)-one A solution of 5-amino-6-bromo-4-chloro-2-(2-methyl-2H-indazol-5-yl)pyridazin-3(2H)-one (1 g, 2.8 mmol, 1.0 eq.), ethyl (Z)-4,4,4-trifluoro-3-(tributylstannyl)but-2-enoate (Ref: Synlett, 2012, 23, 755-759) (2.6 g, 5.6 mmol, 2.0 eq.), Pd(PPh$_3$)$_4$ (655 mg, 0.567 mmol, 0.2 eq.) and CuI (216 mg, 1.13 mmol, 0.4 eq.) in DMF (10 mL) under N$_2$ atmosphere was stirred at 100° C. for 16 hrs. The reaction mixture was quenched with CsF (sat. aq.) (30 mL) and stirred for additional 30 min, the resulting suspension was filtered, the precipitate was collected and triturated with EtOAc (20 mL) to afford 4-chloro-6-hydroxy-2-(2-methyl-2H-indazol-5-yl)-8-(trifluoromethyl)pyrido[3,2-c]pyridazin-3(2H)-one (800 mg, 71% yield) as a yellow solid. LC-MS (ESI): m/z 396 [M+H]$^+$.

6-(2,2-difluoroethoxy)-4-(4-(difluoromethoxy)phenyl)-2-(2-methyl-2H-indazol-5-yl)-8-(trifluoromethyl)pyrido[3,2-c]pyridazin-3(2H)-one (Example 102) was synthesized from 2-(4-(difluoromethoxy)phenyl)-4,4,5,5-tetramethyl-1,3,2-dioxaborolane and 2,2-difluoroethyl trifluoromethanesulfonate via general procedure I (Step E, F).

$^1$H NMR (400 MHz, DMSO-d$_6$) δ: 8.56 (s, 1H), 8.07 (s, 1H), 7.87 (d, J=8.8 Hz, 2H), 7.76 (d, J=9.2 Hz, 1H), 7.61 (s, 1H), 7.50 (dd, J=9.2 Hz, 1.6 Hz, 1H), 7.38 (t, J$_{HF}$=73.6 Hz, 1H), 7.29 (d, J=8.4 Hz, 2H), 6.43 (tt, J$_{HF}$=54.0 Hz, J=2.8 Hz, 1H), 4.63 (td, J$_{HF}$=14.8 Hz, J=2.8 Hz, 2H), 4.25 (s, 3H).

LC-MS (ESI): m/z 568 [M+H]$^+$.

Preparation of Example 103 Via General Procedure I (Method C)

Method C:

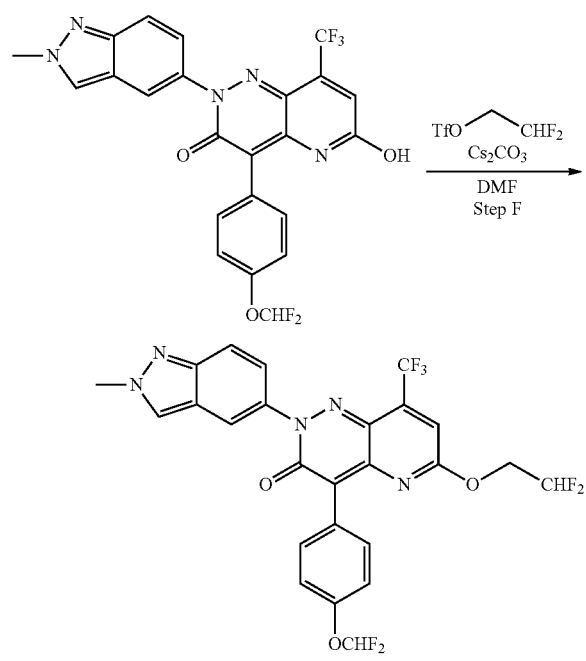

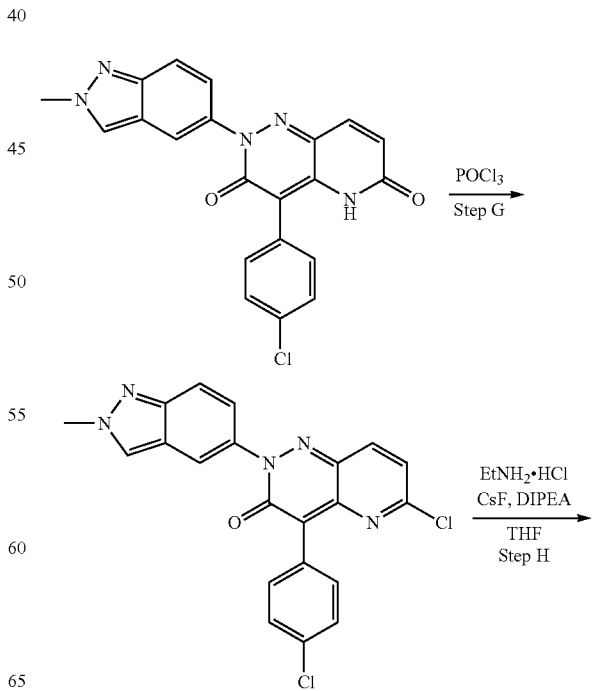

93
-continued

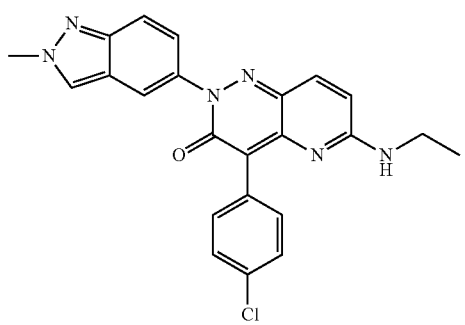

Step G: 6-chloro-4-(4-chlorophenyl)-2-(2-methyl-2H-indazol-5-yl)pyrido[3,2-c]pyridazin-3(2H)-one A solution of 4-(4-chlorophenyl)-2-(2-methyl-2H-indazol-5-yl)pyrido[3,2-c]pyridazine-3,6(2H,5H)-dione (100 mg, 0.284 mmol 1.0 eq.) in POCl$_3$ (5 mL) was stirred at 80° C. for 2 hrs. Excess POCl$_3$ was removed under reduced pressure and the residue was poured into ice cooled NaHCO$_3$ (sat. aq.) (10 mL) carefully, the resulting mixture was extracted with DCM (10 mL×3), the combined organic layers were washed with brine (10 mL) and dried over Na$_2$SO$_4$, concentrated under reduced pressure, the crude residue was purified by flash column chromatography on silica gel to give 6-chloro-4-(4-chlorophenyl)-2-(2-methyl-2H-indazol-5-yl)pyrido[3,2-c]pyridazin-3(2H)-one (60 mg, 57% yield) as a red solid. LC-MS (ESI): m/z 422 [M+H]$^+$.

Step H: 4-(4-chlorophenyl)-6-(ethylamino)-2-(2-methyl-2H-indazol-5-yl)pyrido[3,2-c]pyridazin-3(2H)-one A solution of 6-chloro-4-(4-chlorophenyl)-2-(2-methyl-2H-indazol-5-yl)pyrido[3,2-c]pyridazin-3(2H)-one (60 mg, 0.142 mmol, 1.0 eq.), ethylamine hydrochloride (58 mg, 0.71 mmol, 5.0 eq.), CsF (108 mg, 0.71 mmol 5.0 eq.), and DIPEA (92 mg, 0.71 mmol, 5.0 eq.) in THF (3 mL) was stirred at room temperature for 16 hrs. The reaction mixture was concentrated under reduced pressure, the crude residue was purified by prep-HPLC to give 4-(4-chlorophenyl)-6-(ethylamino)-2-(2-methyl-2H-indazol-5-yl)pyrido[3,2-c]pyridazin-3(2H)-one (Example 103).

$^1$H NMR (400 MHz, DMSO-d$_6$) δ: 8.46 (s, 1H), 8.34 (t, J=5.2 Hz, 1H), 7.94 (d, J=1.2 Hz, 1H), 7.82 (d, J=8.4 Hz, 2H), 7.67 (d, J=9.2 Hz, 1H), 7.61 (d, J=9.2 Hz, 1H), 7.45-7.40 (m, 3H), 6.79 (d, J=9.2 Hz, 1H), 4.22 (s, 3H), 3.37-3.30 (m, 2H), 1.15 (t, J=7.2 Hz, 3H).

LC-MS (ESI): m/z 431 [M+H]$^+$.

94

Preparation of Example 301 Via General Procedure I (Method D)

Method D:

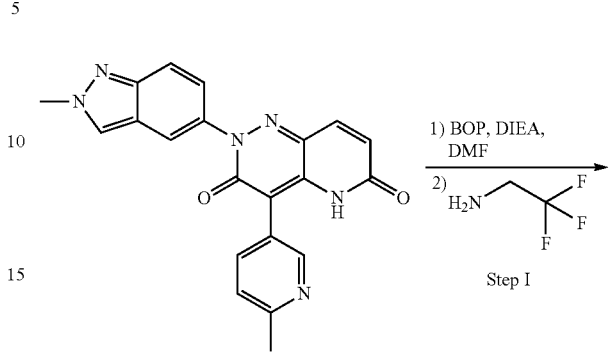

Step I

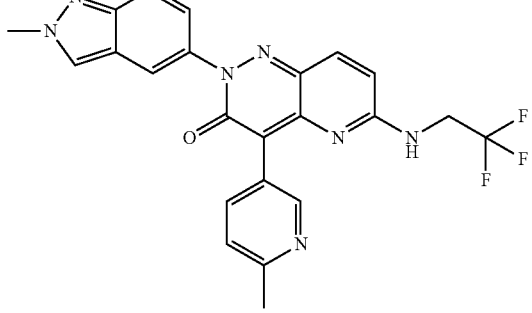

Step I: 2-(2-methyl-2H-indazol-5-yl)-4-(6-methylpyridin-3-yl)-6-((2,2,2-trifluoroethyl)amino)pyrido[3,2-c]pyridazin-3(2H)-one (Example 301)

To a solution of 6-hydroxy-2-(2-methyl-2H-indazol-5-yl)-4-(6-methylpyridin-3-yl)pyrido[3,2-c]pyridazin-3(2H)-one (100 mg, 0.26 mmol, 1.0 eq.), BOP (173 mg, 0.39 mmol, 1.5 eq.), in DMF (5 mL) was added DIEA (0.13 mL, 0.78 mmol, 3.0 eq.). The resulting mixture was stirred at room temperature for 30 min, then 2,2,2-trifluoroethan-1-amine (0.06 mL, 0.78 mmol, 3.0 eq.) was added and stirred for additional 2 hrs. at room temperature. After the completion, the reaction was quenched by adding ice water (10 mL) and extracted with EtOAc (10 ml×3), dried over Na$_2$SO$_4$ and concentrated under reduced pressure, the residue was purified by flash column chromatography on silica gel to give 2-(2-methyl-2H-indazol-5-yl)-4-(6-methylpyridin-3-yl)-6-((2,2,2-trifluoroethyl)amino)pyrido[3,2-c]pyridazin-3(2H)-one (Example 301).

$^1$H NMR (400 MHz, DMSO-d$_6$) δ: 8.86 (s, 1H), 8.80 (s, 1H), 8.47 (s, 1H), 8.02 (d, J=7.5 Hz, 1H), 7.96 (s, 1H), 7.77 (d, J=9.5 Hz, 1H), 7.68 (d, J=8.8 Hz, 1H), 7.42 (d, J=9.7 Hz, 1H), 7.28 (d, J=8.1 Hz, 1H), 6.92 (d, J=9.6 Hz, 1H), 4.30-4.22 (m, 2H), 4.21 (s, 3H), 2.51 (s, 3H).

LC-MS (ESI): m/z 466 [M+H]$^+$.

The procedure set forth above for General Procedure I (Method A) was used to synthesize the following compounds by using appropriate starting materials:

| Cpd No. | Structure | Characterization |
|---|---|---|
| Example 104 | 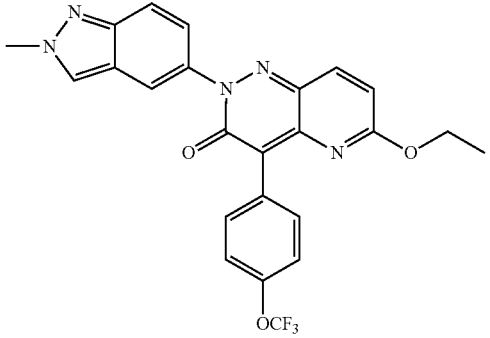<br>6-ethoxy-2-(2-methyl-2H-indazol-5-yl)-4-(4-(trifluoromethoxy)phenyl)pyrido[3,2-c]pyridazin-3(2H)-one | LC-MS (ESI): m/z 482.1 [M + H]+.<br>1H NMR (400 MHz, DMSO-$d_6$) δ: 8.50 (s, 1H), 8.02 (d, J = 1.6 Hz, 1H), 7.99 (d, J = 9.6 Hz, 1H), 7.92 (d, J = 8.8 Hz, 2H), 7.71 (d, J = 9.2 Hz, 1H), 7.47 (d, J = 2.0 Hz, 1H), 7.44 (d, J = 8.0 Hz, 2H), 6.96 (d, J = 9.6 Hz, 1H), 4.34 (q, J = 6.8 Hz, 2H), 4.23 (s, 3H), 1.31 (t, J = 7.2 Hz, 3H). |
| Example 105 | 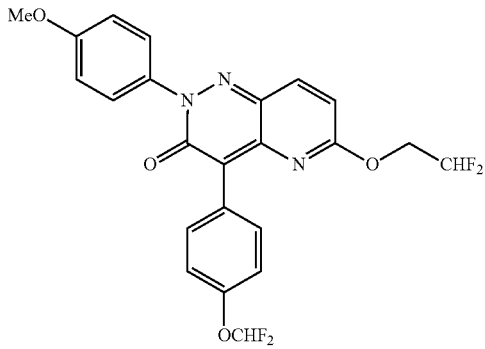<br>6-(2,2-difluoroethoxy)-4-(4-(difluoromethoxy)phenyl)-2-(4-methoxyphenyl)pyrido[3,2-c]pyridazin-3(2H)-one | LC-MS (ESI): m/z 476.1 [M + H]+.<br>1H NMR (400 MHz, DMSO-$d_6$) δ: 7.99 (d, J = 9.6 Hz, 1H), 7.82 (d, J = 8.8 Hz, 2H), 7.57 (d, J = 8.8 Hz, 2H), 7.30 (t, $J_{HF}$ = 73.6 Hz, 1H), 7.23 (d, J = 8.4 Hz, 2H), 7.07 (d, J = 8.8 Hz, 2H), 7.01 (d, J = 9.2 Hz, 1H), 6.36 (t, $J_{HF}$ = 54.4 Hz, 1H), 4.55 (td, $J_{HF}$ = 15.2 Hz, J = 2.8 Hz, 2H), 3.82 (s, 3H). |
| Example 106 | 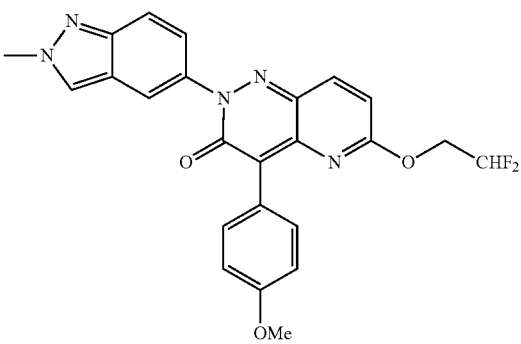<br>6-(2,2-difluoroethoxy)-4-(4-methoxyphenyl)-2-(2-methyl-2H-indazol-5-yl)pyrido[3,2-c]pyridazin-3(2H)-one | LC-MS (ESI): m/z 464.2 [M + H]+.<br>1H NMR (400 MHz, DMSO-$d_6$) δ: 8.50 (s, 1H), 8.03 (d, J = 9.2 Hz, 1H), 8.01 (s, 1H), 7.80 (d, J = 8.8 Hz, 2H), 7.71 (d, J = 9.2 Hz, 1H), 7.50-7.41 (m, 1H), 7.05 (d, J = 9.6 Hz, 1H), 7.01 (d, J = 8.8 Hz, 2H), 6.41 (t, $J_{HF}$ = 54.4 Hz, 1H), 4.60 (td, $J_{HF}$ = 14.8 Hz, J = 2.8 Hz, 2H), 4.23 (s, 3H), 3.83 (s, 3H). |

| Cpd No. | Structure | Characterization |
|---|---|---|
| Example 107 | 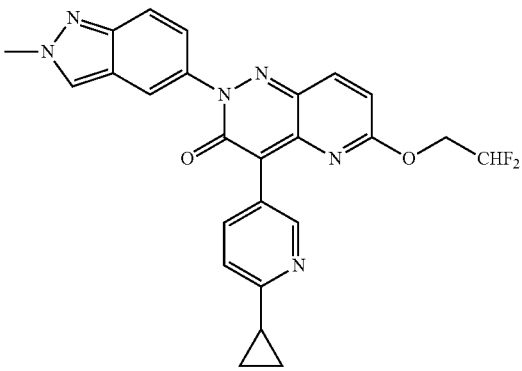<br>4-(6-cyclopropylpyridin-3-yl)-6-(2,2-difluoroethoxy)-2-(2-methyl-2H-indazol-5-yl)pyrido[3,2-c]pyridazin-3(2H)-one | LC-MS (ESI): m/z 475.2 [M + H]+.<br>1H NMR (400 MHz, DMSO-$d_6$) δ:<br>8.81 (d, J = 2.0 Hz, 1H), 8.52 (s, 1H), 8.09 (s, 1H), 8.07 (d, J = 1.2 Hz, 1H), 8.04 (s, 1H), 7.73 (d, J = 9.2 Hz, 1H), 7.48 (dd, J = 8.8 Hz, 1.6 Hz, 1H), 7.41 (d, J = 8.0 Hz, 1H), 7.09 (d, J = 9.2 Hz, 1H), 6.42 (tt, $J_{HF}$ = 54.5 Hz, J = 3.2 Hz, 1H), 4.62 (td, $J_{HF}$ = 15.2, J = 3.2 Hz, 2H), 4.24 (s, 3H), 2.23-2.13 (m, 1H), 1.04-0.98 (m, 4H). |
| Example 108 | 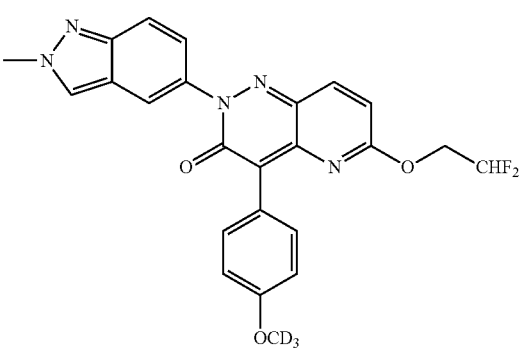<br>6-(2,2-difluoroethoxy)-4-(4-(methoxy-d3)phenyl)-2-(2-methyl-2H-indazol-5-yl)pyrido[3,2-c]pyridazin-3(2H)-one | LC-MS (ESI): m/z 467.2 [M + H]+.<br>1H NMR (400 MHz, DMSO-$d_6$) δ:<br>8.49 (s, 1H), 8.03 (d, J = 9.6 Hz, 1H), 8.01 (d, J = 1.6 Hz, 1H), 7.80 (d, J = 8.8 Hz, 2H), 7.71 (d, J = 9.2 Hz, 1H), 7.45 (dd, J = 9.2 Hz, 2.0 Hz, 1H), 7.04 (d, J = 9.6 Hz, 1H), 7.01 (d, J = 8.8 Hz, 2H), 6.41 (tt, $J_{HF}$ = 54.4 Hz, J = 3.2 Hz, 1H), 4.60 (td, $J_{HF}$ = 15.2 Hz, 3.2 Hz, 2H), 4.22 (s, 3H). |
| Example 109 | 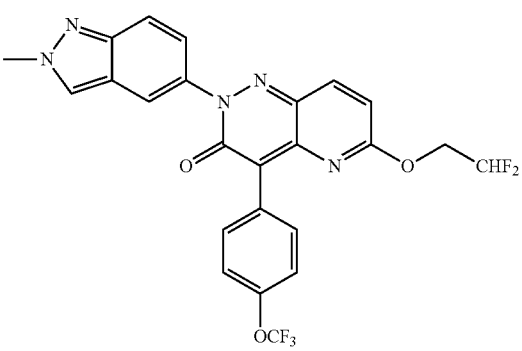<br>6-(2,2-difluoroethoxy)-2-(2-methyl-2H-indazol-5-yl)-4-(4-(trifluoromethoxy)phenyl)pyrido[3,2-c]pyridazin-3(2H)-one | LC-MS (ESI): m/z 518.1 [M + H]+.<br>1H NMR (400 MHz, DMSO-$d_6$) δ:<br>8.51 (s, 1H), 8.08 (d, J = 9.2 Hz, 1H), 8.04 (d, J = 1.6 Hz, 1H), 7.92 (d, J = 8.8 Hz, 2H), 7.72 (d, J = 9.2 Hz, 1H), 7.48 (dd, J = 9.2 Hz, 2.0 Hz, 1H), 7.45 (d, J = 8.4 Hz, 2H), 7.08 (d, J = 9.2 Hz, 1H), 6.39 (tt, $J_{HF}$ = 54.4 Hz, J = 3.6 Hz, 1H), 4.58 (td, $J_{HF}$ = 15.2 Hz, J = 3.2 Hz, 2H), 4.23 (s, 3H). |

| Cpd No. | Structure | Characterization |
|---|---|---|
| Example 110 | 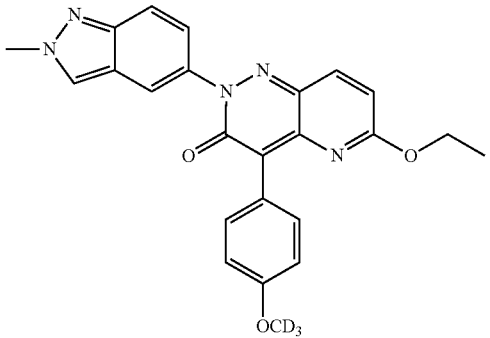<br>6-ethoxy-4-(4-(methoxy-d₃)phenyl)-2-(2-methyl-2H-indazol-5-yl)pyrido[3,2-c]pyridazin-3(2H)-one | LC-MS (ESI): m/z 431.2 [M + H]+.<br>1H NMR (400 MHz, DMSO-$d_6$) δ: 8.49 (s, 1H), 7.99 (s, 1H), 7.94 (d, J = 9.2 Hz, 1H), 7.79 (d, J = 8.4 Hz, 2H), 7.70 (d, J = 8.8 Hz, 1H), 7.44 (d, J = 8.4 Hz, 1H), 7.00 (d, J = 8.0 Hz, 2H), 6.93 (d, J = 9.2 Hz, 1H), 4.35 (d, J = 6.8 Hz, 2H), 4.22 (s, 3H), 1.33 (t, J = 6.8 Hz, 3H). |
| Example 111 | 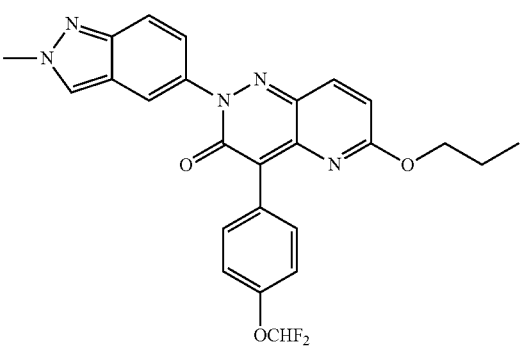<br>4-(4-(difluoromethoxy)phenyl)-2-(2-methyl-2H-indazol-5-yl)-6-propoxypyrido[3,2-c]pyridazin-3(2H)-one | LC-MS (ESI): m/z 478.2 [M + H]+.<br>1H NMR (400 MHz, DMSO-$d_6$) δ: 8.50 (s, 1H), 8.01 (d, J = 1.6 Hz, 1H), 7.97 (d, J = 9.2 Hz, 1H), 7.85 (d, J = 8.8 Hz, 2H), 7.71 (d, J = 9.2 Hz, 1H), 7.46 (dd, J = 9.2 Hz, 2.0 Hz, 1H), 7.34 (t, $J_{HF}$ = 74.0 Hz, 1H), 7.25 (d, J = 8.8 Hz, 2H), 6.96 (d, J = 9.2 Hz, 1H), 4.25 (t, J = 6.8 Hz, 2H), 4.23 (s, 3H), 1.72 (q, J = 7.2 Hz, 2H), 0.92 (t, J = 7.6 Hz, 3H). |
| Example 112 | 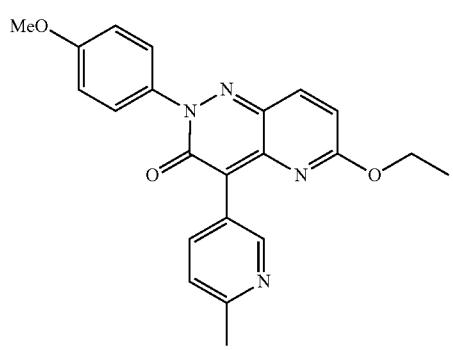<br>6-ethoxy-2-(4-methoxyphenyl)-4-(6-methylpyridin-3-yl)pyrido[3,2-c]pyridazin-3(2H)-one | LC-MS (ESI): m/z 389.2 [M + H]+.<br>1H NMR (400 MHz, DMSO-$d_6$) δ: 8.82 (d, J = 2.0 Hz, 1H), 8.06 (dd, J = 8.0 Hz, 2.0 Hz, 1H), 7.97 (d, J = 9.2 Hz, 1H), 7.59 (dd, J = 7.2 Hz, 2.0 Hz, 2H), 7.34 (d, J = 8.0 Hz, 1H), 7.08 (dd, J = 6.8 Hz, 2.0 Hz, 2H), 6.95 (d, J = 9.6 Hz, 1H), 4.32 (q, J = 6.8 Hz, 2H), 3.83 (s, 3H), 2.51 (s, 3H), 1.31 (t, J = 7.2 Hz, 3H). |

| Cpd No. | Structure | Characterization |
|---|---|---|
| Example 113 | 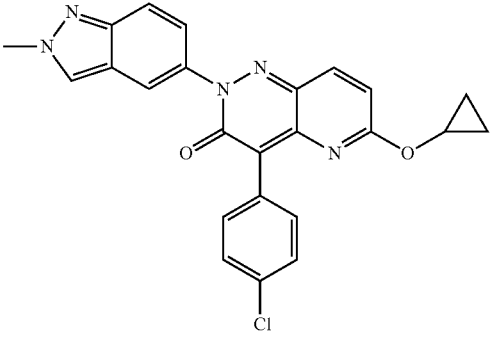<br>4-(4-chlorophenyl)-6-cyclopropoxy-2-(2-methyl-2H-indazol-5-yl)pyrido[3,2-c]pyridazin-3(2H)-one | LC-MS (ESI): m/z 444.1 [M + H]+.<br>1H NMR (400 MHz, DMSO-$d_6$) δ: 8.51 (s, 1H), 8.02 (d, J = 1.6 Hz, 1H), 7.99 (d, J = 9.6 Hz, 1H), 7.93 (dd, J = 6.8 Hz, 1.6 Hz, 2H), 7.71 (d, J = 9.3 Hz, 1H), 7.53 (dd, J = 6.8 Hz, 2.0 Hz, 2H), 7.47 (dd, J = 8.8 Hz, 1.6 Hz, 1H), 6.93 (d, J = 9.2 Hz, 1H), 4.28-4.24 (m, 1H), 4.29 (s, 3H), 0.91-0.83 (m, 4H). |
| Example 114 | 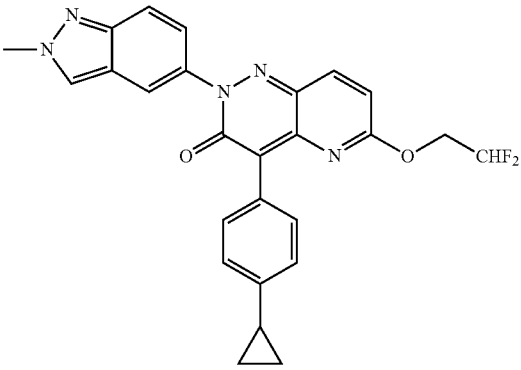<br>4-(4-cyclopropylphenyl)-6-(2,2-difluoroethoxy)-2-(2-methyl-2H-indazol-5-yl)pyrido[3,2-c]pyridazin-3(2H)-one | LC-MS (ESI): m/z 474.2 [M + H]+.<br>1H NMR (400 MHz, DMSO-$d_6$) δ: 8.50 (s, 1H), 8.03 (d, J = 9.6 Hz, 1H), 8.01 (d, J = 2.0 Hz, 1H), 7.72-7.68 (m, 3H), 7.45 (dd, J = 9.2 Hz, 2.0 Hz, 1H), 7.14 (d, J = 8.8 Hz, 2H), 7.04 (d, J = 9.6 Hz, 1H), 6.40 (tt, $J_{HF}$ = 54.4 Hz, J = 3.6 Hz, 1H), 4.58 (td, $J_{HF}$ = 15.2 Hz, J = 3.2 Hz, 2H), 4.22 (s, 3H), 2.01-1.95 (m, 1H), 1.04-0.97 (m, 2H), 0.77-0.70 (m, 2H). |
| Example 115 | 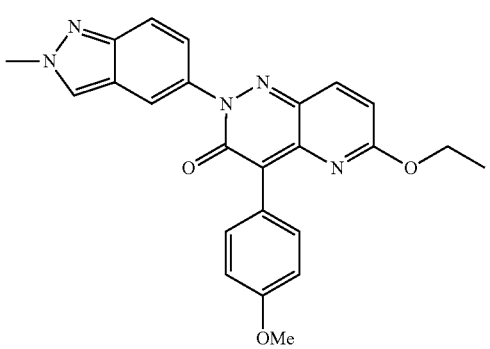<br>6-ethoxy-4-(4-methoxyphenyl)-2-(2-methyl-2H-indazol-5-yl)pyrido[3,2-c]pyridazin-3(2H)-one | LC-MS (ESI): m/z 428.2 [M + H]+.<br>1H NMR (400 MHz, DMSO-$d_6$) δ: 8.49 (s, 1H), 7.99 (d, J = 1.6 Hz, 1H), 7.94 (d, J = 9.6 Hz, 1H), 7.80 (d, J = 8.8 Hz, 2H), 7.70 (d, J = 9.2 Hz, 1H), 7.45 (dd, J = 9.2 Hz, 2.0 Hz, 1H), 7.00 (d, J = 8.8 Hz, 2H), 6.93 (d, J = 9.2 Hz, 1H), 4.35 (q, J = 7.2 Hz, 2H), 4.22 (s, 3H), 3.82 (s, 3H), 1.33 (t, J = 7.2 Hz, 3H). |

| Cpd No. | Structure | Characterization |
|---|---|---|
| Example 116 | 4-(4-chlorophenyl)-2-(2-methyl-2H-indazol-5-yl)-6-(2,2,2-trifluoroethoxy)pyrido[3,2-c]pyridazin-3(2H)-one | LC-MS (ESI): m/z 486.1 [M + H]+. 1H NMR (400 MHz, DMSO-$d_6$) δ: 8.50 (s, 1H), 8.11 (d, J = 9.4 Hz, 1H), 8.03 (s, 1H), 7.84 (d, J = 8.4 Hz, 2H), 7.71 (d, J = 9.2 Hz, 1H), 7.52 (d, J = 8.4 Hz, 2H), 7.47 (d, J = 9.7 Hz, 1H), 7.12 (d, J = 9.4 Hz, 1H), 4.99 (q, $J_{HF}$ = 8.9 Hz, 2H), 4.22 (s, 3H). |
| Example 117 | 4-(4-chlorophenyl)-6-ethoxy-2-(4-methoxyphenyl)pyrido[3,2-c]pyridazin-3(2H)-one | LC-MS (ESI): m/z 408.1 [M + H]+. 1H NMR (400 MHz, DMSO-$d_6$) δ: 7.95 (d, J = 9.3 Hz, 1H), 7.79 (d, J = 8.2 Hz, 2H), 7.59 (d, J = 8.6 Hz, 2H), 7.50 (d, J = 8.2 Hz, 2H), 7.08 (d, J = 8.6 Hz, 2H), 6.93 (d, J = 9.4 Hz, 1H), 4.32 (q, J = 6.8 Hz, 2H), 3.84 (s, 3H), 1.31 (t, J = 6.9 Hz, 3H). |
| Example 118 | 4-(4-chlorophenyl)-2-(4-methoxyphenyl)-6-(2,2,2-trifluoroethoxy)pyrido[3,2-c]pyridazin-3(2H)-one | LC-MS (ESI): m/z 462.1 [M + H]+. 1H NMR (400 MHz, DMSO-$d_6$) δ: 8.09 (d, J = 9.4 Hz, 1H), 7.82 (d, J = 8.5 Hz, 2H), 7.61 (d, J = 8.9 Hz, 2H), 7.52 (d, J = 8.5 Hz, 2H), 7.14-7.07 (m, 3H), 4.98 (q, $J_{HF}$ = 8.9 Hz, 2H), 3.84 (s, 3H). |
| Example 119 | 4-(4-chlorophenyl)-6-ethoxy-2-(2-methyl-2H-indazol-5-yl)pyrido[3,2-c]pyridazin-3(2H)-one | LC-MS (ESI): m/z 432.1 [M + H]+. 1H NMR (400 MHz, DMSO-$d_6$) δ: 8.50 (s, 1H), 8.01 (d, J = 1.6 Hz, 1H), 7.98 (d, J = 9.4 Hz, 1H), 7.81 (d, J = 9.7 Hz, 2H), 7.71 (d, J = 9.1 Hz, 1H), 7.51 (d, J = 8.5 Hz, 2H), 7.46 (dd, J = 9.1 Hz, 1.8 Hz, 1H), 6.95 (d, J = 9.4 Hz, 1H), 4.34 (q, 2H), 4.23 (s, 3H), 1.32 (t, J = 7.0 Hz, 3H). |

| Cpd No. | Structure | Characterization |
|---|---|---|
| Example 120 | 4-(6-(difluoromethoxy)pyridin-3-yl)-6-ethoxy-2-(2-methyl-2H-indazol-5-yl)pyrido[3,2-c]pyridazin-3(2H)-one | LC-MS (ESI): m/z 465.1 [M + H]+. 1H NMR (400 MHz, DMSO-d$_6$) δ: 8.70 (d, J = 2.1 Hz, 1H), 8.52 (s, 1H), 8.36 (dd, J = 8.5 Hz, 2.2 Hz, 1H), 8.02 (d, J = 9.7 Hz, 2H), 7.82 (t, J$_{HF}$ = 72.0 Hz, 1H), 7.74 (d, J = 9.1 Hz, 1H), 7.49 (dd, J = 9.0 Hz, 1.9 Hz, 1H), 7.22 (d, J = 8.5 Hz, 1H), 7.00 (d, J = 9.4 Hz, 1H), 4.38 (q, J = 7.0 Hz, 2H), 4.24 (s, 3H), 1.35 (t, J = 7.0 Hz, 3H). |
| Example 121 | 6-ethoxy-2-(2-methyl-2H-indazol-5-yl)-4-(6-(trifluoromethoxy)pyridin-3-yl)pyrido[3,2-c]pyridazin-3(2H)-one | LC-MS (ESI): m/z 483.1 [M + H]+. 1H NMR (400 MHz, DMSO-d$_6$) δ: 8.78 (d, J = 2.0 Hz, 1H), 8.52 (s, 1H), 8.49-8.42 (m, 1H), 8.04 (d, J = 9.3 Hz, 2H), 7.74 (d, J = 9.0 Hz, 1H), 7.49 (d, J = 9.1 Hz, 1H), 7.43 (d, J = 8.5 Hz, 1H), 7.01 (d, J = 9.5 Hz, 1H), 4.37 (q, J = 7.0 Hz, 2H), 4.24 (s, 3H), 1.34 (t, J = 7.0 Hz, 3H). |
| Example 122 | 4-(6-(difluoromethoxy)pyridin-3-yl)-6-ethoxy-2-(4-methoxyphenyl)pyrido[3,2-c]pyridazin-3(2H)-one | LC-MS (ESI): m/z 441.1 [M + H]+. 1H NMR (400 MHz, DMSO-d$_6$) δ: 8.66 (d, J = 1.9 Hz, 1H), 8.32 (dd, J = 8.6 Hz, 2.4 Hz, 1H), 7.98 (d, J = 9.4 Hz, 1H), 7.80 (t, J$_{HF}$ = 72 Hz, 1H), 7.67-7.57 (m, 2H), 7.24-7.15 (m, 1H), 7.15-7.05 (m, 2H), 6.97 (d, J = 9.4 Hz, 1H), 4.35 (q, J = 7.1 Hz, 2H), 3.84 (s, 3H), 1.32 (t, J = 7.1 Hz, 3H). |

| Cpd No. | Structure | Characterization |
|---|---|---|
| Example 123 | 4-(4-(difluoromethoxy)phenyl)-2-(2-methyl-2H-indazol-5-yl)-6-(2,2,2-trifluoroethoxy)pyrido[3,2-c]pyridazin-3(2H)-one | LC-MS (ESI): m/z 518.1 [M + H]+. 1H NMR (400 MHz, DMSO-$d_6$) δ: 8.50 (s, 1H) 8.10 (d, J = 9.4 Hz, 1H), 8.03 (d, J = 1.4 Hz, 1H), 7.88 (d, J = 8.0 Hz, 2H), 7.71 (d, J = 9.2 Hz, 1H), 7.47 (dd, J = 9.1 Hz, 2.0 Hz, 1H), 7.35 (t, $J_{HF}$ = 72.0 Hz, 1H), 7.25 (d, $J_{HF}$ = 8.8 Hz, 2H), 7.11 (d, J = 9.4 Hz, 1H), 5.00 (q, J = 9.0 Hz, 2H), 4.22 (s, 3H). |
| Example 124 | 4-(4-chlorophenyl)-6-(2,2-difluoroethoxy)-2-(2-methyl-2H-indazol-5-yl)pyrido[3,2-c]pyridazin-3(2H)-one | LC-MS (ESI): m/z 468.0 [M + H]+. 1H NMR (400 MHz, DMSO-$d_6$) δ: 8.50 (s, 1H), 8.07 (d, J = 9.2 Hz, 1H), 8.02 (d, J = 1.6 Hz, 1H), 7.83 (d, J = 8.4 Hz, 2H), 7.71 (d, J = 9.2 Hz, 1H), 7.52 (d, J = 8.4 Hz, 2H), 7.47 (dd, J = 9.2 Hz, 2.0 Hz, 1H), 7.07 (d, J = 9.6 Hz, 1H), 6.38 (tt, $J_{HF}$ = 54.4 Hz, J = 3.2 Hz, 1H), 4.59 (td, $J_{HF}$ = 15.2 Hz, J = 3.2 Hz, 2H), 4.23 (s, 3H). |
| Example 125 | 6-(2,2-difluoroethoxy)-4-(4-(difluoromethoxy)phenyl)-2-(2-methyl-2H-indazol-5-yl)pyrido[3,2-c]pyridazin-3(2H)-one | LC-MS (ESI): m/z 500.0 [M + H]+. 1H NMR (400 MHz, DMSO-$d_6$) δ: 8.50 (s, 1H), 8.06 (d, J = 9.6 Hz, 1H), 8.02 (d, J = 1.2 Hz, 1H), 7.87 (d, J = 8.8 Hz, 2H), 7.71 (d, J = 9.2 Hz, 1H), 7.46 (dd, J = 9.2 Hz, 2.0 Hz, 1H), 7.34 (t, $J_{HF}$ = 74.0 Hz, 1H), 7.25 (d, J = 8.8 Hz, 2H), 7.06 (d, J = 9.6 Hz, 1H), 6.40 (tt, $J_{HF}$ = 54.4 Hz, J = 3.2 Hz, 1H), 4.59 (td, $J_{HF}$ = 15.2 Hz, J = 3.2 Hz, 2H), 4.22 (s, 3H). |
| Example 126 | 6-(2,2-difluoroethoxy)-4-(6-(difluoromethoxy)pyridin-3-yl)-2-(2-methyl-2H-indazol-5-yl)pyrido[3,2-c]pyridazin-3(2H)-one | LC-MS (ESI): m/z 501.0 [M + H]+. 1H NMR (400 MHz, DMSO-$d_6$) δ: 8.68 (d, J = 2.4 Hz, 1H), 8.51 (s, 1H), 8.34 (dd, J = 8.4 Hz, 2.4 Hz, 1H), 8.09 (d, J = 9.2 Hz, 1H), 8.03 (d, J = 1.6 Hz, 1H), 7.80 (t, $J_{HF}$ = 74.0 Hz, 1H), 7.72 (d, J = 9.2 Hz, 1H), 7.47 (dd, J = 9.2 Hz, 1.6 Hz, 1H), 7.20 (d, 1H), 7.09 (d, J = 8.8 Hz, 1H), 6.41 (tt, $J_{HF}$ = 54.4 Hz, J = 3.2 Hz, 1H), 4.61 (td, $J_{HF}$ = 15.2 Hz, J = 3.2 Hz, 2H), 4.22 (s, 3H). |

| Cpd No. | Structure | Characterization |
|---|---|---|
| Example 127 | 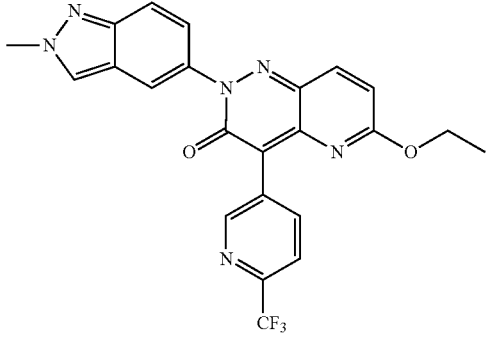<br>6-ethoxy-2-(2-methyl-2H-indazol-5-yl)-4-(6-(trifluoromethyl)pyridin-3-yl)pyrido[3,2-c]pyridazin-3(2H)-one | LC-MS (ESI): m/z 467.0 [M + H]+.<br>1H NMR (400 MHz, DMSO-d$_6$) δ: 9.15 (s, 1H), 8.52 (s, 1H), 8.49 (d, J = 6.8 Hz, 1H), 8.06-8.02 (m, 3H), 7.73 (d, J = 8.8 Hz, 1H), 7.49 (dd, J = 8.8 Hz, 1.6 Hz, 1H), 7.01 (d, J = 9.6 Hz, 1H), 4.35 (q, J = 7.2 Hz, 2H), 4.23 (s, 3H), 1.32 (t, J = 7.2 Hz, 3H). |
| Example 128 | 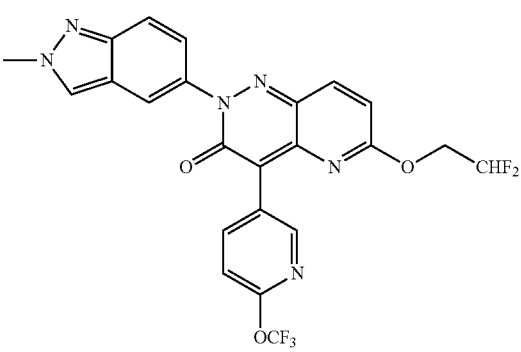<br>6-(2,2-difluoroethoxy)-2-(2-methyl-2H-indazol-5-yl)-4-(6-(trifluoromethoxy)pyridin-3-yl)pyrido[3,2-c]pyridazin-3(2H)-one | LC-MS (ESI): m/z 519.0 [M + H]+.<br>1H NMR (400 MHz, DMSO-d$_6$) δ: 8.77 (s, 1H), 8.51 (s, 1H), 8.43 (dd, J = 8.8 Hz, 2.0 Hz, 1H), 8.10 (d, J = 9.6 Hz, 1H), 8.04 (s, 1H), 7.72 (d, J = 9.2 Hz, 1H), 7.47 (dd, J = 8.8 Hz, 1.6 Hz, 1H), 7.40 (d, J = 8.8 Hz, 1H), 7.10 (d, J = 9.6 Hz, 1H), 6.40 (tt, J$_{HF}$ = 54.4 Hz, J = 3.2 Hz, 1H), 4.60 (td, J$_{HF}$ = 15.2 Hz, J = 3.2 Hz, 2H), 4.22 (s, 3H). |
| Example 129 | 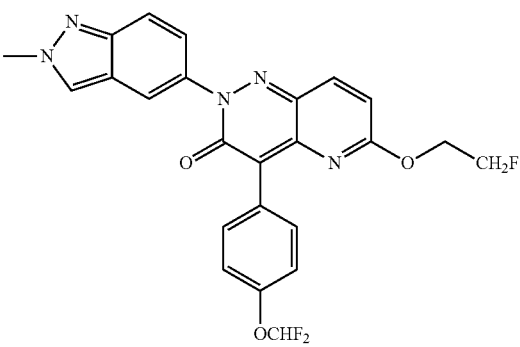<br>4-(4-(difluoromethoxy)phenyl)-6-(2-fluoroethoxy)-2-(2-methyl-2H-indazol-5-yl)pyrido[3,2-c]pyridazin-3(2H)-one | LC-MS (ESI): m/z 482.0 [M + H]+.<br>1H NMR (400 MHz, DMSO-d$_6$) δ: 8.50 (s, 1H), 8.03-8.01 (m, 2H), 7.86 (dd, J = 6.8 Hz, 2.0 Hz, 2H), 7.70 (d, J = 8.8 Hz, 1H), 7.45 (dd, J = 9.2 Hz, 2.0 Hz, 1H), 7.34 (t, J$_{HF}$ = 74.0 Hz, 1H), 7.25 (d, J = 8.8 Hz, 2H), 7.02 (d, J = 9.6 Hz, 1H), 4.82-4.80 (m, 1H), 4.70-4.69 (m, 1H), 4.58-4.56 (m, 1H), 4.51-4.49 (m, 1H), 4.22 (s, 3H). |

| Cpd No. | Structure | Characterization |
|---|---|---|
| Example 130 | 6-(2,2-difluoroethoxy)-4-(6-methoxypyridin-3-yl)-2-(2-methyl-2H-indazol-5-yl)pyrido[3,2-c]pyridazin-3(2H)-one | LC-MS (ESI): m/z 465.0 [M + H]+. 1H NMR (400 MHz, DMSO-$d_6$) δ: 8.64 (d, J = 1.2 Hz, 1H), 8.51 (s, 1H), 8.16 (dd, J = 8.4 Hz, 2.0 Hz, 1H), 8.06 (d, J = 9.6 Hz, 1H), 8.03 (s, 1H), 7.72 (d, J = 8.8 Hz, 1H), 7.47 (dd, J = 9.2 Hz, 1.2 Hz, 1H), 7.08 (d, J = 9.6 Hz, 1H), 6.92 (d, J = 8.4 Hz, 1H), 6.42 (t, $J_{HF}$ = 54.4 Hz, 1H), 4.62 (td, $J_{HF}$ = 14.8 Hz, J = 2.8 Hz, 2H), 4.23 (s, 3H), 3.93 (s, 3H). |
| Example 131 | 6-(cyclobutylmethoxy)-4-(4-(difluoromethoxy)phenyl)-2-(2-methyl-2H-indazol-5-yl)pyrido[3,2-c]pyridazin-3(2H)-one | LC-MS (ESI): m/z 504.0 [M + H]+. 1H NMR (400 MHz, DMSO-$d_6$) δ: 8.50 (s, 1H), 8.01 (d, J = 1.6 Hz, 1H), 7.97 (d, J13.6 Hz, 1H), 7.86 (d, J = 8.8 Hz, 2H), 7.71 (d, J = 8.8 Hz, 1H), 7.46 (dd, J = 9.2 Hz, 2.0 Hz, 1H), 7.35 (t, $J_{HF}$ = 74.0 Hz, 1H), 7.25 (d, J = 8.8 Hz, 2H), 6.96 (d, J = 9.2 Hz, 1H), 4.30 (d, J = 6.8 Hz, 2H), 4.23 (s, 3H), 2.8-2.63 (m, 1H), 2.11-1.97 (m, 2H), 1.92-1.70 (m, 4H). |
| Example 132 | 4-(4-(difluoromethoxy)phenyl)-2-(2-methyl-2H-indazol-5-yl)-6-(3,3,3-trifluoropropoxy)pyrido[3,2-c]pyridazin-3(2H)-one-one | LC-MS (ESI): m/z 532.0 [M + H]+. 1H NMR (400 MHz, DMSO-$d_6$) δ: 8.51 (s, 1H), 8.03 (d, J = 9.6 Hz, 1H), 8.02 (d, J = 1.6 Hz, 1H), 7.86 (d, J = 8.8 Hz, 2H), 7.71 (d, J = 9.2 Hz, 1H), 7.46 (dd, J = 9.2 Hz, 2.0 Hz, 1H), 7.34 (t, $J_{HF}$ = 72.0 Hz, 1H), 7.25 (d, J = 8.8 Hz, 2H), 6.97 (d, J = 9.6 Hz, 1H), 4.53 (t, J = 6.0 Hz, 2H), 4.23 (s, 3H), 2.87-2.75 (m, 2H). |
| Example 133 | 6-(2,2-difluoroethoxy)-2-(2-methyl-2H-indazol-5-yl)-4-phenylpyrido[3,2-c]pyridazin-3(2H)-one | LC-MS (ESI): m/z 434.0 [M + H]+. 1H NMR (400 MHz, DMSO-$d_6$) δ: 8.50 (s, 1H), 8.06 (d, J = 9.2 Hz, 1H), 8.02 (d, J = 2.0 Hz, 1H), 7.76 (d, J = 8.0 Hz, 2H), 7.71 (d, J = 8.8 Hz, 1H), 7.48-7.39 (m, 4H), 7.06 (d, J = 9.6 Hz, 1H), 6.39 (tt, $J_{HF}$ = 54.4 Hz, J = 3.2 Hz, 1H), 4.56 (td, $J_{HF}$ = 15.2 Hz, J = 3.6 Hz, 2H), 4.22 (s, 3H). |

| Cpd No. | Structure | Characterization |
|---|---|---|
| Example 134 | 6-(2,2-difluoroethoxy)-2-(2-methyl-2H-indazol-5-yl)-4-(pyridin-4-yl)pyrido[3,2-c]pyridazin-3(2H)-one | LC-MS (ESI): m/z 435.0 [M + H]+. 1H NMR (400 MHz, DMSO-$d_6$) δ: 8.67 (d, J = 5.6 Hz, 2H), 8.51 (s, 1H), 8.10 (d, J = 9.6 Hz, 1H), 8.04 (d, J = 1.2 Hz, 1H), 7.75 (d, J = 6.0 Hz, 1H), 7.72 (d, J = 9.2 Hz, 1H), 7.72 (d, J = 9.2 Hz, 1H), 7.47 (dd, J = 8.8 Hz, 2.0 Hz, 1H), 7.09 (d, J = 9.2 Hz, 1H), 6.40 (tt, $J_{HF}$ = 54.0 Hz, J = 3.2 Hz, 1H), 4.59 (td, $J_{HF}$ = 15.2 Hz, J = 3.2 Hz, 2H), 4.22 (s, 3H). |
| Example 135 | 4-(4-(difluoromethoxy)phenyl)-6-ethoxy-2-(4-methoxyphenyl)pyrido[3,2-c]pyridazin-3(2H)-one | LC-MS (ESI): m/z 440.1 [M + H]+. 1H NMR (400 MHz, DMSO-$d_6$) δ: 8.01 (d, J = 9.6 Hz, 1H), 7.90 (d, J = 8.8 Hz, 2H), 7.65 (d, J = 8.8 Hz, 2H), 7.41 (t, $J_{HF}$ = 74.0 Hz, 1H), 7.30 (d, J = 8.8 Hz, 2H), 7.15 (d, J = 9.2 Hz, 2H), 7.00 (d, J = 9.2 Hz, 1H), 4.39 (q, J = 7.2 Hz, 2H), 3.90 (s, 3H), 1.37 (t, J = 7.2 Hz, 3H). |
| Example 136 | 6-ethoxy-2-(4-methoxyphenyl)-4-(6-(trifluoromethoxy)pyridin-3-yl)pyrido[3,2-c]pyridazin-3(2H)-one | LC-MS (ESI): m/z 459.1 [M + H]+. 1H NMR (400 MHz, DMSO-$d_6$) δ: 8.74 (d, J = 2.4 Hz, 1H), 8.40 (dd, J = 8.8 Hz, 2.0 Hz, 1H), 8.00 (d, J = 9.2 Hz, 1H), 7.60 (d, J = 9.2 Hz, 2H), 7.40 (d, J = 8.4 Hz, 1H), 7.09 (d, J = 8.8 Hz, 2H), 6.98 (d, J = 9.2 Hz, 1H), 4.34 (q, J = 7.2 Hz, 2H), 3.84 (s, 3H), 1.31 (t, J = 7.2 Hz, 3H). |
| Example 137 | 6-(cyclopropylmethoxy)-4-(4-(difluoromethoxy)phenyl)-2-(2-methyl-2H-indazol-5-yl)pyrido[3,2-c]pyridazin-3(2H)-one | LC-MS (ESI): m/z 490.2 [M + H]+. 1H NMR (400 MHz, DMSO-$d_6$) δ: 8.49 (s, 1H), 8.00 (dd, J = 2.0 Hz, 0.8 Hz, 1H), 7.97 (d, J = 9.2 Hz, 1H), 7.84 (d, J = 8.8 Hz, 2H), 7.70 (d, J = 8.8 Hz, 1H), 7.45 (dd, J = 9.2 Hz, 2.0 Hz, 1H), 7.34 (t, $J_{HF}$ = 74.0 Hz, 1H), 7.24 (d, J = 8.8 Hz, 2H), 6.98 (d, J = 9.2 Hz, 1H), 4.22 (s, 3H), 4.15 (d, J = 7.2 Hz, 2H), 1.28-1.08 (m, 1H), 0.62-0.42 (m, 2H), 0.32-0.13 (m, 2H). |

| Cpd No. | Structure | Characterization |
|---|---|---|
| Example 138 | 4-(4-(difluoromethoxy)phenyl)-6-isopropoxy-2-(2-methyl-2H-indazol-5-yl)pyrido[3,2-c]pyridazin-3(2H)-one | LC-MS (ESI): m/z 478.2 [M + H]+. 1H NMR (400 MHz, DMSO-d₆) δ: 8.49 (s, 1H), 8.00 (dd, J = 2.0 Hz, 0.8 Hz, 1H), 7.96 (d, J = 9.2 Hz, 1H), 7.82 (d, J = 8.8 Hz, 2H), 7.70 (d, J = 8.8 Hz, 1H), 7.45 (dd, J = 9.2 Hz, 2.0 Hz, 1H), 7.34 (t, $J_{HF}$ = 74.0 Hz, 1H), 7.24 (d, J = 8.8 Hz, 2H), 6.90 (d, J = 9.2 Hz, 1H), 5.23-5.08 (m, 1H), 4.22 (s, 3H), 1.30 (d, J = 6.0 Hz, 6H). |
| Example 139 | 6-(2,2-difluoroethoxy)-4-(6-(methoxy-d₃)pyridin-3-yl)-2-(2-methyl-2H-indazol-5-yl)pyrido[3,2-c]pyridazin-3(2H)-one | LC-MS (ESI): m/z 468.2 [M + H]+. 1H NMR (400 MHz, DMSO-d₆) δ: 8.64 (d, J = 1.2 Hz, 1H), 8.51 (s, 1H), 8.16 (dd, J = 8.4 Hz, 2.0 Hz, 1H), 8.07 (d, J = 9.6 Hz, 1H), 8.03 (s, 1H), 7.72 (d, J = 9.2 Hz, 1H), 7.47 (dd, J = 9.2 Hz, 2.0 Hz, 1H), 7.08 (d, J = 9.6 Hz, 1H), 6.92 (d, J = 8.8 Hz, 1H), 6.43 (tt, $J_{HF}$ = 54.4 Hz, J = 3.2 Hz, 1H), 4.62 (td, $J_{HF}$ = 15.2 Hz, J = 3.2 Hz, 2H), 4.23 (s, 3H). |
| Example 140 | 4-(3-chlorophenyl)-6-(2,2-difluoroethoxy)-2-(2-methyl-2H-indazol-5-yl)pyrido[3,2-c]pyridazin-3(2H)-one | LC-MS (ESI): m/z 468.1 [M + H]+. 1H NMR (400 MHz, DMSO-d₆) δ 8.50 (s, 1H), 8.07 (d, J = 9.2 Hz, 1H), 8.03 (s, 1H), 7.84 (s, 1H), 7.75-7.74 (m, 1H), 7.71 (d, J = 9.2 Hz, 1H), 7.48-7.46 (m, 3H), 7.07 (d, J = 9.2 Hz, 1H), 6.40 (t, $J_{HF}$ = 54.4 Hz, 1H), 4.58 (t, $J_{HF}$ = 14.0 Hz, 2H), 4.22 (s, 3H). |
| Example 141 | 4-(4-(difluoromethoxy)phenyl)-6-isobutoxy-2-(2-methyl-2H-indazol-5-yl)pyrido[3,2-c]pyridazin-3(2H)-one | LC-MS (ESI): m/z 492.5 [M + H]+. 1H NMR (400 MHz, DMSO-d₆) δ: 8.49 (s, 1H), 8.00 (d, J = 2.4 Hz, 1H), 7.97 (d, J = 9.2 Hz, 1H), 7.85 (d, J = 9.6 Hz, 2H), 7.70 (d, J = 9.2 Hz, 1H), 7.45 (dd, J = 9.2 Hz, 2.0 Hz, 1H), 7.33 (t, $J_{HF}$ = 74.0 Hz, 1H), 7.22 (d, J = 8.8 Hz, 2H), 6.96 (d, J = 9.2 Hz, 1H), 4.22 (s, 3H), 4.09 (d, J = 6.8 Hz, 2H), 2.10-1.98 (m, 1H), 0.92 (d, J = 6.7 Hz, 6H). |

| Cpd No. | Structure | Characterization |
|---|---|---|
| Example 142 (Synthesized using (E)-methyl 4-(tetrahydro-2H-pyran-2-yloxy)-3-(4,4,5,5-tetramethyl-1,3,2-dioxaborolan-2-yl)but-2-enoate (Ref: Tetrahedron 2012, 68, 3444-3449) | 6-(2,2-difluoroethoxy)-4-(4-(difluoromethoxy)phenyl)-2-(2-methyl-2H-indazol-5-yl)-8-(((tetrahydro-2H-pyran-2-yl)oxy)methyl)pyrido[3,2-c]pyridazin-3(2H)-one | LC-MS (ESI): m/z 614.0 [M + H]+. 1H NMR (400 MHz, DMSO-d$_6$) δ: 8.51 (s, 1H), 8.03 (d, J = 1.6 Hz, 1H), 7.85 (d, J = 8.8 Hz, 2H), 7.71 (d, J = 9.2 Hz, 1H), 7.48 (dd, J = 9.2 Hz, 2.0 Hz, 1H), 7.34 (t, J$_{HF}$ = 74.0 Hz, 1H), 7.25 (d, J = 8.8 Hz, 2H), 6.95 (s, 1H), 6.40 (tt, J$_{HF}$ = 54.4 Hz, J = 3.2 Hz, 1H), 4.98 (d, J = 16.4 Hz, 1H), 4.83 (d, J = 16.4 Hz, 2H), 4.59 (td, J$_{HF}$ = 15.2 Hz, J = 3.2 Hz, 2H), 4.23 (s, 3H), 3.79-3.74 (m, 1H), 3.49-3.40 (m, 1H), 1.83-1.45 (m, 6H). |
| Example 143 | 2-(benzo[d]thiazol-6-yl)-4-(4-chlorophenyl)-6-(2,2-difluoroethoxy)pyrido[3,2-c]pyridazin-3(2H)-one | LC-MS (ESI): m/z 471 [M + H]+. 1H NMR (400 MHz, DMSO-d$_6$) δ 9.55 (s, 1H), 8.55 (d, J = 2.1 Hz, 1H), 8.26 (d, J = 8.7 Hz, 1H), 8.08 (d, J = 9.4 Hz, 1H), 7.92-7.79 (m, 3H), 7.60-7.47 (m, 2H), 7.11 (d, J = 9.4 Hz, 1H), 6.42 (tt, J = 54.3, 3.3 Hz, 1H), 4.61 (td, J = 15.2, 3.3 Hz, 2H). |
| Example 144 | 2-(benzo[d]thiazol-6-yl)-6-(2,2-difluoroethoxy)-4-(4-methoxyphenyl)pyrido[3,2-c]pyridazin-3(2H)-one | LC-MS (ESI): m/z 467 [M + H]+. 1H NMR (400 MHz, DMSO-d$_6$) δ 9.54 (s, 1H), 8.53 (s, 1H), 8.24 (d, J = 8.7 Hz, 1H), 8.03 (d, J = 9.4 Hz, 1H), 7.94-7.70 (m, 3H), 7.12-6.96 (m, 3H), 6.42 (t, J = 54.3 Hz, 1H), 4.61 (td, J = 15.2, 3.3 Hz, 2H), 3.83 (s, 3H). |

| Cpd No. | Structure | Characterization |
|---|---|---|
| Example 145 | 2-(benzo[d]thiazol-6-yl)-4-(4-(difluoromethoxy)phenyl)-6-ethoxypyrido[3,2-c]pyridazin-3(2H)-one | LC-MS (ESI): m/z 467 [M + H]+. 1H NMR (400 MHz, DMSO-d$_6$) δ 9.53 (s, 1H), 8.53 (d, J = 2.1 Hz, 1H), 8.24 (d, J = 8.7 Hz, 1H), 7.97 (d, J = 9.4 Hz, 1H), 7.91-7.80 (m, 3H), 7.35 (t, J = 74.0 Hz, 1H), 7.25 (d, J = 8.8 Hz, 2H), 6.97 (d, J = 9.4 Hz, 1H), 4.34 (q, J = 7.1 Hz, 2H), 1.32 (t, J = 7.1 Hz, 3H). |
| Example 146 | 2-(benzo[d]thiazol-6-yl)-4-(4-(difluoromethoxy)phenyl)-6-isopropoxypyrido[3,2-c]pyridazin-3(2H)-one | LC-MS (ESI): m/z 481 [M + H]+. 1H NMR (400 MHz, DMSO-d$_6$) δ 9.53 (s, 1H), 8.52 (d, J = 2.1 Hz, 1H), 8.24 (d, J = 8.7 Hz, 1H), 7.96 (d, J = 9.4 Hz, 1H), 7.83 (m, 3H), 7.35 (t, J = 74.0 Hz, 1H), 7.25 (d, J = 8.8 Hz, 2H), 6.92 (d, J = 9.4 Hz, 1H), 5.16 (hept, J = 6.6 Hz, 1H), 1.31 (d, J = 6.2 Hz, 6H). |
| Example 147 | 2-(benzo[d]thiazol-6-yl)-4-(6-cyclopropylpyridin-3-yl)-6-(2,2-difluoroethoxy)pyrido[3,2-c]pyridazin-3(2H)-one | LC-MS (ESI): m/z 478 [M + H]+. 1H NMR (400 MHz, DMSO-d$_6$) δ 9.59 (s, 1H), 8.86 (d, J = 2.1 Hz, 1H), 8.59 (d, J = 2.1 Hz, 1H), 8.31 (d, J = 8.7 Hz, 1H), 8.18-8.02 (m, 2H), 7.90 (dd, J = 8.7, 2.1 Hz, 1H), 7.45 (d, J = 8.1 Hz, 1H), 7.15 (d, J = 9.4 Hz, 1H), 6.46 (tt, J = 54.3, 3.4 Hz, 1H), 4.66 (td, J = 15.1, 3.4 Hz, 2H), 2.23 (tt, J = 7.7, 5.0 Hz, 1H), 1.10-0.98 (m, 4H). |

| Cpd No. | Structure | Characterization |
|---|---|---|
| Example 148 | 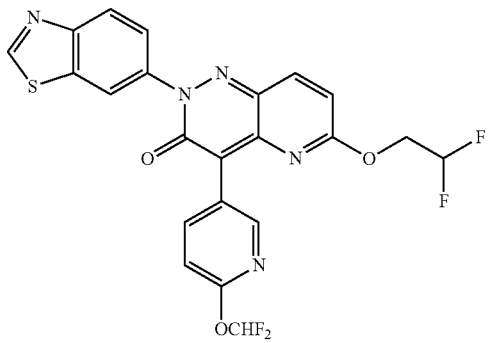<br>2-(benzo[d]thiazol-6-yl)-6-(2,2-difluoroethoxy)-4-(6-(difluoromethoxy)pyridin-3-yl)pyrido[3,2-c]pyridazin-3(2H)-one | LC-MS (ESI): m/z 504 [M + H]+.<br>1H NMR (400 MHz, DMSO-d$_6$) δ 9.54 (s, 1H), 8.69 (d, J = 2.4 Hz, 1H), 8.54 (d, J = 2.2 Hz, 1H), 8.35 (dd, J = 8.6, 2.4 Hz, 1H), 8.25 (d, J = 8.8 Hz, 1H), 8.09 (d, J = 9.4 Hz, 1H), 7.86 (dd, J = 8.7, 2.2 Hz, 1H), 7.80 (t, J = 72.8 Hz, 1H), 7.21 (d, J = 8.6 Hz, 1H), 7.11 (d, J = 9.4 Hz, 1H), 6.41 (tt, J = 54.2, 3.3 Hz, 1H), 4.62 (td, J = 15.1, 3.4 Hz, 3H). |
| Example 149 | 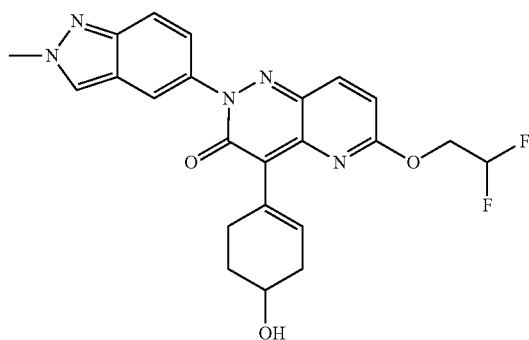<br>6-(2,2-difluoroethoxy)-4-(4-hydroxycyclohex-1-en-1-yl)-2-(2-methyl-2H-indazol-5-yl)pyrido[3,2-c]pyridazin-3(2H)-one | LC-MS: m/z 454.2 (M + H)+.<br>1H NMR (400 MHz, DMSO-d$_6$) δ: 8.47 (s, 1H), 7.99-7.94 (m, 2H), 7.68 (d, J = 9.2 Hz, 1H), 7.39 (dd, J = 9.2 Hz, 2.0 Hz, 1H), 7.00 (d, J = 9.6 Hz, 1H), 6.46 (tt, J$_{HF}$ = 54.4 Hz, 3.6 Hz, 1H), 5.86-5.80 (m, 1H), 4.74 (d, J = 4.0 Hz, 1H), 4.71 (td, J = 14.8 Hz, 3.6 Hz, 2H), 4.19 (s, 3H), 3.92-3.79 (m, 1H), 2.51-2.41 (m, 3H), 2.15-2.02 (m, 1H), 1.95-1.85 (m, 1H), 1.65-1.53 (m, 1H). |
| Example 150 | 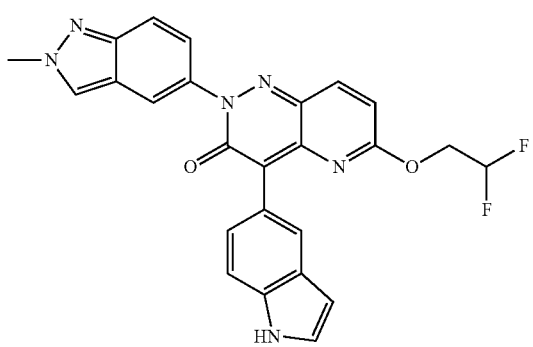<br>6-(2,2-difluoroethoxy)-4-(1H-indol-5-yl)-2-(2-methyl-2H-indazol-5-yl)pyrido[3,2-c]pyridazin-3(2H)-one | LC-MS: m/z 473.1 (M + H)+.<br>1H NMR (400 MHz, DMSO-d$_6$) δ: 11.18 (br s, 1H), 8.49 (s, 1H), 8.06-8.01 (m, 3H), 7.71 (d, J = 9.2 Hz, 1H), 7.56 (dd, J = 8.4 Hz, 1.6 Hz, 1H), 7.47 (dd, J = 9.2 Hz, 2.0 Hz, 1H), 7.42 (d, J = 8.8 Hz, 1H), 7.36 (t, J = 2.8 Hz, 1H), 7.03 (d, J = 9.2 Hz, 1H), 6.49-6.46 (m, 1H), 6.40 (tt, J$_{HF}$ = 54.8 Hz, 3.6 Hz, 1H), 4.56 (td, J = 14.8 Hz, 3.6 Hz, 2H), 4.22 (s, 3H). |

-continued

| Cpd No. | Structure | Characterization |
|---|---|---|
| Example 151 | 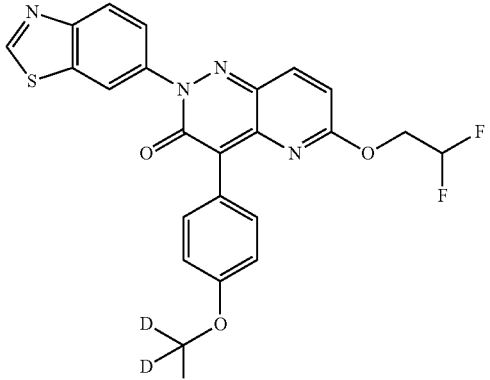<br>2-(benzo[d]thiazol-6-yl)-6-(2,2-difluoroethoxy)-4-(4-methoxy-d$_3$-phenyl)pyrido[3,2-c]pyridazin-3(2H)-one | LC-MS: m/z 470.1 (M + H)+.<br>1H NMR (400 MHz, DMSO-d$_6$) δ: 9.52 (s, 1H), 8.52 (s, 1H), 8.24 (d, J = 8.8 Hz, 1H), 8.03 (d, J = 9.2 Hz, 1H), 7.87-7.76 (m, 3H), 7.06 (d, J = 9.6 Hz, 1H), 7.01 (d, J = 8.8 Hz, 2H), 6.41 (tt, J$_{HF}$ = 54.4 Hz, 3.2 Hz, 1H), 4.60 (td, J = 14.8 Hz, 3.2 Hz, 2H). |
| Example 152 | 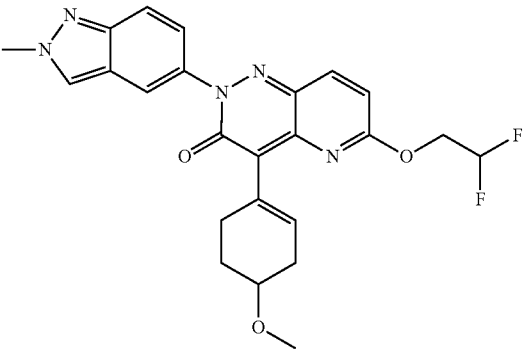<br>6-(2,2-difluoroethoxy)-4-(4-methoxycyclohex-1-en-1-yl)-2-(2-methyl-2H-indazol-5-yl)pyrido[3,2-c]pyridazin-3(2H)-one | LC-MS: m/z 468.2 (M + H)+.<br>1H NMR (400 MHz, DMSO-d$_6$) δ: 8.47 (s, 1H), 7.99-7.93 (m, 2H), 7.68 (d, J = 9.2 Hz, 1H), 7.39 (dd, J = 9.2 Hz, 2.0 Hz, 1H), 7.01 (d, J = 9.6 Hz, 1H), 6.46 (tt, J$_{HF}$ = 56.4 Hz, 3.6 Hz, 1H), 5.88-5.82 (m, 1H), 4.71 (td, J$_{HF}$ = 15.2 Hz, 3.6 Hz, 2H), 4.21 (s, 3H), 3.60-3.51 (m, 1H), 3.31 (s, 3H), 2.61-2.41 (m, 3H) 2.21-2.09 (m, 1H), 2.04-1.94 (m, 1H), 1.72-1.58 (m, 1H). |
| Example 153 | 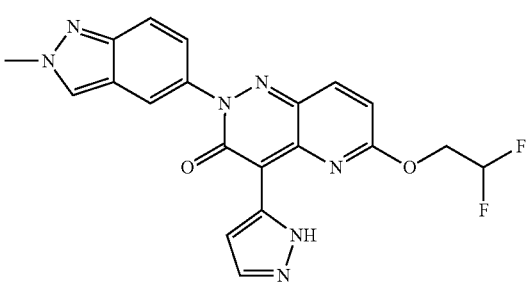<br>6-(2,2-difluoroethoxy)-2-(2-methyl-2H-indazol-5-yl)-4-(1H-pyrazol-5-yl)pyrido[3,2-c]pyridazin-3(2H)-one (synthesized from 4-chloro-2-(2-methyl-2H-indazol-5-yl)pyrido[3,2-c]pyridazine-3,6(2H,5H)-dione & tert-butyl 5-(4,4,5,5-tetramethyl-1,3,2-dioxaborolan-2-yl)-1H-pyrazole-1-carboxylate, then de-Boc with TFA-DCM) | LC-MS: m/z 424.1 (M + H)+.<br>1H NMR (400 MHz, DMSO-d$_6$) δ: 13.31 (br s, 1H), 8.52 (s, 1H), 8.13 (d, J = 9.2 Hz, 1H), 8.02 (d, J = 1.2 Hz, 1H), 7.76-7.69 (m, 2H), 7.56-7.50 (m, 1H), 7.47 (dd, J = 9.2 Hz, 1.6 Hz, 1H), 6.78 (d, J = 9.2 Hz, 1H), 6.55 (tt, J$_{HF}$ = 54.0 Hz, 3.2 Hz, 1H), 4.92 (td, J = 14.8 Hz, 3.2 Hz, 2H), 4.23 (s, 3H). |

-continued

| Cpd No. | Structure | Characterization |
|---|---|---|
| Example 302 | 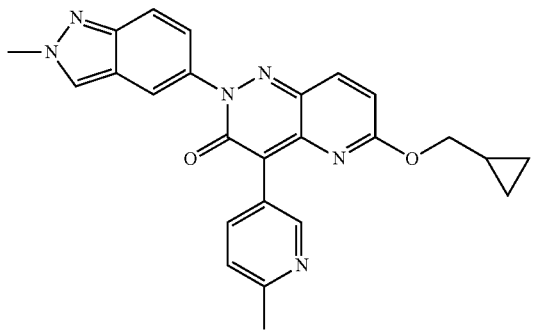 [SMILES: Cc1ccc(-c2c(=O)n(-c3ccc4nn(C)cc4c3)nc3ccc(OCC4CC4)nc23)cn1]<br>6-(cyclopropylmethoxy)-2-(2-methyl-2H-indazol-5-yl)-4-(6-methylpyridin-3-yl)pyrido[3,2-c]pyridazin-3(2H)-one | LC-MS: m/z 439 (M + H)+.<br>1H NMR (400 MHz, DMSO-d$_6$) δ: 8.82 (d, J = 1.8 Hz, 1H), 8.49 (s, 1H), 8.07 (dd, J = 8.0 Hz, 2.2 Hz, 1H), 8.01 (dd, J = 2.0 Hz, 0.7 Hz, 1H), 7.99 (d, J = 9.4 Hz, 1H), 7.70 (d, J = 9.1 Hz, 1H), 7.45 (dd, J = 9.1 Hz, 2.0 Hz, 1H), 7.34 (d, J = 8.1 Hz, 1H), 6.99 (d, J = 9.4 Hz, 1H), 2H), 2.53 (s, 3H), 1.27-1.17 (m, 1H), 0.58-0.50 (m, 2H), 0.33-0.25 (m, 2H). |
| Example 303 | 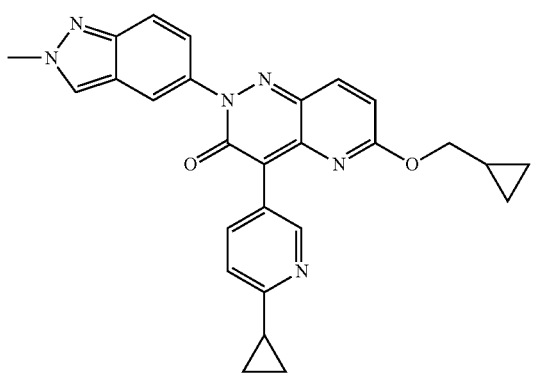 [SMILES: Cn1cc2cc(-n3nc4ccc(OCC5CC5)nc4c(-c4ccc(C5CC5)nc4)c3=O)ccc2n1]<br>6-(cyclopropylmethoxy)-4-(6-cyclopropylpyridin-3-yl)-2-(2-methyl-2H-indazol-5-yl)pyrido[3,2-c]pyridazin-3(2H)-one | LC-MS: m/z 465 (M + H)+.<br>1H NMR (400 MHz, DMSO-d$_6$) δ: 8.77 (d, J = 1.8 Hz, 1H), 8.49 (s, 1H), 8.03 (dd, J = 8.1 Hz, 2.2 Hz, 1H), 8.00 (d, J = 1.3 Hz, 1H), 7.98 (d, J = 9.4 Hz, 1H), 7.70 (d, J = 9.2 Hz, 1H), 7.45 (dd, J = 9.2 Hz, 2.0 Hz, 1H), 7.37 (d, J = 7.6 Hz, 1H), 6.99 (d, J = 9.4 Hz, 1H), 4.22 (s, 3H), 4.16 (d, J = 7.3 Hz, 2H), 2.21-2.11 (m, 1H), 1.25-1.21 (m, 1H), 1.05-0.93 (m, 4H), 0.59-0.47 (m, 2H), 0.33-0.22 (m, 2H). |
| Example 304 | 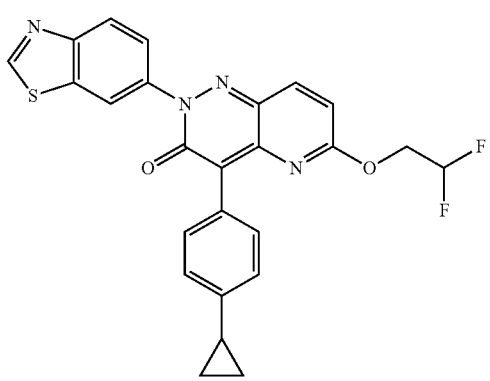<br>2-(benzo[d]thiazol-6-yl)-4-(4-cyclopropylphenyl)-6-(2,2-difluoroethoxy)pyrido[3,2-c]pyridazin-3(2H)-one | LC-MS: m/z 477 (M + H)+.<br>1H NMR (400 MHz, DMSO-d$_6$) δ: 9.53 (s, 1H), 8.52 (d, J = 2.1 Hz, 1H), 8.23 (d, J = 8.7 Hz, 1H), 8.03 (d, J = 9.4 Hz, 1H), 7.83 (dd, J = 8.7 Hz, 2.1 Hz, 1H), 7.70 (d, J = 8.3 Hz, 2H), 7.15 (d, J = 8.4 Hz, 2H), 7.07 (d, J = 9.4 Hz, 1H), 6.40 (tt, J$_{HF}$ = 54.4 Hz, J = 3.3 Hz, 1H), 4.59 (td, J$_{HF}$ = 15.1 Hz, J = 3.3 Hz, 2H), 2.07-1.90 (m, 1H), 1.08-0.95 (m, 2H), 0.84-0.64 (m, 2H). |

The procedure set forth above for General Procedure I (Method C) was used to synthesize the following compounds by using appropriate starting materials:

| Cpd No. | Structure | Characterization |
|---|---|---|
| Example 154 | 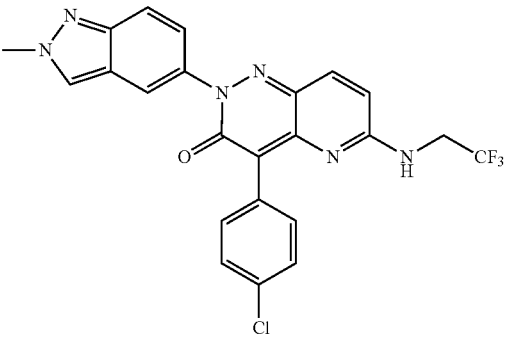<br>4-(4-chlorophenyl)-2-(2-methyl-2H-indazol-5-yl)-6-((2,2,2-trifluoroethyl)amino)pyrido[3,2-c]pyridazin-3(2H)-one | LC-MS (ESI): m/z 485.0 [M + H]+.<br>1H NMR (400 MHz, DMSO-$d_6$) δ: 8.83 (t, J = 6.0 Hz, 1H), 8.47 (s, 1H), 7.96 (d, J = 1.2 Hz, 1H), 7.78-7.76 (m, 3H), 7.68 (d, J = 9.2 Hz, 1H), 7.45-7.41 (m, 3H), 6.92 (d, J = 9.2 Hz, 1H), 4.27-4.17 (m, 2H), 4.21 (s, 3H). |
| Example 155 | 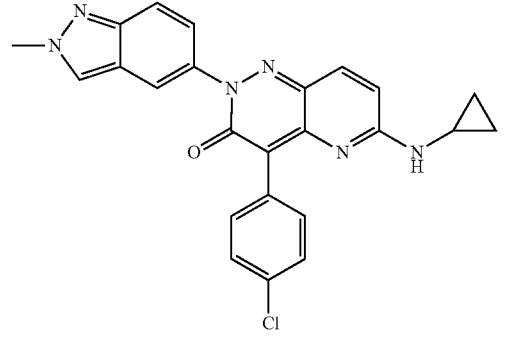<br>4-(4-chlorophenyl)-6-(cyclopropylamino)-2-(2-methyl-2H-indazol-5-yl)pyrido[3,2-c]pyridazin-3(2H)-one | LC-MS (ESI): m/z 443.0 [M + H]+.<br>1H NMR (400 MHz, DMSO-$d_6$) δ: 8.46 (s, 1H), 8.45 (s, 1H), 7.97-7.95 (m, 3H), 7.67 (d, J = 9.2 Hz, 1H), 7.61 (d, J = 9.2 Hz, 1H), 7.45-7.41 (m, 3H), 6.73 (d, J = 8.4 Hz, 1H), 4.22 (s, 3H), 2.88-2.86 (m, 1H), 0.76-0.74 (m, 2H), 0.59-0.54 (m, 2H). |
| Example 156 | 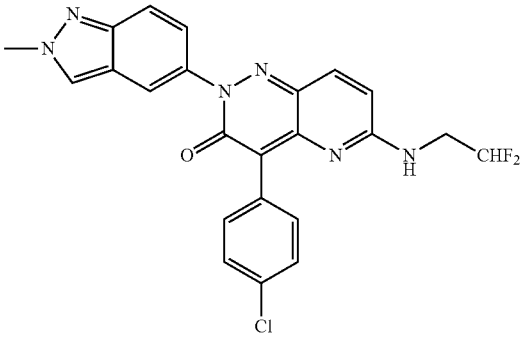<br>4-(4-chlorophenyl)-6-((2,2-difluoroethyl)amino)-2-(2-methyl-2H-indazol-5-yl)pyrido[3,2-c]pyridazin-3(2H)-one | LC-MS (ESI): m/z 467.0 [M + H]+.<br>1H NMR (400 MHz, DMSO-$d_6$) δ: 8.67 (t, J = 6.0 Hz, 1H), 8.47 (s, 1H), 7.96 (d, J = 2.0 Hz, 1H), 7.79 (d, J = 8.8 Hz, 2H), 7.73 (d, J = 9.2 Hz, 1H), 7.68 (d, J = 9.2 Hz, 1H), 7.45-7.41 (m, 3H), 6.90 (d, J = 9.2 Hz, 1H), 6.17 (tt, $J_{HF}$ = 56.0 Hz, J = 3.6 Hz, 1H), 4.22 (s, 3H), 3.79-3.69 (m, 2H). |

| Cpd No. | Structure | Characterization |
|---|---|---|
| Example 157 | 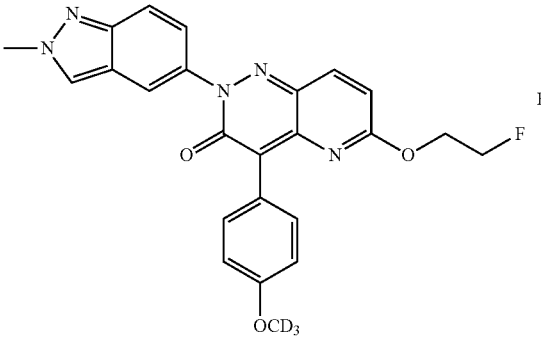<br>6-(2-fluoroethoxy)-4-(4-(methoxy-d3)phenyl)-2-(2-methyl-2H-indazol-5-yl)pyrido[3,2-c]pyridazin-3(2H)-one | LC-MS (ESI): m/z 449.0 [M + H]+. 1H NMR (400 MHz, DMSO-d$_6$) δ: 8.49 (s, 1H), 8.00-7.98 (m, 2H), 7.79 (d, J = 8.8 Hz, 2H), 7.71 (d, J = 9.2 Hz, 1H), 7.45 (dd, J = 9.2 Hz, 2.0 Hz, 1H), 7.01-6.99 (m, 3H), 4.83 (t, J = 4.0 Hz, 1H), 4.71 (t, J = 4.0 Hz, 1H), 4.59 (t, J = 4.0 Hz, 1H), 4.51 (t, J = 4.0 Hz, 1H), 4.23 (s, 3H). |
| Example 158 | 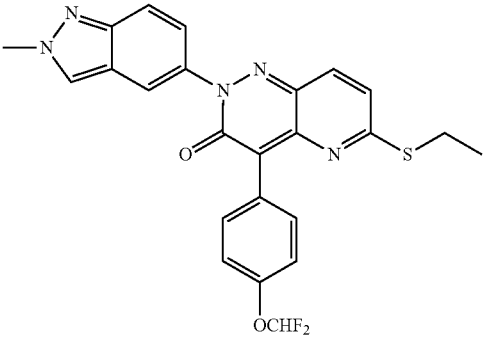<br>4-(4-(difluoromethoxy)phenyl)-6-(ethylthio)-2-(2-methyl-2H-indazol-5-yl)pyrido[3,2-c]pyridazin-3(2H)-one | LC-MS (ESI): m/z 480.2 [M + H]+. 1H NMR (400 MHz, DMSO-d$_6$) δ: 8.50 (s, 1H), 8.03 (d, J = 1.6 Hz, 1H), 7.86-7.83 (m, 3H), 7.71 (d, J = 9.2 Hz, 1H), 7.47 (dd, J = 8.8 Hz, 1.6 Hz, 1H), 7.34 (t, J$_{HF}$ = 74.0 Hz, 1H), 7.26 (d, J = 8.8 Hz, 2H), 7.21 (d, J = 9.2 Hz, 1H), 4.23 (s, 3H), 3.08 (q, J = 7.2 Hz, 2H), 1.22 (t, J = 7.2 Hz, 3H). |
| Example 159 | 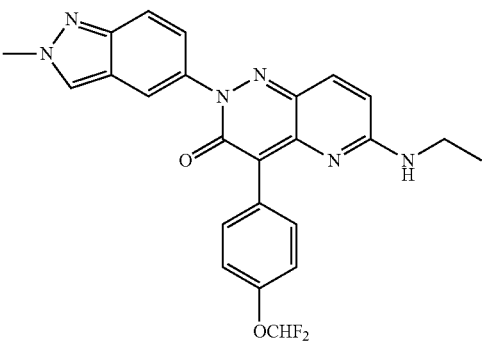<br>4-(4-(difluoromethoxy)phenyl)-6-(ethylamino)-2-(2-methyl-2H-indazol-5-yl)pyrido[3,2-c]pyridazin-3(2H)-one | LC-MS (ESI): m/z 463.0 [M + H]+. 1H NMR (400 MHz, DMSO-d$_6$) δ: 8.46 (s, 1H), 8.32 (t, J = 5.2 Hz, 1H), 7.94 (d, J = 1.2 Hz, 1H), 7.86 (d, J = 8.8 Hz, 2H), 7.67 (d, J = 9.2 Hz, 1H), 7.61 (d, J = 9.6 Hz, 1H), 7.41 (dd, J = 9.2 Hz, 2.0 Hz, 1H), 7.31 (t, J$_{HF}$ = 74.0 Hz, 1H), 7.18 (d, J = 8.8 Hz, 2H), 6.79 (d, J = 9.6 Hz, 1H), 4.22 (s, 3H), 3.45-3.21 (m, 2H), 1.15 (t, J = 7.2 Hz, 3H). |

| Cpd No. | Structure | Characterization |
|---|---|---|
| Example 160 | 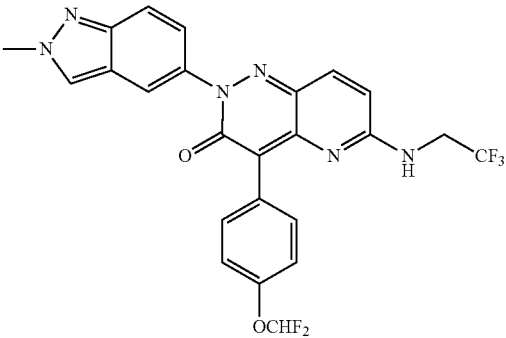<br>4-(4-(difluoromethoxy)phenyl)-2-(2-methyl-2H-indazol-5-yl)-6-((2,2,2-trifluoroethyl)amino)pyrido[3,2-c]pyridazin-3(2H)-one | LC-MS (ESI): m/z 517.1 [M + H]+.<br>1H NMR (400 MHz, DMSO-$d_6$) δ: 8.80 (t, J = 6.4 Hz, 1H) 8.47 (s, 1H), 7.96 (d, J = 2.0 Hz, 1H), 7.81 (d, J = 8.8 Hz, 2H), 7.77 (d, J = 9.6 Hz, 1H), 7.68 (d, J = 9.2 Hz, 1H), 7.42 (dd, J = 9.2 Hz, 2.0 Hz, 1H), 7.32 (t, $J_{HF}$ = 74.0 Hz, 1H), 7.18 (d, J = 8.8 Hz, 2H), 6.91 (d, J = 9.6 Hz, 1H), 4.27-4.18 (m, 2H), 4.21 (s, 3H). |
| Example 161 | 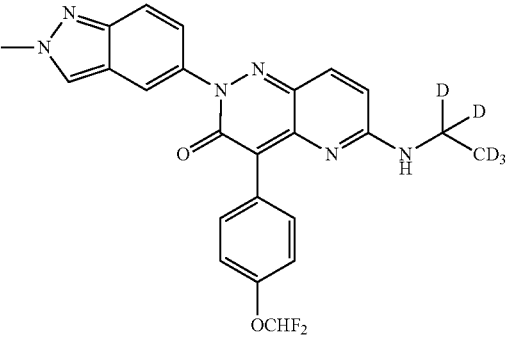<br>4-(4-(difluoromethoxy)phenyl)-6-(ethoxy-$d_5$)-2-(2-methyl-2H-indazol-5-yl)pyrido[3,2-c]pyridazin-3(2H)-one | LC-MS (ESI): m/z 469.0 [M + H]+.<br>1H NMR (400 MHz, DMSO-$d_6$) δ: 8.43 (s, 1H), 7.94 (d, J = 1.6 Hz, 1H), 7.91 (d, J = 9.2 Hz, 1H), 7.80 (d, J = 8.8 Hz, 2H), 7.64 (d, J = 9.2 Hz, 1H), 7.39 (dd, J = 8.8 Hz, 2.0 Hz, 1H), 7.28 (t, $J_{HF}$ = 74.0 Hz, 1H), 7.18 (d, J = 8.8 Hz, 2H), 6.88 (d, J = 9.6 Hz, 1H), 4.16 (s, 3H). |
| Example 162 | 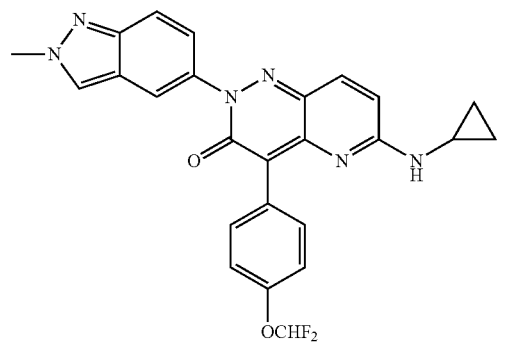<br>6-(cyclopropylamino)-4-(4-(difluoromethoxy)phenyl)-2-(2-methyl-2H-indazol-5-yl)pyrido[3,2-c]pyridazin-3(2H)-one | LC-MS (ESI): m/z 475.1 [M + H]+.<br>1H NMR (400 MHz, DMSO-$d_6$) δ: 8.47 (s, 1H), 8.42 (d, J = 4.4 Hz, 1H), 8.00 (d, J = 9.2 Hz, 2H), 7.95 (d, J = 1.2 Hz, 1H), 7.68 (d, J = 9.2 Hz, 1H), 7.61 (d, J = 9.6 Hz, 1H), 7.42 (dd, J = 9.2 Hz, 2.0 Hz, 1H), 7.30 (t, $J_{HF}$ = 74.0 Hz, 1H), 7.18 (d, J = 8.8 Hz, 2H), 6.73 (d, J = 9.6 Hz, 1H), 4.22 (s, 3H), 2.89-2.86 (m, 1H) 0.77-0.73 (m, 2H), 0.58-0.54 (m, 2H). |

| Cpd No. | Structure | Characterization |
|---|---|---|
| Example 163 | 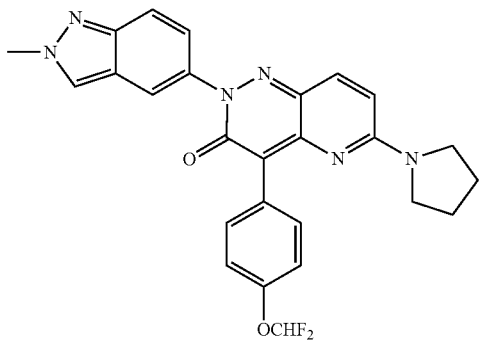<br>4-(4-(difluoromethoxy)phenyl)-2-(2-methyl-2H-indazol-5-yl)-6-(pyrrolidin-1-yl)pyrido[3,2-c]pyridazin-3(2H)-one | 1H NMR (400 MHz, DMSO-$d_6$) δ 8.46 (s, 1H), 7.95 (d, J = 2.0 Hz, 1H), 7.92 (d, J = 8.8 Hz, 2H), 7.73 (d, J = 9.7 Hz, 1H), 7.67 (d, J = 9.2 Hz, 1H), 7.43 (dd, J = 9.1, 2.0 Hz, 1H), 7.31 (t, J = 74.3 Hz, 1H), 7.20-7.15 (m, 2H), 7.06 (d, J = 9.7 Hz, 1H), 4.21 (s, 3H), 3.64 (t, J = 6.8 Hz, 2H), 3.55 (t, J = 6.8 Hz, 2H), 1.99 (p, J = 6.2 Hz, 2H), 1.89 (p, J = 6.4 Hz, 2H). |
| Example 164 | 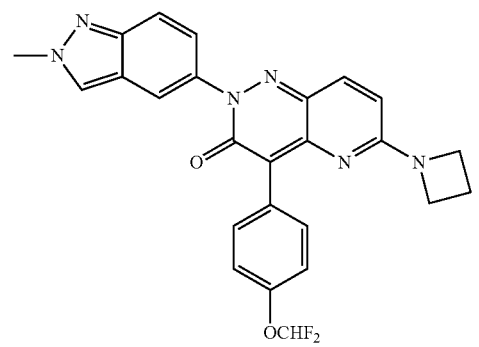<br>6-(azetidin-1-yl)-4-(4-(difluoromethoxy)phenyl)-2-(2-methyl-2H-indazol-5-yl)pyrido[3,2-c]pyridazin-3(2H)-one | 1H NMR (400 MHz, DMSO-$d_6$) δ 8.46 (s, 1H), 7.94 (dd, J = 2.0, 0.8 Hz, 1H), 7.92-7.84 (m, 2H), 7.70 (d, J = 9.5 Hz, 1H), 7.70-7.63 (m, 1H), 7.42 (dd, J = 9.2, 2.0 Hz, 1H), 7.30 (t, J = 74.2 Hz, 1H), 7.16 (d, J = 8.9 Hz, 2H), 6.80 (d, J = 9.5 Hz, 1H), 4.36-4.26 (m, 2H), 4.21 (s, 3H), 4.14-4.04 (m, 2H), 2.34 (h, J = 7.3 Hz, 2H). |
| Example 165 | 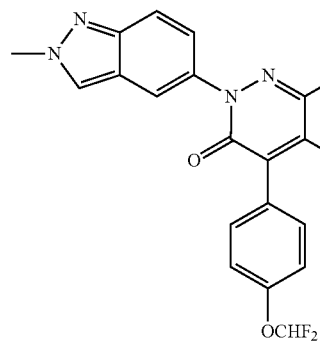<br>4-(4-(difluoromethoxy)phenyl)-2-(2-methyl-2H-indazol-5-yl)-6-((2,2,2-trifluoroethyl)thio)pyrido[3,2-c]pyridazin-3(2H)-one | LC-MS: m/z 534.1 (M + H)+.<br>1H NMR (400 MHz, DMSO-$d_6$) δ: 8.51 (s, 1H), 8.04 (d, J = 1.2 Hz, 1H), 7.99 (d, J = 9.2 Hz, 2H), 7.80 (d, J = 8.8 Hz, 2H), 7.71 (d, J = 9.2 Hz, 1H), 7.48 (dd, J = 9.2, 2.0 Hz, 1H), 7.38 (d, J = 9.2 Hz, 1H), 7.33 (t, $J_{HF}$ = 74.0 Hz, 1H), 7.24 (d, J = 8.8 Hz, 2H), 4.22 (s, 3H), 4.19 (q, J = 10.4 Hz, 2H). |
| Example 305 | 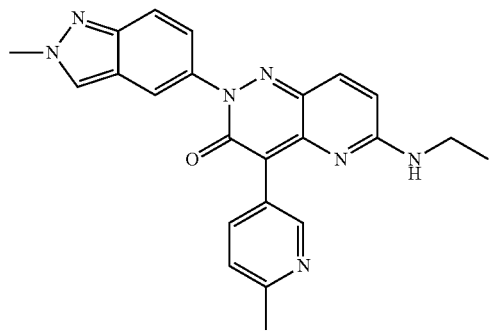 [SMILES: CCNc1ccc2nn(-c3ccc4nn(C)cc4c3)c(=O)c(-c3ccc(C)nc3)c2n1]<br>6-(ethylamino)-2-(2-methyl-2H-indazol-5-yl)-4-(6-methylpyridin-3-yl)pyrido[3,2-c]pyridazin-3(2H)-one | LC-MS: m/z 412 (M + H)+.<br>1H NMR (400 MHz, DMSO-$d_6$) δ: 8.84 (d, J = 2.0 Hz, 1H), 8.46 (s, 1H), 8.36 (t, J = 5.3 Hz, 1H), 8.07 (dd, J = 8.0, 2.2 Hz, 1H), 7.93 (d, J = 1.4 Hz, 1H), 7.66 (d, J = 9.2 Hz, 1H), 7.62 (d, J = 9.2 Hz, 1H), 7.41 (dd, J = 9.2, 2.0 Hz, 1H), 7.27 (d, J = 8.1 Hz, 1H), 6.80 (d, J = 9.5 Hz, 1H), 4.21 (s, 3H), 3.21 (br, 2H), 2.5 (s, 3H), 1.13 (t, J = 7.2 Hz, 3H). |

| Cpd No. | Structure | Characterization |
|---|---|---|
| Example 306 | 6-(cyclopropylamino)-2-(2-methyl-2H-indazol-5-yl)-4-(6-methylpyridin-3-yl)pyrido[3,2-c]pyridazin-3(2H)-one | LC-MS: m/z 424 (M + H)+.<br>1H NMR (400 MHz, DMSO-$d_6$) δ: 8.95 (s, 1H), 8.52 (d, J = 4.1 Hz, 1H), 8.46 (s, 1H), 8.19 (dd, J = 8.1 Hz, 2.1 Hz, 1H), 7.94 (s, 1H), 7.67 (d, J = 9.2 Hz, 1H), 7.61 (d, J = 9.4 Hz, 1H), 7.41 (dd, J = 9.2 Hz, 2.0 Hz, 1H), 7.27 (d, J = 8.2 Hz, 1H), 6.75 (d, J = 9.5 Hz, 1H), 4.21 (s, 3H), 2.89-2.82 (m, 1H), 2.51 (s, 3H), 0.76-0.72 (m, 2H), 0.59-0.54 (m, 2H). |
| Example 307 | 6-(ethylamino)-4-(6-methoxypyridin-3-yl)-2-(2-methyl-2H-indazol-5-yl)pyrido[3,2-c]pyridazin-3(2H)-one | LC-MS: m/z 428 (M + H)+.<br>1H NMR (400 MHz, DMSO-$d_6$) δ: 8.61 (d, J = 2.3 Hz, 1H), 8.45 (s, 1H), 8.36 (d, J = 5.8 Hz, 1H), 8.13 (dd, J = 8.6 Hz, 2.3 Hz, 1H), 7.93 (d, J = 1.3 Hz, 1H), 7.66 (d, J = 9.1 Hz, 1H), 7.60 (d, J = 9.5 Hz, 1H), 7.40 (dd, J = 9.1 Hz, 2.0 Hz, 1H), 6.85 (d, J = 8.9 Hz, 1H), 6.82 (d, J = 8.9 Hz, 1H), 4.21 (s, 3H), 3.89 (s, 3H), 3.45 (s, 2H), 1.14 (t, J = 7.2 Hz, 3H). |
| Example 308 | 6-(cyclopropylamino)-4-(6-methoxypyridin-3-yl)-2-(2-methyl-2H-indazol-5-yl)pyrido[3,2-c]pyridazin-3(2H)-one | LC-MS: m/z 440 (M + H)+.<br>1H NMR (400 MHz, DMSO-$d_6$) δ: 8.72 (s, 1H), 8.60 (s, 1H), 8.46 (s, 1H), 8.27 (d, J = 8.4 Hz, 1H), 7.94 (s, 1H), 7.67 (d, J = 9.1 Hz, 1H), 7.60 (d, J = 9.4 Hz, 1H), 7.41 (dd, J = 9.2 Hz, 1.9 Hz, 1H), 6.83 (s, 1H), 6.78 (s, 1H), 4.21 (s, 3H), 3.88 (s, 3H), 2.89-2.82 (m, 1H), 0.76-0.72 (m, 2H), 0.59-0.54 (m, 2H). |

| Cpd No. | Structure | Characterization |
|---|---|---|
| Example 309 | 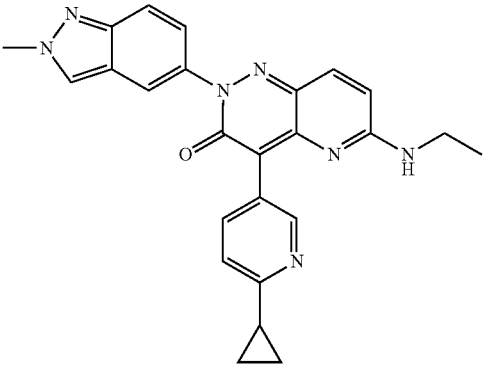 [SMILES: CCNc1ccc2nn(-c3ccc4nn(C)cc4c3)c(=O)c(-c3ccc(C4CC4)nc3)c2n1]<br>4-(6-cyclopropylpyridin-3-yl)-6-(ethylamino)-2-(2-methyl-2H-indazol-5-yl)pyrido[3,2-c]pyridazin-3(2H)-one | LC-MS: m/z 438 (M + H)+.<br>1H NMR (400 MHz, DMSO-$d_6$) δ: 8.77 (d, J = 2.0 Hz, 1H), 8.45 (s, 1H), 8.33 (d, J = 5.5 Hz, 1H), 8.03 (dd, J = 8.1 Hz, 2.2 Hz, 1H), 7.93 (d, J = 1.4 Hz, 1H), 7.66 (d, J = 9.1 Hz, 1H), 7.60 (d, J = 9.5 Hz, 1H), 7.40 (dd, J = 9.2 Hz, 2.0 Hz, 1H), 7.30 (d, J = 8.2 Hz, 1H), 6.78 (d, J = 9.6 Hz, 1H), 4.20 (s, 3H), 3.24 (br, 2H), 2.14-2.11 (m, 1H), 1.14 (t, J = 7.2 Hz, 3H), 0.97-0.94 (m, 4H). |
| Example 310 | 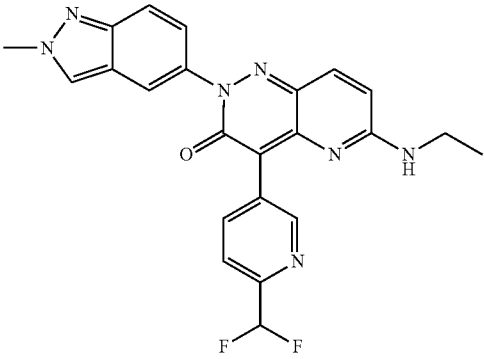 [SMILES: CCNc1ccc2nn(-c3ccc4nn(C)cc4c3)c(=O)c(-c3ccc(C(F)F)nc3)c2n1]<br>4-(6-(difluoromethyl)pyridin-3-yl)-6-(ethylamino)-2-(2-methyl-2H-indazol-5-yl)pyrido[3,2-c]pyridazin-3(2H)-one | LC-MS: m/z 448 (M + H)+.<br>1H NMR (400 MHz, DMSO-$d_6$) δ: 9.06 (s, 1H), 8.52-8.43 (m, 2H), 8.38 (dd, J = 8.1 Hz, 1.9 Hz, 1H), 7.96 (d, J = 1.4 Hz, 1H), 7.73 (d, J = 8.2 Hz, 1H), 7.67 (d, J = 9.2 Hz, 1H), 7.65 (d, J = 9.6 Hz, 1H), 7.42 (dd, J = 9.1 Hz, 2.0 Hz, 1H), 6.99 (t, $J_{HF}$ = 55.1 Hz, 1H), 6.82 (d, J = 9.6 Hz, 1H), 4.21 (s, 3H), 3.34 (br, 2H), 1.14 (t, J = 7.2 Hz, 3H). |
| Example 311 | 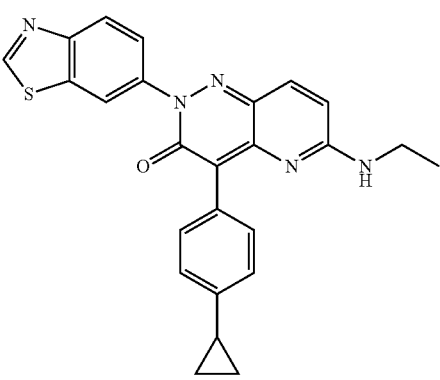 [SMILES: CCNc1ccc2nn(-c3ccc4ncsc4c3)c(=O)c(-c3ccc(C4CC4)cc3)c2n1]<br>2-(benzo[d]thiazol-6-yl)-4-(4-cyclopropylphenyl)-6-(ethylamino)pyrido[3,2-c]pyridazin-3(2H)-one | LC-MS: m/z 440 (M + H)+.<br>1H NMR (400 MHz, DMSO-$d_6$) δ: 9.49 (s, 1H), 8.46 (d, J = 2.0 Hz, 1H), 8.29 (t, J = 5.7 Hz, 1H), 8.19 (d, J = 8.6 Hz, 1H), 7.77 (dd, J = 8.8 Hz, 2.1 Hz, 1H), 7.69 (d, J = 8.3 Hz, 2H), 7.59 (d, J = 9.5 Hz, 1H), 7.07 (d, J = 8.3 Hz, 2H), 6.79 (d, J = 9.6 Hz, 1H), 3.41 (br, 2H), 1.98-1.92 (m, 1H), 1.14 (t, J = 7.2 Hz, 3H), 1.02-0.91 (m, 2H), 0.76-0.62 (m, 2H). |

| Cpd No. | Structure | Characterization |
|---|---|---|
| Example 312 | 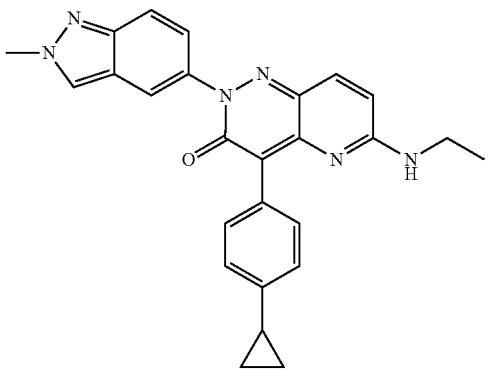 [SMILES: CCNc1ccc2nn(-c3ccc4nn(C)cc4c3)c(=O)c(-c3ccc(C4CC4)cc3)c2n1]<br>4-(4-cyclopropylphenyl)-6-(ethylamino)-2-(2-methyl-2H-indazol-5-yl)pyrido[3,2-c]pyridazin-3(2H)-one | LC-MS: m/z 437 (M + H)+.<br>1H NMR (400 MHz, DMSO-$d_6$) δ: 8.45 (s, 1H), 8.22 (t, J = 5.6 Hz, 1H), 7.91 (s, 1H), 7.67 (t, J = 9.3 Hz, 3H), 7.58 (d, J = 9.5 Hz, 1H), 7.39 (dd, J = 9.1 Hz, 2.0 Hz, 1H), 7.06 (d, J = 8.4 Hz, 2H), 6.76 (d, J = 9.5 Hz, 1H), 4.21 (s, 3H), 3.30 (br, 2H), 2.02-1.87 (m, 1H), 1.14 (t, J = 7.2 Hz, 3H), 1.02-0.90 (m, 2H), 0.77-0.64 (m, 2H). |
| Example 313 | 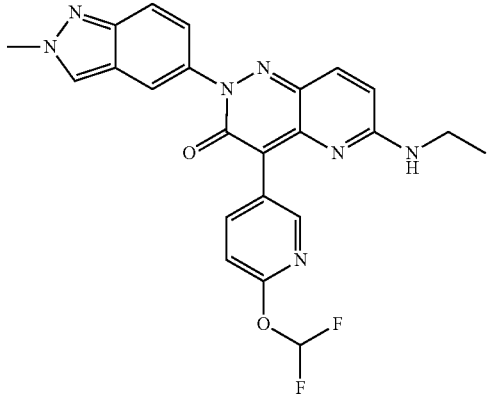 [SMILES: CCNc1ccc2nn(-c3ccc4nn(C)cc4c3)c(=O)c(-c3ccc(OC(F)F)nc3)c2n1]<br>4-(6-(difluoromethoxy)pyridin-3-yl)-6-(ethylamino)-2-(2-methyl-2H-indazol-5-yl)pyrido[3,2-c]pyridazin-3(2H)-one | LC-MS: m/z 464 (M + H)+.<br>1H NMR (400 MHz, DMSO-$d_6$) δ: 8.63 (d, J = 2.3 Hz, 1H), 8.43 (s, 1H), 8.30 (dd, J = 8.6 Hz, 2.3 Hz, 1H), 7.92 (s, 1H), 1.12 (t, $J_{HF}$ = 73.2 Hz, 1H), 7.66 (d, J = 9.1 Hz, 1H), 7.61 (d, J = 9.5 Hz, 1H), 7.40 (dd, J = 9.1 Hz, 2.0 Hz, 1H), 7.11 (d, J = 8.6 Hz, 1H), 6.79 (d, J = 9.5 Hz, 1H), 4.18 (s, 3H), 3.34 (q, J = 7.2 Hz, 2H), 1.12 (t, J = 7.2 Hz, 3H). |
| Example 314 | 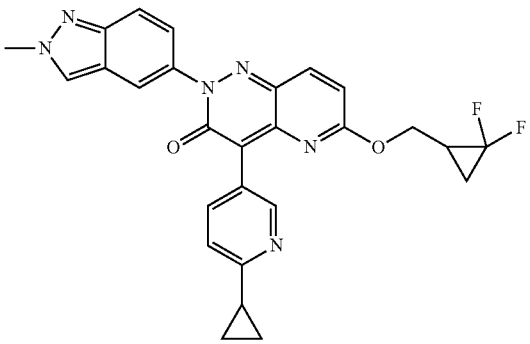<br>4-(6-cyclopropylpyridin-3-yl)-6-((2,2-difluorocyclopropyl)methoxy)-2-(2-methyl-2H-indazol-5-yl)pyrido[3,2-c]pyridazin-3(2H)-one | LC-MS: m/z 501 (M + H)+.<br>1H NMR (400 MHz, DMSO-$d_6$) δ: 8.77 (d, J = 1.9 Hz, 1H), 8.50 (s, 1H), 8.07-7.98 (m, 3H), 7.70 (d, J = 9.1 Hz, 1H), 7.45 (dd, J = 9.2 Hz, 2.0 Hz, 1H), 7.38 (d, J = 7.8 Hz, 1H), 7.02 (d, J = 9.4 Hz, 1H), 4.57-4.46 (m, 1H), 4.35-4.14 (m, 4H), 2.26-2.11 (m, 2H), 1.71-1.98 (m, 1H), 1.50-1.45 (m, 1H), 1.02-0.83 (m, 4H). |

The procedure set forth above for General Procedure I (Method D) was used to synthesize the following compounds by using appropriate starting materials:

| Cpd No. | Structure | Characterization |
|---|---|---|
| Example 315 | 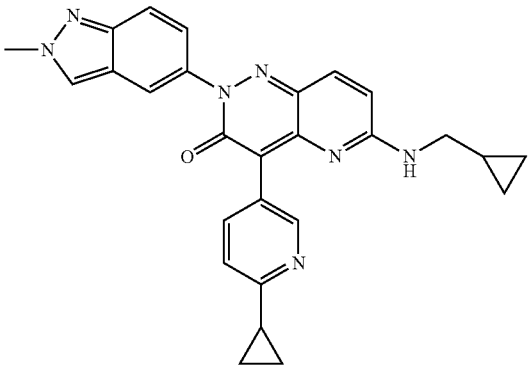 [SMILES: Cn1cc2cc(-n3nc4ccc(NCC5CC5)nc4c(-c4ccc(C5CC5)nc4)c3=O)ccc2n1]<br>6-((cyclopropylmethyl)amino)-4-(6-cyclopropylpyridin-3-yl)-2-(2-methyl-2H-indazol-5-yl)pyrido[3,2-c]pyridazin-3(2H)-one | LC-MS: m/z 464 (M + H)+.<br>1H NMR (400 MHz, DMSO-$d_6$) δ: 8.75 (d, J = 2.2 Hz, 1H), 8.48 (t, J = 5.7 Hz, 1H), 8.45 (s, 1H), 8.00 (dd, J = 8.1 Hz, 2.1 Hz, 1H), 7.93 (d, J = 1.3 Hz, 1H), 7.66 (d, J = 9.0 Hz, 1H), 7.61 (d, J = 9.5 Hz, 1H), 7.40 (dd, J = 9.2 Hz, 1.9 Hz, 1H), 7.30 (d, J = 8.0 Hz, 1H), 6.85 (d, J = 9.5 Hz, 1H), 4.20 (s, 3H), 3.20 (t, J = 6.2 Hz, 2H), 2.15-2.09 (m, 1H), 1.12-0.86 (m, 5H), 0.50-0.36 (m, 2H), 0.22-0.09 (m, 2H). |
| Example 316 | 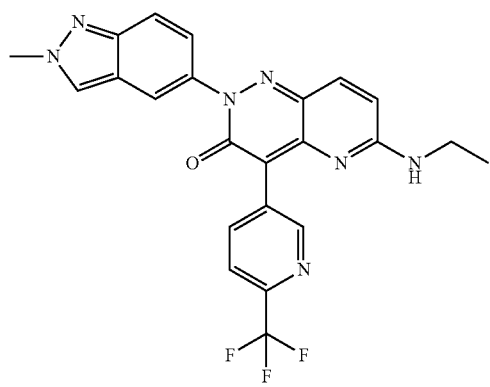 [SMILES: CCNc1ccc2nn(-c3ccc4nn(C)cc4c3)c(=O)c(-c3ccc(C(F)(F)F)nc3)c2n1]<br>6-(ethylamino)-2-(2-methyl-2H-indazol-5-yl)-4-(6-(trifluoromethyl)pyridin-3-yl)pyrido[3,2-c]pyridazin-3(2H)-one | LC-MS: m/z 466 (M + H)+.<br>1H NMR (400 MHz, DMSO-$d_6$) δ: 9.15 (s, 1H), 8.53 (t, J = 5.2 Hz, 1H), 8.48 (d, J = 7.2 Hz, 2H), 8.01-7.88 (m, 2H), 7.66 (t, J = 8.4 Hz, 2H), 7.43 (dd, J = 9.2 Hz, 1.9 Hz, 1H), 6.83 (d, J = 9.6 Hz, 1H), 4.21 (s, 3H), 3.31 (br, 2H), 1.14 (t, J = 7.2 Hz, 3H). |
| Example 317 | 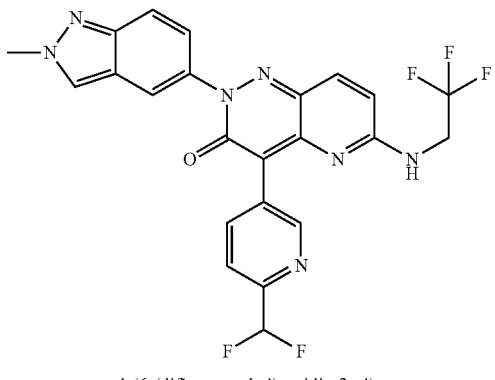<br>4-(6-(difluoromethyl)pyridin-3-yl)-2-(2-methyl-2H-indazol-5-yl)-6-((2,2,2-trifluoroethyl)amino)pyrido[3,2-c]pyridazin-3(2H)-one | LC-MS: m/z 502 (M + H)+.<br>1H NMR (400 MHz, DMSO-$d_6$) δ: 9.06 (s, 1H), 9.01 (s, 1H), 8.48 (s, 1H), 8.33 (d, J = 9.7 Hz, 1H), 7.98 (d, J = 1.7 Hz, 1H), 7.81 (d, J = 9.3 Hz, 1H), 7.73 (d, J = 7.9 Hz, 1H), 7.69 (d, J = 9.2 Hz, 1H), 7.44 (d, J = 9.1 Hz, 1.9 Hz, 1H), 7.00 (d, J = 3.6 Hz, 1H), 6.92 (t, $J_{HF}$ = 55.2 Hz, 1H), 4.21 (s, 5H). |

| Cpd No. | Structure | Characterization |
|---|---|---|
| Example 318 | 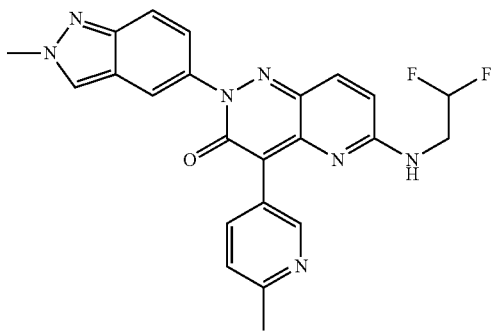 [SMILES: Cc1ccc(-c2c(=O)n(-c3ccc4nn(C)cc4c3)nc3ccc(NCC(F)F)nc23)cn1]<br>6-((2,2-difluoroethyl)amino)-2-(2-methyl-2H-indazol-5-yl)-4-(6-methylpyridin-3-yl)pyrido[3,2-c]pyridazin-3(2H)-one | LC-MS: m/z 448 (M + H)+.<br>1H NMR (400 MHz, DMSO-$d_6$) δ: 8.79 (d, J = 1.8 Hz, 1H), 8.73 (t, J = 5.2 Hz, 1H), 8.46 (s, 1H), 8.04 (dd, J = 8.0 Hz, 2.2 Hz, 1H), 7.95 (d, J = 1.4 Hz, 1H), 7.71 (d, J = 9.2 Hz, 1H), 7.68 (dd, J = 9.2 Hz, 1H), 7.41 (dd, J = 9.2 Hz, 2.0 Hz, 1H), 7.27 (d, J = 8.2 Hz, 1H), 6.92 (d, J = 9.6 Hz, 1H), 6.15 (tt, $J_{HF}$ = 56.0 Hz, J = 3.8 Hz, 1H), 4.21 (s, 3H), 3.75 (t, $J_{HF}$ = 15.8 Hz, 2H), 2.51 (s, 3H). |
| Example 319 | 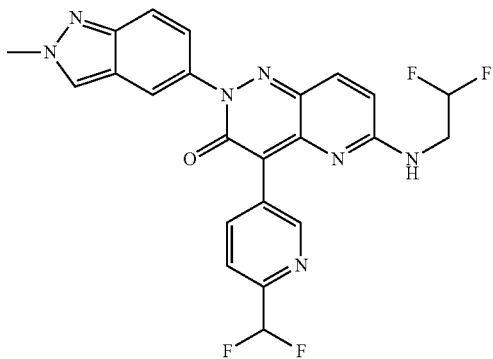 [SMILES: Cn1cc2cc(-n3nc4ccc(NCC(F)F)nc4c(-c4ccc(C(F)F)nc4)c3=O)ccc2n1]<br>6-(ethylamino)-2-(2-methyl-2H-indazol-5-yl)-4-(6-(methyl-$d_3$)pyridin-3-yl)pyrido[3,2-c]pyridazin-3(2H)-one | LC-MS: m/z 484 (M + H)+.<br>1H NMR (400 MHz, DMSO-$d_6$) δ: 9.02 (s, 1H), 8.81 (t, J = 5.2 Hz, 1H), 8.48 (s, 1H), 8.36 (d, J = 9.7 Hz, 1H), 7.98 (d, J = 1.3 Hz, 1H), 7.76 (d, J = 9.5 Hz, 1H), 7.73 (d, J = 8.2 Hz, 1H), 7.69 (d, J = 9.1 Hz, 1H), 7.43 (dd, J = 9.1 Hz, 1.9 Hz, 1H), 7.00 (t, $J_{HF}$ = 55.0 Hz, 1H), 6.94 (d, J = 9.5 Hz, 1H), 6.16 (tt, $J_{HF}$ = 56.4 Hz, J = 3.8 Hz, 1H), 4.21 (s, 3H), 3.75 (t, $J_{HF}$ = 15.8 Hz, 2H). |
| Example 320 | 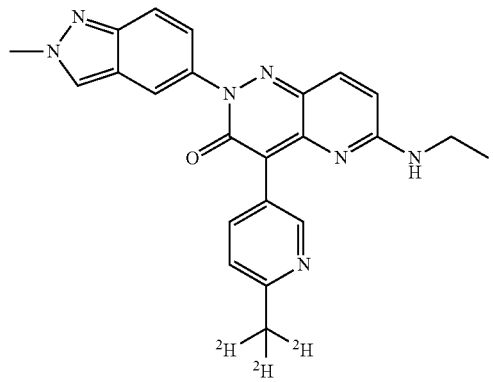 [SMILES: [2H]C([2H])([2H])c1ccc(-c2c(=O)n(-c3ccc4nn(C)cc4c3)nc3ccc(NCC)nc23)cn1]<br>6-(ethylamino)-2-(2-methyl-2H-indazol-5-yl)-4-(6-(methyl-$d_3$)pyridin-3-yl)pyrido[3,2-c]pyridazin-3(2H)-one<br>Prepared using Intermediate (6-(methyl-$d_3$)pyridin-3-yl)boronic acid as described. | LC-MS: m/z 415 (M + H)+.<br>1H NMR (400 MHz, DMSO-$d_6$) δ (ppm): 8.85 (d, J = 1.5 Hz, 1H), 8.46 (s, 1H), 8.38 (s, 1H), 8.07 (dd, J = 8.1 Hz, 2.2 Hz, 1H), 7.94 (d, J = 1.4 Hz, 1H), 7.66 (d, J = 9.2 Hz, 1H), 7.61 (d, J = 9.6 Hz, 1H), 7.41 (dd, J = 9.1 Hz, 2.0 Hz, 1H), 7.27 (d, J = 8.1 Hz, 1H), 6.80 (d, J = 9.5 Hz, 1H), 4.21 (s, 3H), 3.33 (q, J = 7.2 Hz, 2H, overlapped with H2O peak), 1.14 (t, J = 7.2 Hz, 3H). |

Synthesis of Intermediate
(6-(methyl-d₃)pyridin-3-yl)boronic Acid

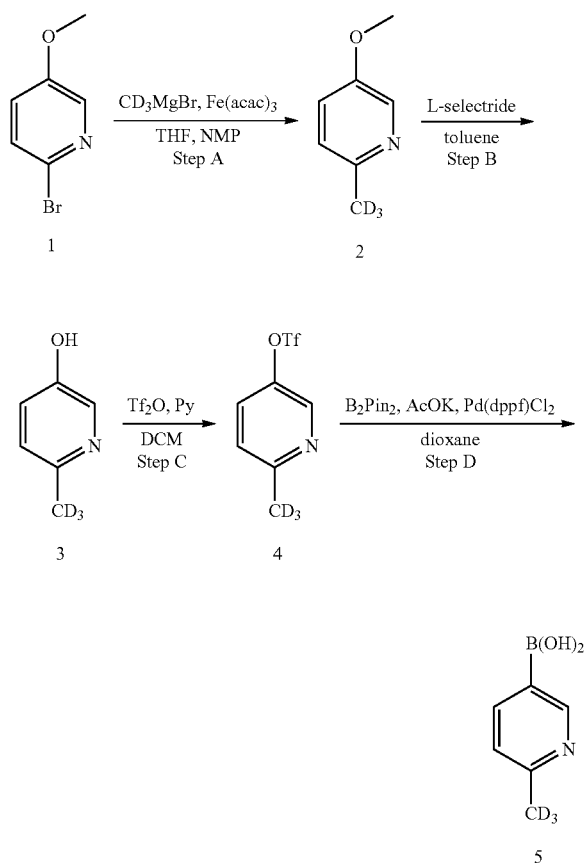

Step A: 5-methoxy-2-(methyl-d₃)pyridine

To a solution of 2-bromo-5-methoxypyridine (7 g, 37.2 mmol, 1.0 eq.) and Fe(acac)₃ (1.31 g, 3.71 mmol, 0.1 eq.) in anhydrous THF (70 mL) was added CD₃MgI (1 M in THF) (93 mL, 93 mmol, 2.5 eq.) dropwise at 0° C. under N₂ atmosphere, the resulting mixture was stirred for 3 hrs at 0° C. After the completion, the reaction was quenched by adding NH₄Cl (sat. aq.) (200 mL), then extracted with EtOAc (70 mL×3), the combined organic layers were washed with brine (100 mL), dried over Na₂SO₄ and concentrated under reduced pressure, the residue was purified by flash column chromatography on silica gel to give 5-methoxy-2-(methyl-d₃)pyridine (4 g, 85%) as a colorless oil. LC-MS (ESI): m/z 127 [M+H]$^+$.

Step B: 6-(methyl-d₃)pyridin-3-ol

To a solution of 5-methoxy-2-(methyl-d₃)pyridine (1.6 g, 12.6 mmol, 1.0 eq.) in dry toluene (20 mL) was added L-Selectride (1 M in THF) (37.8 mL, 37.8 mmol, 3.0 eq.) via dropping funnel at 0° C. dropwise, after the addition, the reaction mixture was allowed to warm to room temperature, then moved to pre-heated oil bath (110° C.) stirred for additional 3 hrs. After the completion, the reaction was cooled down to 0° C. again, quenched by adding MeOH (10 mL) carefully, the resulting mixture was concentrated under reduced pressure, the residue was purified by flash column chromatography on silica gel to give 6-(methyl-d₃)pyridin-3-ol (1.2 g, 84.3%) as a pale-yellow solid. LC-MS (ESI): m/z 113 [M+H]$^+$.

Step C: 6-(methyl-d₃)pyridin-3-yl trifluoromethanesulfonate

To a solution of 6-(methyl-d₃)pyridin-3-ol (500 mg, 4.46 mmol, 1.0 eq.) and pyridine (0.54 mL, 6.69 mmol, 1.5 eq.) in dry DCM (10 mL), was added triflic anhydride (1.13 mL, 6.69 mmol, 1.5 eq.) via the syringe at 0° C. dropwise. The resulting mixture was allowed to warm to room temperature and stirred for additional 2 hrs. After completion, the reaction was quenched by adding H₂O (20 mL), then extracted with EtOAc (20 mL×3), the combined organic layers were washed with dilute HCl (0.5 N, aq.) (20 mL), brine (20 mL), dried over Na₂SO₄ and concentrated under reduced pressure, the residue was purified by flash column chromatography on silica gel to give 6-(methyl-d₃)pyridin-3-yl trifluoromethanesulfonate (1.0 g, 91%) as a colorless oil. LC-MS (ESI): m/z 245 [M+H]$^+$.

Step D: (6-(methyl-d₃)pyridin-3-yl)boronic acid

To a solution of 6-(methyl-d₃)pyridin-3-yl trifluoromethanesulfonate (1.0 g, 4.09 mmol, 1.0 eq.) in dry 1,4-dioxane (10 ml), was added bis(pinacolato)diboron (2.08 g, 8.2 mmol, 2.0 eq.), KOAc (1.6 g, 16.4 mmol, 4.0 eq.) and Pd(dppf)Cl₂ (300 mg, 0.41 mmol, 0.1 eq.). The resulting mixture was stirred at 100° C. under N₂ atmosphere for 16 hrs. After the completion, the crude mixture was filtered through a short pad of Celite®, the filtrate was concentrated under reduced pressure, the residue was purified by RP-prep-HPLC to give (6-(methyl-d₃)pyridin-3-yl)boronic acid (460 mg, 80%). LC-MS (ESI): m/z 141 [M+H]$^+$.

General Procedure II:

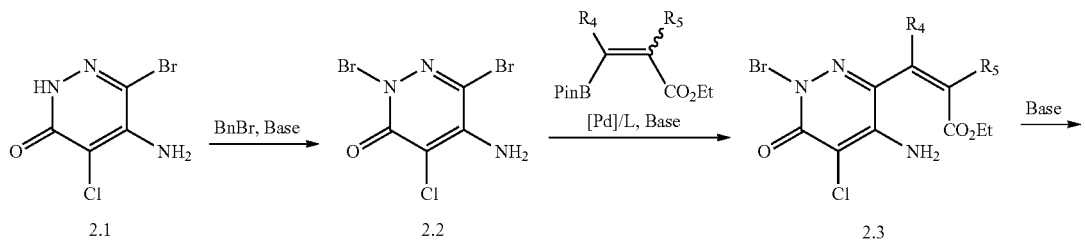

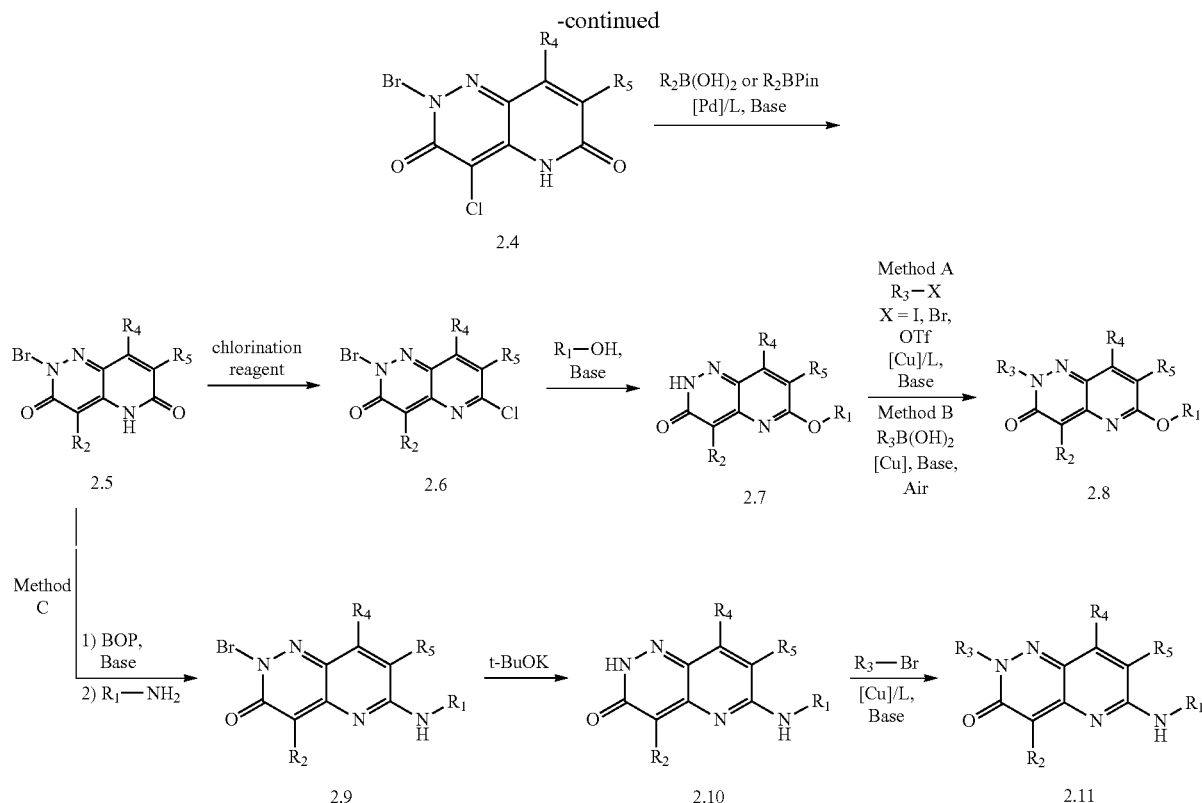

Compounds of structure 2.8 and 2.11 were obtained through the scheme depicted as General Procedure II. Beginning with pyridazinone 2.1, the heterocycle was benzylated to generated compound 2.2. The desired $R_4$ and $R_5$ groups were introduced using a Suzuki cross-coupling to afford compounds of structure 2.3. Compound 2.3 was then cyclized under basic conditions to generate bicyclic compound 2.4. The desired $R_2$ group was introduced using a Suzuki coupling to generate compound 2.5. Compound 2.5 was then chlorinated to generate aryl-chloride 2.6. The desired $R_1$ group was introduced via nucleophilic aromatic substitution, which concurrently debenzylated the heterocyclic core to generate compound 2.7. Lastly, the desired $R_3$ group was introduced using an Ullmann coupling (Method A) or a Chan-Lam coupling (Method B) to afford compounds of structure 2.8. Alternatively, Compound 2.5 could be activated with BOP and reacted with the desired $R_1$-amine to afford heterocycle 2.9 (Method C). The benzyl group was removed using t-BuOK to afford heterocycle 2.10 and the desired $R_3$ group was introduced using an Ullmann coupling to afford compounds of structure 2.11.

General Procedure IIa (Method C):

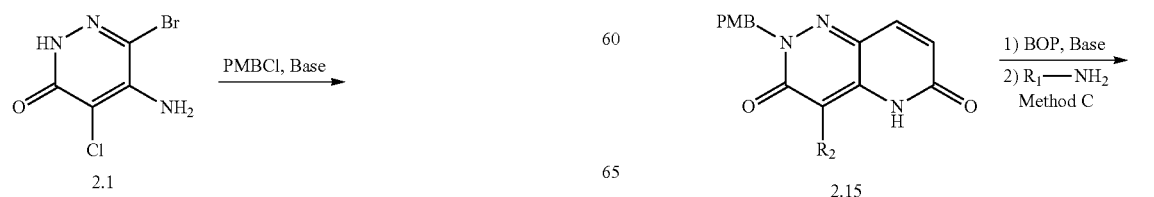

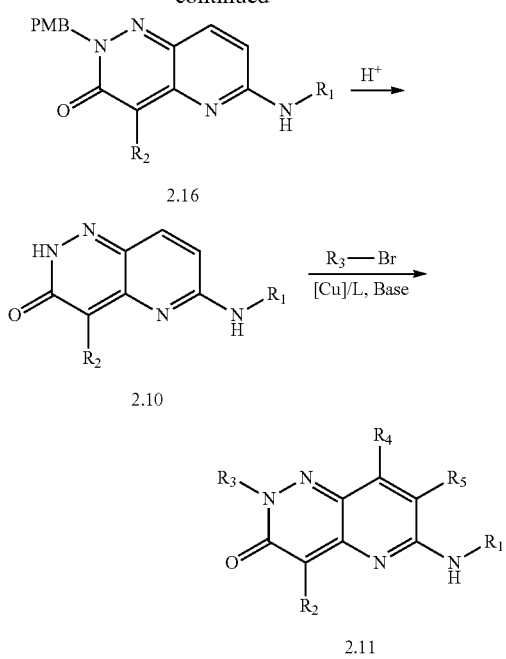

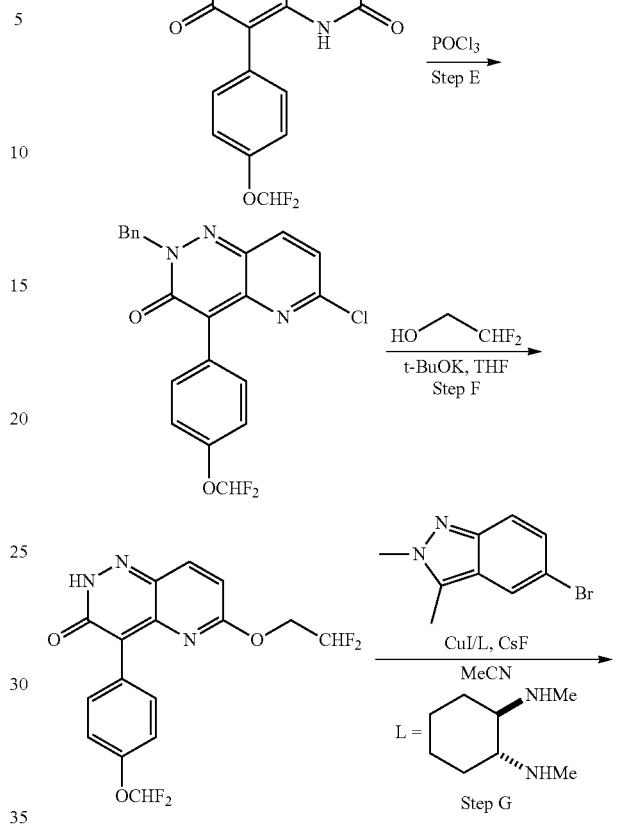

General Procedure IIa (Method C) was later developed using PMB as an alternative protecting group to the Bn protecting group shown in General Procedure II (Method C). Deprotection of heterocycle 2.16 under acidic conditions led to a convergent synthesis of compound structures 2.11.

Preparation of Example 166 Via General Procedure II (Method A)

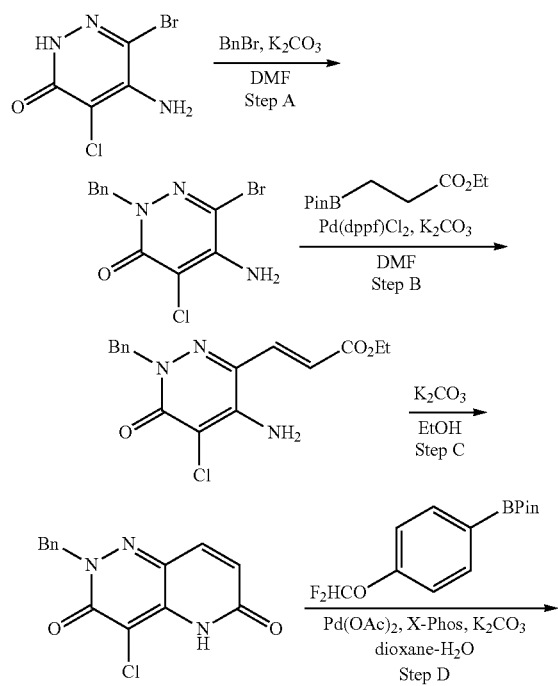

Step A: 5-amino-2-benzyl-6-bromo-4-chloro-pyridazin-3(2H)-one

To a solution of 5-amino-6-bromo-4-chloropyridazin-3(2H)-one (3 g, 13.4 mmol, 1.0 eq.), $K_2CO_3$ (3.7 g, 26.8 mmol, 2.0 eq.) in DMF (50 mL) was added BnBr (2.5 g, 14.7 mmol, 1.1 eq.), the reaction mixture stirred at 80° C. overnight. The reaction mixture was diluted with water (50 mL) and extracted with EtOAc (50 mL×3), the combined organic layers were washed with brine (50 mL), dried over $Na_2SO_4$ and concentrated under reduced pressure, the residue was purified by flash column chromatography on silica gel to afford 5-amino-2-benzyl-6-bromo-4-chloropyridazin-3(2H)-one as a white solid (2.46 g, 59% yield).

LC-MS (ESI) m/z 314, 316 [M+H]+.

Step B: ethyl (E)-3-(4-amino-1-benzyl-5-chloro-6-oxo-1,6-dihydropyridazin-3-yl)acrylate To a solution of 5-amino-2-benzyl-6-bromo-4-chloropyridazin-3(2H)-one (2.46 g, 7.8 mmol, 1.0 eq.), $K_2CO_3$ (2.2 g, 15.6 mmol, 2.0 eq.), ethyl (E)-3-(4,4,5,5-tetramethyl-1,3,2-dioxaborolan-2-yl)acrylate (1.94 g, 8.6 mmol, 1.1 eq.) in DMF (40 mL) was added $Pd(dppf)Cl_2$ (0.57 g, 0.8 mmol, 0.1 eq.) under $N_2$ atmosphere, the reaction mixture stirred at 100° C. for 3 hrs. The reaction mixture was diluted with $H_2O$ (50 mL) and extracted with EtOAc (50 mL×3), the combined organic layers were washed with brine (50 mL), dried over $Na_2SO_4$ and concentrated under reduced pressure, the residue was purified by column chromatography to afford on silica gel to give ethyl (E)-3-(4-amino-1-benzyl-5-chloro-6-oxo-1,6-dihydropyridazin-3-yl)acrylate as a brown solid (1.89 g, 71% yield). LC-MS (ESI): m/z 334 [M+H]$^+$.

Step C: 2-benzyl-4-chloropyrido[3,2-c]pyridazine-3,6(2H,5H)-dione

To a stirred solution of ethyl (E)-3-(4-amino-1-benzyl-5-chloro-6-oxo-1,6-dihydropyridazin-3-yl)acrylate (1.89 g, 5.66 mmol, 1.0 eq.) in EtOH (20 mL) was added $K_2CO_3$ (2.34 g, 16.98 mmol, 3.0 eq.), the reaction mixture stirred at 80° C. overnight. The reaction mixture was diluted with water (30 mL) and extracted with EtOAc (30 mL×3), the combined organic layers were dried over $Na_2SO_4$ and concentrated under reduced pressure to give crude 2-benzyl-4-chloropyrido[3,2-c]pyridazine-3,6(2H,5H)-dione as a brown solid (1.5 g), which used in next step without further purification. LC-MS (ESI): m/z 288 [M+H]$^+$.

Step D: 2-benzyl-4-(4-(difluoromethoxy)phenyl)pyrido[3,2-c]pyridazine-3,6(2H,5H)-dione To a stirred solution of 2-benzyl-4-chloropyrido[3,2-c]pyridazine-3,6(2H,5H)-dione (1.5 g, 5.2 mmol, 1.0 eq.), 2-(4-(difluoromethoxy)phenyl)-4,4,5,5-tetramethyl-1,3,2-dioxaborolane (2 g, 7.2 mmol, 1.4 eq.), $K_2CO_3$ (1.54 g, 11.1 mmol, 2.1 eq.), X-Phos (0.52 g, 1.1 mmol, 0.2 eq.) in dioxane/$H_2O$ mixture (88 mL, 10/1, v/v) was added $Pd(OAc)_2$ (0.12 g, 0.55 mmol, 0.1 eq.) under $N_2$ atmosphere. The reaction mixture stirred at 110° C. overnight.

The reaction mixture was concentrated under reduced pressure, purified by column chromatography on silica gel to afford 2-benzyl-4-(4-(difluoromethoxy)phenyl)pyrido[3,2-c]pyridazine-3,6(2H,5H)-dione (1.4 g, 68% yield) as a white solid. LC-MS (ESI): m/z 396 [M+H]$^+$.

Step E: 2-benzyl-6-chloro-4-(4-(difluoromethoxy)phenyl)pyrido[3,2-c]pyridazin-3(2H)-one 2-benzyl-4-(4-(difluoromethoxy)phenyl)pyrido[3,2-c]pyridazine-3,6(2H,5H)-dione (400 mg, 1.01 mmol, 1.0 eq) was dissolved in $POCl_3$ (4 mL), the resulting mixture stirred at 80° C. for 4 hrs. Excess $POCl_3$ was removed under reduced pressure and the residue was pour onto ice-cooled $NaHCO_3$ (sat. aq.) (20 mL) and extracted with DCM (30 mL×3), the combined organic layers were dried over $Na_2SO_4$ and concentrated under reduced pressure to give crude 2-benzyl-6-chloro-4-(4-(difluoromethoxy)phenyl)pyrido[3,2-c]pyridazin-3(2H)-one, as a yellow solid (400 mg, 95% yield). LC-MS (ESI): m/z 414 [M+H]$^+$.

Step F: 6-(2,2-difluoroethoxy)-4-(4-(difluoromethoxy)phenyl)pyrido[3,2-c]pyridazin-3(2H)-one To a solution of 2-benzyl-6-chloro-4-(4-(difluoromethoxy)phenyl)pyrido[3,2-c]pyridazin-3(2H)-one (400 mg, 0.97 mmol, 1.0 eq.), 2,2-difluoroethan-1-ol (396 mg, 4.8 mmol, 5.0 eq.) in anhy. THF (8 mL) was added t-BuOK (541 mg, 4.8 mmol, 5.0 eq.) in several portions at 0° C., after addition, the reaction mixture stirred at room temperature overnight. The reaction mixture was diluted with $H_2O$ (10 mL) and extracted with EtOAc (30 mL×3), the combined organic layers were dried over $Na_2SO_4$ and concentrated under reduced pressure, the residue was purified by flash column chromatography on silica gel to give 6-(2,2-difluoroethoxy)-4-(4-(difluoromethoxy)phenyl)pyrido[3,2-c]pyridazin-3(2H)-one as a yellow solid (150 mg, 42% yield). LC-MS (ESI): m/z 370 [M+H]$^+$.

Step G: 6-(2,2-difluoroethoxy)-4-(4-(difluoromethoxy)phenyl)-2-(2,3-dimethyl-2H-indazol-5-yl)pyrido[3,2-c]pyridazin-3(2H)-one (Method A)

To a stirred suspension of 6-(2,2-difluoroethoxy)-4-(4-(difluoromethoxy)phenyl)pyrido[3,2-c]pyridazin-3(2H)-one (70 mg, 0.19 mmol, 1.0 eq.) in MeCN (3 mL) was added 5-bromo-2,3-dimethyl-2H-indazole (64.0 mg, 0.28 mmol, 1.5 eq.), CuI (36.2 mg, 0.19 mmol, 1.0 eq.), $N^1,N^2$-dimethylcyclohexane-1,2-diamine (26.9 mg, 0.19 mmol, 1.0 eq.) and CsF (57.6 mg, 0.38 mmol, 2.0 eq.). The reaction was stirred in a seal tube at 85° C. overnight under $N_2$ atmosphere and concentrated under reduced pressure. The residue was purified by prep-HPLC to afford 6-(2,2-difluoroethoxy)-4-(4-(difluoromethoxy)phenyl)-2-(2,3-dimethyl-2H-indazol-5-yl)pyrido[3,2-c]pyridazin-3(2H)-one (Example 166).

$^1$H NMR (400 MHz, DMSO-d$_6$) δ: 8.07 (d, J=9.4 Hz, 1H), 7.98 (d, J=1.4 Hz, 1H), 7.87 (d, J=8.0 Hz, 2H), 7.62 (d, J=8.0 Hz, 1H), 7.42 (dd, J=9.1 Hz, 2.0 Hz, 1H), 7.35 (t, $J_{HF}$=72.0 Hz, 1H), 7.26 (d, J=8.8 Hz, 2H), 7.06 (d, J=9.4 Hz, 1H), 6.41 (tt, $J_{HF}$=54.4 Hz, J=3.3 Hz, 1H), 4.59 (td, $J_{HF}$=15.1 Hz, J=3.3 Hz, 2H), 4.10 (s, 3H), 2.64 (s, 3H).

LC-MS (ESI): m/z 514 [M+H]$^+$.

Preparation of Example 167 Via General Procedure II (Method B)

Method B:

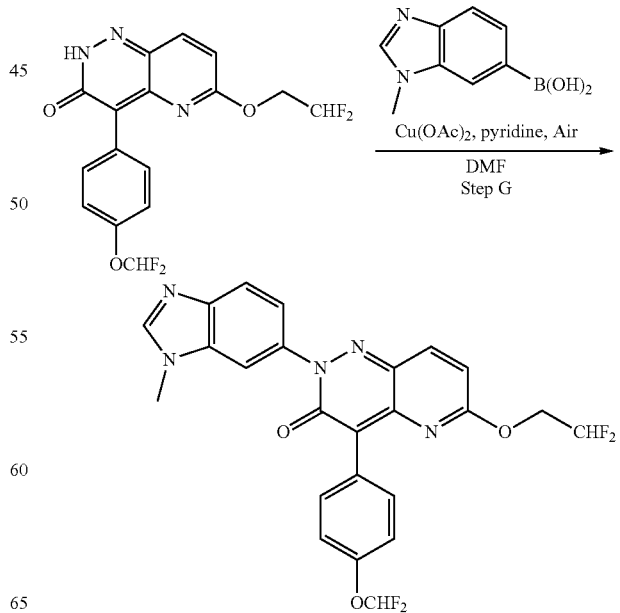

Step G: 6-(2,2-difluoroethoxy)-4-(4-(difluoromethoxy)phenyl)-2-(1-methyl-1H-benzo[d]imidazol-6-yl)pyrido[3,2-c]pyridazin-3(2H)-one (Method B)

To a suspension of 6-(2,2-difluoroethoxy)-4-(4-(difluoromethoxy)phenyl)pyrido[3,2-c]pyridazin-3(2H)-one (70 mg, 0.19 mmol, 1.0 eq.) in DMF (5 mL) was added 1-methyl-1H-benzo[d]imidazol-6-ylboronic acid (33.4 mg, 0.23 mmol, 1.2 eq.), Cu(OAc)$_2$ (34.5 mg, 0.19 mmol, 1.0 eq.) and pyridine (30.0 mg, 0.38 mmol, 2.0 eq.). After the mixture was stirred at 50° C. overnight under air atmosphere, the reaction mixture was quenched by adding H$_2$O (10 mL) and extracted with EtOAc (10 mL×3). The combined organic layer was dried over anhydrous Na$_2$SO$_4$ and concentrated under reduced pressure, the residue was purified by prep-HPLC to afford 6-(2,2-difluoroethoxy)-4-(4-(difluoromethoxy)phenyl)-2-(1-methyl-1H-benzo[d]imidazol-6-yl)pyrido[3,2-c]pyridazin-3(2H)-one (Example 167).

$^1$H NMR (400 MHz, DMSO-d$_6$) δ: 8.34 (s, 1H), 8.06 (d, J=9.4 Hz, 1H), 7.92 (d, J=1.8 Hz, 1H), 7.88 (d, J=8.0 Hz, 2H), 7.79 (d, J=8.6 Hz, 1H), 7.47 (dd, J=8.6 Hz, 2.0 Hz, 1H), 7.35 (t, J$_{HF}$=72.0 Hz, 1H), 7.26 (d, J=8.8 Hz, 2H), 7.07 (d, J=9.4 Hz, 1H), 6.41 (tt, J$_{HF}$=54.4 Hz, 3.3 Hz, 1H), 4.60 (td, J$_{HF}$=15.1 Hz, 3.3 Hz, 2H), 3.88 (s, 3H).

LC-MS (ESI): m/z 500 [M+H]$^+$.

Preparation of Example 321 Via General Procedure II (Method C)

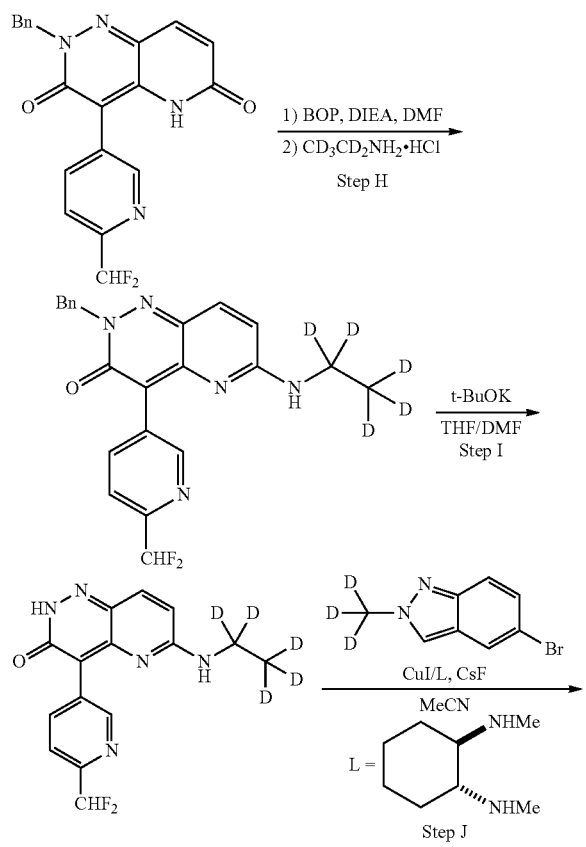

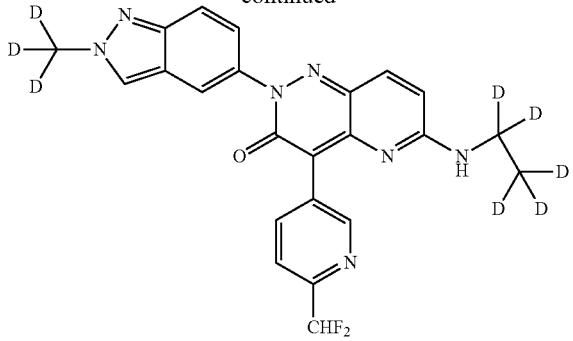

Step H: 2-benzyl-4-(6-(difluoromethyl)pyridin-3-yl)-6-((ethyl-d$_5$)amino)pyrido[3,2-c]pyridazin-3(2H)-one To a solution of 2-benzyl-4-(6-(difluoromethyl)pyridin-3-yl)pyrido[3,2-c]pyridazine-3,6(2H,5H)-dione (250 mg, 0.66 mmol, 1.0 eq.) in DMF (2 mL) was added BOP (436 mg, 0.99 mmol, 1.5 eq.) and DIEA (584 µL, 3.29 mmol, 5.0 eq.), the reaction mixture was stirred at room temperature for 1 hour, then added ethylamine-d$_5$ hydrochloride (86 mg, 0.99 mmol, 1.5 eq.), the resulting mixture was stirred at room temperature for additional 0.5 hour. After the completion, the reaction was quenched by adding ice water (10 mL) and extracted with EtOAc (10 ml×3), dried over Na$_2$SO$_4$ and concentrated under reduced pressure, the residue was purified by flash column chromatography on silica gel to give 4-(6-(difluoromethyl)pyridin-3-yl)-6-((ethyl-d$_5$)amino)pyridopyridazin-3(2H)-one (234 mg, 86%) as a yellow solid. LC-MS (ESI): m/z 413 [M+H]$^+$.

Step I: 4-(6-(difluoromethyl)pyridin-3-yl)-6-((ethyl-d$_5$)amino)pyrido[3,2-c]pyridazin-3(2H)-one To a solution of 2-benzyl-4-(6-(difluoromethyl)pyridin-3-yl)-6-((ethyl-d$_5$)amino)pyridopyridazin-3(2H)-one (185 mg, 0.45 mmol, 1.0 eq.) in THF/DMF (2 mL, 1/1) was added t-BuOK (251 mg, 2.25 mmol, 5.0 eq.), the reaction mixture was stirred at 70° C. for 8 hrs. After the completion, the pH was adjusted to ~7 by adding 1 N HCl (aq.), then the mixture was extracted with DCM (10 mL×3). The combined organic layers were washed with brine (20 mL) and dried over Na$_2$SO$_4$, concentrated under reduced pressure, the residue was purified by flash chromatography to give 4-(6-(difluoromethyl)pyridin-3-yl)-6-((ethyl-d$_5$)amino)pyridopyridazin-3(2H)-one (50 mg) as a yellow solid. LC-MS (ESI): m/z 323 [M+H]$^+$.

Step J: 4-(6-(difluoromethyl)pyridin-3-yl)-6-((ethyl-d$_5$)amino)-2-(2-(methyl-d$_3$)-2H-indazol-5-yl)pyrido[3,2-c]pyridazin-3(2H)-one To a solution of 4-(6-(difluoromethyl)pyridin-3-yl)-6-((ethyl-d$_5$)amino)pyridopyridazin-3(2H)-one (50 mg, 0.16 mmol, 1.0 eq.) and 5-bromo-2-(methyl-d$_3$)-2H-indazole (50 mg, 0.23 mmol, 1.5 eq.) in ACN (1 mL) was added CuI (30 mg, 0.16 mmol, 1.0 eq.), CsF (47 mg, 0.31 mmol, 2.0 eq.), N1,N2-dimethylcyclohexane-1,2-diamine (22 mg, 0.16 mmol, 1.0 eq.), the resulting mixture was stirred at 85° C. for 14 hrs. After the completion, the reaction mixture was diluted with H$_2$O (5 mL), extracted with EtOAc (10 mL×3). The combined organic layers were washed with brine (20 mL) and dried over Na₂SO₄, concentrated under reduced pressure, the residue was purified by RP-prep-HPLC to give 4-(6-(difluoromethyl)pyridin-3-yl)-6-((ethyl-d₅)amino)-2-(2-(methyl-d₃)-2H-indazol-5-yl)pyridopyridazin-3(2H)-one (Example 321).

¹H NMR (400 MHz, DMSO-d₆) δ (ppm): 9.06 (s, 1H), 8.46 (d, J=2.6 Hz, 2H), 8.39 (d, J=8.0 Hz, 1H), 7.95 (s, 1H), 7.73 (d, J=8.2 Hz, 1H), 7.66 (dd, J=11.5, 9.4 Hz, 2H), 7.42 (dd, J=9.2, 1.9 Hz, 1H), 6.99 (t, J=55.1 Hz, 1H), 6.82 (d, J=9.6 Hz, 1H).

LC-MS (ESI): m/z 456 [M+H]⁺.

Preparation of Example 322 Via General Procedure IIa (Method C)

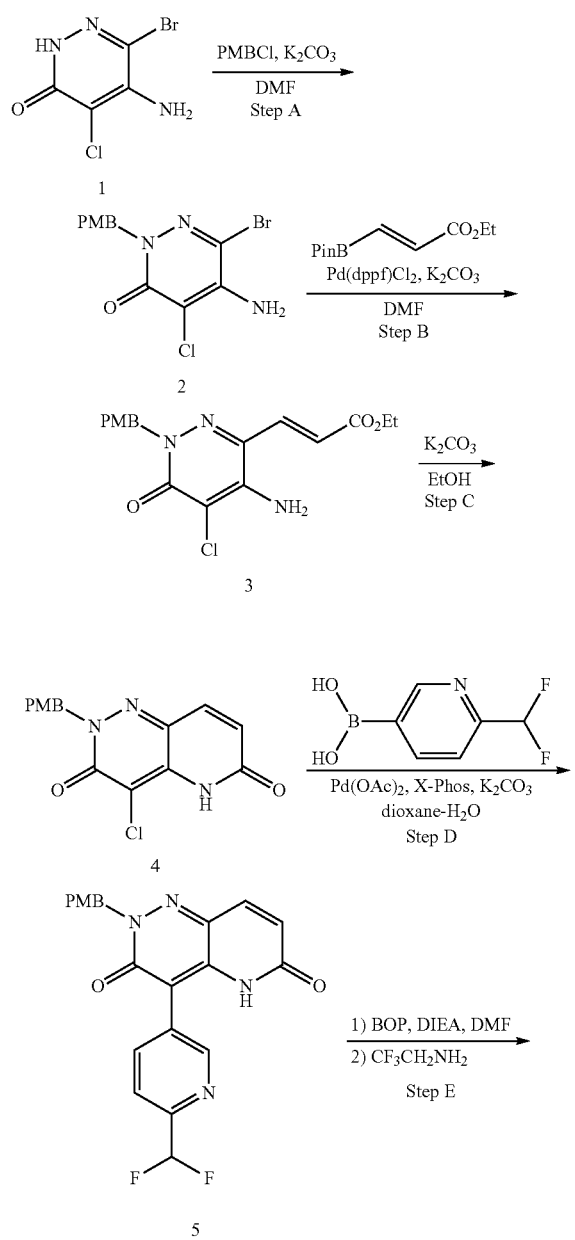

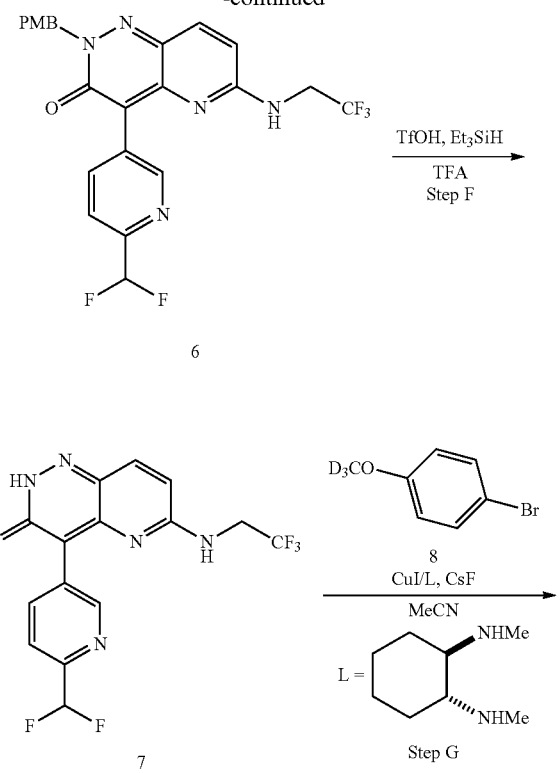

Step A: 5-amino-6-bromo-4-chloro-2-(4-methoxybenzyl)pyridazin-3(2H)-one

To a solution of 5-amino-6-bromo-4-chloropyridazin-3(2H)-one (2.0 g, 8.91 mmol, 1.0 eq.) and K₂CO₃ (2.5 g, 17.8 mmol, 2.0 eq.) in DMF (20 mL) was added PMBCl (1.3 mL, 9.8 mmol, 1.1 eq.), the reaction mixture stirred at 80° C. for 14 hrs. After completion, the reaction mixture was diluted with water (50 mL) and extracted with EtOAc (50 mL×3), the combined organic layers were washed with brine (50 mL), dried over Na₂SO₄ and concentrated under reduced pressure, the residue was purified by flash column chromatography on silica gel to give 5-amino-6-bromo-4-chloro-2-(4-methoxybenzyl)pyridazin-3(2H)-one (2.0 g, 45%) as a white solid. LC-MS (ESI): m/z 344 [M+H]⁺.

Step B: ethyl (E)-3-(4-amino-5-chloro-1-(4-methoxybenzyl)-6-oxo-1,6-dihydropyridazin-3-yl)acrylate To a solution of 5-amino-6-bromo-4-chloro-2-(4-methoxybenzyl)pyridazin-3(2H)-one (2.0 g, 5.8 mmol, 1.0 eq.), $K_2CO_3$ (2.0 g, 14.5 mmol, 2.5 eq.) and ethyl (E)-3-(4,4,5,5-tetramethyl-1,3,2-dioxaborolan-2-yl)acrylate (1.44 g, 6.4 mmol, 1.1 eq.) in DMF (20 mL) was added Pd(dppf)Cl$_2$ (0.43 g, 0.6 mmol, 0.1 eq.), the reaction mixture stirred at 100° C. under $N_2$ atmosphere for 5 hrs. The reaction mixture was diluted with $H_2O$ (30 mL) and extracted with EtOAc (50 mL×3), the combined organic layers were washed with brine (40 mL), dried over $Na_2SO_4$ and concentrated under reduced pressure, the residue was purified by column chromatography to afford on silica gel to give ethyl (E)-3-(4-amino-5-chloro-1-(4-methoxybenzyl)-6-oxo-1,6-dihydropyridazin-3-yl)acrylate as a brown solid (1.4 g, 53%).

LC-MS (ESI): m/z 364 [M+H]$^+$.

Step C: 4-chloro-2-(4-methoxybenzyl)pyrido[3,2-c]pyridazine-3,6(2H,5H)-dione To a stirred solution of ethyl (E)-3-(4-amino-5-chloro-1-(4-methoxybenzyl)-6-oxo-1,6-dihydropyridazin-3-yl)acrylate (1.4 g, 3.85 mmol, 1.0 eq.) in EtOH (20 mL) was added $K_2CO_3$ (1.6 g, 11.54 mmol, 3.0 eq.), the reaction mixture stirred at 80° C. for 14 hrs. The reaction mixture was diluted with water (30 mL) and extracted with EtOAc (30 mL×3), the combined organic layers were dried over $Na_2SO_4$ and concentrated under reduced pressure to give crude 4-chloro-2-(4-methoxybenzyl)pyrido[3,2-c]pyridazine-3,6(2H,5H)-dione (0.6 g, crude) as a brown solid, which used in next step without further purification.

LC-MS (ESI): m/z 318 [M+H]$^+$.

Step D: 4-(6-(difluoromethyl)pyridin-3-yl)-2-(4-methoxybenzyl)pyrido[3,2-c]pyridazine-3,6(2H,5H)-dione To a solution of 4-chloro-2-(4-methoxybenzyl)pyrido[3,2-c]pyridazine-3,6(2H,5H)-dione (0.2 g, 0.63 mmol, 1.0 eq.), 2-(4-(difluoromethoxy)phenyl)-4,4,5,5-tetramethyl-1,3,2-dioxaborolane (152 mg, 0.88 mmol, 1.4 eq.), $K_2CO_3$ (217 mg, 1.57 mmol, 2.5 eq.) and X-Phos (33 mg, 0.06 mmol, 0.1 eq.) in 1,4-dioxane/$H_2O$ mixture (8 mL, 10/1, v/v) was added Pd(OAc)$_2$ (15 mg, 0.06 mmol, 0.1 eq.), the reaction mixture stirred at 110° C. under $N_2$ atmosphere overnight. After completion, the reaction mixture was concentrated under reduced pressure, the residue was purified by column chromatography on silica gel to give 4-(6-(difluoromethyl)pyridin-3-yl)-2-(4-methoxybenzyl)pyrido[3,2-c]pyridazine-3,6(2H,5H)-dione (120 mg, 46%) as a white solid. LC-MS (ESI): m/z 411 [M+H]$^+$.

Step E: 4-(6-(difluoromethyl)pyridin-3-yl)-2-(4-methoxybenzyl)-6-((2,2,2-trifluoroethyl)amino)pyrido[3,2-c]pyridazin-3(2H)-one To a solution of 4-(6-(difluoromethyl)pyridin-3-yl)-2-(4-methoxybenzyl)pyrido[3,2-c]pyridazine-3,6(2H,5H)-dione (100 mg, 0.24 mmol, 1.0 eq.) in DMF (2 mL) was added BOP (180 mg, 0.36 mmol, 1.5 eq.) and DIEA (157 mg, 1.22 mmol, 5.0 eq.), the reaction mixture was stirred at room temperature for 1 hr, then 2,2,2-trifluoroethan-1-amine (36 mg, 0.36 mmol, 1.5 eq.) was added, the resulting mixture was stirred at room temperature for additional 0.5 hr. After the completion, the reaction was quenched by adding ice water (10 mL) and extracted with EtOAc (10 mL×3), dried over $Na_2SO_4$ and concentrated under reduced pressure, the residue was purified by flash column chromatography on silica gel to give 4-(6-(difluoromethyl)pyridin-3-yl)-2-(4-methoxybenzyl)-6-((2,2,2-trifluoroethyl)amino)pyrido[3,2-c]pyridazin-3(2H)-one (80 mg, 67%) as a yellow solid.

LC-MS (ESI): m/z 492 [M+H]$^+$.

Step F: 4-(6-(difluoromethyl)pyridin-3-yl)-6-((2,2,2-trifluoroethyl)amino)pyrido[3,2-c]pyridazin-3(2H)-one To a solution of 4-(6-(difluoromethyl)pyridin-3-yl)-2-(4-methoxybenzyl)-6-((2,2,2-trifluoroethyl)amino)pyrido[3,2-c]pyridazin-3(2H)-one (80 mg, 0.16 mmol, 1.0 eq.) in TFA (2 mL) was added TfOH (142 μL, 1.6 mmol, 10.0 eq.) and Et$_3$SiH (128 μL, 0.8 mmol, 5.0 eq.), the reaction mixture was stirred at room temperature for 2 hrs. After the completion, the reaction was quenched with 10 mL of NaHCO$_3$ (sat. aq.), extracted with EtOAc (10 mL×3). The combined organic layers were washed with brine (20 mL) and dried over $Na_2SO_4$, concentrated under reduced pressure, the residue was purified by flash chromatography on silica gel to give 4-(6-(difluoromethyl)pyridin-3-yl)-6-((2,2,2-trifluoroethyl)amino)pyrido[3,2-c]pyridazin-3(2H)-one (40 mg, 66%) as a yellow solid. LC-MS (ESI): m/z 372 [M+H]$^+$.

Step G: 4-(6-(difluoromethyl)pyridin-3-yl)-2-(4-(methoxy-d$_3$)phenyl)-6-((2,2,2-trifluoroethyl)amino)pyrido[3,2-c]pyridazin-3(2H)-one (Example 322)

4-(6-(difluoromethyl)pyridin-3-yl)-2-(4-(methoxy-d$_3$)phenyl)-6-((2,2,2-trifluoroethyl)amino)pyrido[3,2-c]pyridazin-3(2H)-one (Example 322) was synthesized from 4-(6-(difluoromethyl)pyridin-3-yl)-6-((2,2,2-trifluoroethyl)amino)pyrido[3,2-c]pyridazin-3(2H)-one & 1-bromo-4-(methoxy-d$_3$)benzene via General Procedure II (Method C, Step J).

$^1$H NMR (400 MHz, DMSO-d$_6$) δ (ppm): 8.98 (s, 1H), 8.93 (t, J=5.9 Hz, 1H), 8.30 (dd, J=8.0 Hz, 1.6 Hz, 1H), 7.79 (d, J=9.5 Hz, 1H), 7.73 (d, J=8.2 Hz, 1H), 7.59-7.53 (m, 2H), 7.09-7.04 (m, 2H), 7.00 (t, J$_{HF}$=56.0 Hz, 1H), 6.93 (d, J=9.5 Hz, 1H), 4.23-4.15 (m, 2H).

LC-MS (ESI): m/z 481 [M+H]$^+$.

The procedure set forth above for General Procedure II (Method A) was used to synthesize the following compounds by using appropriate starting materials:

| Cpd No. | Structure | Characterization |
|---|---|---|
| Example 168 | 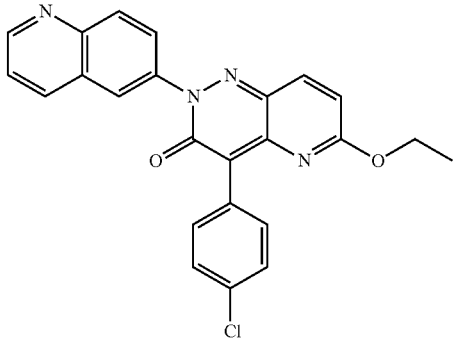<br>4-(4-chlorophenyl)-6-ethoxy-2-(quinolin-6-yl)pyrido[3,2-c]pyridazin-3(2H)-one | LC-MS (ESI): m/z 491 [M + H]+.<br>1H NMR (400 MHz, DMSO-$d_6$) δ: 9.00 (dd, J = 4.4 Hz, 1.6 Hz, 1H), 8.51 (d, J = 7.2 Hz, 1H), 8.37 (d, J = 2.4 Hz, 1H), 8.17 (d, J = 9.2 Hz, 1H), 8.07 (dd, J = 8.8 Hz, J = 2.4 Hz, 1H), 8.01 (d, J = 9.2 Hz, 1H), 7.83 (d, J = 8.8 Hz, 2H), 7.64 (dd, J = 8.4 Hz, 4.4 Hz, 1H), 7.52 (d, J = 8.8 Hz, 2H), 7.0 (d, J = 9.2 Hz, 1H), 4.34 (q, J = 6.8 Hz, 2H), 1.32 (t, J = 7.2 Hz, 3H). |
| Example 169 | 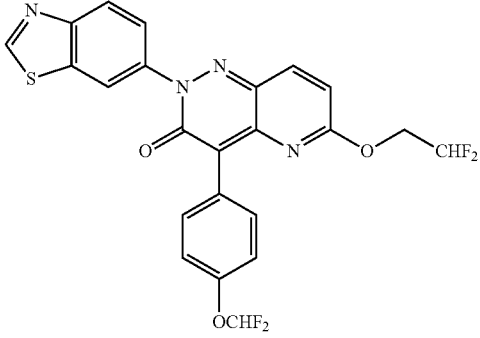<br>2-(benzo[d]thiazol-6-yl)-6-(2,2-difluoroethoxy)-4-(4-(difluoromethoxy)phenyl)pyrido[3,2-c]pyridazin-3(2H)-one | LC-MS (ESI): m/z 503.0 [M + H]+.<br>1H NMR (400 MHz, DMSO-$d_6$) δ: 9.53 (s, 1H), 8.54 (d, J = 2.0 Hz, 1H), 8.24 (d, J = 8.4 Hz, 1H), 8.06 (d, J = 9.2 Hz, 1H), 7.88 (d, J = 8.8 Hz, 2H), 7.85 (dd, J = 8.8 Hz, 2.4 Hz, 1H), 7.35 (t, $J_{HF}$ = 74.0 Hz, 1H), 7.26 (d, J = 8.8 Hz, 2H), 7.09 (d, J = 9.6 Hz, 1H), 6.41 (tt, $J_{HF}$ = 54.4 Hz, J = 3.2 Hz, 1H), 4.60 (td, $J_{HF}$ = 15.2 Hz, J = 3.2 Hz, 2H). |
| Example 170 | 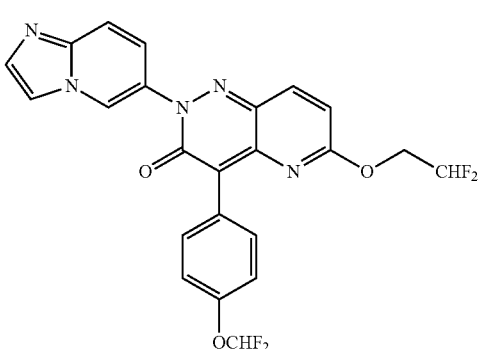<br>6-(2,2-difluoroethoxy)-4-(4-(difluoromethoxy)phenyl)-2-(imidazo[1,2-a]pyridin-6-yl)pyrido[3,2-c]pyridazin-3(2H)-one | LC-MS (ESI): m/z 486.0 [M + H]+.<br>1H NMR (400 MHz, DMSO-$d_6$) δ: 9.13 (s, 1H), 8.11 (s, 1H), 8.06 (d, J = 9.6 Hz, 1H), 7.87 (d, J = 8.8 Hz, 2H), 7.73 (d, J = 9.6 Hz, 1H), 7.70 (s, 1H), 7.58 (dd, J = 9.6 Hz, 1.6 Hz, 1H), 7.35 (t, $J_{HF}$ = 74.0 Hz, 1H), 7.26 (d, J = 8.8 Hz, 2H), 7.10 (d, J = 9.2 Hz, 1H), 6.37 (tt, $J_{HF}$ = 54.4 Hz, J = 3.2 Hz, 1H), 4.60 (td, $J_{HF}$ = 15.2 Hz, J = 3.2 Hz, 2H). |

-continued

| Cpd No. | Structure | Characterization |
| --- | --- | --- |
| Example 171 (synthesized using 5-bromo-3-methoxy-2-methyl-2H-indazole (Ref: Organic Letters, 2011, 13, 3138-3141)) | 6-(2,2-difluoroethoxy)-4-(4-(difluoromethoxy)phenyl)-2-(3-methoxy-2-methyl-2H-indazol-5-yl)pyrido[3,2-c]pyridazin-3(2H)-one | LC-MS (ESI): m/z 530.0 [M + H]+. 1H NMR (400 MHz, DMSO-d$_6$) δ: 8.12 (d, J = 1.6 Hz, 1H), 8.07 (d, J = 9.6 Hz, 1H), 7.86 (d, J = 8.8 Hz, 2H), 7.49 (d, J = 9.2 Hz, 1H), 7.37 (dd, J = 9.2 Hz, 2.0 Hz, 1H), 7.34 (t, J$_{HF}$ = 74.0 Hz, 1H), 7.25 (d, J = 8.8 Hz, 2H), 7.06 (d, J = 9.2 Hz, 1H), 6.40 (tt, J$_{HF}$ = 54.4 Hz, J = 3.2 Hz, 1H), 4.59 (td, J$_{HF}$ = 15.2 Hz, J = 3.2 Hz, 2H), 4.29 (s, 3H), 3.91 (s, 3H). |
| Example 172 (synthesized using 6-bromo-2-methoxy-1-methyl-1H-benzo[d]imidazole (Ref: Heterocycles, 2008, 75, 1907-1911)) | 6-(2,2-difluoroethoxy)-4-(4-(difluoromethoxy)phenyl)-2-(2-methoxy-1-methyl-1H-benzo[d]imidazol-6-yl)pyrido[3,2-c]pyridin-3(2H)-one | LC-MS (ESI): m/z 530.0 [M + H]+. 1H NMR (400 MHz, DMSO-d$_6$) δ: 8.05 (d, J = 9.2 Hz, 1H), 7.86 (d, J = 8.4 Hz, 2H), 7.68 (d, J = 2.0 Hz, 1H), 7.52 (d, J = 8.4 Hz, 1H), 7.34 (dd, J = 8.4 Hz, 2.0 Hz, 1H), 7.34 (t, J$_{HF}$ = 74.0 Hz, 1H), 7.24 (d, J = 8.4 Hz, 2H), 7.06 (d, J = 9.2 Hz, 1H), 6.36 (tt, J$_{HF}$ = 54.4 Hz, J = 3.2 Hz, 1H), 4.60 (td, J$_{HF}$ = 15.2 Hz, J = 3.2 Hz, 2H), 4.15 (s, 3H), 3.57 (s, 3H). |
| Example 173 | 4-(4-chlorophenyl)-6-(2,2-difluoroethoxy)-2-(2,3-dimethyl-2H-indazol-5-yl)pyrido[3,2-c]pyridazin-3(2H)-one | LC-MS (ESI): m/z 482.1 [M + H]+. 1H NMR (400 MHz, DMSO-d$_6$) δ: 8.07 (d, J = 9.2 Hz, 1H), 7.98 (d, J = 2.0 Hz, 1H), 7.82 (d, J = 8.4 Hz, 2H), 7.61 (d, J = 9.2 Hz, 1H), 7.51 (d, J = 8.8 Hz, 2H), 7.41 (dd, J = 9.2 Hz, 2.0 Hz, 1H), 7.07 (d, J = 9.2 Hz, 1H), 6.41 (tt, J$_{HF}$ = 54.2 Hz, J = 3.2 Hz, 1H), 4.59 (td, J$_{HF}$ = 15.2 Hz, J = 3.2 Hz, 2H), 4.10 (s, 3H), 2.64 (s, 3H). |

| Cpd No. | Structure | Characterization |
|---|---|---|
| Example 174 (synthesized using 5-bromo-3-methoxy-2-methyl-2H-indazole (Ref: Organic Letters, 2011, 13, 3138-3141) | 4-(4-chlorophenyl)-6-(2,2-difluoroethoxy)-2-(3-methoxy-2-methyl-2H-indazol-5-yl)pyrido[3,2-c]pyridazin-3(2H)-one | LC-MS (ESI): m/z 498.1 [M + H]+. 1H NMR (400 MHz, DMSO-$d_6$) δ: 8.12 (d, J = 2.0 Hz, 1H), 8.08 (d, J = 9.2 Hz, 1H), 7.82 (d, J = 8.4 Hz, 2H), 7.51 (d, J = 8.4 Hz, 2H), 7.48 (s, 1H), 7.36 (dd, J = 9.2 Hz, 2.0 Hz, 1H), 7.07 (d, J = 9.2 Hz, 1H), 6.40 (tt, $J_{HF}$ = 54.4 Hz, J = 3.2 Hz, 1H), 4.58 (td, $J_{HF}$ = 15.2 Hz, J = 3.2 Hz, 2H), 4.29 (s, 3H), 3.91 (s, 3H). |
| Example 175 (synthesized using 5-bromo-3-(methoxy-$d_3$)-2-methyl-2H-indazole (Ref: Organic Letters, 2011, 13, 3138-3141) | 6-(2,2-difluoroethoxy)-4-(4-(difluoromethoxy)phenyl)-2-(3-(methoxy-$d_3$)-2-methyl-2H-indazol-5-yl)pyrido[3,2-c]pyridazin-3(2H)-one | LC-MS (ESI): m/z 533.2 [M + H]+. 1H NMR (400 MHz, DMSO-$d_6$) δ: 8.12 (d, J = 1.2 Hz, 1H), 8.07 (d, J = 9.6 Hz, 1H), 7.87 (d, J = 8.8 Hz, 2H), 7.50 (d, J = 9.2 Hz, 1H), 7.37 (dd, J = 9.2 Hz, 1.6 Hz, 1H), 7.34 (t, $J_{HF}$ = 74.0 Hz, 1H), 7.25 (d, J = 8.8 Hz, 2H), 7.07 (d, J = 9.2 Hz, 1H), 6.40 (tt, $J_{HF}$ = 54.2 Hz, J = 3.2 Hz, 1H), 4.59 (td, $J_{HF}$ = 15.2 Hz, J = 3.2 Hz, 2H), 3.91 (s, 3H). |
| Example 176 | 2-(cinnolin-6-yl)-6-(2,2-difluoroethoxy)-4-(4-(difluoromethoxy)phenyl)pyrido[3,2-c]pyridazin-3(2H)-one | LC-MS (ESI): m/z 498 [M + H]+. 1H NMR (400 MHz, DMSO-$d_6$) δ 9.48 (d, J = 5.9 Hz, 1H), 8.63 (d, J = 9.2 Hz, 1H), 8.51 (d, J = 2.2 Hz, 1H), 8.38 (d, J = 5.8 Hz, 1H), 8.30 (dd, J = 9.1, 2.3 Hz, 1H), 8.08 (d, J = 9.4 Hz, 1H), 7.94-7.86 (m, 2H), 7.36 (t, J = 73.9 Hz, 1H), 7.32-7.22 (m, 2H), 7.12 (d, J = 9.4 Hz, 1H), 6.41 (tt, J = 54.3, 3.3 Hz, 1H), 4.61 (td, J = 15.1, 3.3 Hz, 2H). |

| Cpd No. | Structure | Characterization |
|---|---|---|
| Example 177 | 6-(2,2-difluoroethoxy)-4-(4-(difluoromethoxy)phenyl)-2-(2,3-dihydrobenzo[b][1,4]dioxin-6-yl)pyrido[3,2-c]pyridazin-3(2H)-one | LC-MS (ESI): m/z 504 [M + H]+. 1H NMR (400 MHz, DMSO-$d_6$) δ 8.02 (d, J = 9.4 Hz, 1H), 7.84 (d, J = 8.8 Hz, 2H), 7.34 (t, J = 74.0 Hz, 1H), 7.24 (d, J = 8.7 Hz, 2H), 7.20 (d, J = 2.5 Hz, 1H), 7.12 (dd, J = 8.7, 2.5 Hz, 1H), 7.05 (d, J = 9.4 Hz, 1H), 7.00 (d, J = 8.7 Hz, 1H), 6.39 (tt, J = 54.1, 3.3 Hz, 1H), 4.57 (td, J = 15.1 3.4 Hz, 2H), 4.31 (s, 4H). |
| Example 178 | 6-(2,2-difluoroethoxy)-4-(4-(difluoromethoxy)phenyl)-2-(2,3-dihydrobenzofuran-5-yl)pyrido[3,2-c]pyridazin-3(2H)-one | LC-MS (ESI): m/z 488 [M + H]+. 1H NMR (400 MHz, DMSO-$d_6$) δ 8.03 (d, J = 9.4 Hz, 1H), 7.84 (d, J = 8.8 Hz, 2H), 7.51 (d, J = 2.2 Hz, 1H), 7.39-7.35 (m, 1H), 7.35 (t, J = 74.2 Hz, 1H), 7.24 (d, J = 8.8 Hz, 2H), 7.05 (d, J = 9.4 Hz, 1H), 6.89 (d, J = 8.5 Hz, 1H), 6.39 (tt, J = 54.4, 3.3 Hz, 1H), 4.67-4.51 (m, 4H), 3.26 (t, J = 8.8 Hz, 2H). |
| Example 179 | 6-(2,2-difluoroethoxy)-4-(4-(difluoromethoxy)phenyl)-2-(quinazolin-6-yl)pyrido[3,2-c]pyridazin-3(2H)-one | LC-MS (ESI): m/z 498 [M + H]+. 1H NMR (400 MHz, DMSO-$d_6$) δ 9.76 (s, 1H), 9.41 (s, 1H), 8.58 (d, J = 2.4 Hz, 1H), 8.38 (dd, J = 9.0, 2.4 Hz, 1H), 8.20 (d, J = 9.0 Hz, 1H), 8.09 (d, J = 9.4 Hz, 1H), 7.90 (d, J = 8.7 Hz, 2H), 7.35 (t, J = 73.8 Hz, 1H), 7.27 (d, J = 8.8 Hz, 2H), 7.12 (d, J = 9.4 Hz, 1H), 6.41 (t, J = 54.4 Hz, 1H), 4.61 (td, J = 15.1, 3.3 Hz, 2H). |

| Cpd No. | Structure | Characterization |
|---|---|---|
| Example 180 | 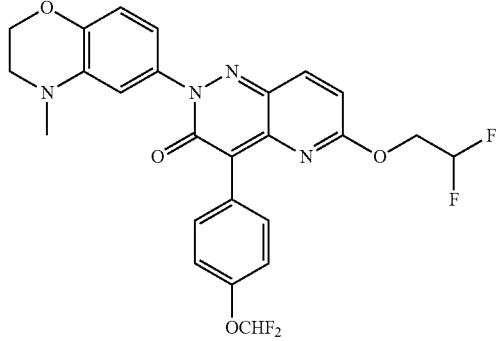<br>6-(2,2-difluoroethoxy)-4-(4-(difluoromethoxy)phenyl)-2-(4-methyl-3,4-dihydro-2H-benzo[b][1,4]oxazin-6-yl)pyrido[3,2-c]pyridazin-3(2H)-one | LC-MS (ESI): m/z 517 [M + H]+.<br>1H NMR (400 MHz, DMSO-d$_6$) δ 8.01 (d, J = 9.4 Hz, 1H), 7.87-7.79 (m, 2H), 7.32 (t, J = 74.0 Hz, 1H), 7.24 (d, J = 8.8 Hz, 2H), 7.03 (d, J = 9.4 Hz, 1H), 6.92 (s, 1H), 6.79 (br s, 2H), 6.38 (tt, J = 54.4, 3.4 Hz, 1H), 4.57 (td, J = 15.1, 3.4 Hz, 2H), 4.29 (dd, J = 5.3, 3.5 Hz, 2H), 3.29 (t, J = 4.4 Hz, 2H), 2.83 (s, 3H). |
| Example 181 | 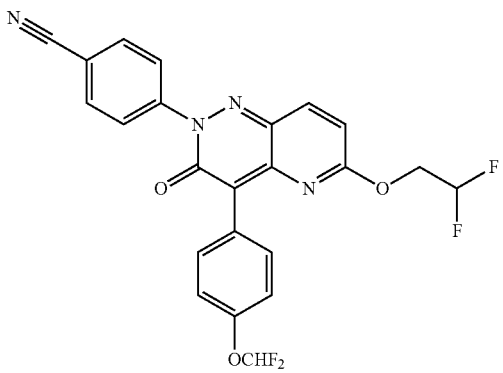<br>4-(6-(2,2-difluoroethoxy)-4-(4-(difluoromethoxy)phenyl)-3-oxopyrido[3,2-c]pyridazin-2(3H)-yl)benzonitrile | LC-MS (ESI): m/z 471 [M + H]+.<br>1H NMR (400 MHz, DMSO-d$_6$) δ 8.10-8.01 (m, 3H), 7.95 (d, J = 8.3 Hz, 2H), 7.85 (d, J = 8.8 Hz, 2H), 7.35 (t, J = 74.0 Hz, 1H), 7.25 (d, J = 8.5 Hz, 2H), 7.10 (d, J = 9.4 Hz, 1H), 6.40 (tt, J = 54.3, 3.4 Hz, 1H), 4.59 (td, J = 15.1, 3.4 Hz, 2H). |
| Example 182 | 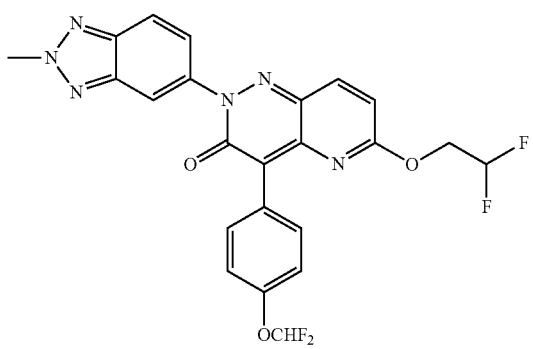<br>6-(2,2-difluoroethoxy)-4-(4-(difluoromethoxy)phenyl)-2-(2-methyl-2H-benzo[d][1,2,3]triazol-5-yl)pyrido[3,2-c]pyridazin-3(2H)-one | LC-MS: m/z 501.1 (M + H)+.<br>1H NMR (400 MHz, DMSO-d$_6$) δ: 8.27 (d, J = 1.2 Hz, 1H), 8.07 (d, J = 9.2 Hz, 1H), 7.87 (d, J = 8.8 Hz, 2H), 7.70 (dd, J = 9.2 Hz, 2.0 Hz, 1H), 7.34 (t, J$_{HF}$ = 74.0 Hz, 1H), 7.25 (d, J = 8.8 Hz, 2H), 7.08 (d, J = 9.6 Hz, 1H), 6.40 (tt, J$_{HF}$ = 54.4 Hz, 3.2 Hz, 1H), 4.58 (td, J = 14.8 Hz, 3.6 Hz, 2H), 4.56 (s, 3H). |

-continued

| Cpd No. | Structure | Characterization |
|---|---|---|
| Example 183 | 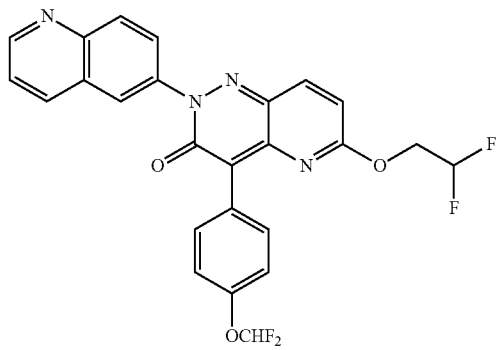<br>6-(2,2-difluoroethoxy)-4-(4-(difluoromethoxy)phenyl)-2-(quinolin-6-yl)pyrido[3,2-c]pyridazin-3(2H)-one | LC-MS: m/z 497.1 (M + H)+.<br>1H NMR (400 MHz, DMSO-d$_6$) δ: 9.01 (s, 1H), 8.51 (d, J = 8.4 Hz, 1H), 8.37 (s, 1H), 8.12-8.02 (m, 1H), 7.89 (d, J = 8.0 Hz, 2H), 7.68-7.59 (m, 1H), 7.35 (t, J$_{HF}$ = 74.0 Hz, 1H), 7.26 (d, J = 8.0 Hz, 2H), 7.10 (d, J = 9.6 Hz, 1H), 6.41 (tt, J$_{HF}$ = 54.4 Hz, 3.6 Hz, 1H), 4.60 (td, J = 14.8 Hz, 3.6 Hz, 2H). |
| Example 184 | 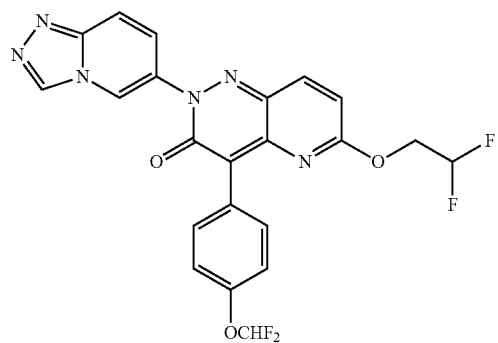<br>2-([1,2,4]triazolo[4,3-a]pyridin-6-yl)-6-(2,2-difluoroethoxy)-4-(4-(difluoromethoxy)phenyl)pyrido[3,2-c]pyridazin-3(2H)-one | LC-MS: m/z 487.1 (M + H)+.<br>1H NMR (400 MHz, DMSO-d$_6$) δ: 9.41 (s, 1H), 9.18 (s, 1H), 8.06 (d, J = 9.2 Hz, 1H), 7.94 (d, J = 9.6 Hz, 1H), 7.87 (d, J = 8.4 Hz, 2H), 7.75 (dd, J = 9.2 Hz, 2.0 Hz, 1H), 7.35 (t, J$_{HF}$ = 74.0 Hz, 1H), 7.26 (d, J = 8.4 Hz, 2H), 7.12 (d, J = 9.2 Hz, 1H), 6.40 (tt, J$_{HF}$ = 54.4 Hz, 3.6 Hz, 1H), 4.60 (td, J = 14.8 Hz, 3.6 Hz, 2H). |
| Example 185 | 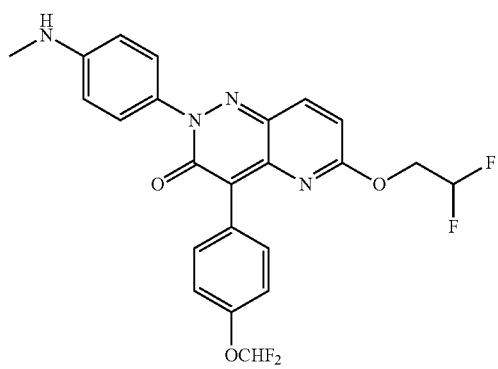<br>6-(2,2-difluoroethoxy)-4-(4-(difluoromethoxy)phenyl)-2-(4-(methylamino)phenyl)pyrido[3,2-c]pyridazin-3(2H)-one | LC-MS: m/z 475.1 (M + H)+.<br>1H NMR (400 MHz, DMSO-d$_6$) δ: 8.02 (d, J = 9.2 Hz, 1H), 7.83 (d, J = 8.8 Hz, 2H), 7.40 (d, J = 8.8 Hz, 2H), 7.33 (t, J$_{HF}$ = 74.0 Hz, 1H), 7.23 (d, J = 8.8 Hz, 2H), 7.03 (d, J = 9.2 Hz, 1H), 6.62 (d, J = 8.8 Hz, 2H), 6.39 (tt, J$_{HF}$ = 54.4 Hz, 3.2 Hz, 1H), 6.06 (q, J = 4.8 Hz, 1H), 4.56 (td, J$_{HF}$ = 14.8 Hz, 3.2 Hz, 2H), 2.73 (d, J = 4.8 Hz, 3H). |

| Cpd No. | Structure | Characterization |
|---|---|---|
| Example 186 | 6-(2,2-difluoroethoxy)-4-(4-(difluoromethoxy)phenyl)-2-(thiazol-5-yl)pyrido[3,2-c]pyridazin-3(2H)-one | LC-MS: m/z 466.1 (M + H)+.<br>1H NMR (400 MHz, DMSO-$d_6$) δ: 9.05 (s, 1H), 8.66 (s, 1H), 8.12 (d, J = 9.2 Hz, 1H), 7.85 (d, J = 8.8 Hz, 2H), 7.37 (t, $J_{HF}$ = 74.0 Hz, 1H), 7.28 (d, J = 8.8 Hz, 2H), 7.17 (d, J = 9.2 Hz, 1H), 6.40 (tt, $J_{HF}$ = 54.4 Hz, 3.2 Hz, 1H), 4.58 (td, $J_{HF}$ = 15.2 Hz, 3.2 Hz, 2H). |
| Example 187 (synthesized using 4-methoxycyclohex-1-en-1-yl trifluoro-methanesulfonate (Ref: Journal of the American Chemical Society, 2018, 140, 2446-2449) | 6-(2,2-difluoroethoxy)-4-(4-(difluoromethoxy)phenyl)-2-(4-methoxycyclohex-1-en-1-yl)pyrido[3,2-c]pyridazin-3(2H)-one | LC-MS: m/z 480.1 (M + H)+.<br>1H NMR (400 MHz, DMSO-$d_6$) δ: 8.03 (d, J = 9.2 Hz, 1H), 7.81 (d, J = 8.4 Hz, 2H), 7.33 (t, $J_{HF}$ = 74.0 Hz, 1H), 7.32 (d, J = 8.8 Hz, 2H), 7.02 (d, J = 9.6 Hz, 1H), 6.37 (tt, $J_{HF}$ = 54.4 Hz, 3.2 Hz, 1H), 5.94-5.89 (m, 1H), 4.55 (td, $J_{HF}$ = 14.8 Hz, 3.2 Hz, 2H), 3.63-3.52 (m, 1H), 3.31 (s, 3H), 2.61-2.41 (m, 3H), 2.24-2.15 (m, 1H), 2.03-1.92 (m, 1H), 1.85-1.71 (m, 1H). |

The procedure set forth above for General Procedure II (Method B) was used to synthesize the following compounds by using appropriate starting materials:

| Cpd No. | Structure | Characterization |
|---|---|---|
| Example 188 | 6-(2,2-difluoroethoxy)-4-(4-(difluoromethoxy)phenyl)-2-(pyridin-4-yl)pyrido[3,2-c]pyridazin-3(2H)-one | LC-MS (ESI): m/z 447 [M + H]+.<br>1H NMR (400 MHz, DMSO-$d_6$) δ 8.82-8.76 (m, 2H), 8.05 (d, J = 9.5 Hz, 1H), 7.89-7.78 (m, 4H), 7.35 (t, J = 74.0 Hz, 1H), 7.26 (d, J = 8.8 Hz, 2H), 7.10 (d, J = 9.4 Hz, 1H), 6.40 (tt, J = 54.3, 3.3 Hz, 1H), 4.59 (td, J = 15.1, 3.3 Hz, 2H). |

| Cpd No. | Structure | Characterization |
|---|---|---|
| Example 189 | 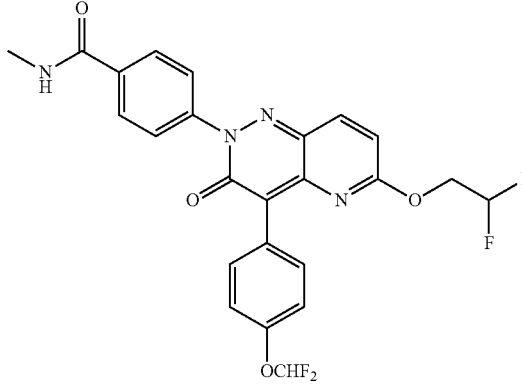<br>4-(6-(2,2-difluoroethoxy)-4-(4-(difluoromethoxy)phenyl)-3-oxopyrido[3,2-c]pyridazin-2(3H)-yl)-N-methylbenzamide | LC-MS: m/z 503.1 (M + H)+.<br>1H NMR (400 MHz, DMSO-$d_6$) δ: 8.59 (q, J = 4.4 Hz, 1H), 8.05 (d, J = 9.6 Hz, 1H), 7.99 (d, J = 8.8 Hz, 2H), 7.85 (d, J = 8.8 Hz, 2H), 7.81 (d, J = 8.4 Hz, 2H), 7.34 (t, $J_{HF}$ = 74.0 Hz, 1H), 7.25 (d, J = 8.8 Hz, 2H), 7.08 (d, J = 9.6 Hz, 1H), 6.39 (tt, $J_{HF}$ = 54.4 Hz, 3.6 Hz, 1H), 4.58 (td, J = 14.8 Hz, 3.2 Hz, 2H), 2.82 (d, J = 4.8 Hz, 3H). |
| Example 190 | 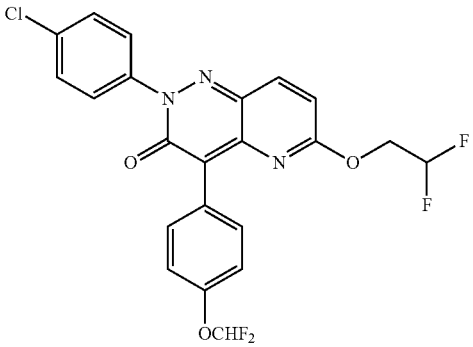<br>2-(4-chlorophenyl)-6-(2,2-difluoroethoxy)-4-(4-(difluoromethoxy)phenyl)pyrido[3,2-c]pyridazin-3(2H)-one | LC-MS: m/z 480.1 (M + H)+.<br>1H NMR (400 MHz, DMSO-$d_6$) δ: 8.04 (d, J = 9.6 Hz, 1H), 7.84 (d, J = 8.8 Hz, 1H), 7.73 (d, J = 8.8 Hz, 2H), 7.63 (d, J = 8.8 Hz, 2H), 7.34 (t, $J_{HF}$ = 74.0 Hz, 1H), 7.24 (d, J = 8.8 Hz, 2H), 7.07 (d, J = 9.6 Hz, 1H), 6.39 (tt, $J_{HF}$ = 54.0 Hz, 3.2 Hz, 1H), 4.58 (td, J = 15.2 Hz, 3.2 Hz, 2H). |
| Example 191 | 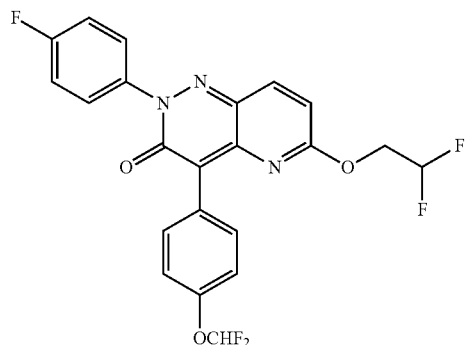<br>6-(2,2-difluoroethoxy)-4-(4-(difluoromethoxy)phenyl)-2-(4-fluorophenyl)pyrido[3,2-c]pyridazin-3(2H)-one | LC-MS: m/z 464.1 (M + H)+.<br>1H NMR (400 MHz, DMSO-$d_6$) δ: 8.04 (d, J = 9.6 Hz, 1H), 7.85 (d, J = 8.8 Hz, 2H), 7.76-7.71 (m, 2H), 7.40 (t, J = 8.8 Hz, 2H), 7.35 (t, $J_{HF}$ = 74.0 Hz, 1H), 7.25 (d, J = 8.4 Hz, 2H), 7.07 (d, J = 9.2 Hz, 1H), 6.40 (tt, $J_{HF}$ = 54.0 Hz, 3.6 Hz, 1H), 4.58 (td, J = 15.2 Hz, 3.6 Hz, 2H). |

| Cpd No. | Structure | Characterization |
|---|---|---|
| Example 192 | 6-(2,2-difluoroethoxy)-4-(4-(difluoromethoxy)phenyl)-2-(quinoxalin-6-yl)pyrido[3,2-c]pyridazin-3(2H)-one | LC-MS: m/z 498.1 (M + H)+.<br>1H NMR (400 MHz, DMSO-$d_6$) δ: 9.06-9.04 (m, 2H), 8.48 (d, J = 2.0 Hz, 1H), 8.27 (d, J = 9.2 Hz, 1H), 8.12 (dd, J = 9.2 Hz, 2.0 Hz, 1H), 8.09 (d, J = 9.6 Hz, 1H), 7.89 (d, J = 8.8 Hz, 2H), 7.35 (t, $J_{HF}$ = 74.0 Hz, 1H), 7.27 (d, J = 8.8 Hz, 2H), 7.11 (d, J = 9.2 Hz, 1H), 6.41 (tt, $J_{HF}$ = 54.4 Hz, 3.2 Hz, 1H), 4.61 (td, J = 14.8 Hz, 3.6 Hz, 2H). |
| Example 193 | 6-(2,2-difluoroethoxy)-4-(4-(difluoromethoxy)phenyl)-2-(1H-pyrazol-4-yl)pyrido[3,2-c]pyridazin-3(2H)-one | LC-MS: m/z 436.1 (M + H)+.<br>1H NMR (400 MHz, DMSO-$d_6$) δ: 13.23 (br s, 1H), 8.60-8.51 (m, 1H), 8.22-8.13 (m, 1H), 8.07 (d, J = 9.2 Hz, 1H), 7.84 (d, J = 8.8 Hz, 2H), 7.34 (t, $J_{HF}$ = 74.0 Hz, 1H), 7.26 (d, J = 8.4 Hz, 2H), 7.08 (d, J = 9.2 Hz, 1H), 6.38 (tt, $J_{HF}$ = 54.4 Hz, 3.2 Hz, 1H), 4.56 (td, J = 14.8 Hz, 3.2 Hz, 2H). |

The procedure set forth above for General Procedure II (Method C) was used to synthesize the following compounds by using appropriate starting materials:

| Cpd No. | Structure | Characterization |
|---|---|---|
| Example 323 | 6-((ethyl-d5)amino)-2-(2-methyl-2H-imidazol-5-yl)-4-(6-methylpyridin-3-yl)pyrido[3,2-c]pyridazin-3(2H)-one | LC-MS: m/z 417 (M + H)+.<br>1H NMR (400 MHz, DMSO-$d_6$) δ: 8.84 (d, J = 1.9 Hz, 1H), 8.46 (s, 1H), 8.34 (s, 1H), 8.06 (dd, J = 8.2 Hz, 2.1 Hz, 1H), 7.94 (d, J = 1.4 Hz, 1H), 7.67 (d, J = 9.2 Hz, 1H), 7.61 (d, J = 9.5 Hz, 1H), 7.41 (dd, J = 9.1 Hz, 2.0 Hz, 1H), 7.27 (d, J = 8.0 Hz, 1H), 6.79 (d, J = 9.6 Hz, 1H), 4.21 (s, 3H), 2.51 (s, 3H). |

| Cpd No. | Structure | Characterization |
|---|---|---|
| Example 324 | 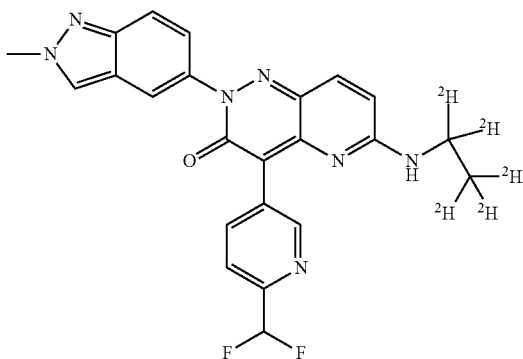<br>4-(6-(difluoromethyl)pyridin-3-yl)-6-((ethyl-d5)amino)-2-(2-methyl-2H-indazol-5-yl)pyrido[3,2-c]pyridazin-3(2H)-one | LC-MS: m/z 453 (M + H)+.<br>1H NMR (400 MHz, DMSO-d$_6$) δ: 9.06 (s, 1H), 8.47 (s, 2H), 8.38 (dd, J = 8.1 Hz, 1.8 Hz, 1H), 7.96 (d, J = 1.4 Hz, 1H), 7.73 (d, J = 8.2 Hz, 1H), 7.66 (t, J = 9.6 Hz, 2H), 7.42 (dd, J = 9.2 Hz, 2.0 Hz, 1H), 6.99 (t, J$_{HF}$ = 55.1 Hz, 1H), 6.82 (d, J = 9.6 Hz, 1H), 4.21 (s, 3H). |
| Example 325 | 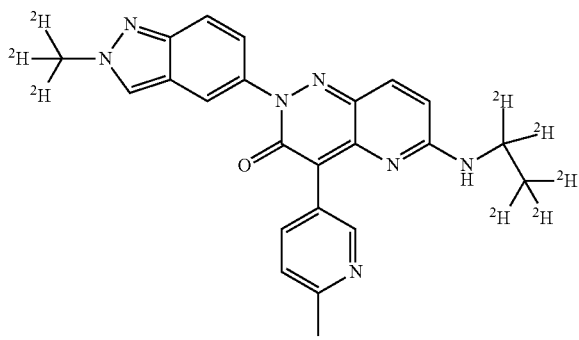<br>6-((ethyl-d5)amino)-2-(2-methyl-d3)-2H-indazol-5-yl)-4-(6-methylpyridin-3-yl)pyrido[3,2-c]pyridazin-3(2H)-one | LC-MS: m/z 420 (M + H)+.<br>1H NMR (400 MHz, DMSO-d$_6$) δ: 8.84 (d, J = 1.5 Hz, 1H), 8.46 (s, 1H), 8.32 (s, 1H), 8.07 (dd, J = 8.1 Hz, 2.1 Hz, 1H), 7.94 (d, J = 1.1 Hz, 1H), 7.67 (d, J = 9.2 Hz, 1H), 7.61 (d, J = 9.5 Hz, 1H), 7.41 (dd, J = 9.1 Hz, 2.0 Hz, 1H), 7.27 (d, J = 8.1 Hz, 1H), 6.79 (d, J = 9.5 Hz, 1H), 2.51 (s, 3H). |
| Example 326 | 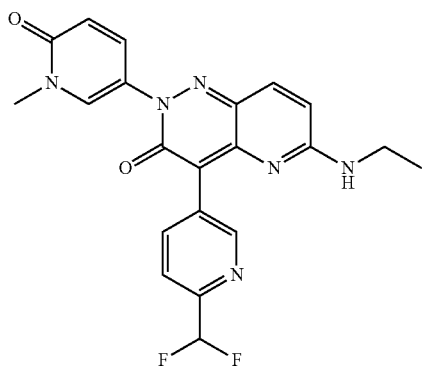 [SMILES: CCNc1ccc2nn(-c3ccc(=O)n(C)c3)c(=O)c(-c3ccc(C(F)F)nc3)c2n1]<br>4-(6-(difluoromethyl)pyridin-3-yl)-6-(ethylamino)-2-(1-methyl-6-oxo-1,6-dihydropyridin-3-yl)pyrido[3,2-c]pyridazin-3(2H)-one | LC-MS: m/z 425 (M + H)+.<br>1H NMR (400 MHz, DMSO-d$_6$) δ: 9.03 (s, 1H), 8.54 (t, J = 5.3 Hz, 1H), 8.35 (d, J = 9.7 Hz, 1H), 8.21 (d, J = 2.8 Hz, 1H), 7.77-7.69 (m, 2H), 7.63 (d, J = 9.5 Hz, 1H), 7.06 (t, J$_{HF}$ = 55.2 Hz, 1H), 6.83 (d, J = 9.6 Hz, 1H), 6.47 (d, J = 9.7 Hz, 1H), 3.49 (s, 3H), 3.31 (q, J = 7.2 Hz, 2H), 1.13 (t, J = 7.2 Hz, 3H). |

| Cpd No. | Structure | Characterization |
|---|---|---|
| Example 327 | 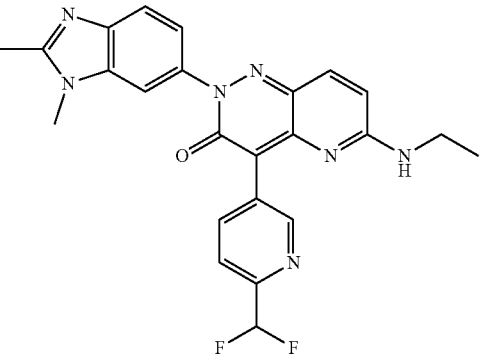 [SMILES: CCNc1ccc2nn(-c3ccc4nc(C)n(C)c4c3)c(=O)c(-c3ccc(C(F)F)nc3)c2n1]<br>4-(6-(difluoromethyl)pyridin-3-yl)-2-(1,2-dimethyl-1H-benzo[d]imidazol-6-yl)-6-(ethylamino)pyrido[3,2-c]pyridazin-3(2H)-one | LC-MS: m/z 462 (M + H)+.<br>1H NMR (400 MHz, DMSO-$d_6$) δ: 9.06 (s, 1H), 8.50 (t, J = 5.7 Hz, 1H), 8.38 (d, J = 9.8 Hz, 1H), 7.76 (d, J = 1.6 Hz, 1H), 7.73 (d, J = 8.4 Hz, 1H), 7.65 (d, J = 9.6 Hz, 1H), 7.60 (d, J = 8.2 Hz, 1H), 7.33 (dd, J = 8.5 Hz, 2.0 Hz, 1H), 6.99 (t, $J_{HF}$ = 55.1 Hz, 1H), 6.83 (d, J = 9.6 Hz, 1H), 3.75 (s, 3H), 3.32 (q, J = 7.2 Hz, 2H), 2.56 (s, 3H), 1.14 (t, J = 7.2 Hz, 3H). |
| Example 328 | 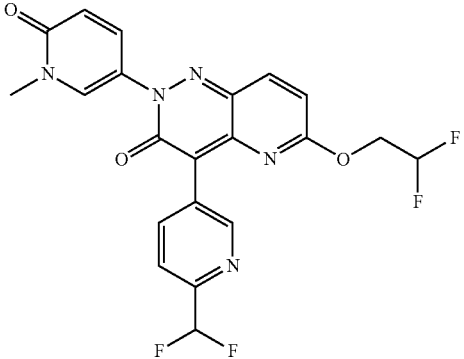 [SMILES: Cn1cc(-n2nc3ccc(OCC(F)F)nc3c(-c3ccc(C(F)F)nc3)c2=O)ccc1=O]<br>6-(2,2-difluoroethoxy)-4-(6-(difluoromethyl)pyridin-3-yl)-2-(1-methyl-6-oxo-1,6-dihydropyridin-3-yl)pyrido[3,2-c]pyridazin-3(2H)-one | LC-MS: m/z 462 (M + H)+.<br>1H NMR (400 MHz, DMSO-$d_6$) δ: 9.03 (s, 1H), 8.38 (d, J = 7.3 Hz, 1H), 8.30 (d, J = 2.6 Hz, 1H), 8.09 (d, J = 9.4 Hz, 1H), 7.82-7.77 (m, 2H), 7.12 (d, J = 9.6 Hz, 1H), 7.04 (t, $J_{HF}$ = 54.8 Hz, 1H), 6.52 (d, J = 9.7 Hz, 1H), 6.39 (t, $J_{HF}$ = 54.4 Hz, 1H), 4.59 (td, $J_{HF}$ = 15.2 Hz, J = 2.8 Hz, 2H), 3.51 (s, 3H). |
| Example 329 | 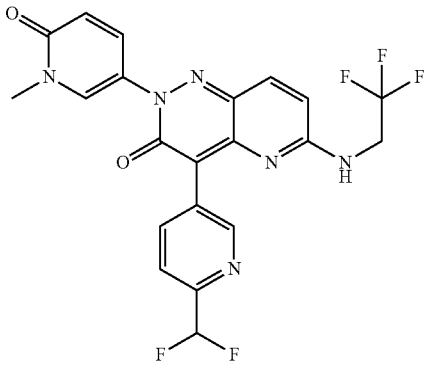 [SMILES: Cn1cc(-n2nc3ccc(NCC(F)(F)F)nc3c(-c3ccc(C(F)F)nc3)c2=O)ccc1=O]<br>4-(6-(difluoromethyl)pyridin-3-yl)-2-(1-methyl-6-oxo-1,6-dihydropyridin-3-yl)-6-((2,2,2-trifluoroethyl)amino)pyrido[3,2-c]pyridazin-3(2H)-one | LC-MS: m/z 479 (M + H)+.<br>1H NMR (400 MHz, DMSO-$d_6$) δ: 9.20 (t, J = 6.4 Hz, 1H), 8.97 (s, 1H), 8.29 (d, J = 8.8 Hz, 1H), 8.23 (d, J = 2.9 Hz, 1H), 7.79 (d, J = 9.4 Hz, 1H), 7.73 (d, J = 9.0 Hz, 2H), 7.01 (d, J = 9.6 Hz, 1H), 7.01 (t, $J_{HF}$ = 55.0 Hz, 1H), 6.48 (d, J = 9.8 Hz, 1H), 4.25-4.18 (m, 2H), 3.50 (s, 3H). |

| Cpd No. | Structure | Characterization |
|---|---|---|
| Example 330 | 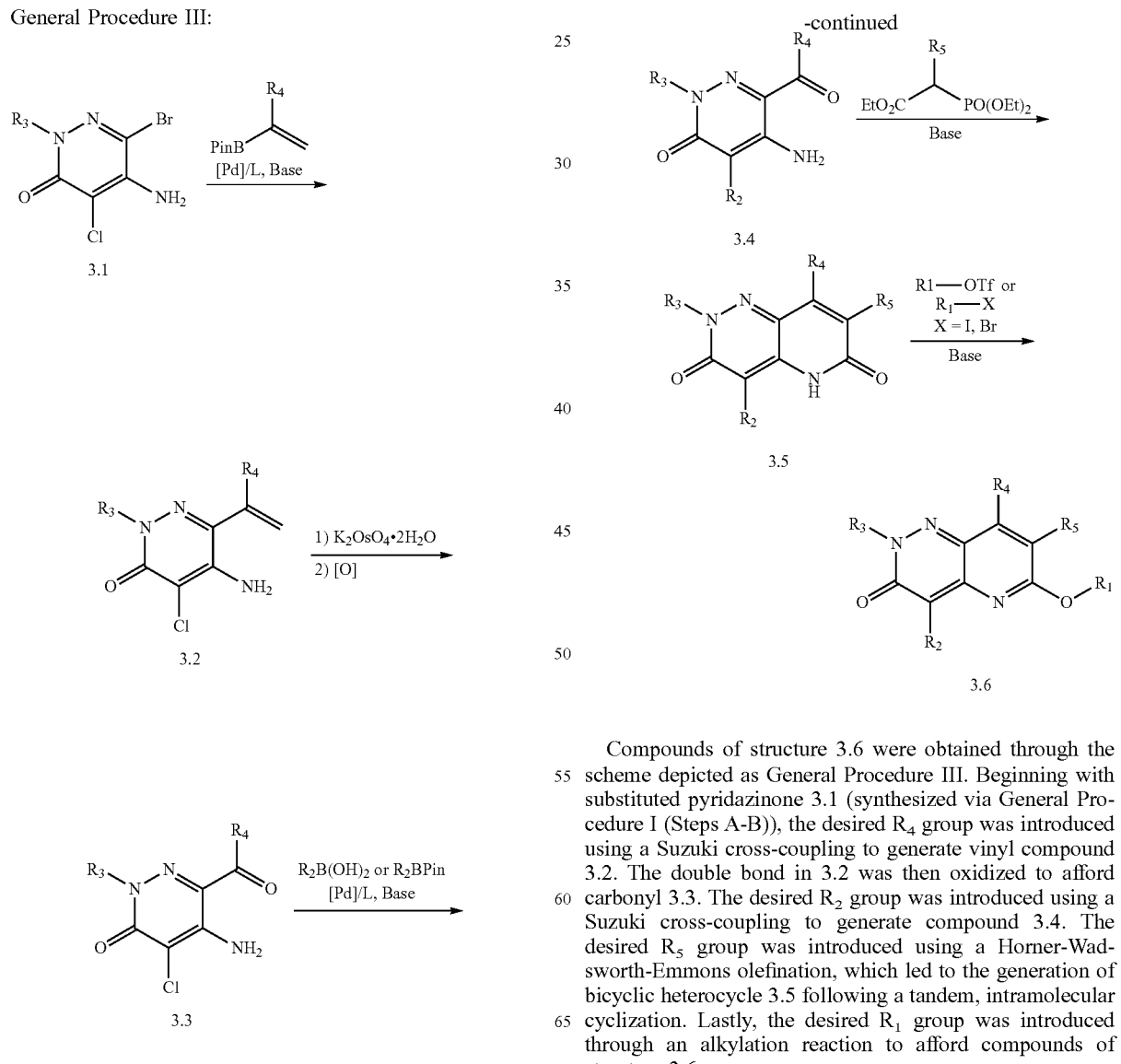<br>6-(ethylamino)-2-(2-(methyl-$d_3$)-2H-indazol-5-yl)-4-(6-methylpyridin-3-yl)pyrido[3,2-c]pyridazin-3(2H)-one | LC-MS: m/z 415 (M + H)+.<br>1H NMR (400 MHz, DMSO-$d_6$) δ: 8.85 (d, J = 1.8 Hz, 1H), 8.46 (s, 1H), 8.35 (t, J = 5.2 Hz, 1H), 8.07 (dd, J = 8.0 Hz, 2.2 Hz, 1H), 7.94 (d, J = 1.4 Hz, 1H), 7.67 (d, J = 9.1 Hz, 1H), 7.61 (d, J = 9.5 Hz, 1H), 7.41 (dd, J = 9.1 Hz, 1.9 Hz, 1H), 7.27 (d, J = 8.1 Hz, 1H), 6.79 (d, J = 9.5 Hz, 1H), 3.36 (q, J = 7.2 Hz, 2H), 2.50 (s, 3H), 1.14 (t, J = 7.2 Hz, 3H). |

General Procedure III:

Compounds of structure 3.6 were obtained through the scheme depicted as General Procedure III. Beginning with substituted pyridazinone 3.1 (synthesized via General Procedure I (Steps A-B)), the desired $R_4$ group was introduced using a Suzuki cross-coupling to generate vinyl compound 3.2. The double bond in 3.2 was then oxidized to afford carbonyl 3.3. The desired $R_2$ group was introduced using a Suzuki cross-coupling to generate compound 3.4. The desired $R_5$ group was introduced using a Horner-Wadsworth-Emmons olefination, which led to the generation of bicyclic heterocycle 3.5 following a tandem, intramolecular cyclization. Lastly, the desired $R_1$ group was introduced through an alkylation reaction to afford compounds of structure 3.6.

Preparation of Example 194 Via General Procedure III

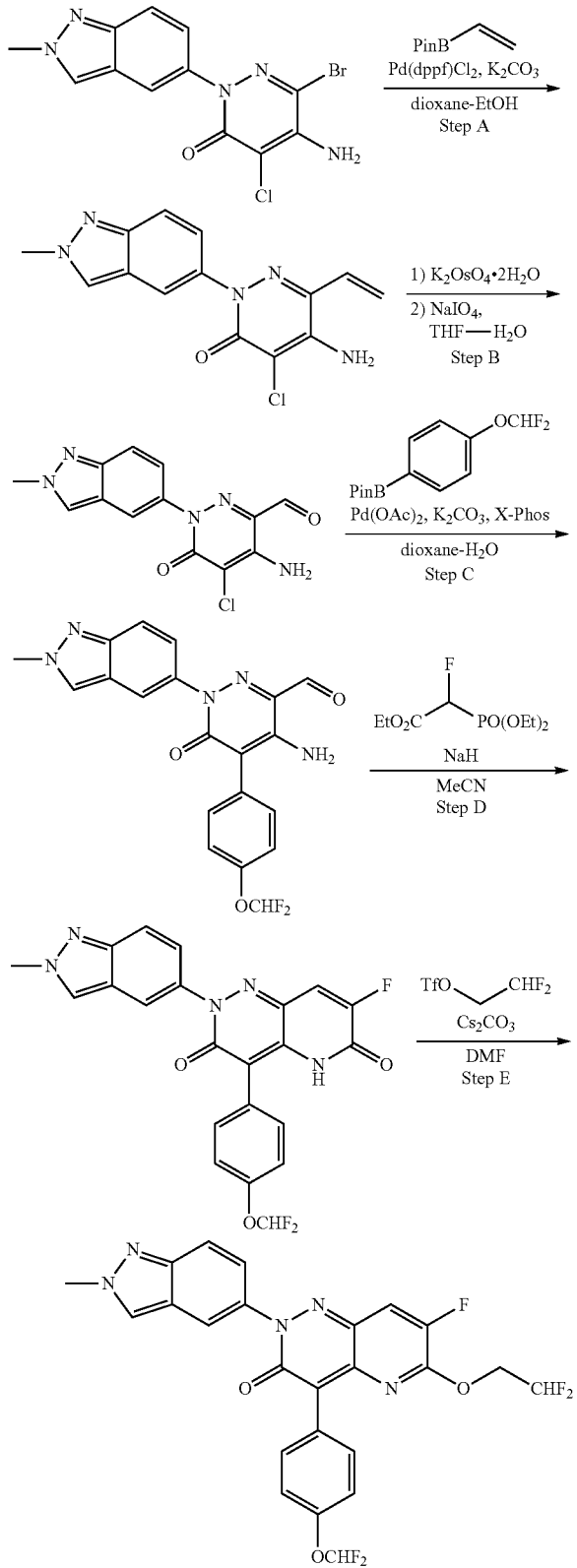

Step A: 5-amino-4-chloro-2-(2-methyl-2H-indazol-5-yl)-6-vinylpyridazin-3(2H)-one A solution of 5-amino-6-bromo-4-chloro-2-(2-methyl-2H-indazol-5-yl)pyridazin-3(2H)-one (2 g, 5.67 mmol, 1.0 eq., General Procedure I, (Steps A-B)), 4,4,5,5-tetramethyl-2-vinyl-1,3,2-dioxaborolane (1.738 g, 11.34 mmol, 2.0 eq.), Pd(dppf)Cl$_2$ (0.826 g, 1.13 mmol, 0.2 eq.), K$_2$CO$_3$ (2.336 g, 16.99 mmol, 3.0 eq.) in dioxane/EtOH (48 mL, 3/1, v/v) under N$_2$ atmosphere was stirred at 80° C. for 16 hrs. The reaction mixture was filtered and concentrated under reduced pressure, the residue was purified by flash column chromatography on silica gel to give 5-amino-4-chloro-2-(2-methyl-2H-indazol-5-yl)-6-vinylpyridazin-3(2H)-one (1.02 g, 60% yield) as a yellow solid. LC-MS (ESI): m/z 302 [M+H]$^+$.

Step B: 4-amino-5-chloro-1-(2-methyl-2H-indazol-5-yl)-6-oxo-1,6-dihydropyridazine-3-carbaldehyde A solution of 5-amino-4-chloro-2-(2-methyl-2H-indazol-5-yl)-6-vinylpyridazin-3(2H)-one (1.6 g, 5.3 mmol, 1.0 eq.), NaIO$_4$ (3.4 g, 15.9 mmol, 3.0 eq.) and K$_2$OsO$_4$·2H$_2$O (98 mg, 0.26 mmol, 0.05 eq.) in THF/H$_2$O (20 mL, 3:1) was stirred at room temperature for 3 hrs, and the resulting mixture was filtered and extracted with DCM (50 mL×3). The filtrate was washed with brine (30 mL) and the combined organic layers were dried over Na$_2$SO$_4$ and concentrated under reduced pressure. The crude residue was purified by flash column chromatography on silica gel to afford 4-amino-5-chloro-1-(2-methyl-2H-indazol-5-yl)-6-oxo-1,6-dihydropyridazine-3-carbaldehyde as a white solid (1 g, 62% yield).

LC-MS (ESI): m/z 304 [M+H]$^+$.

Step C: 4-amino-5-(4-(difluoromethoxy)phenyl)-1-(2-methyl-2H-indazol-5-yl)-6-oxo-1,6-dihydropyridazine-3-carbaldehyde A solution of 4-amino-5-chloro-1-(2-methyl-2H-indazol-5-yl)-6-oxo-1,6-dihydropyridazine-3-carbaldehyde (650 mg, 2.15 mmol, 1.0 eq.), 2-(4-(difluoromethoxy)phenyl)-4,4,5,5-tetramethyl-1,3,2-dioxaborolane (934 mg, 3.46 mmol, 1.6 eq.), Pd(OAc)$_2$ (52 mg, 0.215 mmol, 0.1 eq.), X-Phos (205 mg, 0.43 mmol, 0.2 eq.), K$_2$CO$_3$ (594 mg, 4.3 mmol, 2.0 eq.) in dioxane/H$_2$O (11 mL, 10/1, v/v) was stirred at 110° C. under N$_2$ atmosphere for 3 hrs. H$_2$O was added and the resulting mixture was extracted with EtOAc (30 mL×3), the combined organic layers were dried over Na$_2$SO$_4$, concentrated under reduced pressure, the residue was purified by flash column chromatography on silica gel to give 4-amino-5-(4-(difluoromethoxy)phenyl)-1-(2-methyl-2H-indazol-5-yl)-6-oxo-1,6-dihydropyridazine-3-carbaldehyde (650 mg, 69% yield) as a yellow solid. LC-MS (ESI): m/z 412 [M+H]$^+$.

Step D: 4-(4-(difluoromethoxy)phenyl)-7-fluoro-2-(2-methyl-2H-indazol-5-yl)pyrido[3,2-c]pyridazine-3,6(2H,5H)-dione To a suspension of 4-amino-5-(4-(difluoromethoxy)phenyl)-1-(2-methyl-2H-indazol-5-yl)-6-oxo-1,6-dihydropyridazine-3-carbaldehyde (150 mg, 0.36 mmol, 1.0 eq.) and ethyl 2-(diethoxyphosphoryl)-2-fluoroacetate (132 mg, 0.55 mmol, 1.5 eq.) in MeCN (5 mL) was added NaH (30% suspend in mineral oil, 175 mg, 2.19 mmol, 6.0 eq.) in several portions at 0° C. under N$_2$ atmosphere. After stirring at room temperature overnight, the resulting mixture was poured into ice-cooled NH₄Cl (sat. aq.) (10 mL), then extracted with EtOAc (10 mL×3), the combined organic layers were washed with brine (20 mL) and dried over Na$_2$SO$_4$, concentrated under reduced pressure, the residue was purified by flash column chromatography on silica gel to give 4-(4-(difluoromethoxy)phenyl)-7-fluoro-2-(2-methyl-2H-indazol-5-yl)pyrido[3,2-c]pyridazine-3,6(2H,5H)-dione (120 mg, 73% yield) as a yellow solid. LC-MS (ESI): m/z 454 [M+H]⁺.

6-(2,2-difluoroethoxy)-4-(4-(difluoromethoxy)phenyl)-7-fluoro-2-(2-methyl-2H-indazol-5-yl)pyrido[3,2-c]pyridazin-3(2H)-one (Example 194) was synthesized from 4-(4-(difluoromethoxy)phenyl)-7-fluoro-2-(2-methyl-2H-indazol-5-yl)pyrido[3,2-c]pyridazine-3,6(2H,5H)-dione and 2,2-difluoroethyl trifluoromethanesulfonate via similar procedure described in General Procedure I (Step F).

¹H NMR (400 MHz, DMSO-d₆) δ: 8.56 (s, 1H), 8.10 (d, J=10.0 Hz, 1H), 8.07 (d, J=1.2 Hz, 1H), 7.91 (d, J=9.2 Hz, 2H), 7.77 (d, J=9.2 Hz, 1H), 7.51 (dd, J=9.2 Hz, 2.0 Hz, 1H), 7.41 (t, J$_{HF}$=74.0 Hz, 1H), 7.32 (d, J=9.2 Hz, 2H), 6.50 (tt, J$_{HF}$=54.0 Hz, 3.2 Hz, 1H), 4.71 (td, J$_{HF}$=15.2 Hz, J=3.2 Hz, 2H), 4.28 (s, 3H).

LC-MS (ESI): m/z 518 [M+H]⁺.

The procedure set forth above for General Procedure III was used to synthesize the following compounds by using appropriate starting materials:

| Cpd No. | Structure | Characterization |
|---|---|---|
| Example 195 | 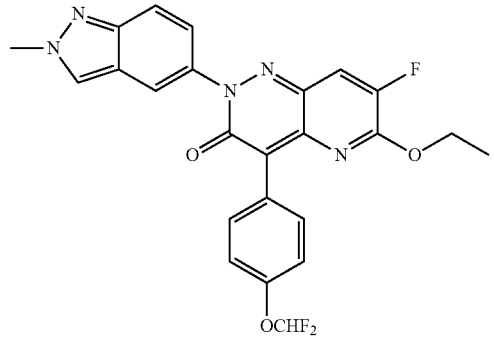 4-(4-(difluoromethoxy)phenyl)-6-ethoxy-7-fluoro-2-(2-methyl-2H-indazol-5-yl)pyrido[3,2-c]pyridazin-3(2H)-one | LC-MS (ESI): m/z 482.1 [M + H]+. 1H NMR (400 MHz, DMSO-d₆) δ: 8.50 (s, 1H), 8.00 (d, J = 1.2 Hz, 1H), 7.94 (d, J = 10.4 Hz, 1H), 7.88-7.83 (m, 2H), 7.71 (d, J = 9.2 Hz, 1H), 7.45 (dd, J = 9.2 Hz, 2.0 Hz, 1H), 7.35 (t, J$_{HF}$ = 74.0 Hz, 1H), 7.28-7.23 (m, 2H), 4.42 (q, J = 7.2 Hz, 2H), 4.23 (s, 3H), 1.36 (t, J = 7.2 Hz, 3H). |
| Example 196 | 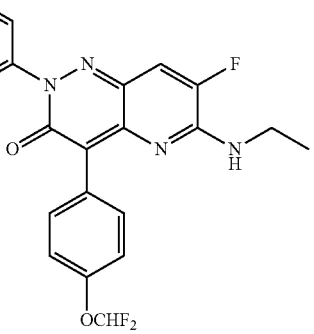 4-(4-(difluoromethoxy)phenyl)-6-(ethylamino)-7-fluoro-2-(2-methyl-2H-indazol-5-yl)pyrido[3,2-c]pyridazin-3(2H)-one | LC-MS (ESI): m/z 481.2 [M + H]+. 1H NMR (400 MHz, DMSO-d₆) δ: 8.58 (t, J = 5.6 Hz, 1H), 8.47 (s, 1H), 7.96-7.91 (m, 1H), 7.90-7.79 (J = 8.4 Hz, 2H), 7.68 (d, J = 9.2 Hz, 1H), 7.58 (d, J = 11.2 Hz, 1H), 7.41 (dd, J = 9.2 Hz, 2.0 Hz, 1H), 7.31 (t, J$_{HF}$ = 74.4 Hz, 1H), 7.20 (d, J = 8.4 Hz, 2H), 4.22 (s, 3H), 3.55-3.33 (m, 2H), 1.15 (t, J = 7.2 Hz, 3H). |

| Cpd No. | Structure | Characterization |
|---|---|---|
| Example 197 | 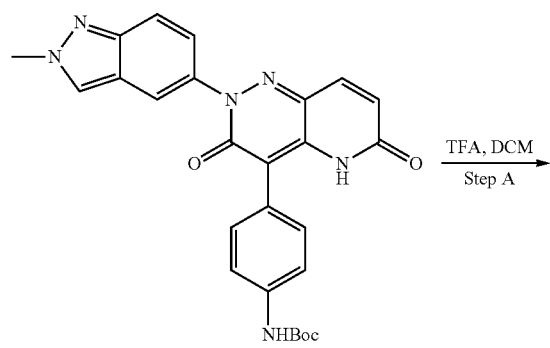

4-(4-(difluoromethoxy)phenyl)-7-fluoro-2-(2-methyl-2H-indazol-5-yl)-6-((2,2,2-trifluoroethyl)amino)pyrido[3,2-c]pyridazin-3(2H)-one | LC-MS (ESI): m/z 535.1 [M + H]+. 1H NMR (400 MHz, DMSO-d$_6$) δ: 9.05 (s, 1H), 8.48 (s, 1H), 7.97 (d, J = 1.2 Hz, 1H), 7.80 (d, J = 8.8 Hz, 2H), 7.77 (d, J = 10.8 Hz, 1H), 7.69 (d, J = 8.8 Hz, 1H), 7.43 (dd, J = 9.2 Hz, 2.0 Hz, 1H), 7.33 (t, J$_{HF}$ = 74.4 Hz, 1H), 7.19 (d, J = 8.8 Hz, 2H), 4.22 (s, 3H), 4.22-4.14 (m, 2H). |

Synthesis of 4-(4-bromophenyl)-6-ethoxy-2-(2-methyl-2H-indazol-5-yl)pyrido[3,2-c]pyridazin-3(2H)-one (Example 198)

Step A: 4-(4-aminophenyl)-2-(2-methyl-2H-indazol-5-yl)pyrido[3,2-c]pyridazine-3,6(2H,5H)-dione

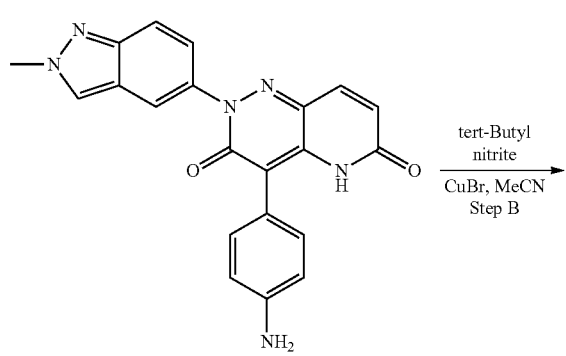

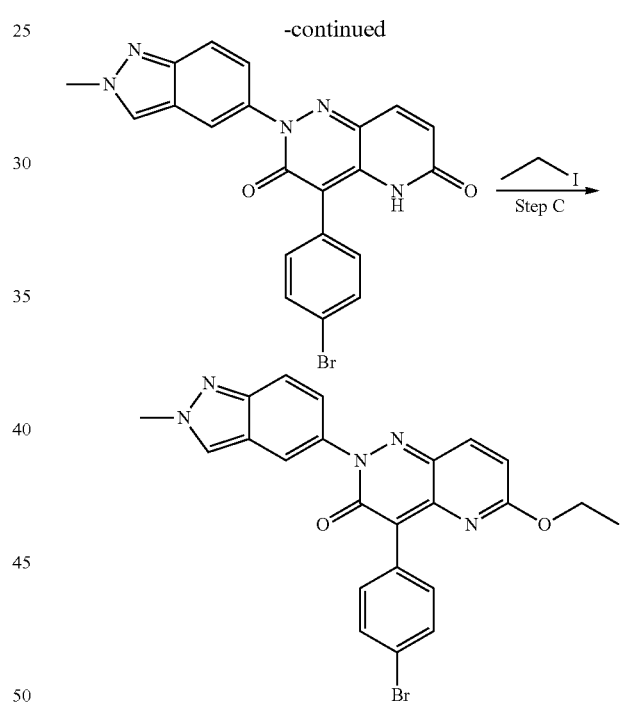

A solution of tert-butyl (4-(2-(2-methyl-2H-indazol-5-yl)-3,6-dioxo-2,3,5,6-tetrahydropyrido[3,2-c]pyridazin-4-yl)phenyl)carbamate (synthesized from 4-chloro-2-(2-methyl-2H-indazol-5-yl)pyrido[3,2-c]pyridazine-3,6(2H,5H)-dione & (4-((tert-butoxycarbonyl)amino)phenyl)boronic acid via General Procedure I (Method A, Step E)) (180 mg, 0.372 mmol) in TFA/DCM (1 mL/5 mL) was stirred at room temperature for 1 hr. The reaction mixture was extracted with EtOAc (20 mL×3). The combined organic layers were washed with brine (20 mL), dried over Na$_2$SO$_4$ and concentrated under reduced pressure, the residue was purified by flash column chromatography on silica gel to give 4-(4-aminophenyl)-2-(2-methyl-2H-indazol-5-yl)pyrido[3,2-c]pyridazine-3,6(2H,5H)-dione (116 mg, 79% yield) as a yellow solid. LC-MS (ESI): m/z 385 [M+H]+.

Step B: 4-(4-bromophenyl)-2-(2-methyl-2H-indazol-5-yl)pyrido[3,2-c]pyridazine-3,6(2H,5H)-dione To a solution of 4-(4-aminophenyl)-2-(2-methyl-2H-indazol-5-yl)pyrido[3,2-c]pyridazine-3,6(2H,5H)-dione (200 mg, 0.52 mmol, 1.0 eq.) and CuBr (299 mg, 2.08 mmol, 4.0 eq.) in ACN (10 mL) was added tert-butyl nitrite (215 mg, 2.08 mmol, 4.0 eq.) at 0° C. drop-wise over 10 min. The reaction mixture was stirred at room temperature for 4 hrs. The resulting mixture was quenched with Na$_2$SO$_3$ (sat. aq.) (20 mL), extracted with EtOAc (10 mL×3). The combined organic layers were washed with brine (20 mL), dried over Na$_2$SO$_4$ and concentrated under reduced pressure, the residue was purified by flash column chromatography on silica gel to afford 4-(4-bromophenyl)-2-(2-methyl-2H-indazol-5-yl)pyrido[3,2-c]pyridazine-3,6(2H,5H)-dione as a yellow solid (70 mg, 30% yield). LC-MS (ESI): m/z 448 [M+H]$^+$.

Step C:

4-(4-Bromophenyl)-6-ethoxy-2-(2-methyl-2H-indazol-5-yl)pyrido[3,2-c]pyridazin-3(2H)-one (Example 198) was synthesized from 4-(4-bromophenyl)-2-(2-methyl-2H-indazol-5-yl)pyrido[3,2-c]pyridazine-3,6(2H,5H)-dione & iodoethane via General Procedure I (Method A, Step F).

$^1$H NMR (400 MHz, DMSO-d$_6$) δ (ppm): 8.49 (s, 1H), 8.00 (d, J=1.6 Hz, 1H), 7.97 (d, J=9.6 Hz, 1H), 7.75 (d, J=8.4 Hz, 2H), 7.70 (d, J=9.2 Hz, 1H), 7.64 (d, J=8.4 Hz, 2H), 7.45 (dd, J=8.8 Hz, 1.6 Hz, 1H), 6.95 (d, J=9.2 Hz, 1H), 4.33 (q, J=7.2 Hz, 2H), 4.22 (s, 3H), 1.32 (t, J=7.2 Hz, 3H).

LC-MS (ESI): m/z 476, 478 [M+H]$^+$.

Synthesis of 4-(4-bromophenyl)-6-isopropoxy-2-(2-methyl-2H-indazol-5-yl)pyrido[3,2-c]pyridazin-3(2H)-one (Example 199)

4-(4-Bromophenyl)-6-isopropoxy-2-(2-methyl-2H-indazol-5-yl)pyrido[3,2-c]pyridazin-3(2H)-one (Example 199) was synthesized from 4-(4-bromophenyl)-2-(2-methyl-2H-indazol-5-yl)pyrido[3,2-c]pyridazine-3,6(2H,5H)-dione & 2-iodopropane via General Procedure I (Method A, Step F).

$^1$H NMR (400 MHz, DMSO-d$_6$) δ (ppm): 8.49 (s, 1H), 8.00 (dd, J=2.0 Hz, 0.8 Hz, 1H), 7.96 (d, J=9.4 Hz, 1H), 7.74-7.68 (m, 3H), 7.64 (d, J=8.6 Hz, 2H), 7.45 (dd, J=9.1 Hz, 2.0 Hz, 1H), 6.90 (d, J=9.4 Hz, 1H), 5.15 (hept, J=6.2 Hz, 1H), 4.22 (s, 3H), 1.30 (d, J=6.2 Hz, 6H).

LC-MS (ESI): m/z 490, 492 [M+H]$^+$.

Synthesis of 4-(4-bromophenyl)-6-(2,2-difluoroethoxy)-2-(2-methyl-2H-indazol-5-yl)pyrido[3,2-c]pyridazin-3(2H)-one (Example 200)

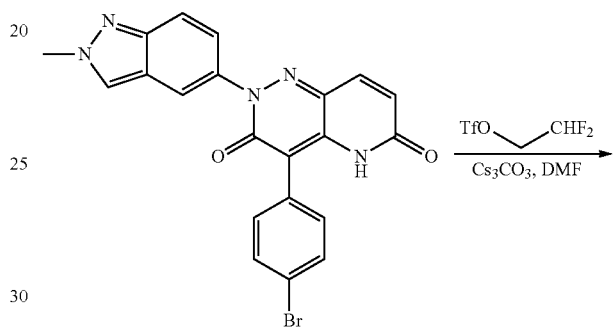

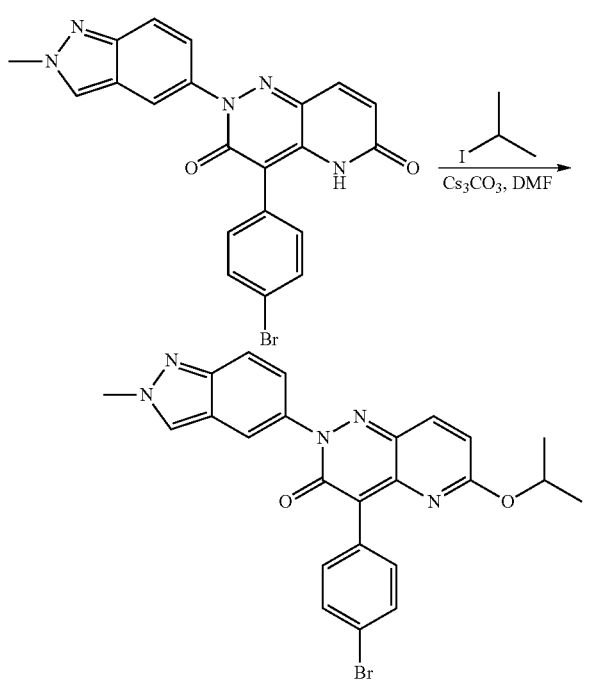

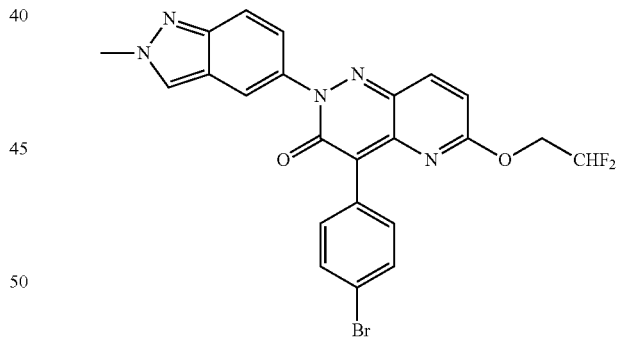

4-(4-bromophenyl)-6-(2,2-difluoroethoxy)-2-(2-methyl-2H-indazol-5-yl)pyrido[3,2-c]pyridazin-3(2H)-one (Example 200) was synthesized from 4-(4-bromophenyl)-2-(2-methyl-2H-indazol-5-yl)pyrido[3,2-c]pyridazine-3,6(2H,5H)-dione & 2,2-difluoroethyl trifluoromethanesulfonate via General Procedure I (Method A, Step F).

$^1$H NMR (400 MHz, DMSO-d$_6$) δ (ppm): 8.51 (s, 1H), 8.07 (d, J=9.2 Hz, 1H), 8.03 (d, J=1.6 Hz, 1H), 7.76 (d, J=8.8 Hz, 2H), 7.72 (d, J=9.2 Hz, 1H), 7.66 (d, J=8.4 Hz, 2H), 7.47 (dd, J=9.2 Hz, 2.0 Hz, 1H), 7.08 (d, J=9.2 Hz, 1H), 6.41 (tt, J$_{HF}$=54.4 Hz, 3.2 Hz, 1H), 4.59 (td, J$_{HF}$=15.2 Hz, J=3.2 Hz, 2H), 4.23 (s, 3H).

LC-MS (ESI): m/z 512, 514 [M+H]$^+$.

Synthesis of 2-(benzo[d]thiazol-6-yl)-4-(4-bromophenyl)-6-(2,2-difluoroethoxy)pyrido[3,2-c]pyridazin-3(2H)-one (Example 201)

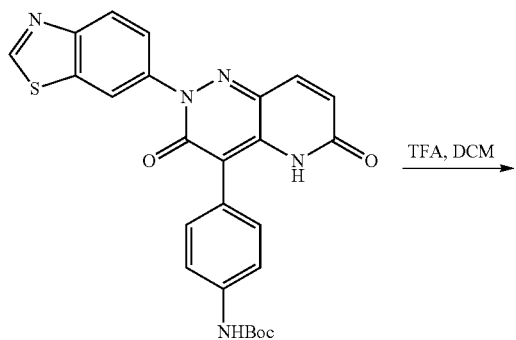

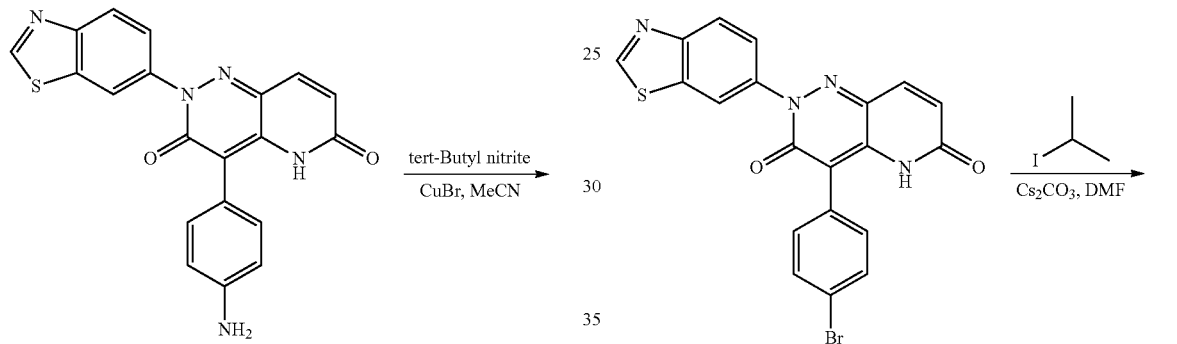

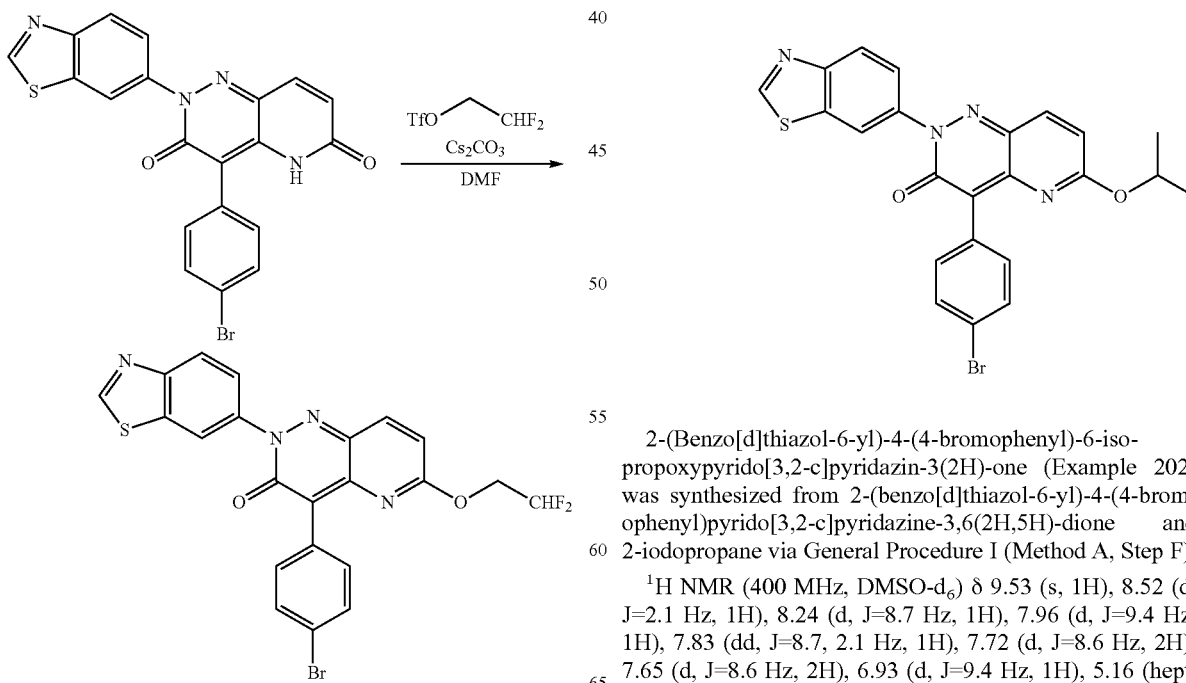

Procedures similar to those described for Example 198 were followed. 2-(Benzo[d]thiazol-6-yl)-4-(4-bromophenyl)-6-(2,2-difluoroethoxy)pyrido[3,2-c]pyridazin-3(2H)-one (Example 201) was synthesized from tert-butyl (4-(2-(benzo[d]thiazol-6-yl)-3,6-dioxo-2,3,5,6-tetrahydropyrido[3,2-c]pyridazin-4-yl)phenyl)carbamate via Step A-B (Example 198) and 2,2-difluoroethyl trifluoromethanesulfonate via General Procedure I (Method A, Step F).

$^1$H NMR (400 MHz, DMSO-d$_6$) δ (ppm): 9.53 (s, 1H), 8.54 (d, J=2.1 Hz, 1H), 8.25 (d, J=8.7 Hz, 1H), 8.07 (d, J=9.4 Hz, 1H), 7.85 (dd, J=8.7 Hz, 2.1 Hz, 1H), 7.76 (d, J=8.6 Hz, 2H), 7.66 (d, J=8.6 Hz, 2H), 7.09 (d, J=9.4 Hz, 1H), 6.41 (tt, J$_{HF}$=54.4, 3.4 Hz, 1H), 4.60 (td, J=15.2, 3.4 Hz, 2H).

LC-MS (ESI): m/z 515, 517 [M+H]$^+$.

Synthesis of 2-(benzo[d]thiazol-6-yl)-4-(4-bromophenyl)-6-isopropoxypyrido[3,2-c]pyridazin-3(2H)-one (Example 202)

2-(Benzo[d]thiazol-6-yl)-4-(4-bromophenyl)-6-isopropoxypyrido[3,2-c]pyridazin-3(2H)-one (Example 202) was synthesized from 2-(benzo[d]thiazol-6-yl)-4-(4-bromophenyl)pyrido[3,2-c]pyridazine-3,6(2H,5H)-dione and 2-iodopropane via General Procedure I (Method A, Step F).

$^1$H NMR (400 MHz, DMSO-d$_6$) δ 9.53 (s, 1H), 8.52 (d, J=2.1 Hz, 1H), 8.24 (d, J=8.7 Hz, 1H), 7.96 (d, J=9.4 Hz, 1H), 7.83 (dd, J=8.7, 2.1 Hz, 1H), 7.72 (d, J=8.6 Hz, 2H), 7.65 (d, J=8.6 Hz, 2H), 6.93 (d, J=9.4 Hz, 1H), 5.16 (hept, J=6.4 Hz, 1H), 1.31 (d, J=6.4 Hz, 6H).

LC-MS (ESI): m/z 493, 495 [M+H]$^+$.

193

Synthesis of 6-(2,2-difluoroethoxy)-4-(4-(difluoromethoxy)phenyl)-2-(3-(dimethylamino)-2-methyl-2H-indazol-5-yl)pyrido[3,2-c]pyridazin-3(2H)-one (Example 203) & 4-(4-(difluoromethoxy)phenyl)-6-(dimethylamino)-2-(3-(dimethylamino)-2-methyl-2H-indazol-5-yl)pyrido[3,2-c]pyridazin-3(2H)-one (Example 204)

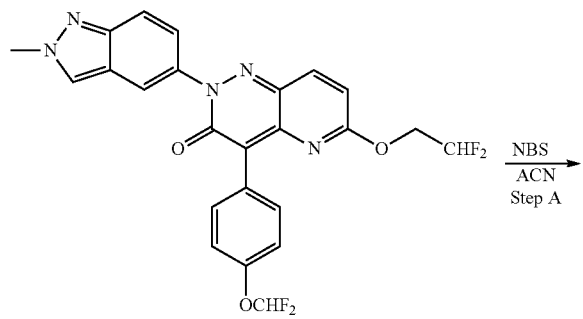

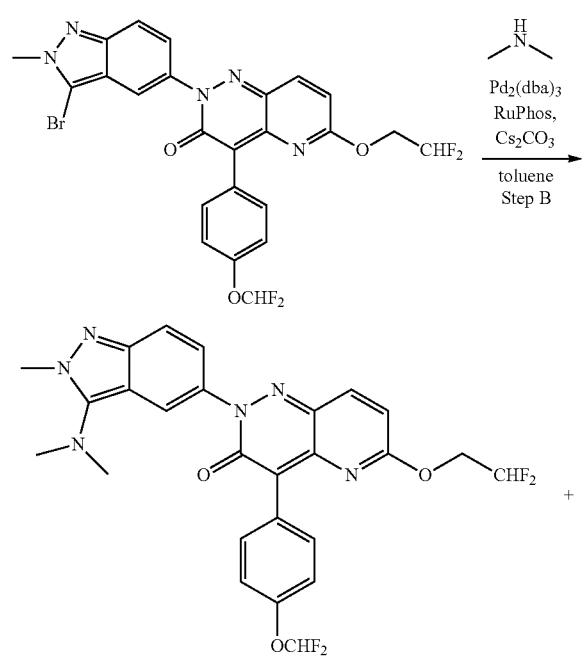

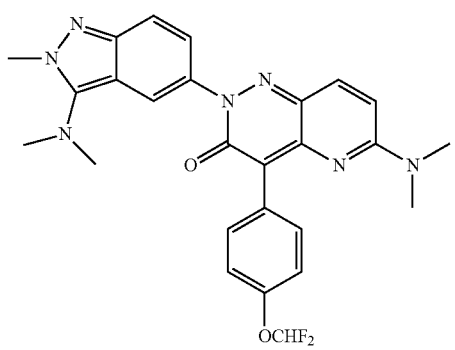

194

Step A: 2-(3-bromo-2-methyl-2H-indazol-5-yl)-6-(2,2-difluoroethoxy)-4-(4-(difluoromethoxy)phenyl)pyrido[3,2-c]pyridazin-3(2H)-one To a suspension of 6-(2,2-difluoroethoxy)-4-(4-(difluoromethoxy)phenyl)-2-(2-methyl-2H-indazol-5-yl)pyrido[3,2-c]pyridazin-3(2H)-one (Example 125) (200 mg, 0.4 mmol, 1.0 eq.) in ACN (4 mL) was added NBS (75 mg, 0.42 mmol, 1.05 eq.). Then the reaction was stirring at 80° C. for 3 hrs. The reaction was concentrated under reduced pressure and the residue was purified directly by flash column chromatography on silica gel to afford 2-(3-bromo-2-methyl-2H-indazol-5-yl)-6-(2,2-difluoroethoxy)-4-(4-(difluoromethoxy)phenyl)pyrido[3,2-c]pyridazin-3(2H)-one (160 mg, 69% yield) as a yellow solid. LC-MS (ESI): m/z 578; 580 [M+H]$^+$.

Step B: 6-(2,2-difluoroethoxy)-4-(4-(difluoromethoxy)phenyl)-2-(3-(dimethylamino)-2-methyl-2H-indazol-5-yl)pyrido[3,2-c]pyridazin-3(2H)-one & 4-(4-(difluoromethoxy)phenyl)-6-(dimethylamino)-2-(3-(dimethylamino)-2-methyl-2H-indazol-5-yl)pyrido[3,2-c]pyridazin-3(2H)-one To a suspension of 2-(3-bromo-2-methyl-2H-indazol-5-yl)-6-(2,2-difluoroethoxy)-4-(4-(difluoromethoxy)phenyl)pyrido[3,2-c]pyridazin-3(2H)-one (160 mg, 0.28 mmol, 1.0 eq.) in toluene (3 mL) was added $Cs_2CO_3$ (90 mg, 0.28 mmol, 1.0 eq.), $Pd_2(dba)_3$ (25 mg, 0.028 mmol, 0.10 eq.), Ru-Phos (26 mg, 0.055 mmol, 0.2 eq.) and dimethylamine (2 M in THF) (1.4 mL, 2.8 mmol, 10.0 eq.). Then the reaction was sealed in a pressure-resistant tube and stirring at 100° C. for 5 hrs under $N_2$ atmosphere. The reaction was cooled to room temperature and concentrated under reduced pressure, and the residue was purified by flash column chromatography on silica gel and RP-prep-HPLC to afford 6-(2,2-difluoroethoxy)-4-(4-(difluoromethoxy)phenyl)-2-(3-(dimethylamino)-2-methyl-2H-indazol-5-yl)pyrido[3,2-c]pyridazin-3(2H)-one (Example 203) and 4-(4-(difluoromethoxy)phenyl)-6-(dimethylamino)-2-(3-(dimethylamino)-2-methyl-2H-indazol-5-yl)pyrido[3,2-c]pyridazin-3(2H)-one (Example 204).

Example 203

$^1$H NMR (400 MHz, DMSO-$d_6$) δ (ppm): 8.11 (s, 1H), 8.08 (d, J=9.4 Hz, 1H), 7.87 (d, J=8.4 Hz, 2H), 7.55 (d, J=9.2 Hz, 1H), 7.36 (d, J=10.6 Hz, 1H), 7.35 (t, $J_{HF}$=74.0 Hz, 1H), 7.26 (d, J=8.2 Hz, 2H), 7.06 (d, J=9.3 Hz, 1H), 6.41 (tt, $J_{HF}$=54.4 Hz, J=3.3 Hz, 1H), 4.59 (td, $J_{HF}$=15.1 Hz, J=3.3 Hz, 2H), 3.99 (s, 3H), 2.97 (s, 6H).

LC-MS (ESI): m/z 543 [M+H]$^+$.

Example 204

$^1$H NMR (400 MHz, DMSO-$d_6$) δ (ppm): 8.04 (dd, J=2.0, 0.8 Hz, 1H), 7.93-7.84 (m, 2H), 7.76 (d, J=9.8 Hz, 1H), 7.52 (dd, J=9.1, 0.8 Hz, 1H), 7.33 (dd, J=9.2, 2.0 Hz, 1H), 7.31 (t, $J_{HF}$=74.2, 1H), 7.27 (d, J=9.8 Hz, 1H), 7.22-7.16 (m, 2H), 3.99 (s, 3H), 3.23 (s, 3H), 3.17 (s, 3H), 2.96 (s, 6H).

LC-MS (ESI): m/z 506 [M+H]$^+$.

Synthesis of 4-(4-(difluoromethoxy)phenyl)-2-(2-methyl-2H-indazol-5-yl)-6-propylpyrido[3,2-c]pyridazin-3(2H)-one (Example 205)

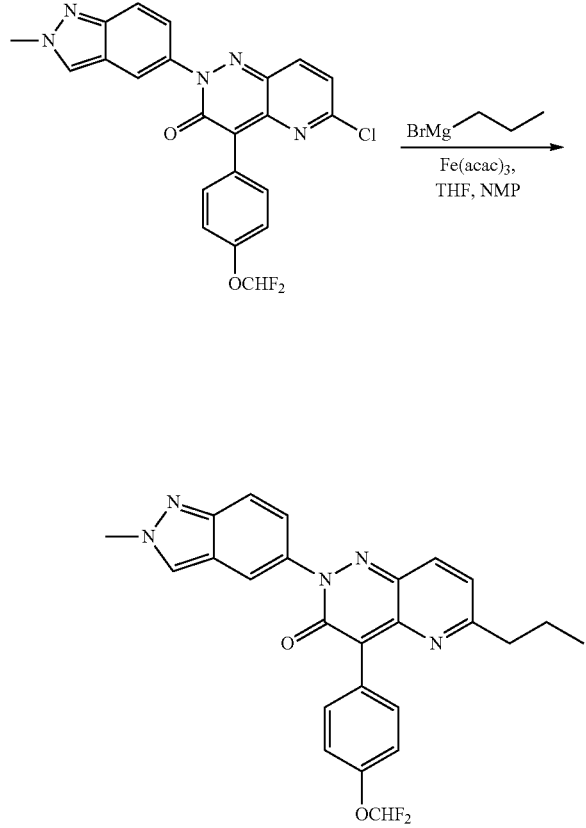

To a mixture of 6-chloro-4-(4-(difluoromethoxy)phenyl)-2-(2-methyl-2H-indazol-5-yl)pyrido[3,2-c]pyridazin-3(2H)-one (synthesized from 4-chloro-2-(2-methyl-2H-indazol-5-yl)pyrido[3,2-c]pyridazine-3,6(2H,5H)-dione & 2-(4-(difluoromethoxy)phenyl)-4,4,5,5-tetramethyl-1,3,2-dioxaborolane via General Procedure I (Method C, Step E, G) (120 mg, 0.26 mmol, 1.0 eq.) and Fe(acac)$_3$ (93 mg, 0.26 mmol, 1.0 eq.) in THF (5 mL) and NMP (1 mL) was added n-propylmagnesium bromide (1 M in diethyl ether) (4.0 mL, 4.0 mmol, 15.4 eq.) drop-wisely at 0° C. under N$_2$ atmosphere. The reaction mixture was stirred at room temperature overnight and quenched carefully with ice water (10 mL). The crude mixture was extracted with EtOAc (10 mL×3). The combined organic layers were washed with brine (20 mL), dried over Na$_2$SO$_4$ and concentrated under reduced pressure. The crude residue was purified by RP-prep-HPLC to give 4-(4-(difluoromethoxy)phenyl)-2-(2-methyl-2H-indazol-5-yl)-6-propylpyrido[3,2-c]pyridazin-3(2H)-one (Example 205).

$^1$H NMR (400 MHz, DMSO-d$_6$) δ (ppm): 8.51 (s, 1H), 8.04 (s, 1H), 7.99 (d, J=9.1 Hz, 1H), 7.83 (d, J=8.6 Hz, 2H), 7.72 (d, J=9.2 Hz, 1H), 7.49 (d, J=9.1 Hz, 1H), 7.35 (t, J$_{HF}$=72.0 Hz, 1H), 7.29 (d, J=9.3 Hz, 1H), 7.26 (d, J=8.6 Hz, 2H), 4.23 (s, 3H), 2.78 (t, J=7.4 Hz, 2H), 1.82-1.61 (m, 2H), 0.94 (t, J=7.4 Hz, 3H).

LC-MS (ESI): m/z 462 [M+H]$^+$.

Synthesis of 4-cyclohexyl-6-(2,2-difluoroethoxy)-2-(2-methyl-2H-indazol-5-yl)pyrido[3,2-c]pyridazin-3(2H)-one (Example 206)

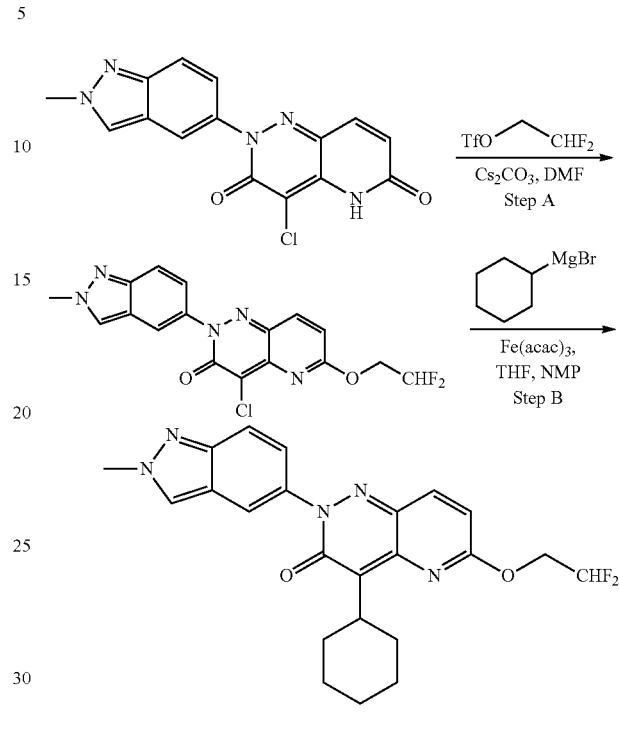

Step A: 4-chloro-6-(2,2-difluoroethoxy)-2-(2-methyl-2H-indazol-5-yl)pyrido[3,2-c]pyridazin-3(2H)-one A mixture of 4,6-dichloro-2-(2-methyl-2H-indazol-5-yl)pyrido[3,2-c]pyridazin-3(2H)-one (300 mg, 0.87 mmol, 1.0 eq., Synthesized via General Procedure I (Method A, Steps A-D), 2,2-difluoroethyl trifluoromethanesulfonate (278 mg, 1.3 mmol, 1.49 eq.) and Cs$_2$CO$_3$ (565 mg, 1.7 mmol, 1.95 eq.) in DMF (8 mL) was stirred at room temperature for 3 hrs and quenched with ice water (10 mL). The crude mixture was extracted with EtOAc (10 mL×3). The combined organic layers were washed with brine (20 mL), dried over Na$_2$SO$_4$ and concentrated under reduced pressure. The crude residue was purified by flash column chromatography on silica gel to afford 4-chloro-6-(2,2-difluoroethoxy)-2-(2-methyl-2H-indazol-5-yl)pyrido[3,2-c]pyridazin-3(2H)-one (250 mg, 74% yield) as a yellow solid. LC-MS (ESI): m/z 392 [M+H]$^+$.

Step B: 4-cyclohexyl-6-(2,2-difluoroethoxy)-2-(2-methyl-2H-indazol-5-yl)pyrido[3,2-c]pyridazin-3(2H)-one A mixture of 4-chloro-6-(2,2-difluoroethoxy)-2-(2-methyl-2H-indazol-5-yl)-2H,3H-pyrido[3,2-c]pyridazin-3-one (100 mg, 0.26 mmol, 1.0 eq.), Fe(acac)$_3$ (90 mg, 0.26 mmol, 1.0 eq.) and NMP/THF mixture (0.5 mL/5 mL) was stirred at 0° C. under N$_2$ atmosphere. cyclohexylmagnesium bromide (1 M in diethyl ether) (2.6 mL, 2.6 mmol, 10.0 eq.) was added drop-wisely at 0° C. Then the mixture was allowed to warm to room temperature and stirred overnight, the reaction was monitored by TLC, after the completion, the reaction was quenched with ice water (10 mL), the crude mixture was extracted with EtOAc (10 mL×3), the combined organic layers were washed with brine (30 mL), dried over Na$_2$SO$_4$ and concentrated under reduced pressure, the crude residue was purified by RP-prep-HPLC to give 4-cyclohexyl-6-(2,2-difluoroethoxy)-2-(2-methyl-2H-indazol-5-yl)pyrido[3,2-c]pyridazin-3(2H)-one (Example 206).

$^1$H NMR (400 MHz, DMSO-d$_6$) δ (ppm) 8.48 (s, 1H), 7.99-7.92 (m, 2H), 7.69 (d, J=9.1 Hz, 1H), 7.39 (dd, J=9.1, 2.0 Hz, 1H), 7.02 (d, J=9.4 Hz, 1H), 6.50 (t, J$_{HF}$=54.2 Hz, 1H), 4.79 (td, J$_{HF}$=15.1, 3.2 Hz, 2H), 4.22 (s, 3H), 2.36-2.32 (m, 1H), 1.88-1.69 (m, 4H), 1.63-1.55 (m, 2H), 1.43-1.19 (m, 4H).

LC-MS (ESI): m/z 439 [M+H]$^+$.

Synthesis of 6-(2,2-difluoroethoxy)-4-(4-hydroxyphenyl)-2-(2-methyl-2H-indazol-5-yl)pyrido[3,2-c]pyridazin-3(2H)-one (Example 207)

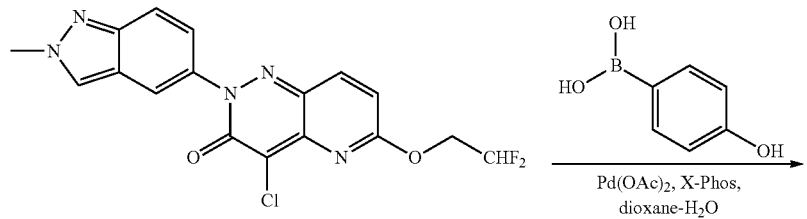

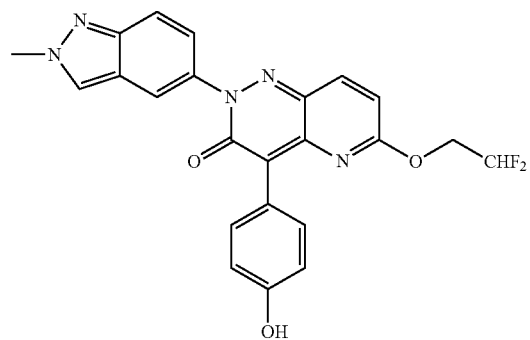

A mixture of 4-chloro-6-(2,2-difluoroethoxy)-2-(2-methyl-2H-indazol-5-yl)pyrido[3,2-c]pyridazin-3(2H)-one (100 mg, 0.25 mmol, 1.0 eq.), Pd(OAc)$_2$ (12 mg, 0.05 mmol, 0.2 eq.), K$_2$CO$_3$ (105 mg, 0.75 mmol, 3.0 eq.) and (4-hydroxyphenyl)boronic acid (53 mg, 0.38 mmol) in dioxane/water mixture (5 mL, 10/1, v/v) was stirred at 100° C. under N$_2$ atmosphere. Then the reaction mixture was poured into ice water (10 mL) and extracted with EtOAc (10 mL×3). The combined organic layers were washed with brine (20 mL), dried over Na$_2$SO$_4$ and concentrated under reduced pressure. The crude residue was purified by RP-prep-HPLC to give 6-(2,2-difluoroethoxy)-4-(4-hydroxyphenyl)-2-(2-methyl-2H-indazol-5-yl)pyrido[3,2-c]pyridazin-3(2H)-one (Example 207).

$^1$H NMR (400 MHz, DMSO-d$_6$) δ (ppm): 8.49 (s, 1H), 8.04-7.97 (m, 2H), 7.77-7.62 (m, 3H), 7.44 (dd, J=9.1, 1.9 Hz, 1H), 7.03 (d, J=9.4 Hz, 1H), 6.83 (d, J=8.4 Hz, 2H), 6.42 (tt, J$_{HF}$=54.5, 3.5 Hz, 1H), 4.61 (td, J=15.0, 3.5 Hz, 2H), 4.22 (s, 3H).

LC-MS (ESI): m/z 450 [M+H]$^+$.

Synthesis of 6-(2,2-difluoroethoxy)-4-(4-(difluoromethoxy)phenyl)-2-(3-ethyl-2-methyl-2H-indazol-5-yl)pyrido[3,2-c]pyridazin-3(2H)-one (Example 208)

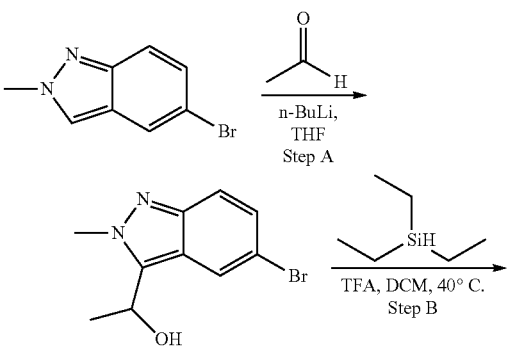

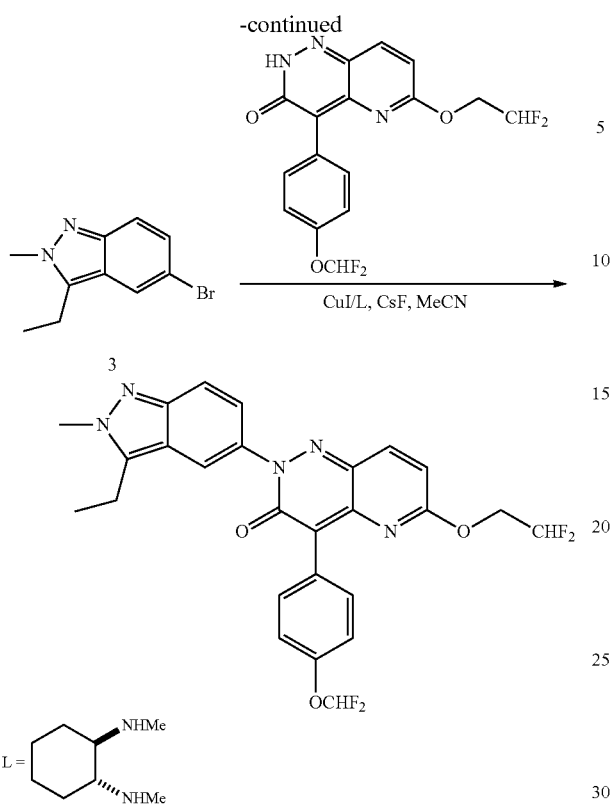

Step A: 1-(5-bromo-2-methyl-2H-indazol-3-yl)ethanol

To a solution of 5-bromo-2-methyl-2H-indazole (500 mg, 2.37 mmol, 1 eq.) in THF (10 mL) was added n-BuLi (2.5 M in hexane) (4.7 mL, 11.85 mmol, 5 eq.) drop-wisely at −65° C. under $N_2$ atmosphere. After 3 hrs, acetaldehyde (5 M in THF) (0.6 mL, 3.0 mmol, 1.27 eq.) was added. Then the reaction was warmed to room temperature slowly and stirred for 16 hrs. The reaction mixture was poured into sat. $NH_4Cl$ aq. (10 mL) and was extracted with EtOAc (10 mL×3). The combined organic layers were washed with brine (20 mL), dried over $Na_2SO_4$ and concentrated under reduced pressure. The crude residue was purified by flash column chromatography on silica gel to give 1-(5-bromo-2-methyl-2H-indazol-3-yl)ethanol (500 mg, 83% yield) as a yellow solid. LC-MS (ESI): m/z 255, 257 $[M+H]^+$.

Step B: 5-bromo-3-ethyl-2-methyl-2H-indazole

A mixture of 1-(5-bromo-2-methyl-2H-indazol-3-yl)ethanol (200 mg, 0.78 mmol, 1 eq.), triethylsilane (453 mg, 3.9 mmol, 5 eq.), TFA (889 mg, 7.8 mmol, 10 eq.) in DCM (5 mL) was stirred at 40° C. for 16 hrs. Then the mixture was poured into sat. $NaHCO_3$ aq. (10 mL) at 0° C., and was extracted with DCM (10 mL×3). The combined organic layers were dried over $Na_2SO_4$, concentrated under reduced pressure. The crude residue was purified by flash column chromatography on silica gel to give 5-bromo-3-ethyl-2-methyl-2H-indazole (80 mg, 43% yield) as a yellow solid. LC-MS (ESI): m/z 239, 241 $[M+H]^+$.

6-(2,2-difluoroethoxy)-4-(4-(difluoromethoxy)phenyl)-2-(3-ethyl-2-methyl-2H-indazol-5-yl)pyrido[3,2-c]pyridazin-3(2H)-one (Example 208) was synthesized from 6-(2,2-difluoroethoxy)-4-(4-(difluoromethoxy)phenyl)pyrido[3,2-c]pyridazin-3(2H)-one and 5-bromo-3-ethyl-2-methyl-2H-indazole via General Procedure II (Method A, Step G).

$^1H$ NMR (400 MHz, DMSO-$d_6$) δ: 8.13 (d, J=9.2 Hz, 1H), 8.07 (dd, J=2.0 Hz, 0.8 Hz, 1H), 7.93 (d, J=8.8 Hz, 2H), 7.68 (dd, J=9.2 Hz, 0.8 Hz, 1H), 7.48 (dd, J=8.8 Hz, 1.6 Hz, 1H), 7.41 (t, $J_{HF}$=74.0 Hz, 1H), 7.31 (d, J=8.8 Hz, 2H), 7.13 (d, J=9.2 Hz, 1H), 6.47 (tt, $J_{HF}$=54.4 Hz, 3.2 Hz, 1H), 4.65 (td, $J_{HF}$=15.2 Hz, 3.2 Hz, 2H), 4.20 (s, 3H), 3.17 (q, J=7.2 Hz, 2H), 1.33 (t, J=7.2 Hz, 3H).

LC-MS (ESI): m/z 528 $[M+H]^+$.

Synthesis of 6-(2,2-difluoroethoxy)-4-(4-(difluoromethoxy)phenyl)-8-(hydroxymethyl)-2-(2-methyl-2H-indazol-5-yl)pyrido[3,2-c]pyridazin-3(2H)-one (Example 209) and 6-(2,2-difluoroethoxy)-4-(4-(difluoromethoxy)phenyl)-8-(difluoromethyl)-2-(2-methyl-2H-indazol-5-yl)pyrido[3,2-c]pyridazin-3(2H)-one (Example 210)

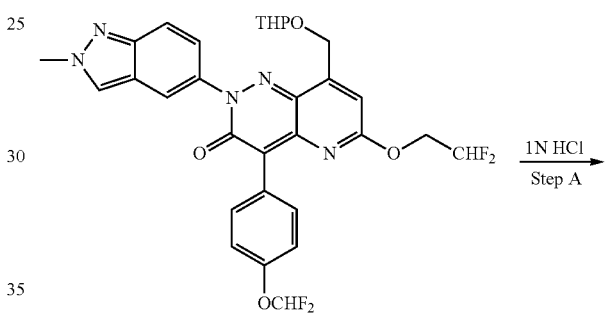

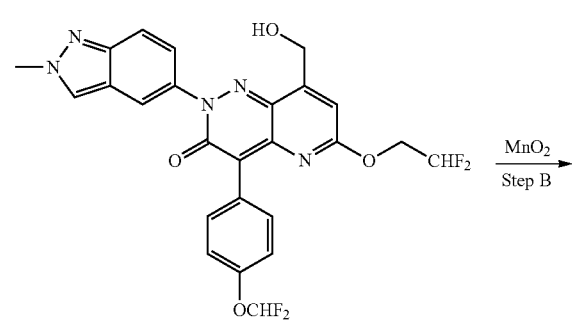

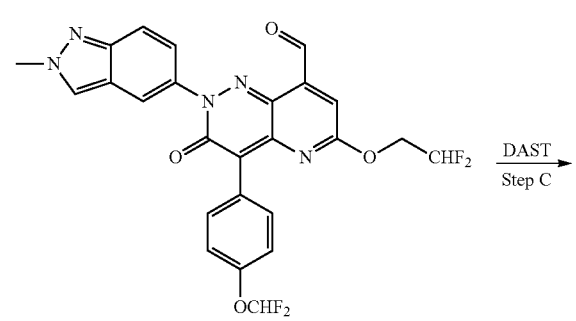

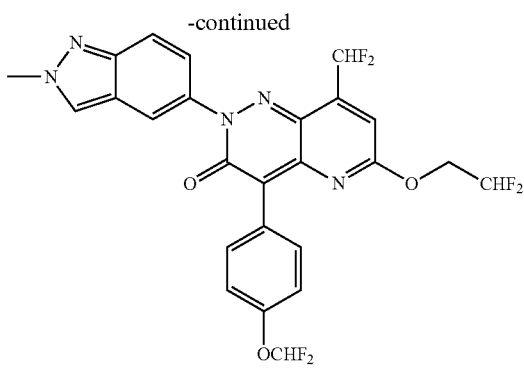

Step A: 6-(2,2-difluoroethoxy)-4-(4-(difluoromethoxy)phenyl)-8-(hydroxymethyl)-2-(2-methyl-2H-indazol-5-yl)pyrido[3,2-c]pyridazin-3(2H)-one To a solution of 6-(2,2-difluoroethoxy)-4-(4-(difluoromethoxy)phenyl)-2-(2-methyl-2H-indazol-5-yl)-8-(((tetrahydro-2H-pyran-2-yl)oxy)methyl)pyrido[3,2-c]pyridazin-3(2H)-one (Example 142, synthesized from (E)-methyl 4-(tetrahydro-2H-pyran-2-yloxy)-3-(4,4,5,5-tetramethyl-1,3,2-dioxaborolan-2-yl)but-2-enoate (Ref: Tetrahedron 2012, 68, 3444-3449) via General Procedure I (Method A, Step E-F) (180 mg, 0.3 mmol, 1.0 eq.) in dioxane (3 mL) was added 1N HCl (aq.) (1 mL, 1 mmol, 3.3 eq.) at room temperature. And the resulting mixture was stirred at room temperature for 2 hrs. Then the reaction was quenched with ice water (20 mL), extracted with EtOAc (20 mL×3). The combined organic layers were washed with brine (20 mL), dried over $Na_2SO_4$ and concentrated under reduced pressure, the residue was purified by flash column chromatography on silica gel to afford 6-(2,2-difluoroethoxy)-4-(4-(difluoromethoxy)phenyl)-8-(hydroxymethyl)-2-(2-methyl-2H-indazol-5-yl)pyrido[3,2-c]pyridazin-3(2H)-one (Example 209).

$^1$H NMR (400 MHz, DMSO-$d_6$) δ (ppm): 8.50 (s, 1H), 8.04 (s, 1H), 7.84 (d, J=8.4 Hz, 2H), 7.70 (d, J=9.6 Hz, 1H), 7.49 (d, J=8.8 Hz, 1H), 7.34 (t, $J_{HF}$=74.0 Hz, 1H), 7.24 (d, J=8.4 Hz, 2H), 6.94 (s, 1H), 6.39 (tt, $J_{HF}$=54.4 Hz, 3.2 Hz, 1H), 5.63 (s, 1H), 4.83 (s, 2H), 4.58 (td, $J_{HF}$=15.2 Hz, 3.2 Hz, 2H), 4.22 (s, 3H).

LC-MS (ESI): m/z 530 [M+H]$^+$.

Step B: 6-(2,2-difluoroethoxy)-4-(4-(difluoromethoxy)phenyl)-2-(2-methyl-2H-indazol-5-yl)-3-oxo-2,3-dihydropyrido[3,2-c]pyridazine-8-carbaldehyde To a solution of 6-(2,2-difluoroethoxy)-4-(4-(difluoromethoxy)phenyl)-8-(hydroxymethyl)-2-(2-methyl-2H-indazol-5-yl)pyrido[3,2-c]pyridazin-3(2H)-one (60 mg, 0.1 mmol, 1.0 eq.) in $CHCl_3$ (5 mL) was added freshly activated $MnO_2$ (96 mg, 1.0 mmol, 10.0 eq.) in one portion. Then the resulting mixture was stirred at room temperature for 16 hrs. The progress of the reaction was monitored by TLC, After completion, the reaction mixture was filtered through a short pad of Celite®, the filtrate was concentrated under reduced pressure to afford crude 6-(2,2-difluoroethoxy)-4-(4-(difluoromethoxy)phenyl)-2-(2-methyl-2H-indazol-5-yl)-3-oxo-2,3-dihydropyrido[3,2-c]pyridazine-8-carbaldehyde (50 mg) as a yellow solid, which used in next step without further purification. LC-MS: m/z 528 [M+H]$^+$.

Step C: 6-(2,2-difluoroethoxy)-4-(4-(difluoromethoxy)phenyl)-8-(difluoromethyl)-2-(2-methyl-2H-indazol-5-yl)pyrido[3,2-c]pyridazin-3(2H)-one To a solution of 6-(2,2-difluoroethoxy)-4-(4-(difluoromethoxy)phenyl)-2-(2-methyl-2H-indazol-5-yl)-3-oxo-2,3-dihydropyrido[3,2-c]pyridazine-8-carbaldehyde (50 mg, crude) in DCM (3 mL) was added DAST (46 mg) at −60° C. After addition, it was allowed to warm to room temperature and stirred for additional 16 hrs. After completion of the reaction, ice water (10 mL) was added and extracted with EtOAc (10 mL×3), The combined organic layers were washed with brine (20 mL), dried over $Na_2SO_4$ and concentrated under reduced pressure, the residue was purified by RP-prep-HPLC to afford 6-(2,2-difluoroethoxy)-4-(4-(difluoromethoxy)phenyl)-8-(difluoromethyl)-2-(2-methyl-2H-indazol-5-yl)pyrido[3,2-c]pyridazin-3(2H)-one (Example 210).

$^1$H NMR (400 MHz, DMSO-$d_6$) δ (ppm): 8.53 (s, 1H), 8.08 (d, J=2.0 Hz, 1H), 7.86 (d, J=8.8 Hz, 2H), 7.73 (d, J=9.2 Hz, 1H), 7.51 (dd, J=9.2 Hz, 2.0 Hz, 1H), 7.45 (t, $J_{HF}$=53.6 Hz, 1H), 7.36 (t, $J_{HF}$=74.0 Hz, 1H), 7.30-7.25 (m, 3H), 6.41 (tt, $J_{HF}$=54.4 Hz, 3.2 Hz, 1H), 4.61 (td, $J_{HF}$=15.2 Hz, 3.2 Hz, 2H), 4.23 (s, 3H).

LC-MS (ESI): m/z 550 [M+H]$^+$.

Synthesis of 6-(2,2-difluoroethoxy)-4-(4-(difluoromethoxy)phenyl)-8-((dimethylamino)methyl)-2-(2-methyl-2H-indazol-5-yl)pyrido[3,2-c]pyridazin-3(2H)-one (Example 211)

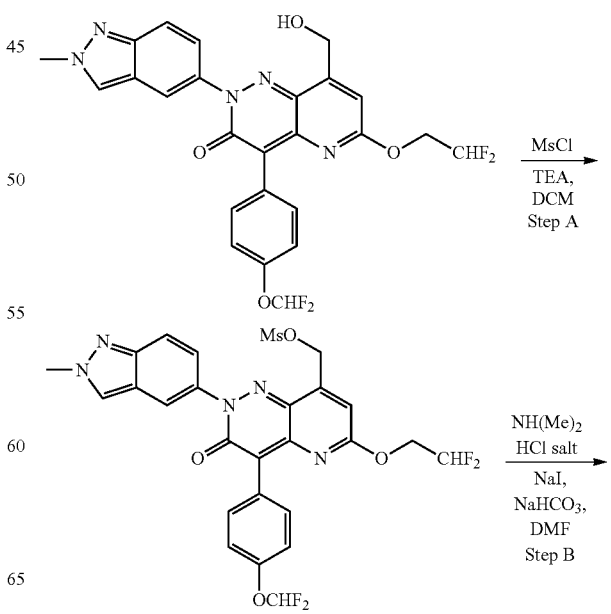

-continued

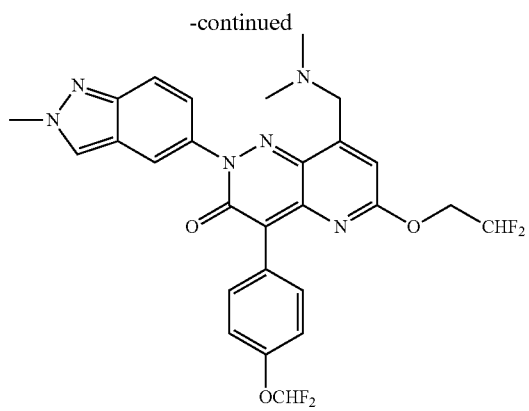

Step A: (6-(2,2-difluoroethoxy)-4-(4-(difluoromethoxy)phenyl)-2-(2-methyl-2H-indazol-5-yl)-3-oxo-2,3-dihydropyrido[3,2-c]pyridazin-8-yl)methyl methanesulfonate To a solution of 6-(2,2-difluoroethoxy)-4-(4-(difluoromethoxy)phenyl)-8-(hydroxymethyl)-2-(2-methyl-2H-indazol-5-yl)pyrido[3,2-c]pyridazin-3(2H)-one (90 mg, 0.17 mmol, 1.0 eq., Example 209) in DCM (3 mL) was added MsCl (29 mg, 0.25 mmol, 1.47 eq.) and TEA (34 mg, 0.34 mmol, 2.0 eq.) at room temperature. And the reaction mixture was stirred at room temperature for 2 hrs. Then the reaction mixture was poured into ice water (10 mL) and extracted with EtOAc (10 mL×3). The combined organic layers were washed with brine (20 mL), dried over $Na_2SO_4$ and concentrated under reduced pressure, The crude residue was purified by flash column chromatography on silica gel to afford (6-(2,2-difluoroethoxy)-4-(4-(difluoromethoxy)phenyl)-2-(2-methyl-2H-indazol-5-yl)-3-oxo-2,3-dihydropyrido[3,2-c]pyridazin-8-yl)methyl methanesulfonate (90 mg, 87% yield) as a yellow solid. LC-MS: m/z 608 [M+H]$^+$.

Step B: 6-(2,2-difluoroethoxy)-4-(4-(difluoromethoxy)phenyl)-8-((dimethylamino)methyl)-2-(2-methyl-2H-indazol-5-yl)pyrido[3,2-c]pyridazin-3(2H)-one To a solution of (6-(2,2-difluoroethoxy)-4-(4-(difluoromethoxy)phenyl)-2-(2-methyl-2H-indazol-5-yl)-3-oxo-2,3-dihydropyrido[3,2-c]pyridazin-8-yl)methyl methanesulfonate (50 mg, 0.08 mmol, 1.0 eq.) in DMSO (3 mL) was added NH(Me)$_2$ HCl salt (33 mg, 0.41 mmol, 5.1 eq.), NaI (23 mg, 0.16 mmol, 2.0 eq.) and NaHCO$_3$ (14 mg, 0.16 mmol, 2.0 eq.) at room temperature. And the reaction mixture was stirred at 80° C. for 2 hrs. Then the reaction mixture was poured into ice water (10 mL) and extracted with EtOAc (10 mL×3). The combined organic layers were washed with brine (20 mL), dried over $Na_2SO_4$ and concentrated under reduced pressure. The crude residue was purified by RP-prep-HPLC to give 6-(2,2-difluoroethoxy)-4-(4-(difluoromethoxy)phenyl)-8-((dimethylamino)methyl)-2-(2-methyl-2H-indazol-5-yl)pyrido[3,2-c]pyridazin-3(2H)-one (Example 211).

$^1$H NMR (400 MHz, DMSO-d$_6$) δ (ppm) 8.52 (s, 1H), 8.05 (d, J=2.0 Hz, 1H), 7.84 (d, J=8.8 Hz, 2H), 7.72 (d, J=9.2 Hz, 1H), 7.49 (dd, J=9.2, 2.0 Hz, 1H), 7.36 (t, J$_{HF}$=74.0 Hz, 1H), 7.25 (d, J=8.8 Hz, 2H), 6.96 (s, 1H), 6.40 (tt, J$_{HF}$=54.4, 3.4 Hz, 1H), 4.23 (s, 3H), 3.77 (s, 2H), 2.29 (s, 6H).
LC-MS (ESI): m/z 557 [M+H]$^+$.

Synthesis of 8-amino-6-(2,2-difluoroethoxy)-4-(4-(difluoromethoxy)phenyl)-2-(2-methyl-2H-indazol-5-yl)pyrido[3,2-c]pyridazin-3(2H)-one (Example 212)

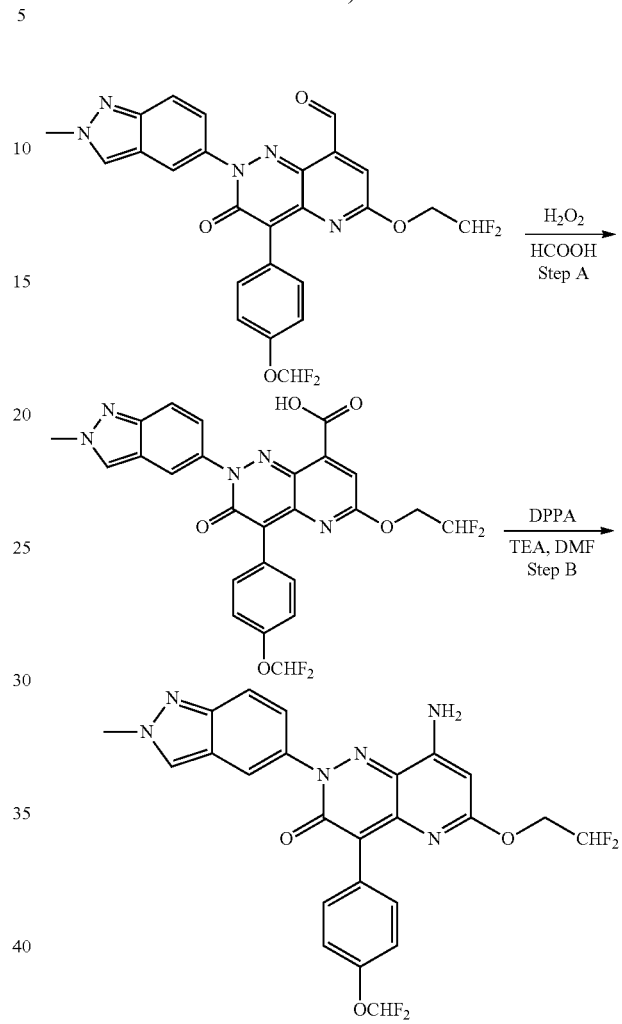

Step A: 6-(2,2-difluoroethoxy)-4-(4-(difluoromethoxy)phenyl)-2-(2-methyl-2H-indazol-5-yl)-3-oxo-2,3-dihydropyrido[3,2-c]pyridazine-8-carboxylic acid To a mixture of 6-(2,2-difluoroethoxy)-4-(4-(difluoromethoxy)phenyl)-2-(2-methyl-2H-indazol-5-yl)-3-oxo-2,3-dihydropyrido[3,2-c]pyridazine-8-carbaldehyde (120 mg, 0.23 mmol, 1.0 eq., synthesized as in Example 210 Step B) and HCO$_2$H (0.1 mL, 2.65 mmol, 11.5 eq.) in H$_2$O (0.5 mL) was slowly added H$_2$O$_2$ (30 wt. % in H$_2$O, 0.1 mL, 1.14 mmol, 5 eq.) at 4° C. And the mixture was stirred at room temperature for 6 hrs. Then the mixture was poured into H$_2$O (10 mL) and extracted with EtOAc (10 mL×3). The combined organic layers were washed with brine (20 mL), dried over Na$_2$SO$_4$ and concentrated under reduced pressure, the crude residue was purified by flash column chromatography on silica gel to afford 6-(2,2-difluoroethoxy)-4-(4-(difluoromethoxy)phenyl)-2-(2-methyl-2H-indazol-5-yl)-3-oxo-2, 3-dihydropyrido[3,2-c]pyridazine-8-carboxylic acid (80 mg, 52% yield) as a yellow solid. LC-MS (ESI): m/z 544 [M+H]⁺.

Step B: 8-amino-6-(2,2-difluoroethoxy)-4-(4-(difluoromethoxy)phenyl)-2-(2-methyl-2H-indazol-5-yl)pyrido[3,2-c]pyridazin-3(2H)-one To a solution of 6-(2,2-difluoroethoxy)-4-(4-(difluoromethoxy)phenyl)-2-(2-methyl-2H-indazol-5-yl)-3-oxo-2,3-dihydropyrido[3,2-c]pyridazine-8-carboxylic acid (80 mg, 0.15 mmol, 1.5 eq.) in DMF (2 mL) was added TEA (22 mg, 0.22 mmol, 1.45 eq.) and DPPA (61 mg, 0.22 mmol, 1.45 eq.). And the mixture was stirred at room temperature for 3 hrs. Then 0.3 mL of water was added to the solution and the reaction mixture was stirred at 100° C. overnight. The reaction was cooled to room temperature, and poured into H₂O (10 mL) and extracted with EtOAc (10 mL×3). The combined organic layers were washed with brine (20 mL), dried over Na₂SO₄ and concentrated under reduced pressure, the crude residue was purified by RP-Prep-TLC to afford 8-amino-6-(2,2-difluoroethoxy)-4-(4-(difluoromethoxy)phenyl)-2-(2-methyl-2H-indazol-5-yl)pyrido[3,2-c]pyridazin-3(2H)-one (Example 212).

¹H NMR (400 MHz, DMSO-d₆) δ (ppm): 8.49 (s, 1H), 8.05 (d, J=1.2 Hz, 1H), 7.83 (d, J=8.8 Hz, 2H), 7.69 (d, J=9.2 Hz, 1H), 7.51 (dd, J=9.2 Hz, 1.6 Hz, 1H), 7.32 (t, J$_{HF}$=74.0 Hz, 1H), 7.23-7.14 (m, 4H), 6.31 (tt, J$_{HF}$=54.0 Hz, 3.6 Hz, 1H), 5.83 (s, 1H), 4.47 (td, J=14.8 Hz, 3.6 Hz, 2H), 4.22 (s, 3H).

LC-MS (ESI): m/z 515 [M+H]⁺.

Synthesis of 6-(2,2-difluoroethoxy)-2-(2-methyl-2H-indazol-5-yl)-4-((trimethylsilyl)ethynyl)pyrido[3,2-c]pyridazin-3(2H)-one (Example 213), 6-(2,2-difluoroethoxy)-4-ethynyl-2-(2-methyl-2H-indazol-5-yl)pyrido[3,2-c]pyridazin-3(2H)-one (Example 214) & 4-((1H-pyrazol-3-yl)ethynyl)-6-(2,2-difluoroethoxy)-2-(2-methyl-2H-indazol-5-yl)pyrido[3,2-c]pyridazin-3(2H)-one (Example 215)

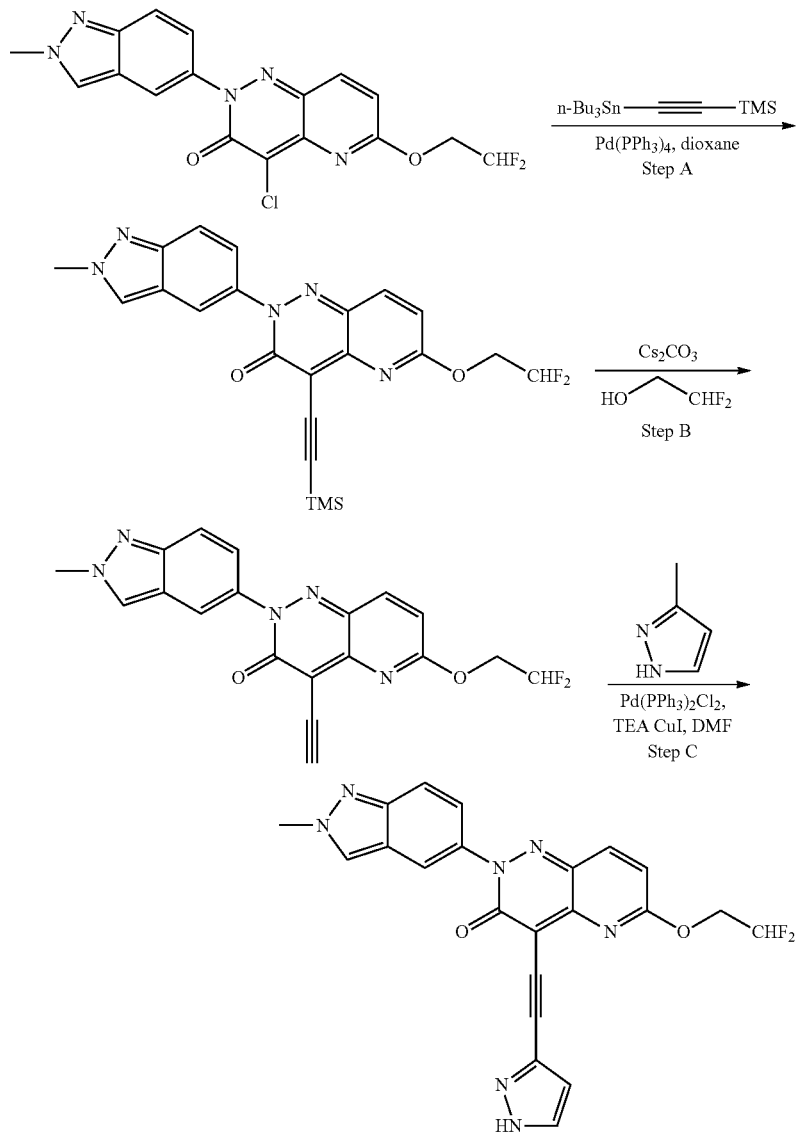

Step A: 6-(2,2-difluoroethoxy)-2-(2-methyl-2H-indazol-5-yl)-4-((trimethylsilyl)ethynyl)pyrido[3,2-c]pyridazin-3(2H)-one A mixture of 4-chloro-6-(2,2-difluoroethoxy)-2-(2-methyl-2H-indazol-5-yl)pyrido[3,2-c]pyridazin-3(2H)-one (180 mg, 0.46 mmol, 1.0 eq., Synthesized as in Example 206 Step A), trimethyl((tributylstannyl)ethynyl)silane (268 mg, 0.69 mmol, 1.5 eq.) and Pd(PPh₃)₄ (58 mg, 0.05 mmol, 0.11 eq.) in dioxane (5 mL) was stirred at 80° C. under N₂ atmosphere for 15 hrs. The reaction mixture was concentrated under reduced pressure, the crude residue was purified by flash column chromatography on silica gel to afford 6-(2,2-difluoroethoxy)-2-(2-methyl-2H-indazol-5-yl)-4-((trimethylsilyl)ethynyl)pyrido[3,2-c]pyridazin-3(2H)-one (Example 213).

$^1$H NMR (400 MHz, DMSO-$d_6$) δ (ppm): 8.50 (s, 1H), 8.08 (d, J=9.6 Hz, 1H), 7.98 (d, J=1.6 Hz, 1H), 7.70 (d, J=9.2 Hz, 1H), 7.41 (dd, J=9.2 Hz, 2.0 Hz, 1H), 7.09 (d, J=9.2 Hz, 1H), 6.54 (tt, $J_{HF}$=54.8 Hz, 3.6 Hz, 1H), 4.82 (td, $J_{HF}$=14.4 Hz, 3.6 Hz, 2H), 4.22 (s, 3H), 0.28 (s, 9H).

LC-MS (ESI): m/z 454 [M+H]⁺.

Step B: 6-(2,2-difluoroethoxy)-4-ethynyl-2-(2-methyl-2H-indazol-5-yl)pyrido[3,2-c]pyridazin-3(2H)-one A mixture of 6-(2,2-difluoroethoxy)-2-(2-methyl-2H-indazol-5-yl)-4-((trimethylsilyl)ethynyl)pyrido[3,2-c]pyridazin-3(2H)-one (126 mg, 0.28 mmol, 1.0 eq.) and Cs₂CO₃ (183 mg, 0.56 mmol, 2.0 eq) in 2,2-difluoroethan-1-ol (4 mL) was stirred at room temperature for 4 hrs. The resulting mixture was poured into H₂O (10 mL) and extracted with EtOAc (10 mL×3). The combined organic layers were washed with brine (20 mL), dried over Na₂SO₄ and concentrated under reduced pressure. The crude residue was purified by flash column chromatography on silica gel to afford 6-(2,2-difluoroethoxy)-4-ethynyl-2-(2-methyl-2H-indazol-5-yl)pyrido[3,2-c]pyridazin-3(2H)-one (Example 214).

$^1$H NMR (400 MHz, DMSO-$d_6$) δ (ppm): 8.51 (s, 1H), 8.08 (d, J=9.2 Hz, 1H), 7.99 (d, J=1.6 Hz, 1H), 7.72 (d, J=9.6 Hz, 1H), 7.41 (dd, J=9.2 Hz, 2.0 Hz, 1H), 7.10 (d, J=9.2 Hz, 1H), 6.52 (tt, $J_{HF}$=54.4 Hz, 3.2 Hz, 1H), 5.02 (s, 1H), 4.83 (td, $J_{HF}$=14.8 Hz, 3.2 Hz, 2H), 4.23 (s, 3H).

LC-MS (ESI): m/z 382 [M+H]⁺.

Step C: 4-((1H-pyrazol-3-yl)ethynyl)-6-(2,2-difluoroethoxy)-2-(2-methyl-2H-indazol-5-yl)pyrido[3,2-c]pyridazin-3(2H)-one A mixture of 6-(2,2-difluoroethoxy)-4-ethynyl-2-(2-methyl-2H-indazol-5-yl)pyrido[3,2-c]pyridazin-3(2H)-one (50 mg, 0.13 mmol, 1.0 eq.), DIPEA (50 mg, 0.39 mmol, 3.0 eq.), Pd(PPh₃)₂Cl₂ (10 mg, 0.013 mmol, 0.1 eq.) and 3-iodo-1H-pyrazole (101 mg, 0.52 mmol, 4.0 eq.) and CuI (25 mg, 0.13 mmol, 1.0 eq.) in DMF (5 mL) was stirred at room temperature under N₂ atmosphere for 4 hrs. Then the reaction mixture was poured into H₂O (10 mL) and extracted with EtOAc (10 mL×3). The combined organic layers were washed with brine (20 mL), dried over Na₂SO₄ and concentrated under reduced pressure. The crude residue was purified by RP-prep-HPLC to afford 4-((1H-pyrazol-3-yl)ethynyl)-6-(2,2-difluoroethoxy)-2-(2-methyl-2H-indazol-5-yl)pyrido[3,2-c]pyridazin-3(2H)-one (Example 215).

$^1$H NMR (400 MHz, DMSO-$d_6$) δ (ppm): 13.39 (br, s, 1H), 8.52 (s, 1H), 8.09 (d, J=9.2 Hz, 1H), 8.01 (s, 1H), 7.91-7.81 (m, 1H), 7.72 (d, J=9.2 Hz, 1H), 7.44 (dd, J=9.2 Hz, 2.0 Hz, 1H), 7.11 (d, J=9.2 Hz, 1H), 6.62 (s, 1H), 6.55 (tt, $J_{HF}$=54.4 Hz, 3.2 Hz, 1H), 4.88 (td, $J_{HF}$=14.8 Hz, 3.2 Hz, 2H), 4.23 (s, 3H).

LC-MS (ESI): m/z 448 [M+H]⁺.

Synthesis of 6-(2,2-difluoroethoxy)-4-(4-(difluoromethoxy)phenyl)-2-(4-oxocyclohexyl)pyrido[3,2-c]pyridazin-3(2H)-one (Example 216)

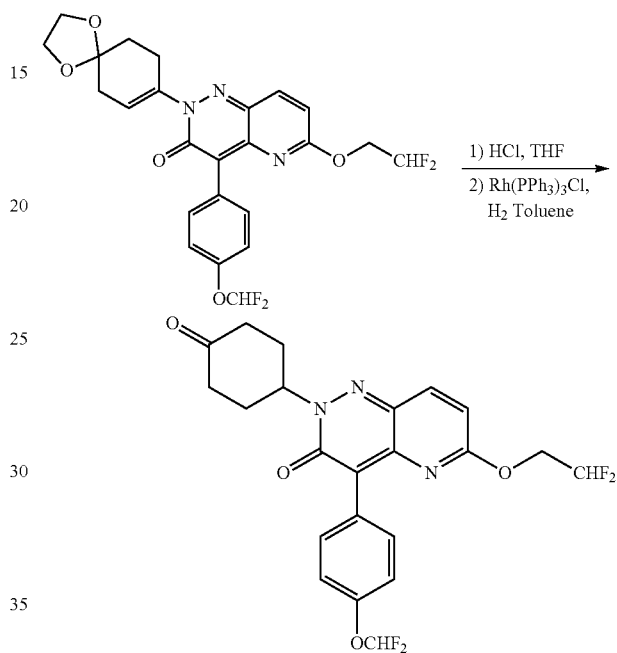

A solution of 6-(2,2-difluoroethoxy)-4-(4-(difluoromethoxy)phenyl)-2-(1,4-dioxaspiro[4.5]dec-7-en-8-yl)pyrido[3,2-c]pyridazin-3(2H)-one (synthesized from 6-(2,2-difluoroethoxy)-4-(4-(difluoromethoxy)phenyl)pyrido[3,2-c]pyridazin-3(2H)-one & 1,4-dioxaspiro[4.5]dec-7-en-8-yl trifluoromethanesulfonate via General Procedure II (Method A, Step G)) (10 mg, 0.0197 mmol) and conc. HCl (0.1 mL) in THF (1.5 mL) was stirred at room temperature for 2 hrs. The reaction was poured into sat. NaHCO₃ aq. (5 mL) and extracted with EA (5 mL×3). The combined organic layers were washed with brine (20 mL), dried over Na₂SO₄ and concentrated under reduced pressure. Then a mixture of the residue and Rh(PPh₃)₃Cl (18 mg, 0.0197 mmol) in toluene (3 mL) was stirred at room temperature overnight under H₂ atmosphere. Then the mixture was poured into H₂O (5 mL) and extracted with EtOAc (5 mL×3). The combined organic layers were washed with brine (10 mL), dried over Na₂SO₄ and concentrated under reduced pressure. The crude residue was purified by RP-prep-HPLC to afford 6-(2,2-difluoroethoxy)-4-(4-(difluoromethoxy)phenyl)-2-(4-oxocyclohexyl)pyrido[3,2-c]pyridazin-3(2H)-one (Example 216).

$^1$H NMR (400 MHz, DMSO-$d_6$) δ (ppm): 8.02 (d, J=9.6 Hz, 1H), 7.82 (d, J=8.8 Hz, 2H), 7.34 (t, $J_{HF}$=74.0 Hz, 1H), 7.24 (d, J=8.8 Hz, 2H), 7.02 (d, J=9.6 Hz, 1H), 6.37 (tt, $J_{HF}$=54.4 Hz, 2.8 Hz, 1H), 5.62 (hept, J=4.8 Hz, 1H), 4.54 (td, $J_{HF}$=14.8 Hz, 2.8 Hz, 2H), 2.78-2.63 (m, 2H). 2.45-2.23 (m, 2H), 2.29-2.14 (m, 1H) (HCO₂H salt).

LC-MS (ESI): m/z 466 [M+H]⁺.

209

Synthesis of 4-(4-(difluoromethoxy)phenyl)-6-ethoxy-2-(2-methyl-2H-indazol-5-yl)pyrido[3,2-c]pyridazin-3(2H)-one (Example 217)

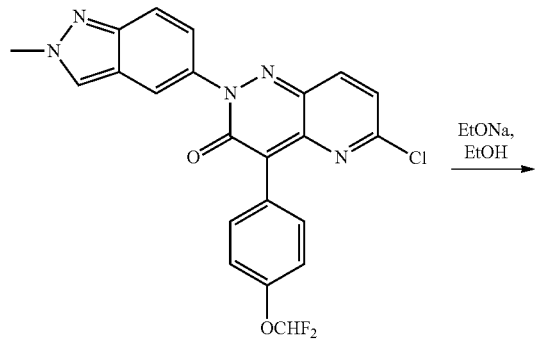

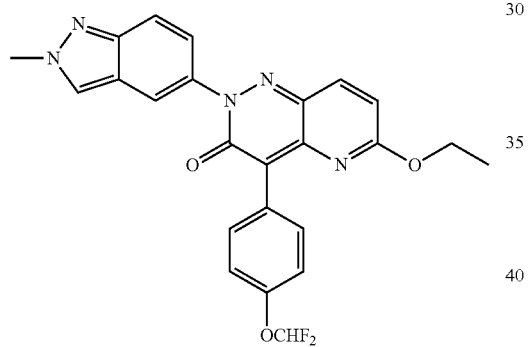

A mixture of 6-chloro-4-(4-(difluoromethoxy)phenyl)-2-(2-methyl-2H-indazol-5-yl)pyrido[3,2-c]pyridazin-3(2H)-one (synthesized from 4-chloro-2-(2-methyl-2H-indazol-5-yl)pyrido[3,2-c]pyridazine-3,6(2H,5H)-dione & 2-(4-(difluoromethoxy)phenyl)-4,4,5,5-tetramethyl-1,3,2-dioxaborolane via General Procedure I (Method C, Step E, G) (120 mg, 0.26 mmol, 1.0 eq.) and EtONa (177 mg, 2.6 mmol, 10.0 eq.) in EtOH (8 mL) was stirred at 40° C. for 3 hrs. Then the reaction mixture was poured into ice water (10 mL) and extracted with DCM (10 mL×3). The combined organic layers were dried over Na$_2$SO$_4$, concentrated under reduced pressure. The crude residue was purified by RP-prep-HPLC to give 4-(4-(difluoromethoxy)phenyl)-6-ethoxy-2-(2-methyl-2H-indazol-5-yl)pyrido[3,2-c]pyridazin-3(2H)-one (Example 217).

$^1$H NMR (400 MHz, DMSO-d$_6$) δ: 8.49 (s, 1H), 8.04 (d, J=1.2 Hz, 1H), 7.97 (d, J=9.2 Hz, 1H), 7.86 (d, J=8.8 Hz, 2H), 7.70 (d, J=9.2 Hz, 1H), 7.45 (dd, J=9.2 Hz, 2.0 Hz, 1H), 7.34 (t, J$_{HF}$=74.0, 1H), 7.24 (d, J=8.8 Hz, 2H), 6.95 (d, J=9.6 Hz, 1H), 4.34 (q, J=7.2 Hz, 2H), 4.22 (s, 3H), 1.32 (t, J=7.2 Hz, 3H).

LC-MS (ESI): m/z 464 [M+H]$^+$.

210

Synthesis of 5-(6-(2,2-difluoroethoxy)-2-(2-methyl-2H-indazol-5-yl)-3-oxo-2,3-dihydropyrido[3,2-c]pyridazin-4-yl)-1H-indole-3-carbonitrile (Example 331)

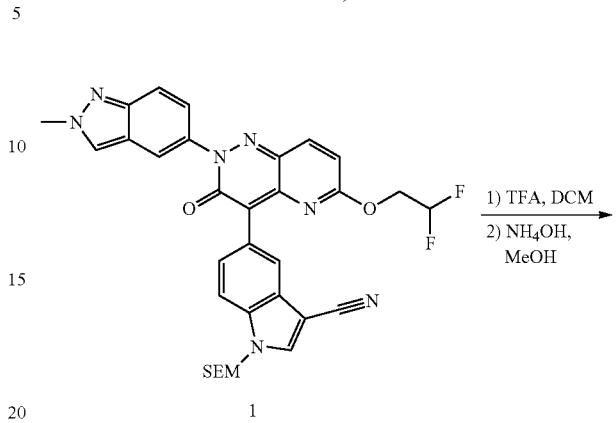

To a solution of 7-(2,2-difluoroethoxy)-3-(2-methyl-2H-indazol-5-yl)-1-(1-((2-(trimethylsilyl)ethoxy)methyl)-1H-indazol-5-yl)-3,4-dihydropyrido[2,3-d]pyrimidin-2(1H)-one (54 mg, 0.09 mmol, 1.0 eq) (synthesized from 4-chloro-2-(2-methyl-2H-indazol-5-yl)pyrido[3,2-c]pyridazine-3,6(2H,5H)-dione & 5-(4,4,5,5-tetramethyl-1,3,2-dioxaborolan-2-yl)-1-((2-(trimethylsilyl)ethoxy)methyl)-1H-indole-3-carbonitrile (Ref: WO2018215316) via General Procedure I (Method A, Step E & F)) in DCM (3 mL) was added TFA (1 mL), the reaction mixture was stirred at room temperature for 3 hrs. Then the reaction mixture was concentrated under reduced pressure, the residue was re-dissolved in MeOH (2 mL) and conc. NH$_4$OH (1 mL), the resulting mixture was stirred at room temperature overnight. After completion, the reaction mixture was concentrated under reduced pressure, the residue was purified by RP-Prep-HPLC to give 5-(6-(2,2-difluoroethoxy)-2-(2-methyl-2H-indazol-5-yl)-3-oxo-2,3-dihydropyrido[3,2-c]pyridazin-4-yl)-1H-indole-3-carbonitrile (Example 331).

$^1$H NMR (400 MHz, DMSO-d$_6$) δ (ppm): δ 12.29 (s, 1H), 8.50 (s, 1H), 8.29 (s, 1H), 8.12 (d, J=0.9 Hz, 1H), 8.10-8.01 (m, 2H), 7.75 (dd, J=8.6 Hz, 1.5 Hz, 1H), 7.71 (d, J=9.2 Hz, 1H), 7.60 (d, J=8.7 Hz, 1H), 7.49 (dd, J=9.1 Hz, 2.0 Hz, 1H), 7.06 (d, J=9.4 Hz, 1H), 6.38 (tt, J$_{HF}$=54.5 Hz, J=3.3 Hz, 1H), 4.54 (td, J$_{HF}$=15.0 Hz, J=3.4 Hz, 2H), 4.22 (s, 3H).

LC-MS (ESI): m/z 498 [M+H]$^+$.

Synthesis of 5-(6-(ethylamino)-2-(2-methyl-2H-indazol-5-yl)-3-oxo-2,3-dihydropyrido[3,2-c]pyridazin-4-yl)-1H-indole-3-carbonitrile (Example 332)

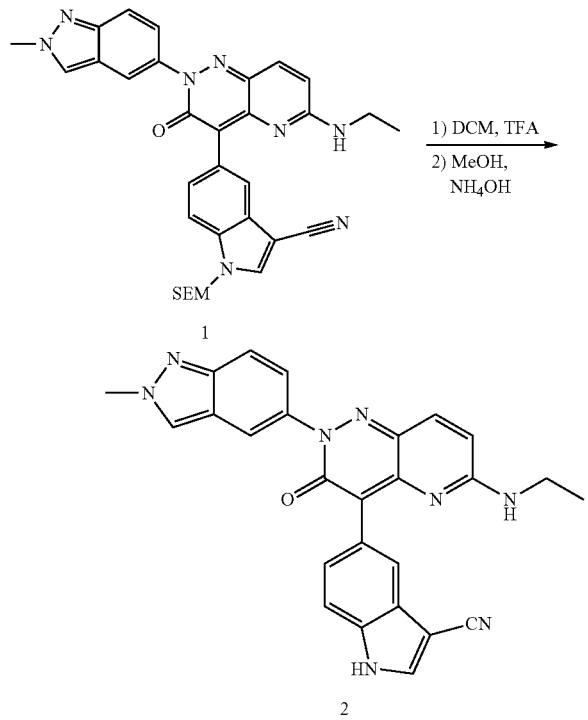

To a solution of 5-(6-(ethylamino)-2-(2-methyl-2H-indazol-5-yl)-3-oxo-2,3-dihydropyrido[3,2-c]pyridazin-4-yl)-1-((2-(trimethylsilyl)ethoxy)methyl)-1H-indole-3-carbonitrile (100 mg, 0.17 mmol) (synthesized from 4-chloro-2-(2-methyl-2H-indazol-5-yl)pyrido[3,2-c]pyridazine-3,6(2H, 5H)-dione & 5-(4,4,5,5-tetramethyl-1,3,2-dioxaborolan-2-yl)-1-((2-(trimethylsilyl)ethoxy)methyl)-1H-indole-3-carbonitrile (Ref: WO2018215316) via General Procedure I (Method A, Step E; Method D, Step I)) in DCM (6 mL) was added TFA (6 mL), the reaction mixture was stirred at room temperature for 12 hrs. Then the reaction mixture was concentrated under reduced pressure, the residue was re-dissolved with MeOH (4 mL) and conc. NH$_4$OH (2 mL), the resulting mixture was stirred at room temperature for additional 6 hrs. After completion, the reaction mixture was concentrated under reduced pressure, the residue was purified by RP-prep-HPLC to give 5-(6-(ethylamino)-2-(2-methyl-2H-indazol-5-yl)-3-oxo-2,3-dihydropyrido[3,2-c]pyridazin-4-yl)-1H-indole-3-carbonitrile (Example 332).

$^1$H NMR (400 MHz, DMSO-d$_6$) (ppm): δ 12.17 (s, 1H), 8.45 (s, 1H), 8.27 (s, 1H), 8.22 (s, 1H), 8.16 (s, 1H), 7.96 (s, 1H), 7.76 (d, J=9.0 Hz, 1H), 7.66 (d, J=9.1 Hz, 1H), 7.64 (d, J=9.1 Hz, 1H), 7.51 (d, J=8.9 Hz, 1H), 7.43 (d, J=8.9 Hz, 1H), 6.78 (d, J=9.3 Hz, 1H), 4.21 (s, 3H), 3.31 (q, J=7.1 Hz, 2H), 1.14 (t, J=7.1 Hz, 3H).

LC-MS (ESI): m/z 461 [M+H]$^+$.

Biochemical Assay

Mat2A protein was expressed by recombinant baculovirus in SF9 infected cells using the Bac to Bac system cloned into the pFASTBAC1 vector (Invitrogen, Carlsbad, CA). Recombinant MAT2A was isolated from the cell lysate of 150 g of infected cells using HP Ni sepharose column chromatography. Recombinant MAT2A homodimer was eluted with 250 and 500 mM imidazole, and fractions containing MAT2A were identified by sodium dodecyl sulfate polyacrylamide gel electrophoresis and pooled.

For determination of the inhibitory potency of compounds against the MAT2A homodimer, protein was diluted to 4 µg/mL in assay buffer (50 mM Tris, pH 8.0, 50 mM KCl, 15 mM MgCl$_2$, 0.3 mM EDTA, 0.005% [w/v] bovine serum albumin [BSA]). Test compound was prepared in 100% dimethyl sulfoxide (DMSO) at 50× the desired final concentration. A 1 µL volume of compound dilution was added to 40 µL of enzyme dilution and the mixture was allowed to equilibrate for 60 minutes at 25° C. The enzymatic assay was initiated by the addition of 10 µL of substrate mix (500 µM ATP, pH 7.0, 400 µM L-methionine in 1× assay buffer), and the mixture was incubated for a further 60 minutes at 25° C. The reaction was halted and the liberated phosphate released by the enzyme in stoichiometric amounts by the production of S-adenosyl methionine (SAM) was measured using the PiColorLock Gold kit (Innova Biosciences, UK). Absolute product amounts were determined by comparison to a standard curve of potassium phosphate buffer, pH 8.0.

Specific compounds disclosed herein were tested in the foregoing assay and they were determined to inhibit MAT2A with an IC$_{50}$ according to the following scores: (A) less than 100 nM (>40% maximum inhibition), (B) between 100 nM and 1 µM (>40% maximum inhibition), and (C) between 1 µM and 10 µM (>40% maximum inhibition), as shown in Table 2 below.

Cellular Assay of Target Engagement (SAM)

Measurement of MAT2A activity in cells was made by direct quantitation of the abundance of the product of its enzymatic activity, SAM. Cancer cells were treated with candidate MAT2A inhibitors for a suitable incubation period, and the cells were then lysed using a reagent which quenched any further enzyme activity. Soluble metabolites including SAM were collected and SAM itself was directly measured from the lysate using quantitative LC-MS/MS.

A typical assay was performed using an HCT116 human colon carcinoma cell line which was genetically engineered to delete the MTAP gene (commercially available from Horizon Discovery). This cell line was utilized because it was determined that loss of the MTAP gene predicts sensitivity to MAT2A inhibitors. Cells were plated in 96-well dishes at appropriate cell density. Following 24 hours, cells were then treated with the candidate MAT2A inhibitor. Prior to addition to cells, the compound was first serially diluted in 100% DMSO, typically as a 3-fold serial dilution starting at 500× top dose with 10 dose points including DMSO only control. Compound was then transferred to a working stock plate in cell culture media by adding 5 µL of compound in DMSO to 495 µL of cell culture media. This working stock was then added to cells via a further 5-fold dilution, by adding 25 µL of working stock to 100 µL of cells in culture media. Following compound addition, cells were incubated at 37° C./5% CO$_2$ for 72 hrs.

To quantitate SAM levels following compound treatment, cells were gently washed once in ammonium carbonate buffer (75 mM at pH 7.4), placed on dry ice, and lysed with metabolite extraction buffer (80% cold methanol and 20% water (v/v) with acetic acid at 1M final concentration with 200 ng/mL deuterated d$_3$-SAM as internal control). Following centrifugation at 4° C. at 3,200 rpm for 30 minutes, the supernatant was collected and stored at −80° C. until analysis by Liquid Chromatography with tandem Mass Spectrometry (LC-MS/MS). LC-MS/MS analysis was performed using an API6500 Mass Spectrometer (Sciex, Framingham, MA, USA) operating in positive ion spray mode and equipped with a Waters UPLC Acquity (Waters, Milford, MA, USA) BEH Amide column. Multiple Reaction Monitoring data was acquired for SAM and the $d_3$-SAM standard, using a mass transition pair at m/z 399.2→250.1 and 402.2→250.1, respectively. In a typical LC-MS/MS analysis, the initial flow rate was 0.5 ml/min of 25% mobile phase A (acetonitrile and water at 5:95 (v/v) with 1% formic acid and 10 mM ammonium acetate) and 75% mobile phase B (acetonitrile and water at 95:5 (v/v) with 1% formic acid and 10 mM ammonium acetate), 0.2-0.5 minutes with 75%-35% mobile phase B, 25%-65% mobile phase A, at 0.5 min 65% mobile phase A and 35% mobile phase B, 1.0-1.1 minutes with 35%-75% mobile phase B, 65%-25% mobile phase A, at 1.1 min 25% mobile phase A and 75% mobile phase B with a total run time of 1.5 minutes.

Specific compounds disclosed herein were tested in the foregoing assay and they were determined to inhibit SAM with an $IC_{50}$ according to the following scores: (A) less than 100 nM (>60% maximum inhibition), (B) between 100 nM and 1 μM (>60% maximum inhibition), (C) greater than or equal to 1 μM (>60% maximum inhibition), and (NT) not tested, as shown in Table 2 below.

Assay for Inhibition of Cellular Proliferation

Test compound impact on cancer cell growth was assessed by treating cancer cells with compound for 4 days and then measuring proliferation using an ATP-based cell proliferation readout (Cell Titer Glo, Promega Corporation).

In a typical assay an isogenic pair of HCT116 human colon carcinoma cell lines which vary only in MTAP deletion status (HCT116 MTAP+/+ and HCT116 MTAP−/−) were plated in 96-well dishes at appropriate cell density. Following 24 hours, cells were then treated with the candidate MAT2A inhibitor. Prior to addition to cells, the compound was first serially diluted in 100% DMSO, typically as a 3-fold serial dilution starting at 500× top dose with 10 dose points including DMSO only control. Compound was then transferred to a working stock plate in cell culture media by adding 5 μL of compound in DMSO to 495 μL of cell culture media. This working stock was then added to cells via a further 5-fold dilution, by adding 25 μL of working stock to 100 μL of cells in culture media. Following compound addition, cells were incubated at 37° C./5% CO2 for 4 days.

To measure inhibition of cellular proliferation, cells were allowed to equilibrate to room temperature for 30 minutes, and were then treated with 125 μL of Cell Titer Glo reagent. The plate was then covered with aluminum foil and shaken for 15 minutes to ensure complete mixing and full cell lysis. Luminescent signal was then measured using a plate-based luminometer Veritas version 1.9.2 using ATP standard curve to confirm assay reproducibility from run to run. This luminescence measure was converted to a proliferation index by subtracting from each data point the ATP luminescence signal measured from a bank (no cells) well and dividing by the ATP luminescence signal measured in 0.2% DMSO control well adjusted for signal in blank well. Compound activity was then represented as a percentage change in proliferation relative to a within-plate DMSO control against log 10 of compound concentration in molar (M) units.

Specific compounds disclosed herein were tested in the foregoing assay and they were determined to inhibit cellular proliferation with an $IC_{50}$ according to the following scores: (A) less than 100 nM (>30% maximum inhibition for MTAP −/−; >10% maximum inhibition for MTAP +/+), (B) between 100 nM and 1 μM (>30% maximum inhibition for MTAP −/−; >10% maximum inhibition for MTAP +/+), (C) greater than or equal to 1 μM, and (NT) not tested, as shown in Table 2 below.

TABLE 2

| Example | Enzyme Inhibition | Cell 72 h SAM Inhibition (MTAP −/−) | 4 Day Relative Growth Inhibition (MTAP −/−) | 4 Day Relative Growth Inhibition (MTAP +/+) |
|---|---|---|---|---|
| 101 | A | A | B | C |
| 102 | A | A | B | C |
| 103 | A | A | A | C |
| 104 | A | B | B | C |
| 105 | A | B | B | C |
| 106 | A | A | A | B |
| 107 | A | A | A | C |
| 108 | A | A | A | C |
| 109 | A | A | A | C |
| 110 | A | A | A | B |
| 111 | A | A | A | C |
| 112 | A | B | B | C |
| 113 | A | A | B | C |
| 114 | A | A | A | C |
| 115 | A | A | A | B |
| 116 | A | A | A | C |
| 117 | A | A | A | C |
| 118 | B | NT | NT | NT |
| 119 | A | A | A | C |
| 120 | A | A | A | C |
| 121 | A | A | A | C |
| 122 | A | B | A | C |
| 123 | A | A | A | B |
| 124 | A | A | A | B |
| 125 | A | A | A | B |
| 126 | A | A | A | C |
| 127 | A | A | A | C |
| 128 | A | A | A | C |
| 129 | A | A | A | C |
| 130 | A | A | A | B |
| 131 | A | B | C | C |
| 132 | A | B | B | C |
| 133 | A | A | B | C |
| 134 | A | B | C | C |
| 135 | A | A | B | C |
| 136 | A | B | B | C |
| 137 | A | A | A | C |
| 138 | A | A | A | C |
| 139 | A | A | A | B |
| 140 | A | B | A | C |
| 141 | A | A | B | C |
| 142 | A | B | B | C |
| 143 | A | A | A | C |
| 144 | A | A | A | C |
| 145 | A | A | A | C |
| 146 | A | A | A | C |
| 147 | A | B | B | C |
| 148 | A | B | B | C |
| 149 | A | A | B | C |
| 150 | A | A | A | C |
| 151 | A | A | A | C |
| 152 | A | A | A | B |
| 153 | B | C | C | C |
| 154 | A | A | A | C |
| 155 | A | A | A | C |
| 156 | A | A | A | C |
| 157 | A | B | B | C |
| 158 | A | A | A | C |
| 159 | A | A | A | C |
| 160 | A | A | A | C |
| 161 | A | A | A | C |
| 162 | A | A | A | C |
| 163 | A | C | C | C |
| 164 | B | NT | NT | NT |
| 165 | A | A | A | B |
| 166 | A | A | A | C |
| 167 | A | A | A | C |
| 168 | A | A | B | C |
| 169 | A | A | A | A |
| 170 | A | A | B | C |

TABLE 2-continued

| Example | Enzyme Inhibition | Cell 72 h SAM Inhibition (MTAP −/−) | 4 Day Relative Growth Inhibition (MTAP −/−) | 4 Day Relative Growth Inhibition (MTAP +/+) |
|---|---|---|---|---|
| 171 | A | A | A | C |
| 172 | A | A | A | C |
| 173 | A | A | A | B |
| 174 | A | A | A | C |
| 175 | A | A | A | B |
| 176 | A | A | B | B |
| 177 | A | A | A | B |
| 178 | A | A | A | B |
| 179 | A | A | B | C |
| 180 | A | A | A | C |
| 181 | C | NT | NT | NT |
| 182 | A | A | A | B |
| 183 | A | A | A | B |
| 184 | A | A | B | C |
| 185 | B | NT | NT | NT |
| 186 | B | NT | NT | NT |
| 187 | A | B | C | C |
| 188 | A | B | B | C |
| 189 | A | B | B | C |
| 190 | C | NT | NT | NT |
| 191 | B | B | C | C |
| 192 | A | A | B | B |
| 193 | A | B | B | C |
| 194 | A | B | A | C |
| 195 | A | A | C | C |
| 196 | A | A | A | C |
| 197 | A | A | A | C |
| 198 | A | A | A | C |
| 199 | A | A | A | C |
| 200 | A | A | A | C |
| 201 | A | A | A | C |
| 202 | A | A | A | C |
| 203 | A | A | A | B |
| 204 | A | NT | NT | NT |
| 205 | A | A | A | C |
| 206 | A | B | B | C |
| 207 | A | A | B | C |
| 208 | A | A | A | B |
| 209 | A | A | A | C |
| 210 | A | A | B | C |
| 211 | A | B | B | C |
| 212 | A | A | A | B |
| 213 | B | NT | C | C |
| 214 | B | C | C | C |
| 215 | A | C | B | C |
| 216 | B | NT | NT | NT |
| 217 | A | A | A | B |
| 301 | A | A | A | C |
| 302 | A | A | A | C |
| 303 | A | A | A | C |
| 304 | A | A | B | B |
| 305 | A | A | A | C |
| 306 | A | NT | NT | NT |
| 307 | A | A | A | C |
| 308 | A | NT | NT | NT |
| 309 | A | A | A | C |
| 310 | A | A | A | C |
| 311 | A | NT | NT | NT |
| 312 | A | NT | NT | NT |
| 313 | A | A | A | B |
| 314 | A | NT | NT | NT |
| 315 | A | A | A | C |
| 316 | A | A | A | C |
| 317 | A | A | A | C |
| 318 | A | A | A | C |
| 319 | A | A | A | C |
| 320 | A | NT | NT | NT |
| 321 | A | A | A | C |
| 322 | A | NT | NT | NT |
| 323 | A | A | A | A |
| 324 | A | NT | NT | NT |
| 325 | A | NT | NT | NT |
| 326 | A | NT | NT | NT |
| 327 | A | A | A | C |
| 328 | B | NT | NT | NT |
| 329 | B | NT | NT | NT |
| 330 | A | NT | NT | NT |
| 331 | A | A | A | C |
| 332 | A | NT | NT | NT |

We claim:
1. A compound according to Formula I:

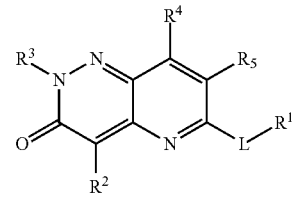

wherein:
L is O, S, NR, or a bond;
R is H or $C_1$-$C_6$-alkyl;
$R^1$ is selected from the group consisting of $C_1$-$C_6$-alkyl, $C_2$-$C_6$-alkenyl, $C_3$-$C_6$-carbocyclyl, —($C_1$-$C_6$-alkyl)($C_3$-$C_6$-carbocyclyl), and —($C_1$-$C_6$-alkyl)($C_3$-$C_6$-cycloalkenyl) wherein
any alkyl in $R^1$ is straight or branched, and
$R^1$ is optionally substituted by 1 to 6 halogen or 1 to 6 deuterium;
or when L is NR, then R and $R^1$ in combination with L represent a 3- to 6-membered heterocycloalkyl (wherein 1-4 ring members are, independently, N, O, or S) optionally substituted by one or more of $R^A$,
$R^2$ and $R^3$ are independently selected from the group consisting of ($C_2$-$C_6$)alkynyl, $C_6$-$C_{10}$-aryl, $C_3$-$C_6$-carbocyclyl, 5- to 10-membered heteroaryl (wherein 1-4 heteroaryl members are, independently, N, O, or S), and 3- to 14-membered heterocycloalkyl (wherein 1-4 heterocycloalkyl members are, independently, N, O, or S),
wherein $R^2$ and $R^3$ are independently and optionally substituted by one or more substituents that are selected from the group consisting of $R^A$, $OR^A$, halogen, —N=N—$R^A$, $NR^AR^B$, —($C_1$-$C_6$-alkyl)$NR^AR^B$, —C(O)$OR^A$, —C(O)$NR^AR^B$, —OC(O)$R^A$, —Si($C_1$-$C_6$-alkyl)$_3$ and —CN;
$R^4$ is selected from the group consisting of H, $C_1$-$C_6$-alkyl (optionally substituted by one or more halogen, hydroxy or 3- to 14-membered heterocycloalkoxy (wherein 1-4 heterocycloalkoxy members are, independently, N, O, or S)), —O($C_1$-$C_6$-alkyl) (optionally substituted by one or more halogen), —OH, halogen, —CN, —($C_1$-$C_6$-alkyl)$NR^AR^B$, and —$NR^AR^B$;
$R^5$ is selected from the group consisting of H, $C_1$-$C_6$-alkyl, $C_1$-$C_6$-alkoxy, $C_2$-$C_6$-alkenyl, $C_2$-$C_6$-alkynyl, halogen, —CN, and —$NR^CR^D$;
$R^A$ and $R^B$ are independently selected from the group consisting of H, —CN, -hydroxy, oxo, $C_1$-$C_6$-alkyl, $C_1$-$C_6$-alkoxy, $C_2$-$C_6$-alkenyl, $C_2$-$C_6$-alkynyl, —NH$_2$, —S(O)$_{0-2}$—($C_1$-$C_6$-alkyl), —S(O)$_{0-2}$—($C_6$-$C_{10}$-aryl), —C(O)($C_1$-$C_6$-alkyl), —C(O)($C_3$-$C_{14}$- carbocyclyl), —$C_3$-$C_{14}$-carbocyclyl, —($C_1$-$C_6$-alkyl)($C_3$-$C_{14}$-carbocyclyl), $C_6$-$C_{10}$-aryl, 3- to 14-membered heterocycloalkyl, (wherein 1-4 heterocycloalkyl members are, independently, N, O, or S), —($C_1$-$C_6$-alkyl)-(3- to 14-membered heterocycloalkyl) (wherein 1-4 heterocycloalkyl members are, independently, N, O, or S), and 5- to 10-membered heteroaryl (wherein 1-4 heteroaryl members are, independently, N, O, or S);

wherein each alkyl, alkoxy, alkenyl, alkynyl, aryl, carbocyclyl, heterocycloalkyl, and heteroaryl moiety of $R^A$ and $R^B$ is optionally substituted with one or more substituents selected from the group consisting of deuterium, hydroxy, halogen, —$NR'_2$ (wherein each R' is independently selected from the group consisting of $C_1$-$C_6$-alkyl, $C_2$-$C_6$-alkenyl, $C_2$-$C_6$-alkynyl, $C_6$-$C_{10}$-aryl, 3- to 14-membered heterocycloalkyl (wherein 1-4 ring members are, independently, N, O, or S), —($C_1$-$C_6$-alkyl)-(3- to 14-membered heterocycloalkyl) (wherein 1-4 ring members are, independently, N, O, or S), 5- to 10-membered heteroaryl (wherein 1-4 heteroaryl members are, independently, N, O, and S)), —NHC(O)(O$C_1$-$C_6$-alkyl), —$NO_2$, —CN, oxo, —C(O)OH, —C(O)O($C_1$-$C_6$-alkyl), —$C_1$-$C_6$-alkyl($C_1$-$C_6$-alkoxy), —C(O)$NH_2$, $C_1$-$C_6$-alkyl, —C(O)$C_1$-$C_6$-alkyl, —O$C_1$-$C_6$-alkyl, —Si($C_1$-$C_6$-alkyl)$_3$, —S(O)$_{0-2}$—($C_1$-$C_6$-alkyl), $C_6$-$C_{10}$-aryl, —($C_1$-$C_6$-alkyl)($C_6$-$C_{10}$-aryl), 3- to 14-membered heterocycloalkyl, and —($C_1$-$C_6$-alkyl)-(3- to 14-membered heterocycle) (wherein 1-4 heterocycle members are, independently, N, O, or S), and —O($C_6$-$C_{14}$-aryl), wherein each alkyl, alkenyl, aryl, and heterocycloalkyl substituent in $R^A$ and $R^B$ is optionally substituted with one or more substituents selected from the group consisting of hydroxy, —O$C_1$-$C_6$-alkyl, halogen, —$NH_2$, —($C_1$-$C_6$-alkyl)$NH_2$, —C(O)OH, CN, and oxo;

$R^C$ and $R^D$ are each, independently, H or $C_1$-$C_6$-alkyl; or a pharmaceutically acceptable salt thereof.

2. The compound according to claim 1, wherein:
$R^4$ is selected from the group consisting of H, $C_1$-$C_6$-alkyl (optionally substituted by one or more halogen, hydroxy or 3- to 14-membered heterocycloalkoxy (wherein 1-4 heterocycloalkoxy members are, independently, N, O, or S)), —O($C_1$-$C_6$-alkyl), —($C_1$-$C_6$-alkyl)$NR^AR^B$, and —$NR^AR^B$ (wherein $R^A$ and $R^B$ are, independently, H or $C_1$-$C_6$-alkyl); and
$R^5$ is selected from the group consisting of H, $C_1$-$C_6$-alkyl, $C_1$-$C_6$-alkoxy, and —$NR^CR^D$.

3. The compound according to claim 1, wherein $R^4$ is H.

4. The compound according to claim 1, wherein $R^5$ is H.

5. The compound according to claim 1, wherein each of $R^4$ and $R^5$ is H.

6. The compound according to claim 1, wherein $R^2$ is optionally substituted $C_6$-$C_{10}$-aryl or optionally substituted 5- to 10-membered heteroaryl (wherein 1-4 heteroaryl members are, independently, N, O, or S).

7. The compound according to claim 6, wherein $R^2$ is optionally substituted $C_6$-$C_{10}$-aryl.

8. The compound according to claim 7, wherein $R^2$ is optionally substituted phenyl.

9. The compound according to claim 6, wherein $R^2$ is optionally substituted 5- to 10-membered heteroaryl, wherein 1 heteroaryl ring member is N.

10. The compound according to claim 9, wherein $R^2$ is optionally substituted 5-membered heteroaryl.

11. The compound according to claim 9, wherein $R^2$ is optionally substituted 6-membered heteroaryl.

12. The compound according to claim 9, wherein $R^2$ is optionally substituted pyridyl.

13. The compound according to claim 1, wherein $R^3$ is optionally substituted 3- to 14-membered heterocycloalkyl (wherein 1-4 heterocycloalkyl members are, independently, N, O, or S) or optionally substituted 5- to 10-membered heteroaryl (wherein 1-4 heteroaryl members are, independently, N, O, or S).

14. The compound according to claim 13, wherein $R^3$ is selected from the group consisting of benzothiazolyl, benzoisothiazolyl, benzoxazolyl, pyridinyl, pyridinonyl, pyridazinyl, benzimidazolyl, benzotriazolyl, indazolyl, quinoxalinyl, quinolinyl, quinazolinyl, imidazopyridinyl, pyrazolopyridinyl, triazolopyridinyl, cinnolinyl, isoxazolyl, pyrazolyl, benzofuranyl, dihydrobenzofuranyl, dihydrobenzodioxinyl, and tetrahydrobenzodioxinyl, each of which is optionally substituted.

15. The compound according to claim 1, wherein $R^3$ is optionally substituted $C_6$-$C_{10}$-aryl.

16. The compound according to claim 15, wherein $R^3$ is optionally substituted phenyl.

17. The compound according to claim 1, wherein $R^2$ is optionally substituted phenyl and $R^3$ is optionally substituted 3- to 14-membered heterocycloalkyl (wherein 1-4 heterocycloalkyl members are, independently, N, O, or S) or optionally substituted 5- to 10-membered heteroaryl (wherein 1-4 heteroaryl members are, independently, N, O, or S).

18. The compound according to claim 1, wherein L is O or NR.

19. The compound according to claim 18, wherein $R^1$ is optionally substituted $C_1$-$C_6$-alkyl or optionally substituted $C_3$-$C_6$-carbocyclyl.

20. The compound according to claim 18, wherein $R^1$ is $C_1$-$C_3$-alkyl that is optionally substituted by 1 to 3 F.

21. The compound according to claim 1, wherein:
L is O or NR and R is H;
$R^1$ is $C_1$-$C_3$-alkyl that is optionally substituted by 1 to 3 F;
$R^2$ is optionally substituted 3- to 14-membered heterocycloalkyl (wherein 1 heteroaryl member is N), optionally substituted 5- to 10-membered heteroaryl (wherein 1 heteroaryl member is N) or optionally substituted $C_6$-$C_{10}$-aryl;
$R^3$ is optionally substituted 3- to 14-membered heterocycloalkyl (wherein 1-4 heterocycloalkyl members are, independently, N, O, or S) or optionally substituted 5- to 10-membered heteroaryl (wherein 1 to 3 heteroaryl members are, independently, N, O, or S; and
each of $R^4$ and $R^5$ is H.

22. The compound according to claim 21, wherein L is NR.

23. The compound according to claim 1 or a pharmaceutically acceptable salt thereof, wherein the compound is:

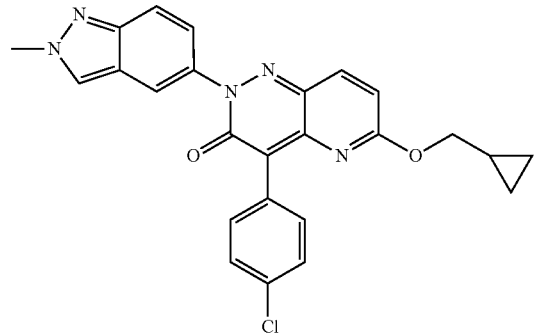 [SMILES: Cn1cc2cc(-n3nc4ccc(OCC5CC5)nc4c(-c4ccc(Cl)cc4)c3=O)ccc2n1]
101
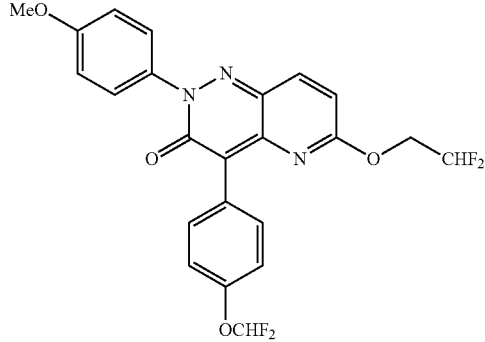
105
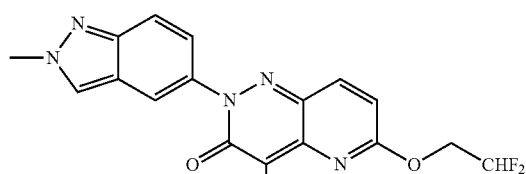
106
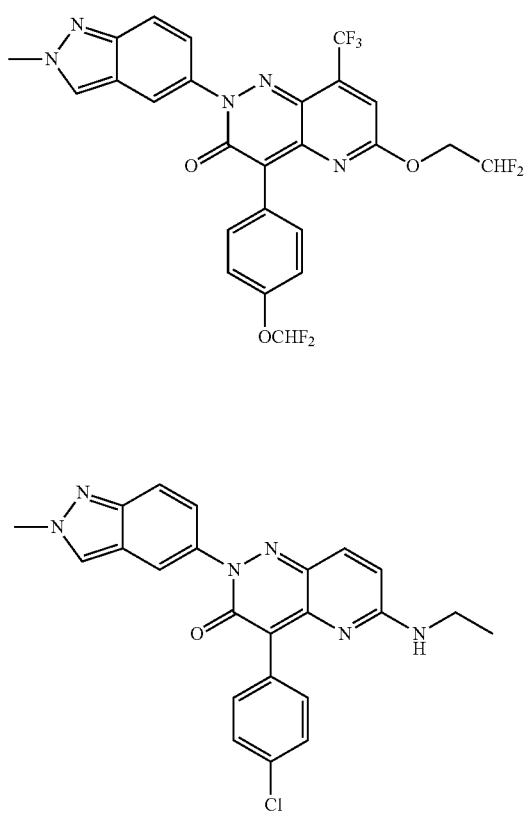
102
103
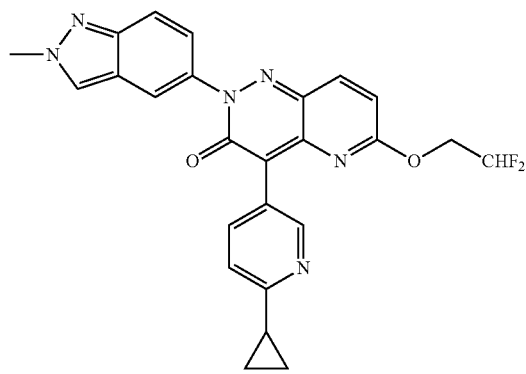
107
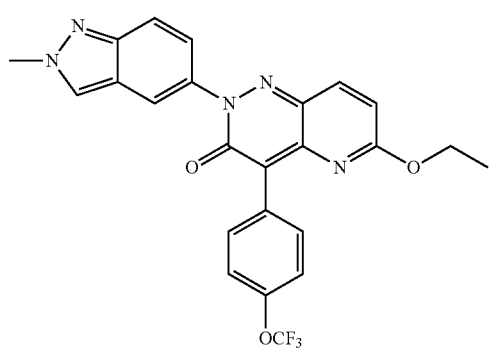
104
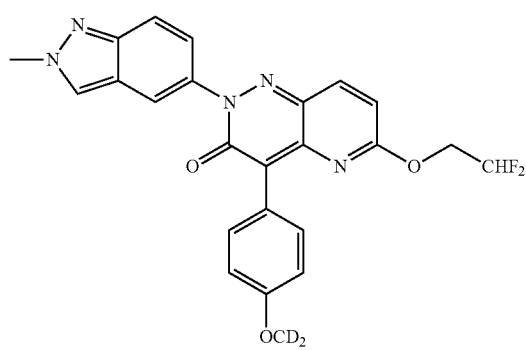
108

-continued
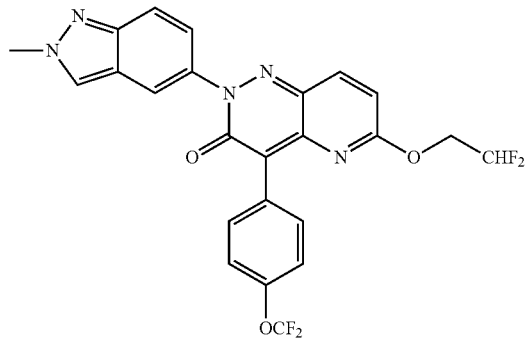
109
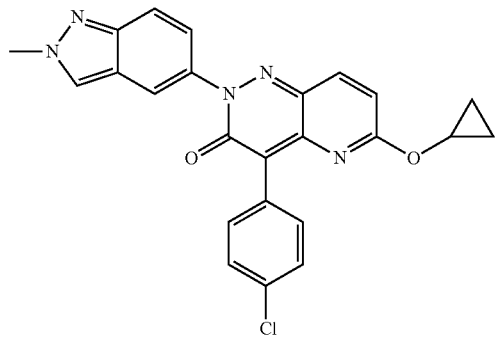 [SMILES: Cn1cc2cc(-n3nc4ccc(OC5CC5)nc4c(-c4ccc(Cl)cc4)c3=O)ccc2n1]
113
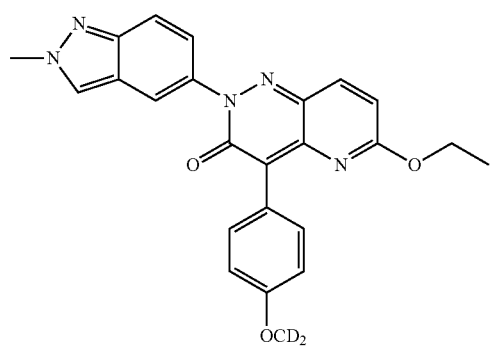
110
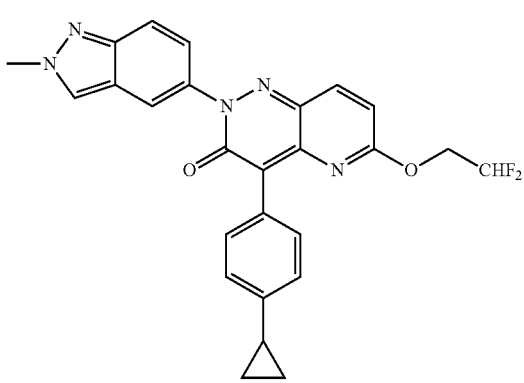
114
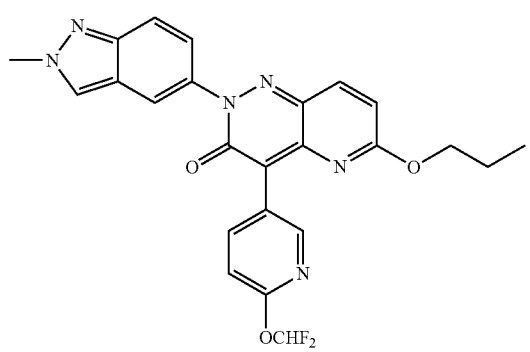
111
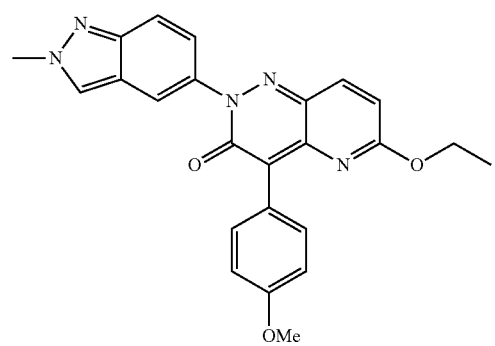 [SMILES: CCOc1ccc2nn(-c3ccc4nn(C)cc4c3)c(=O)c(-c3ccc(OC)cc3)c2n1]
115
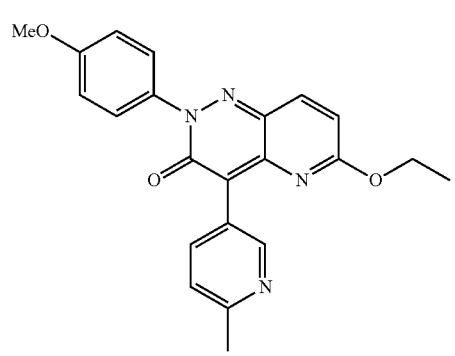
112
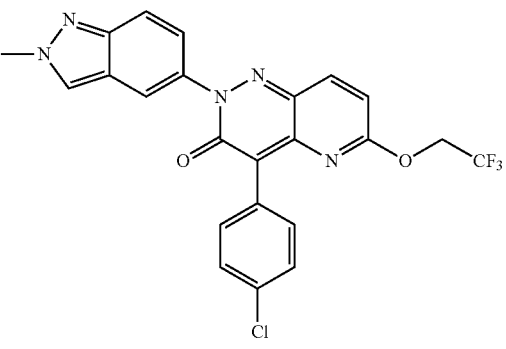 [SMILES: Cn1cc2cc(-n3nc4ccc(OCC(F)(F)F)nc4c(-c4ccc(Cl)cc4)c3=O)ccc2n1]
116

223
-continued
117 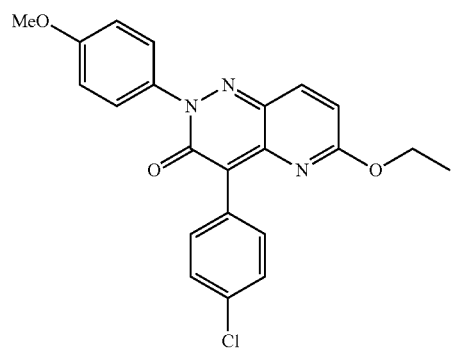 [SMILES: CCOc1ccc2nn(-c3ccc(OC)cc3)c(=O)c(-c3ccc(Cl)cc3)c2n1]
118 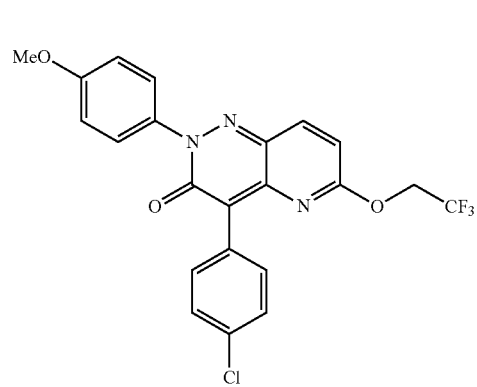 [SMILES: COc1ccc(-n2nc3ccc(OCC(F)(F)F)nc3c(-c3ccc(Cl)cc3)c2=O)cc1]
119 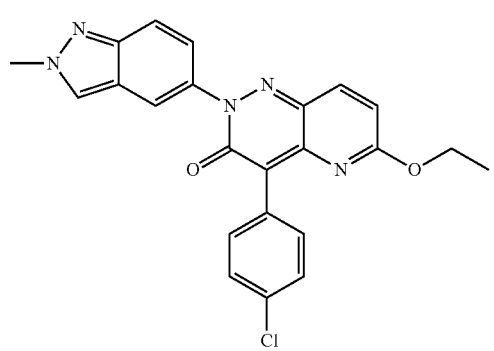 [SMILES: CCOc1ccc2nn(-c3ccc4nn(C)cc4c3)c(=O)c(-c3ccc(Cl)cc3)c2n1]
120 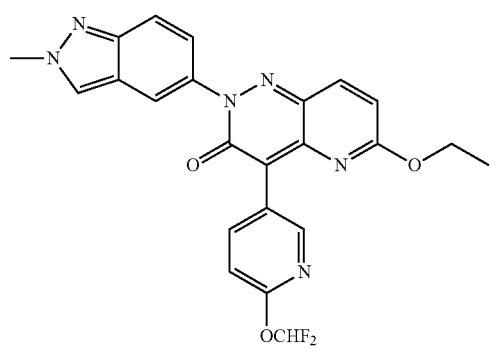
224
-continued
121 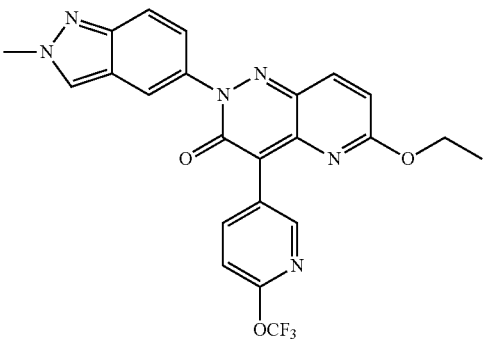
122 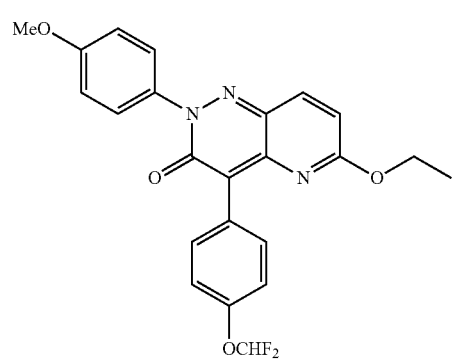
123 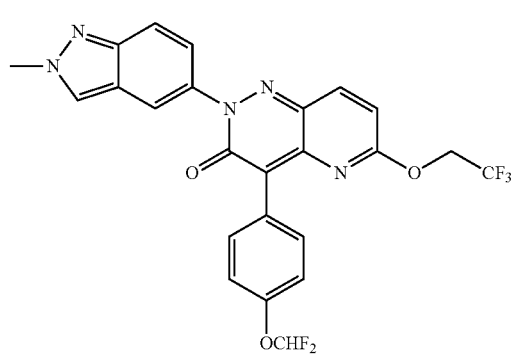 [SMILES: Cn1cc2cc(-n3nc4ccc(OCC(F)(F)F)nc4c(-c4ccc(OC(F)F)cc4)c3=O)ccc2n1]
124 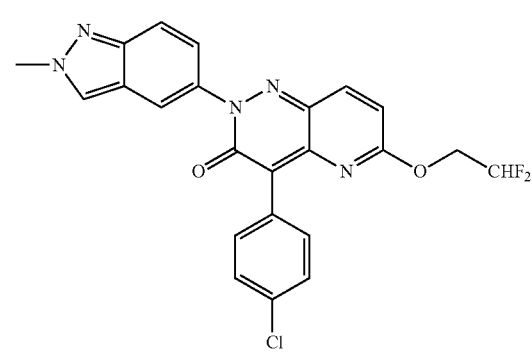

125
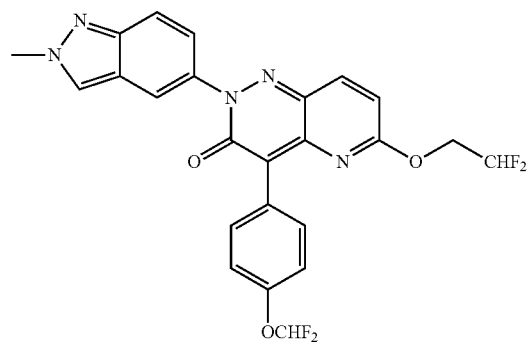
126
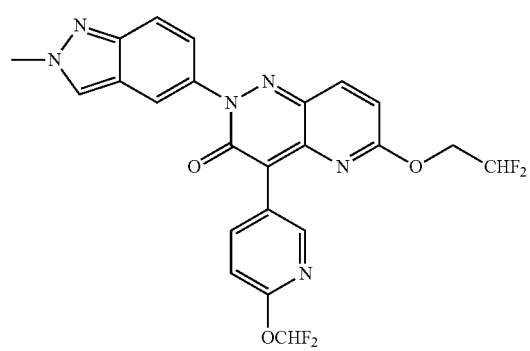
127
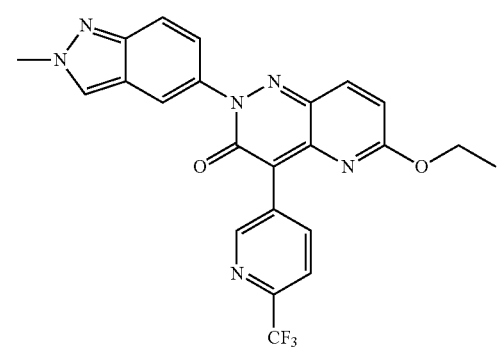
128
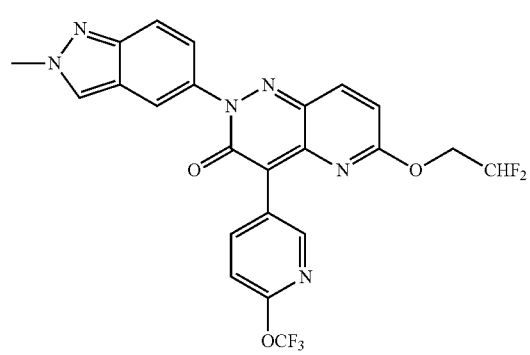
129
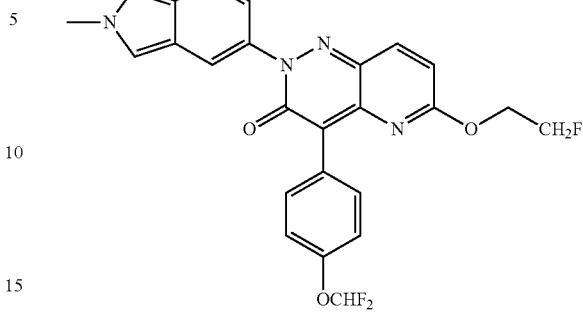
130
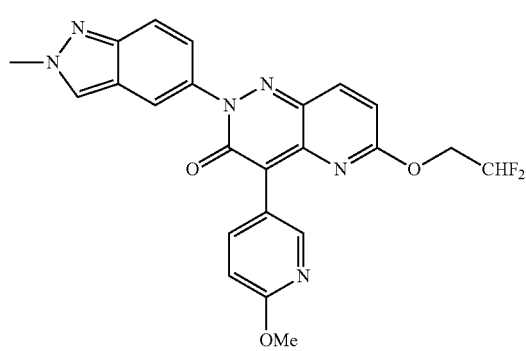
131
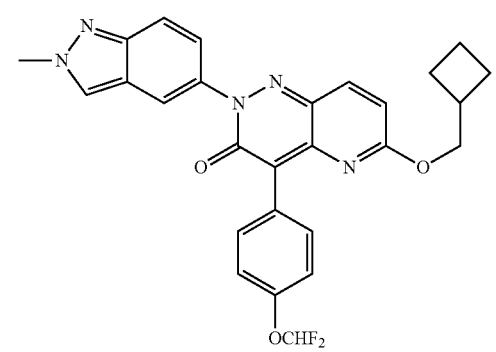 [SMILES: Cn1cc2cc(-n3nc4ccc(OCC5CCC5)nc4c(-c4ccc(OC(F)F)cc4)c3=O)ccc2n1]
132
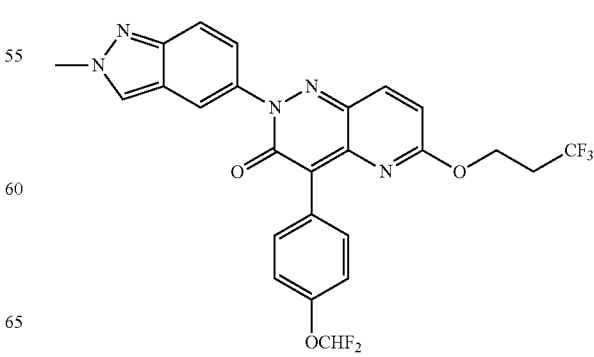

133
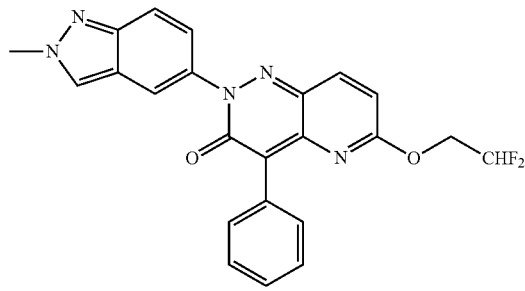
137
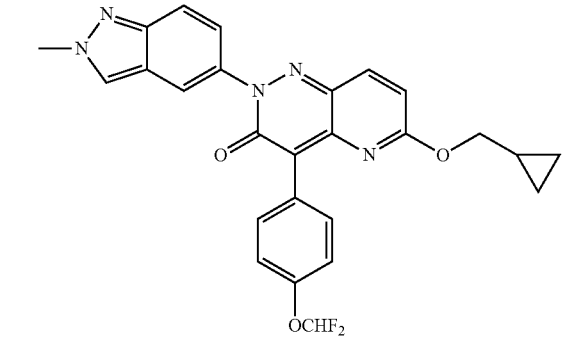
134
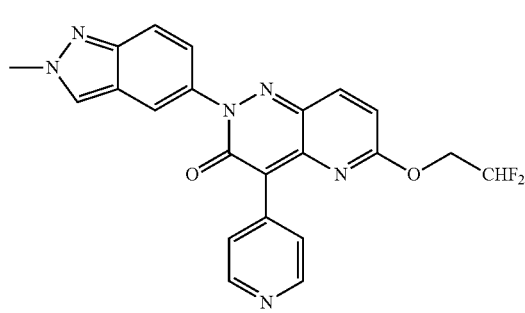
138
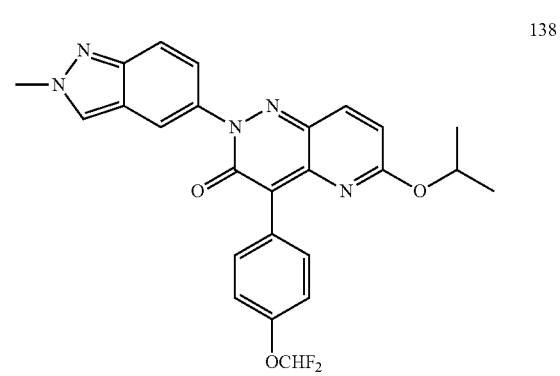
135
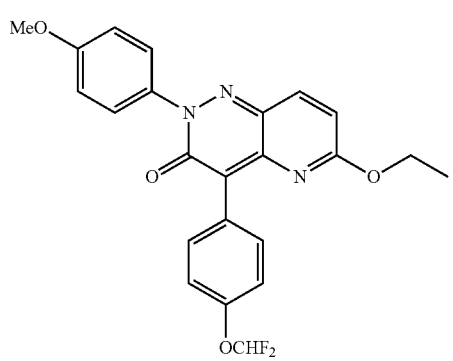 [SMILES: CCOc1ccc2nn(-c3ccc(OC)cc3)c(=O)c(-c3ccc(OC(F)F)cc3)c2n1]
139
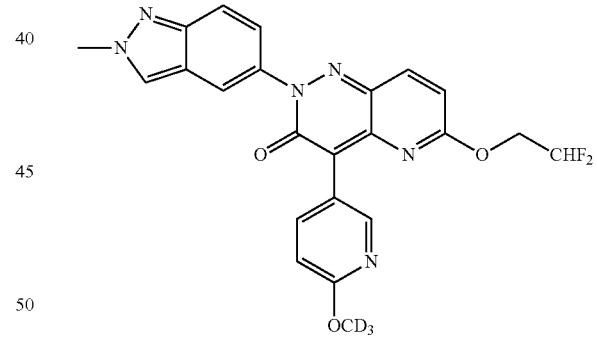
136
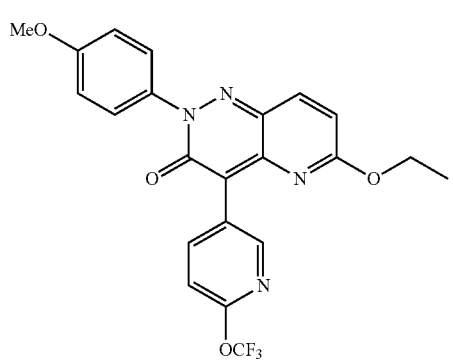 [SMILES: CCOc1ccc2nn(-c3ccc(OC)cc3)c(=O)c(-c3ccc(OC(F)(F)F)nc3)c2n1]
140
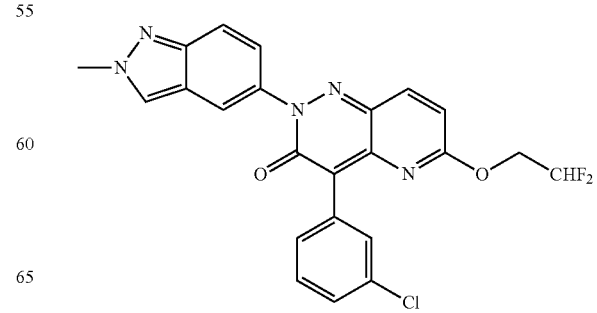

141
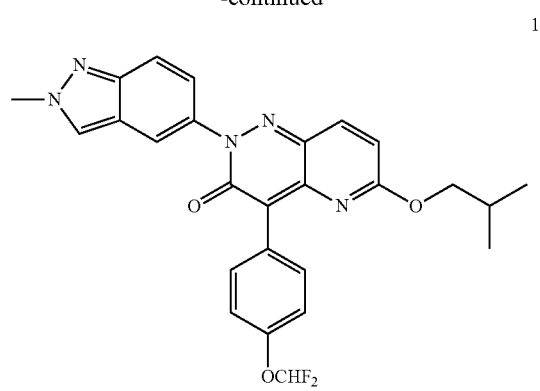
142
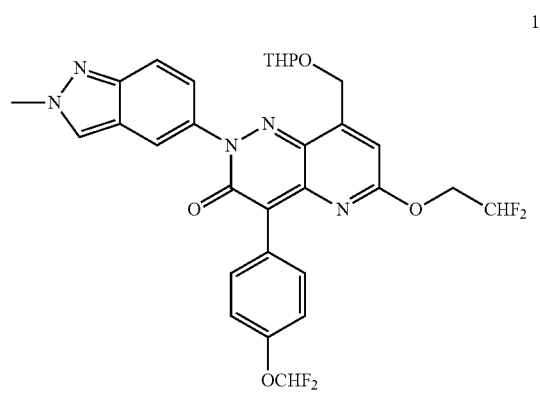
143
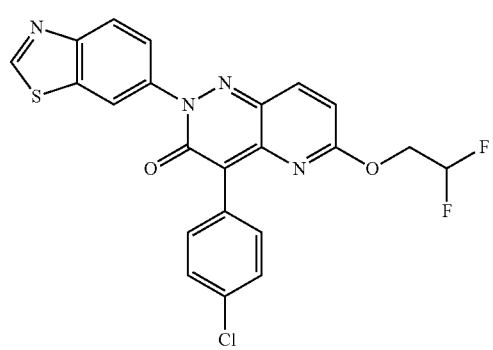 [SMILES: O=c1c(-c2ccc(Cl)cc2)c2nc(OCC(F)F)ccc2nn1-c1ccc2ncsc2c1]
144
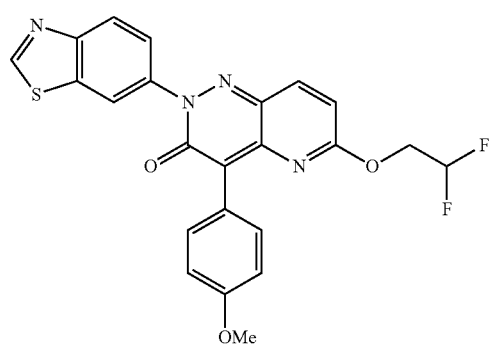 [SMILES: COc1ccc(-c2c(=O)n(-c3ccc4ncsc4c3)nc3ccc(OCC(F)F)nc23)cc1]
145
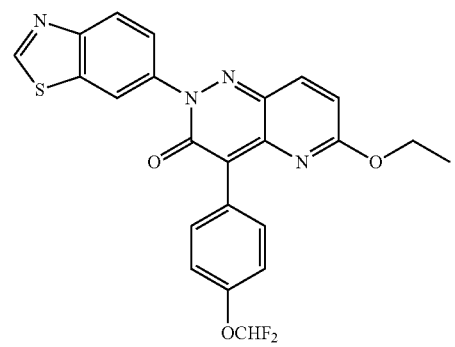
146
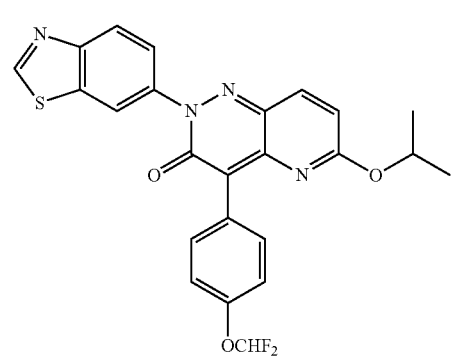 [SMILES: CC(C)Oc1ccc2nn(-c3ccc4ncsc4c3)c(=O)c(-c3ccc(OC(F)F)cc3)c2n1]
147
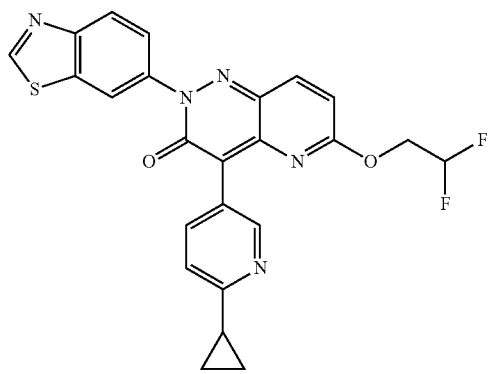 [SMILES: O=c1c(-c2ccc(C3CC3)nc2)c2nc(OCC(F)F)ccc2nn1-c1ccc2ncsc2c1]
148
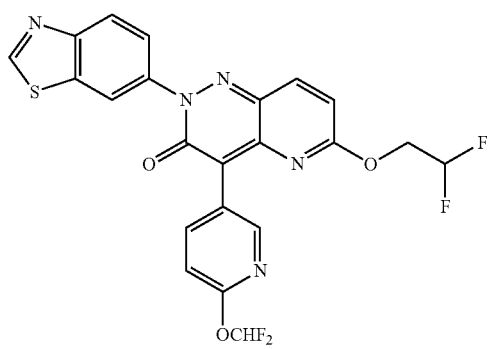 [SMILES: O=c1c(-c2ccc(OC(F)F)nc2)c2nc(OCC(F)F)ccc2nn1-c1ccc2ncsc2c1]

149
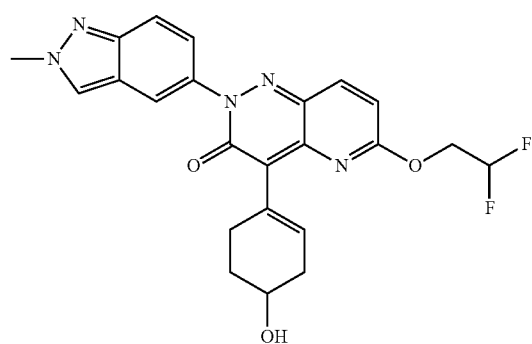
153
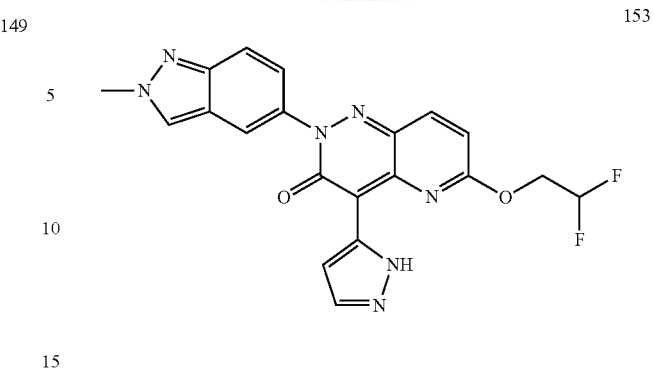
150
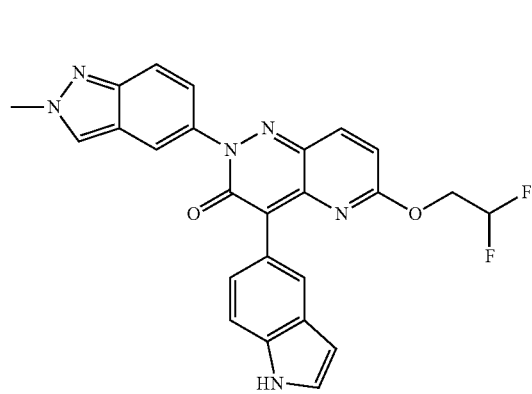
154
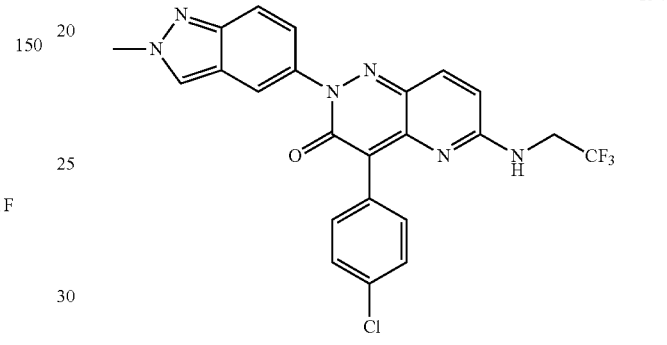
151
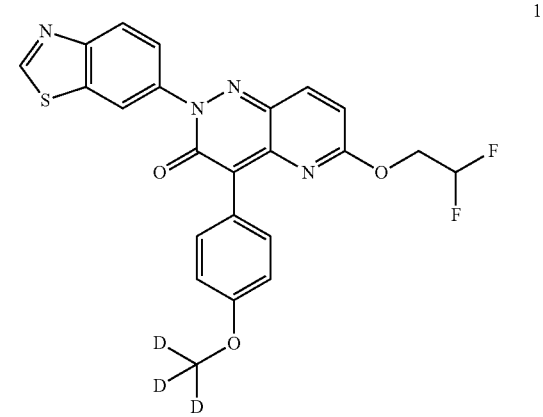
155
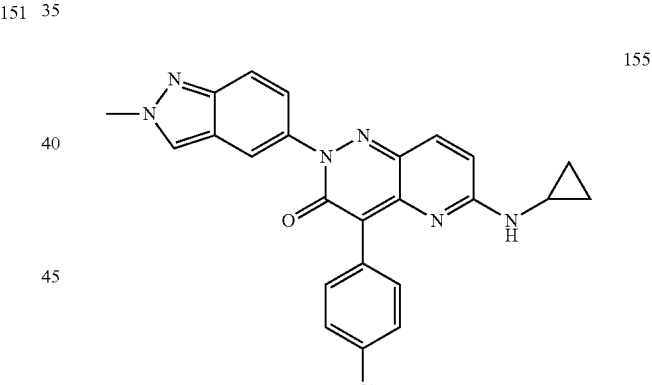
152
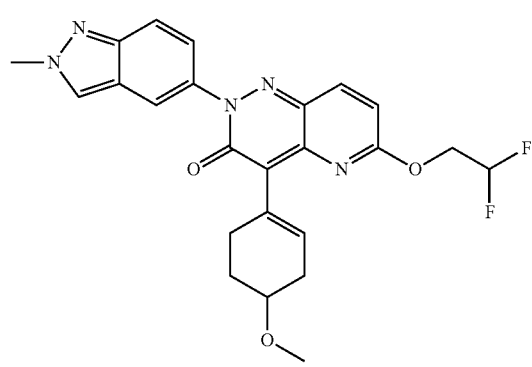 [SMILES: COC1CC=C(c2c(=O)n(-c3ccc4nn(C)cc4c3)nc3ccc(OCC(F)F)nc23)CC1]
156
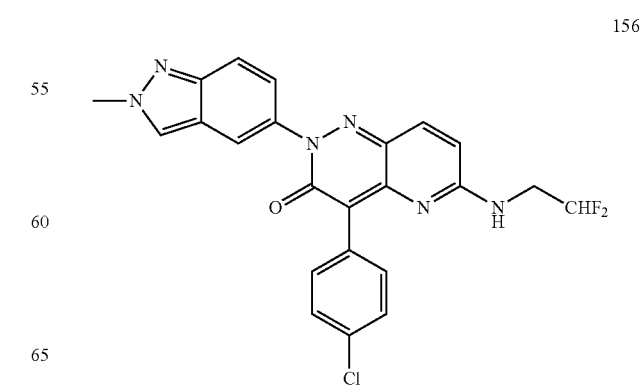

157
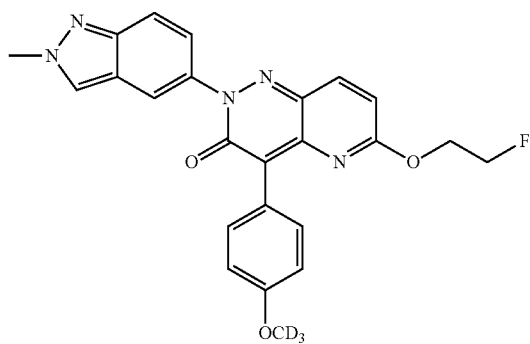
161
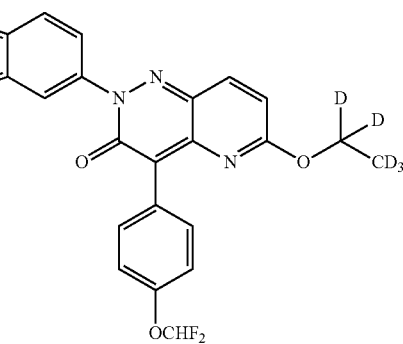
158
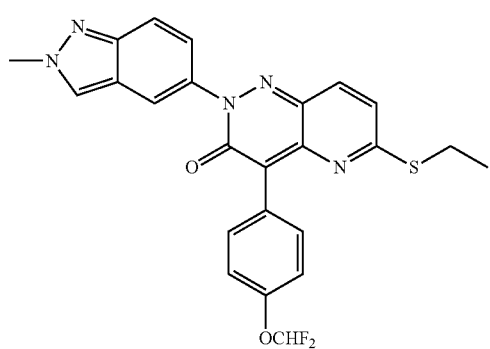
162
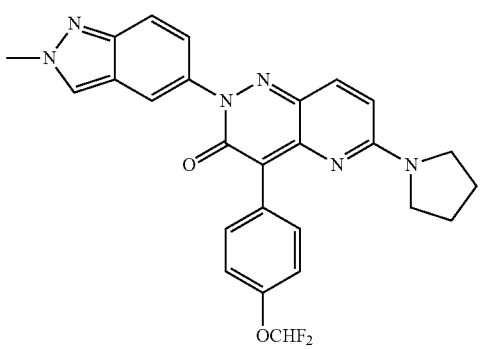 [SMILES: Cn1cc2cc(-n3nc4ccc(N5CCCC5)nc4c(-c4ccc(OC(F)F)cc4)c3=O)ccc2n1]
159
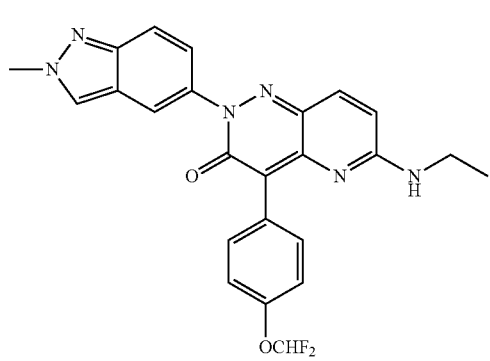
163
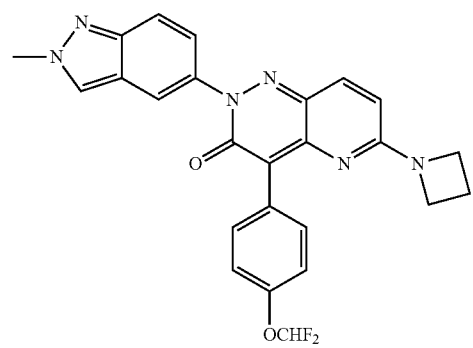 [SMILES: Cn1cc2cc(-n3nc4ccc(N5CCC5)nc4c(-c4ccc(OC(F)F)cc4)c3=O)ccc2n1]
160
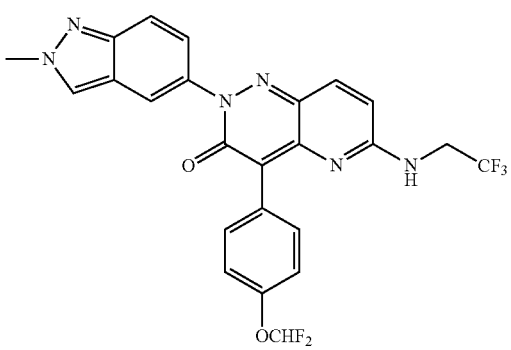
164

165 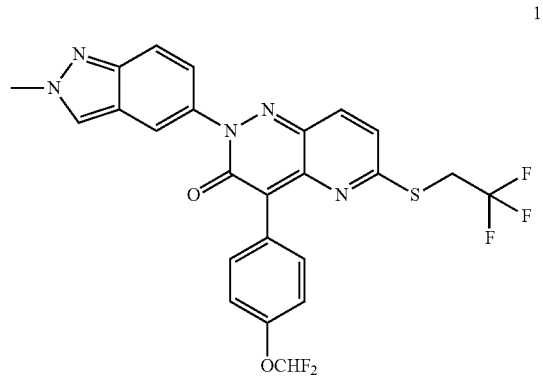
166 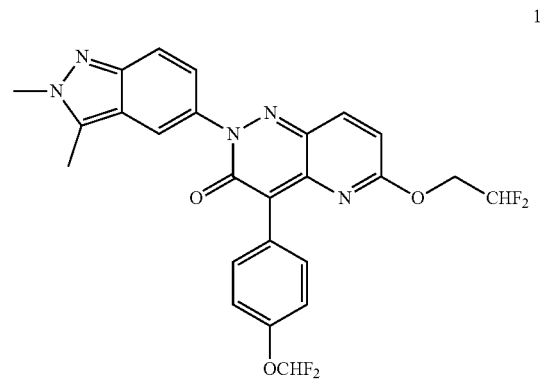
167 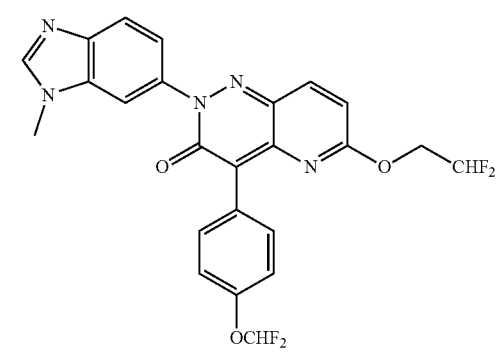
168 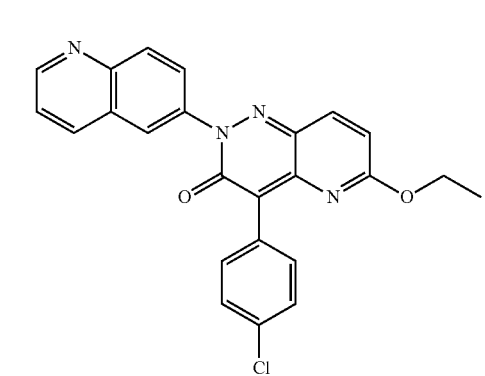 [SMILES: CCOc1ccc2nn(-c3ccc4ncccc4c3)c(=O)c(-c3ccc(Cl)cc3)c2n1]
169 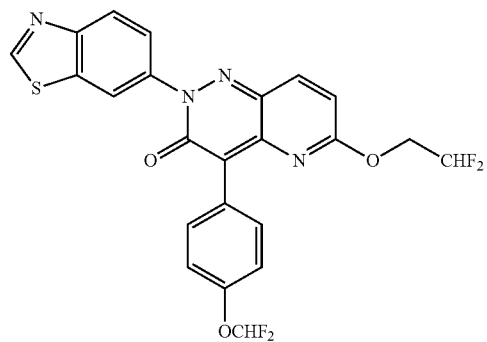
170 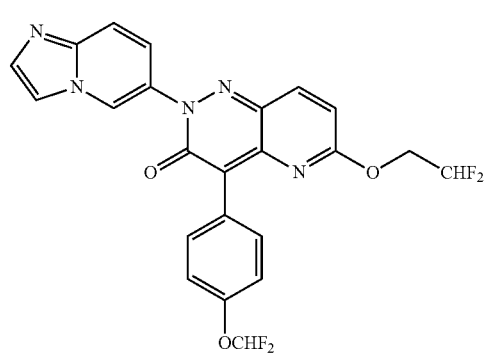 [SMILES: O=c1c(-c2ccc(OC(F)F)cc2)c2nc(OCC(F)F)ccc2nn1-c1ccc2nccn2c1]
171 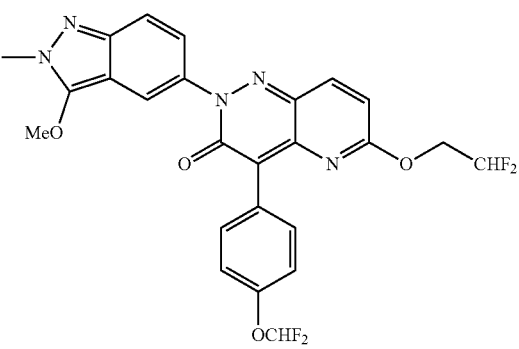
172 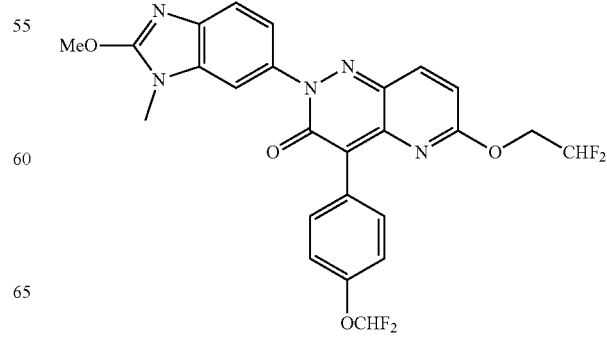

173
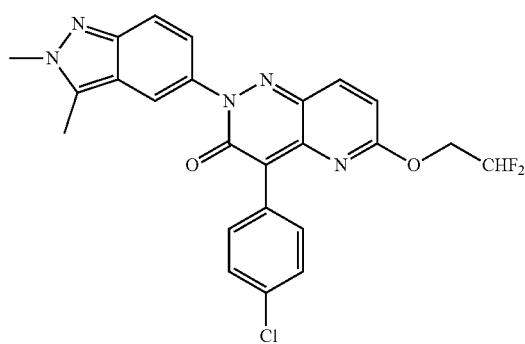
174
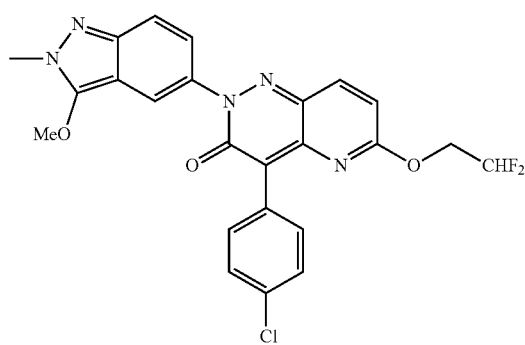
175
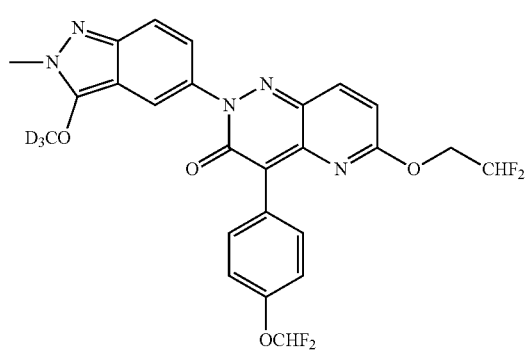
176
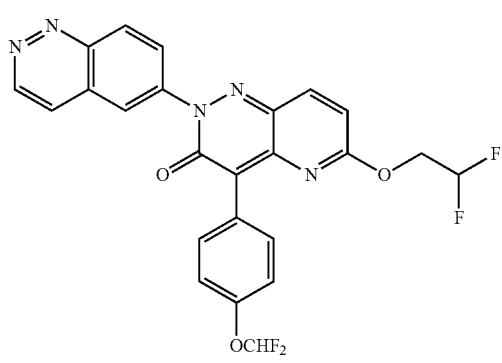 [SMILES: O=c1c(-c2ccc(OC(F)F)cc2)c2nc(OCC(F)F)ccc2nn1-c1ccc2nnccc2c1]
177
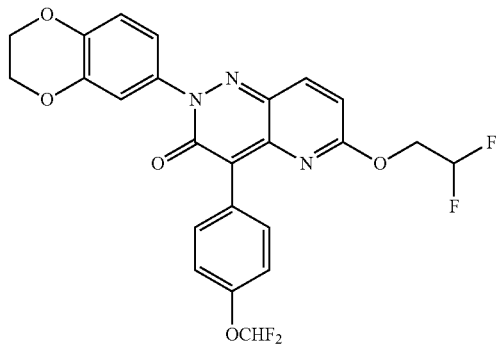 [SMILES: O=c1c(-c2ccc(OC(F)F)cc2)c2nc(OCC(F)F)ccc2nn1-c1ccc2c(c1)OCCO2]
178
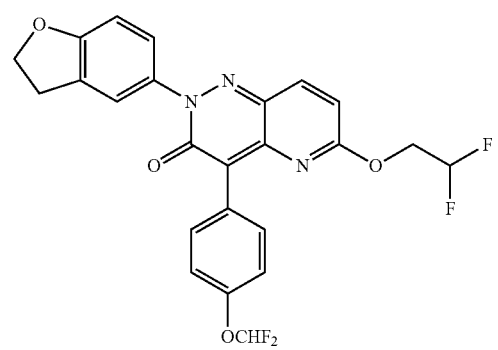 [SMILES: O=c1c(-c2ccc(OC(F)F)cc2)c2nc(OCC(F)F)ccc2nn1-c1ccc2c(c1)CCO2]
179
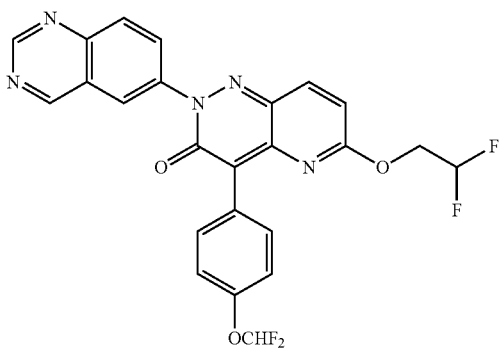 [SMILES: O=c1c(-c2ccc(OC(F)F)cc2)c2nc(OCC(F)F)ccc2nn1-c1ccc2ncncc2c1]
180
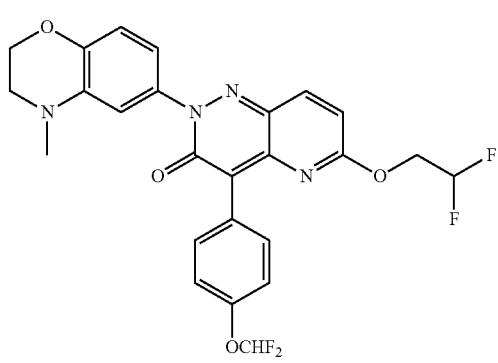 [SMILES: CN1CCOc2ccc(-n3nc4ccc(OCC(F)F)nc4c(-c4ccc(OC(F)F)cc4)c3=O)cc21]

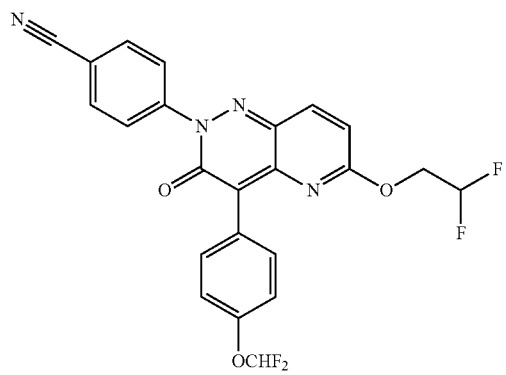 [SMILES: N#Cc1ccc(-n2nc3ccc(OCC(F)F)nc3c(-c3ccc(OC(F)F)cc3)c2=O)cc1]
181
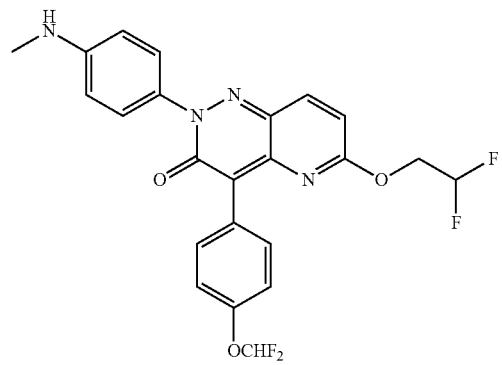 [SMILES: CNc1ccc(-n2nc3ccc(OCC(F)F)nc3c(-c3ccc(OC(F)F)cc3)c2=O)cc1]
185
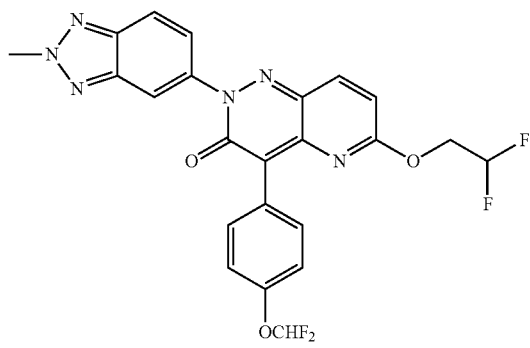
182
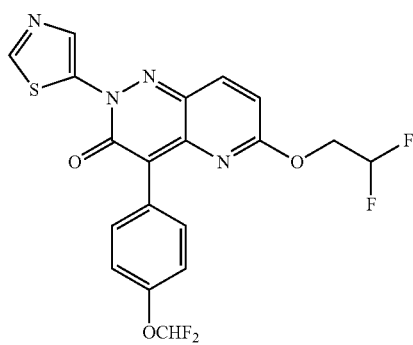 [SMILES: O=c1c(-c2ccc(OC(F)F)cc2)c2nc(OCC(F)F)ccc2nn1-c1cncs1]
186
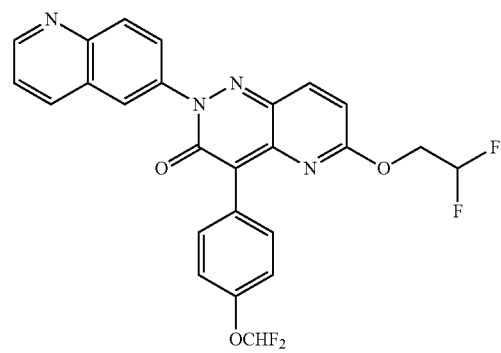
183
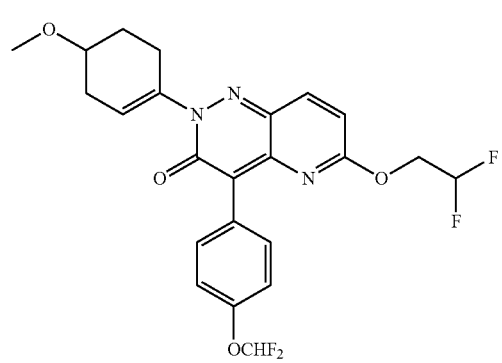 [SMILES: COC1CC=C(n2nc3ccc(OCC(F)F)nc3c(-c3ccc(OC(F)F)cc3)c2=O)CC1]
187
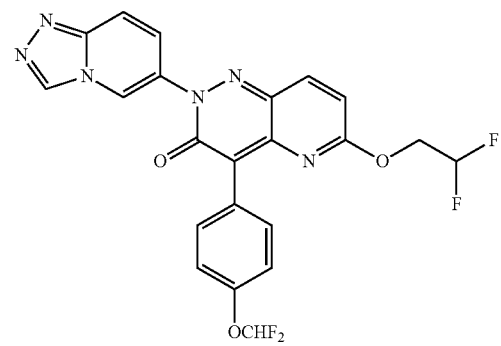
184
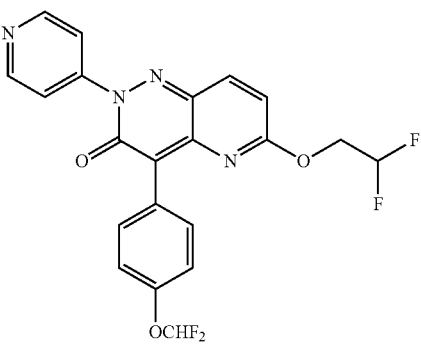 [SMILES: O=c1c(-c2ccc(OC(F)F)cc2)c2nc(OCC(F)F)ccc2nn1-c1ccncc1]
188

189
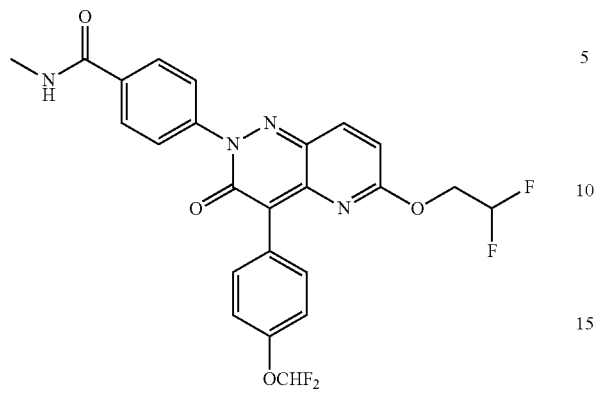
190
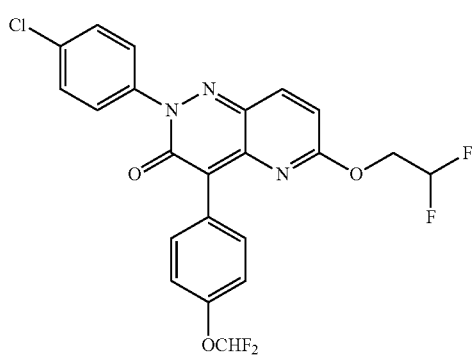 [SMILES: O=c1c(-c2ccc(OC(F)F)cc2)c2nc(OCC(F)F)ccc2nn1-c1ccc(Cl)cc1]
191
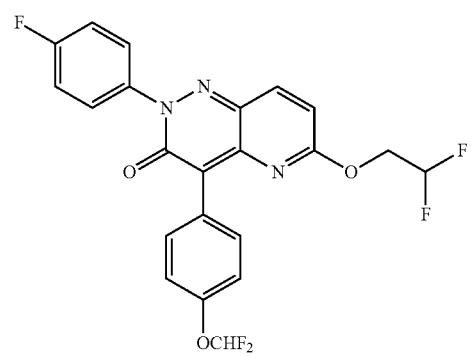 [SMILES: O=c1c(-c2ccc(OC(F)F)cc2)c2nc(OCC(F)F)ccc2nn1-c1ccc(F)cc1]
192
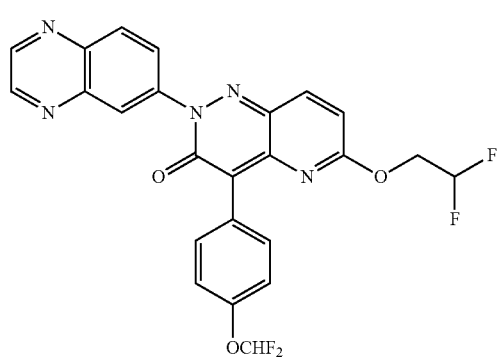 [SMILES: O=c1c(-c2ccc(OC(F)F)cc2)c2nc(OCC(F)F)ccc2nn1-c1ccc2nccnc2c1]
193
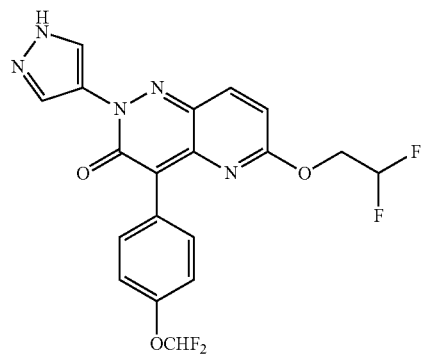 [SMILES: O=c1c(-c2ccc(OC(F)F)cc2)c2nc(OCC(F)F)ccc2nn1-c1cn[nH]c1]
194
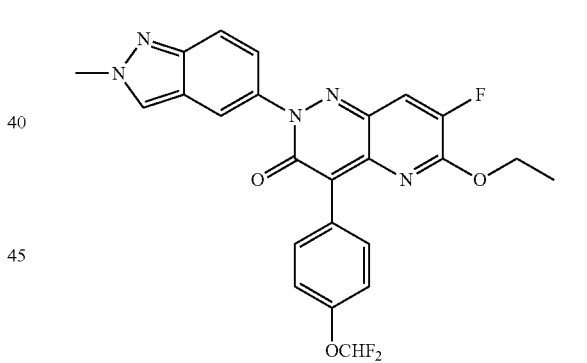
195
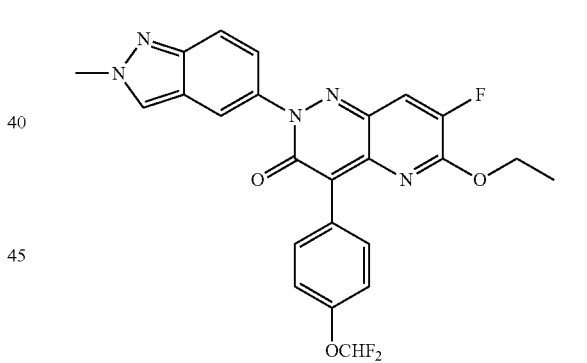
196
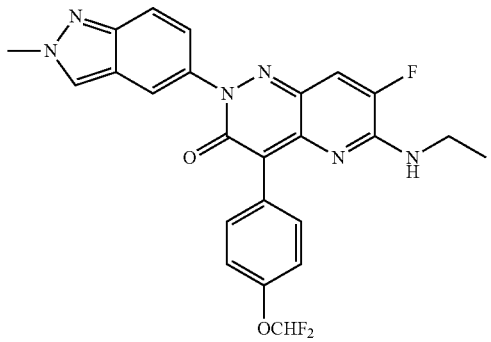

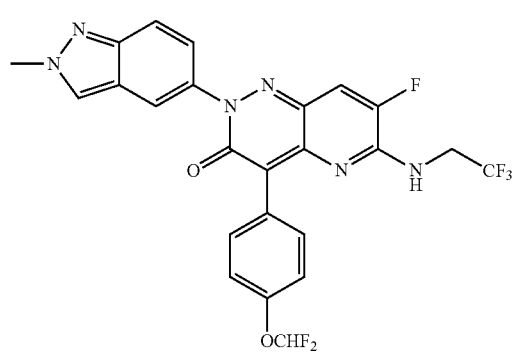 [SMILES: Cn1cc2cc(-n3nc4cc(F)c(NCC(F)(F)F)nc4c(-c4ccc(OC(F)F)cc4)c3=O)ccc2n1]
197
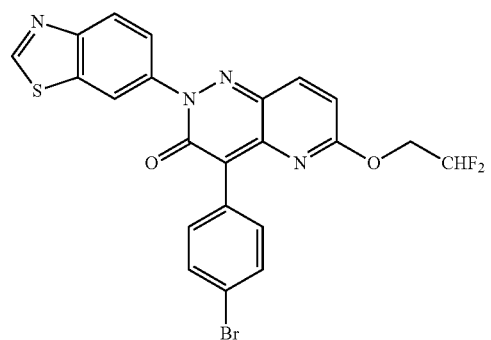
201
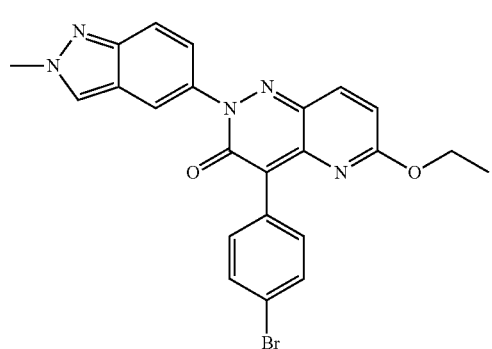 [SMILES: CCOc1ccc2nn(-c3ccc4nn(C)cc4c3)c(=O)c(-c3ccc(Br)cc3)c2n1]
198
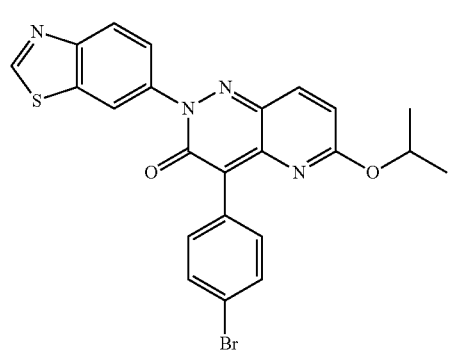
202
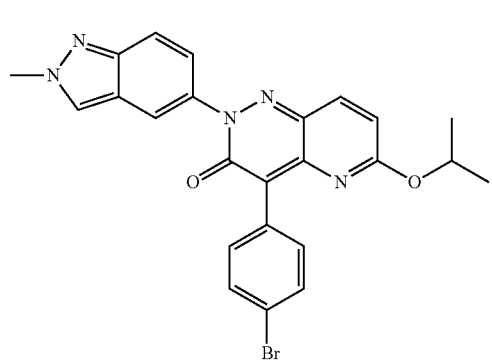 [SMILES: CC(C)Oc1ccc2nn(-c3ccc4nn(C)cc4c3)c(=O)c(-c3ccc(Br)cc3)c2n1]
199
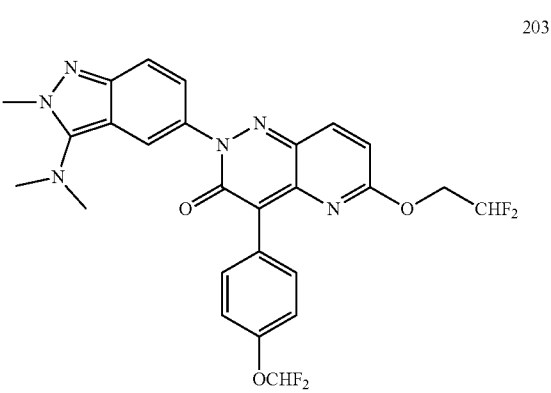
203
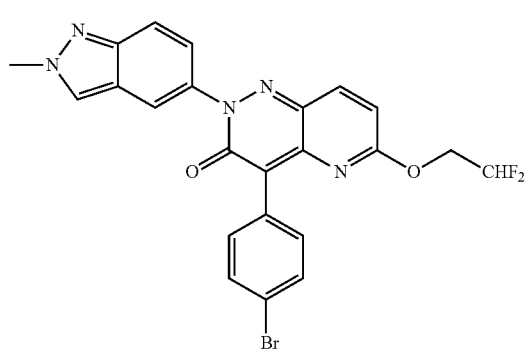
200
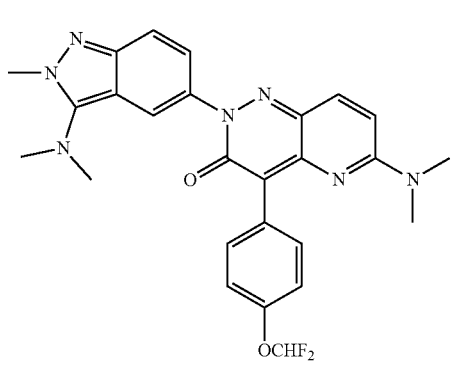
204

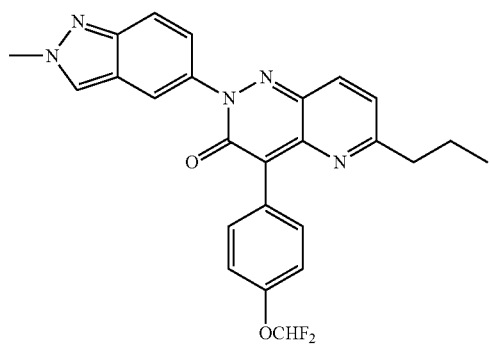 [SMILES: CCCc1ccc2nn(-c3ccc4nn(C)cc4c3)c(=O)c(-c3ccc(OC(F)F)cc3)c2n1]
205
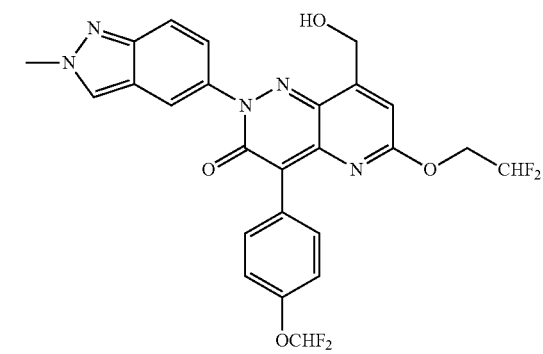
209
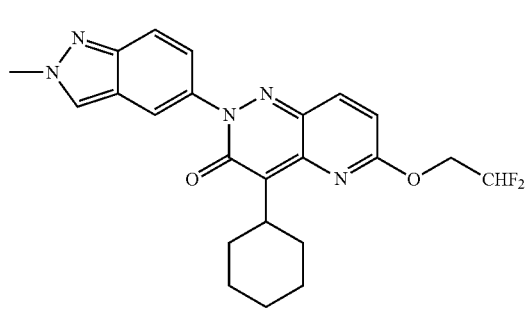
206
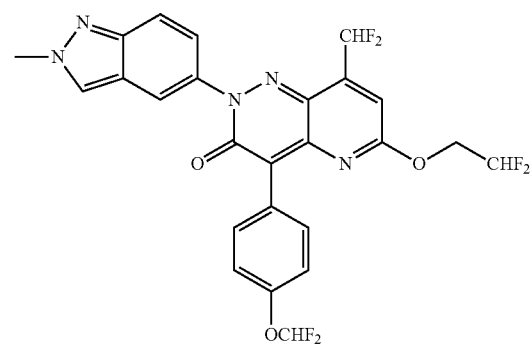
210
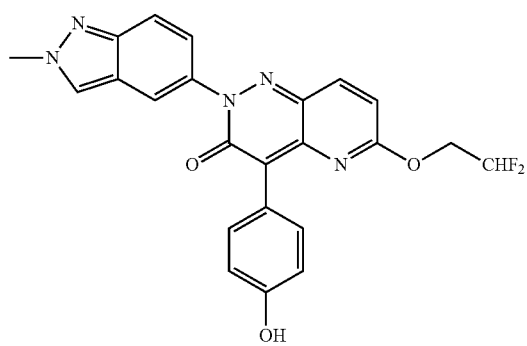
207
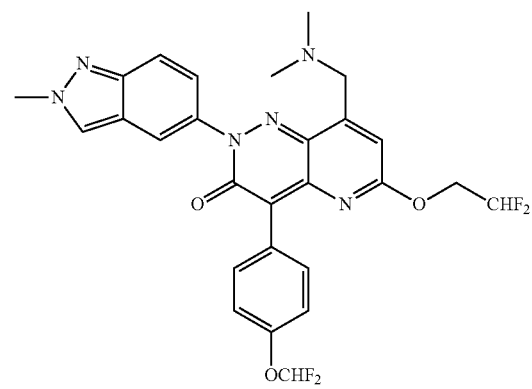
211
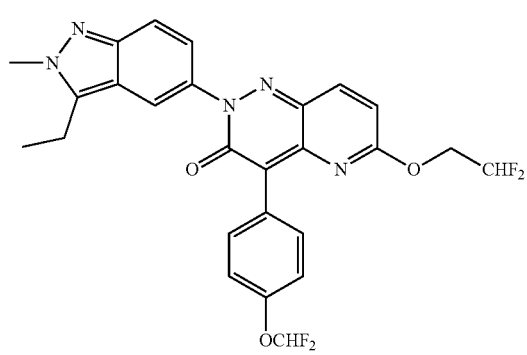
208
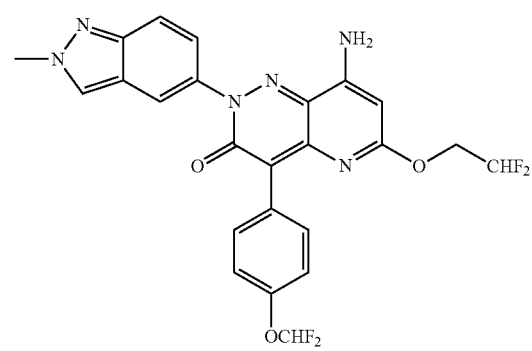
212

213
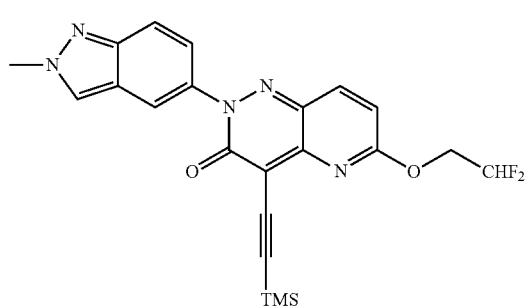
214
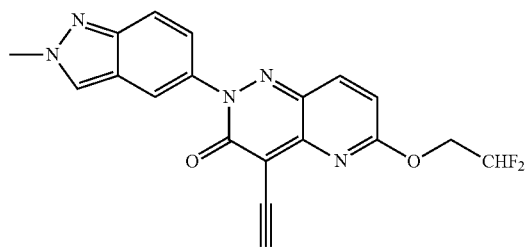
215
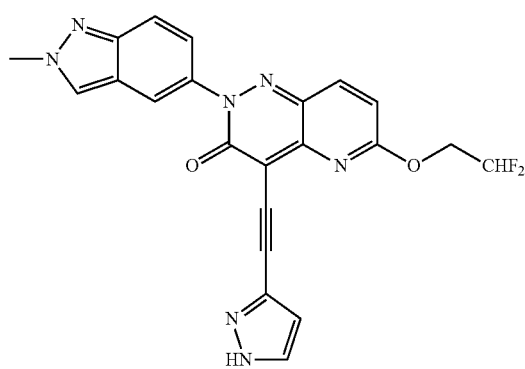
216
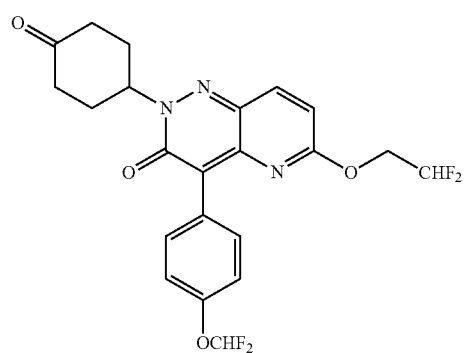 [SMILES: O=C1CCC(n2nc3ccc(OCC(F)F)nc3c(-c3ccc(OC(F)F)cc3)c2=O)CC1]
217
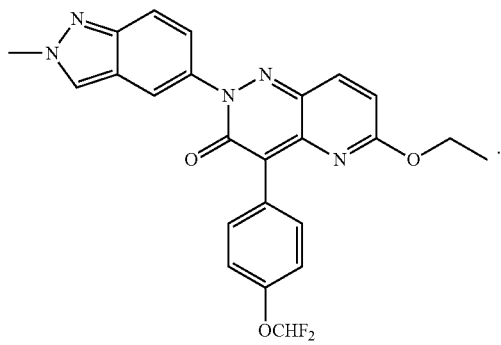
24. The compound according to claim 1 or a pharmaceutically acceptable salt thereof, wherein the compound is:
301
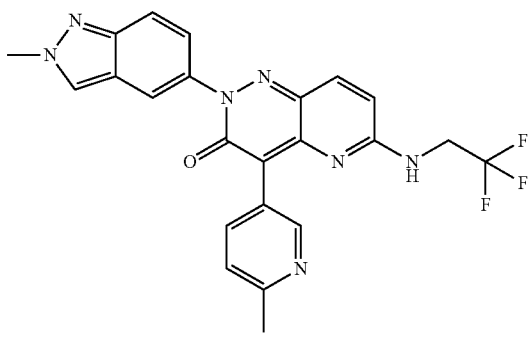
302, 303
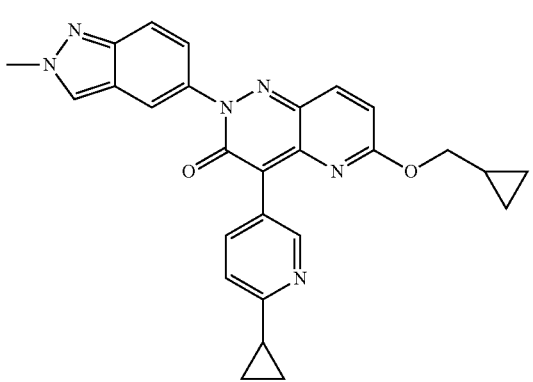

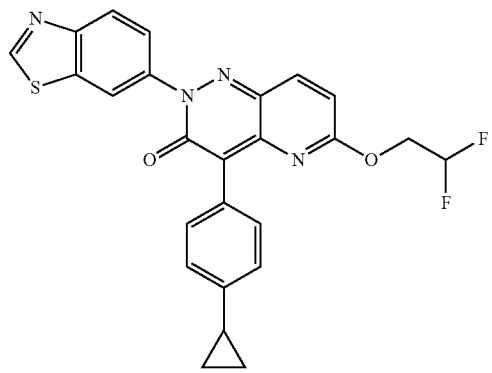
304
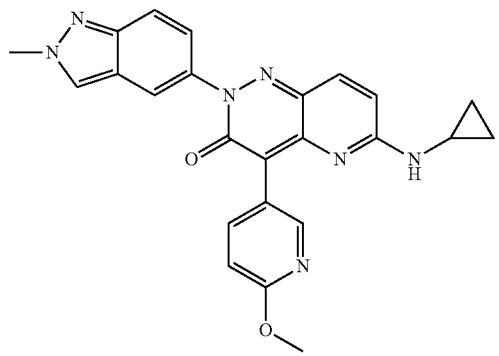
308
305
309
306
310
307
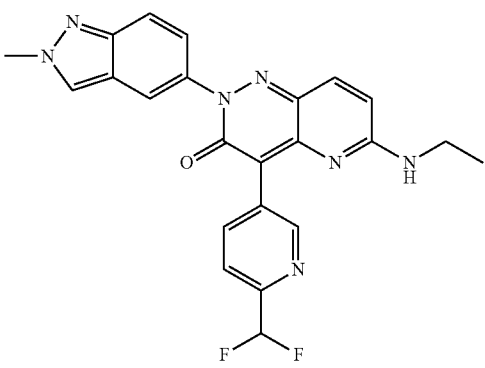
311
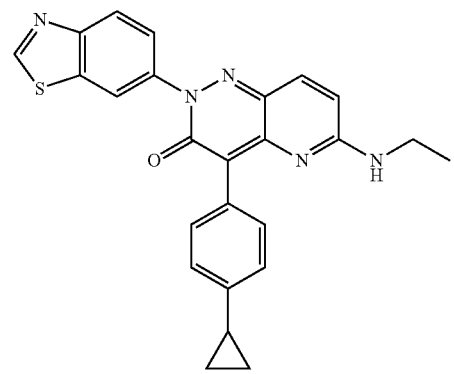

251
-continued
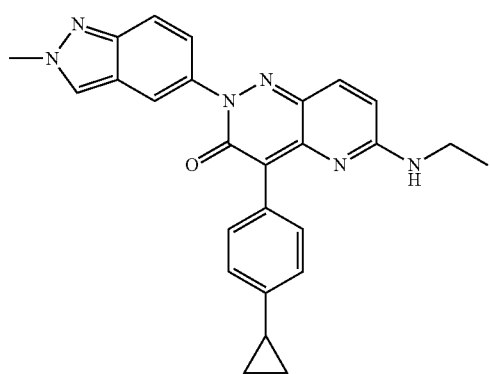
312
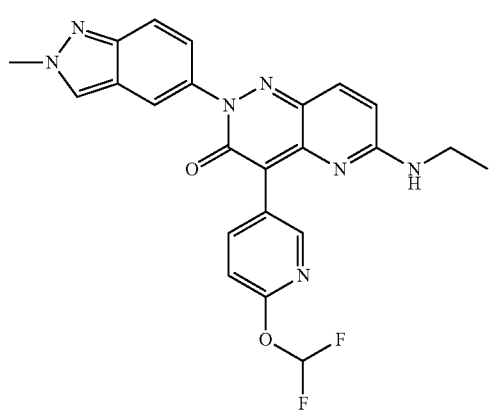
313
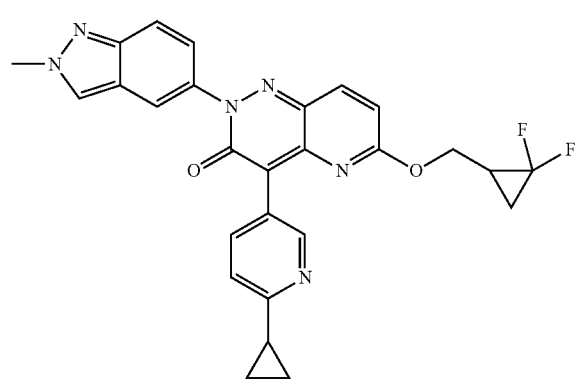
314
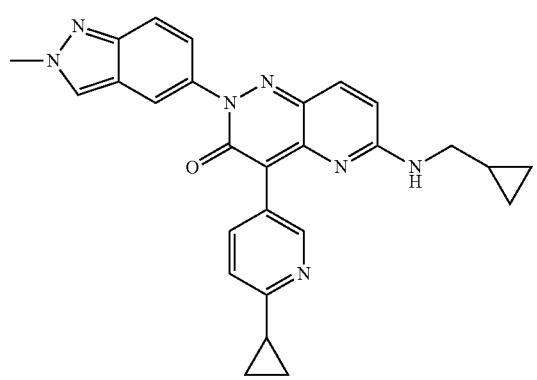
315
252
-continued
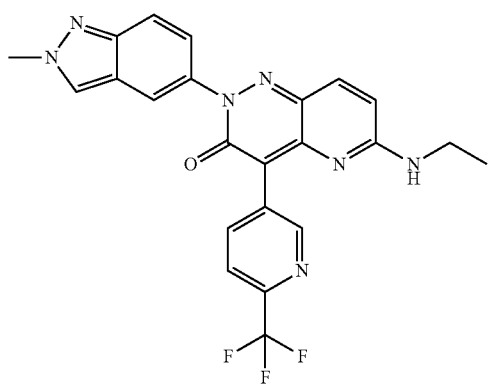
316
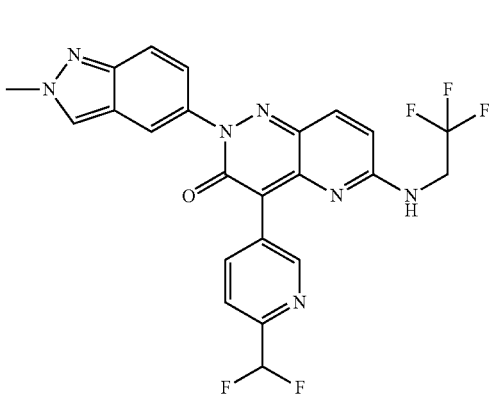
317
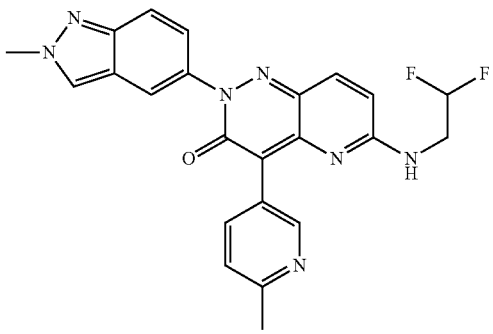
318
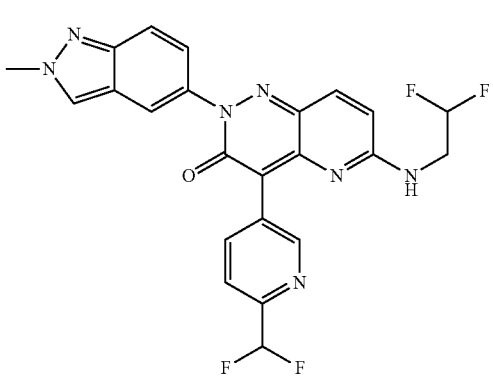
319

253
-continued
320
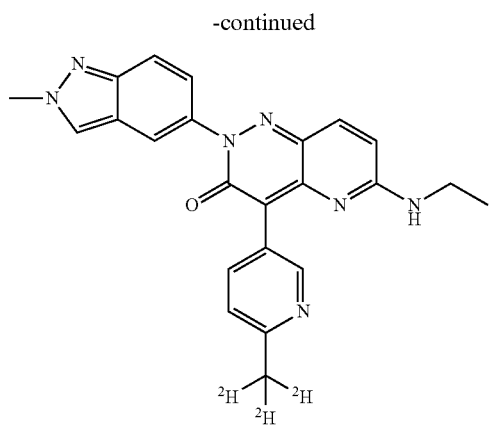
321
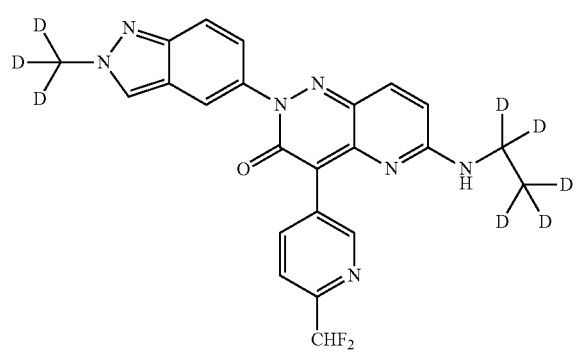
322
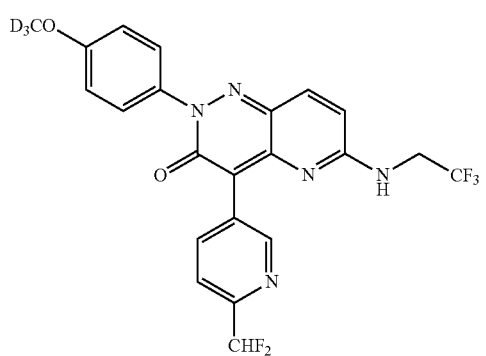
323
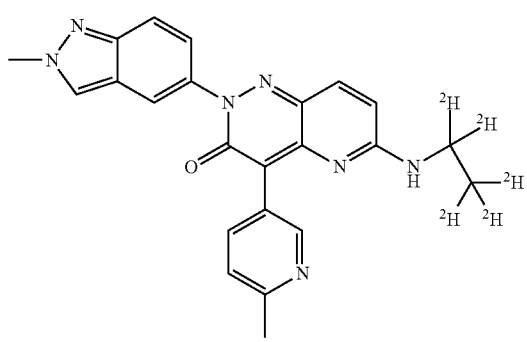
254
-continued
324
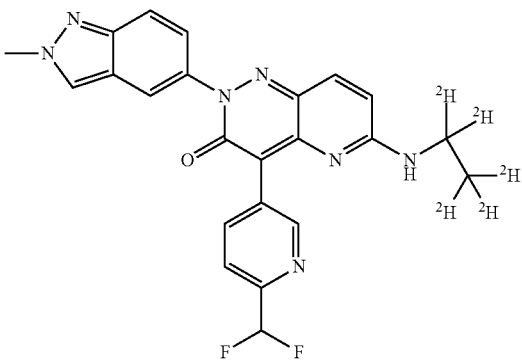
325
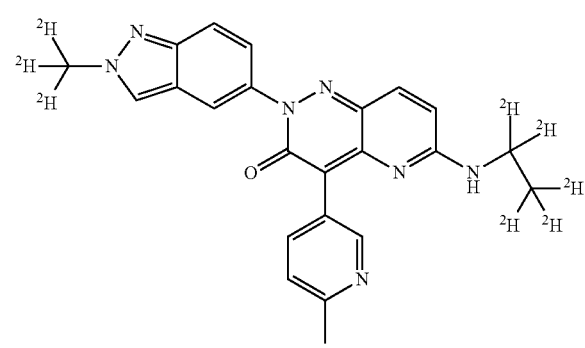
326
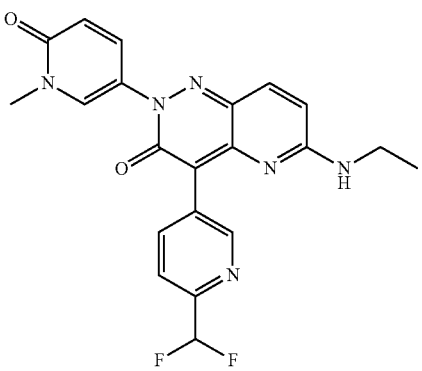
327
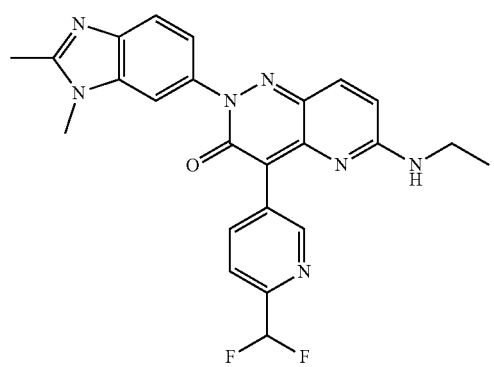

328 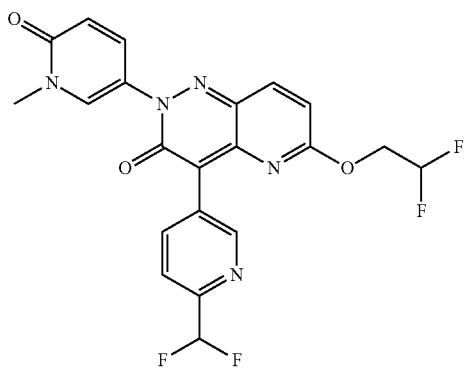

329 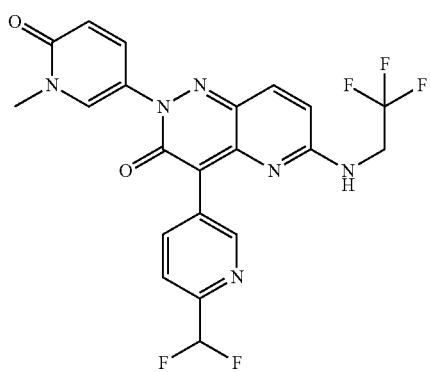

330 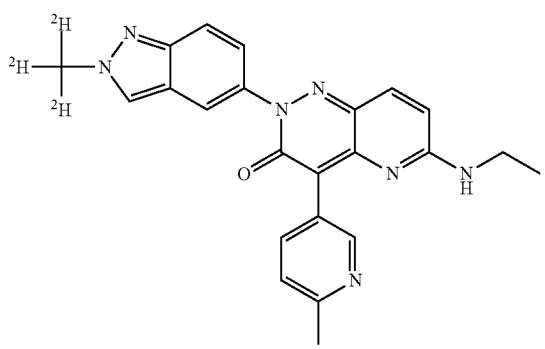

331 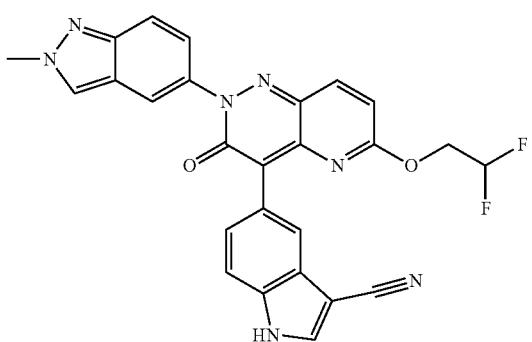

332 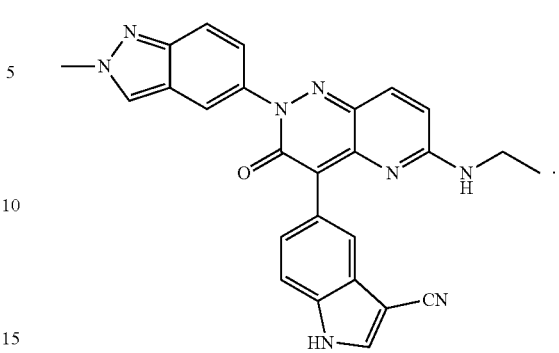

25. A pharmaceutical composition comprising a therapeutically effective amount of a compound according to claim 1 or a pharmaceutically acceptable salt thereof, and a pharmaceutically acceptable carrier.

26. A method for treating a cancer in a subject suffering therefrom, comprising administering to the subject an effective amount of a MAT2A inhibitor compound or a pharmaceutically acceptable salt thereof according to claim 1.

27. The method according to claim 26, wherein the cancer is an MTAP-deleted cancer.

28. A method for treating a cancer in a subject suffering therefrom, comprising administering to the subject an effective amount of a compound or a pharmaceutically acceptable salt thereof according to claim 1.

29. The method according to claim 28, wherein the cancer is an MTAP-deleted cancer.

30. The method according to claim 26, wherein the cancer is selected from the group consisting of mesothelioma, neuroblastoma, rectum carcinoma, colon carcinoma, familiarly adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, bladder carcinoma, testis carcinoma, breast carcinoma, urinary carcinoma, melanoma, brain tumors, lymphoma, head and neck cancer, acute lymphatic leukemia (ALL), chronic lymphatic leukemia (CLL), acute myeloid leukemia (AML), chronic myeloid leukemia (CML), hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, osteosarcoma, chondrosarcoma, myosarcoma, liposarcoma, fibrosarcoma, Ewing sarcoma, and plasmocytoma.

31. The method according to claim 28, wherein the cancer is selected from the group consisting of B-cell acute lymphocytic leukemia (B-ALL), mesothelioma, lymphoma, pancreatic carcinoma, lung cancer, gastric cancer, esophageal cancer, bladder carcinoma, brain cancer, head and neck cancer, melanoma, and breast cancer.

32. The method according to claim 31, wherein the cancer is a lung cancer selected from the group consisting of non-small cell lung cancer, small cell lung cancer, adenocarcinoma of the lung, and squamous cell carcinoma of the lung.

33. The method according to claim 31, wherein cancer is a brain tumor selected from the group consisting of glioma, glioblastoma, astrocytoma, meningioma, medulloblastoma, peripheral neuroectodermal tumors, and craniopharyngioma.

34. The method according to claim 31, wherein the cancer is triple negative breast cancer (TNBC).

35. The method according to claim 31, wherein the cancer is a lymphoma selected from the group consisting of mantle cell lymphoma, Hodgkin lymphoma, non-Hodgkin lymphoma, Burkitt lymphoma, diffuse large B-cell lymphoma, and adult T-cell leukemia/lymphoma.

* * * * *